United States Patent
Kelly et al.

(10) Patent No.: US 7,816,371 B2
(45) Date of Patent: Oct. 19, 2010

(54) BICYCLOHETEROARYL COMPOUNDS AS P2X₇ MODULATORS AND USES THEREOF

(75) Inventors: Michael G. Kelly, Thousand Oaks, CA (US); John Kincaid, Belmont, CA (US); Yunfeng Fang, Foster City, CA (US); Jianhua He, legal representative, Foster City, CA (US); Yeyu Cao, Foster City, CA (US); Carl Kaub, San Mateo, CA (US); Sumithra Gowlugari, San Mateo, CA (US); Zhan Wang, Palo Alto, CA (US)

(73) Assignee: Renovis, Inc., Newark, CA (US)

( * ) Notice: Subject to any disclaimer, the term of this patent is extended or adjusted under 35 U.S.C. 154(b) by 795 days.

(21) Appl. No.: 11/725,153

(22) Filed: Mar. 16, 2007

(65) Prior Publication Data

US 2007/0225324 A1    Sep. 27, 2007

Related U.S. Application Data

(60) Provisional application No. 60/783,121, filed on Mar. 16, 2006, provisional application No. 60/782,923, filed on Mar. 16, 2006, provisional application No. 60/783,590, filed on Mar. 16, 2006, provisional application No. 60/906,049, filed on Mar. 9, 2007, provisional application No. 60/831,416, filed on Jul. 17, 2006.

(51) Int. Cl.
 C07D 217/22    (2006.01)
 A61K 31/4704   (2006.01)
(52) U.S. Cl. .......................... 514/309; 546/143
(58) Field of Classification Search ................. None
 See application file for complete search history.

(56) References Cited

U.S. PATENT DOCUMENTS

| | | | |
|---|---|---|---|
| 2,640,829 | A | 6/1953 | Wilson et al. |
| 3,978,066 | A | 8/1976 | Philipp et al. |
| 6,380,193 | B1 | 4/2002 | Li et al. |
| 2005/0215572 | A1 | 9/2005 | Kelly et al. |
| 2005/0267018 | A1 | 12/2005 | Blatt et al. |
| 2005/0267202 | A1 | 12/2005 | Nguyen et al. |
| 2005/0277643 | A1 | 12/2005 | Kelly et al. |
| 2006/0135557 | A1 | 6/2006 | Nan et al. |

FOREIGN PATENT DOCUMENTS

| | | |
|---|---|---|
| EP | 482939 A1 | 4/1992 |
| WO | WO 99/21836 | 5/1999 |
| WO | WO 00/42040 | 7/2000 |
| WO | WO 01/87855 | 11/2001 |
| WO | WO 02/094790 | 11/2002 |
| WO | WO 03/011285 | 2/2003 |
| WO | 03/080579 A1 | 10/2003 |
| WO | WO 03/080578 | 10/2003 |
| WO | WO 03/082827 | 10/2003 |
| WO | WO 03/093249 | 11/2003 |
| WO | WO 03/099274 | 12/2003 |
| WO | WO 2004/035545 | 4/2004 |
| WO | WO 2004/078176 | 9/2004 |
| WO | 2004106305 A1 | 12/2004 |
| WO | WO 2004/108724 | 12/2004 |
| WO | WO 2005/034939 | 4/2005 |
| WO | WO 2005/035503 | 4/2005 |
| WO | WO 2005/066171 | 7/2005 |
| WO | WO 2005/075429 | 8/2005 |
| WO | WO 2005/105814 | 11/2005 |
| WO | WO 2006/050998 | 5/2006 |
| WO | WO 2006/057270 | 6/2006 |
| WO | WO 2006/066950 | 6/2006 |
| WO | 2006102588 A1 | 9/2006 |
| WO | 2006102610 A2 | 9/2006 |

OTHER PUBLICATIONS

Chan, WN, et al., Evaluation of a Series of Anticonvulsant 1,2,3,4-Tetrahydroisoquinolinyl-benzamides, 2000, Bioorganic & Medical Chemistry, vol. 8, pp. 2085-2094.

*Primary Examiner*—Zinna N Davis
(74) *Attorney, Agent, or Firm*—Klauber & Jackson LLC

(57) ABSTRACT

Bicycloheteroaryl compounds are disclosed that have a formula represented by the following:

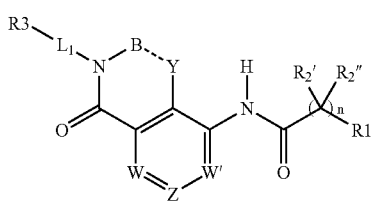

The compounds may be prepared as pharmaceutical compositions, and may be used for the prevention and treatment of a variety of conditions in mammals including humans, including by way of non-limiting example, pain, inflammation, traumatic injury, and others.

56 Claims, No Drawings

BICYCLOHETEROARYL COMPOUNDS AS P2X₇ MODULATORS AND USES THEREOF

CROSS REFERENCE TO RELATED APPLICATIONS

The present application claims the priority of provisional applications U.S. Ser. Nos. 60/783,121, 60/782,923 and 60/783,590, all filed on Mar. 16, 2006, Ser. No. 60/831,416, filed on Jul. 17, 2006, and Ser. No. 60/906,049, filed on Mar. 9, 2007, and the disclosures of such applications are incorporated by reference herein their entireties. Applicants claim the benefits of such applications under 35 U.S.C. §119(e).

FIELD OF THE INVENTION

This invention relates to novel compounds of the class bicycloheteroaryls that are capable of modulating $P2X_7$ receptor activity, and to pharmaceutical compositions containing such compounds. This invention also relates to methods for preventing and/or treating conditions that are causally related to aberrant $P2X_7$ activity, such as inflammation-related conditions in mammals, comprising (but not limited to) rheumatoid arthritis, osteoarthritis, Parkinson's disease, uveitis, asthma, cardiovascular conditions including myocardial infarction, the treatment and prophylaxis of pain syndromes (acute and chronic or neuropathic), traumatic brain injury, acute spinal cord injury, neurodegenerative disorders, inflammatory bowel disease and autoimmune disorders, using the compounds and pharmaceutical compositions of the invention.

BACKGROUND OF THE INVENTION

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members ($P2X_1$-$P2X_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three primary ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, that has been interpreted to indicate that $ATP^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor ($rP2X_7$) thus corresponds to the P2Z receptor. $rP2X_7$ is structurally related to other members of the P2X family but it has a longer cytoplasmic C-terminus domain (there is 35-40% amino acid identity in the corresponding region of homology, but the C-terminus is 239 amino acids long in the $rP2X_7$ receptor compared with 27-20 amino acids in the others). The $rP2X_7$ receptor functions both as a channel permeable to small cations and as a cytolytic pore. Brief applications of ATP (1-2s) transiently open the channel, as is the case of other P2X receptors. Repeated or prolonged applications of agonist cause cell permeabilization reducing the extracellular magnesium concentration potentiates this effect. The unique C-terminal domain of $rP2X_7$ is required for cell permeabilization and the lytic actions of ATP (Suprenant et al, Science 272:735 (1996)).

The P2Z/$rP2X_7$ receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). Certain functional differences exist between rodent and man (Hickman et al, Blood 84:2452 (1994)). The human macrophage $P2X_7$ receptor ($P2X_7$) has now been cloned and its functional properties determined (Rassendren et al, J. Biol. Chem. 272:5482 (1997). When compared with the rat $P2X_7$ receptor, elicited cation-selective currents in the human $P2X_7$ receptor required higher concentrations of agonists, were more potentiated by removal of extracellular magnesium ions, and revised more rapidly on agonist removal. Expression of chimeric molecules indicated that some of the differences between rat and human $P2X_7$ receptors could be revised by exchanging the respective C-terminal domains of the receptor proteins.

It has been reported that certain compounds act as $P2X_7$ antagonists. For example, WO99/29660 and WO99/29661 disclose that certain adamantane derivatives exhibit $P2X_7$ antagonistic activity having therapeutic efficacy in the treatment of rheumatoid arthritis and psoriasis. Similarly, WO99/29686 discloses that certain heterocyclic derivatives are $P2X_7$ receptor antagonists and are useful as immunosuppressive agents and treating rheumatoid arthritis, asthma, septic shock and atheroscelerosis. Finally, WO00/71529 discloses certain substituted phenyl compounds exhibiting immunosuppressing activity. All of the references described herein are incorporated herein by reference in their entirety.

A need therefore exists for therapeutic agents, and corresponding pharmaceutical compositions and related methods of treatment, that address the conditions causally related to aberrant $P2X_7$ activity, and it is toward the fulfillment and satisfaction of that need, that the present invention is directed.

SUMMARY OF THE INVENTION

Bicycloaryl derivatives of formulae I-XIIId, and their pharmaceutical compositions are disclosed as therapeutic agents useful for the treatment of conditions in mammals associated with abnormal or aberrant activity of the $P2X_7$ receptor, including inflammatory-mediated conditions such as (but not limited to) arthritis, myocardial infarction, the treatment and prophylaxis of pain syndromes (acute and chronic [neuropathic]), traumatic brain injury, acute spinal cord injury, neurodegenerative disorders, inflammatory bowel disease and immune dysfunctions such as autoimmune disorders.

It has now been found that the present bicycloheteroaryl compounds are capable of mediating the activity of the $P2X_7$ receptor. This finding leads to novel compounds having therapeutic value. It also leads to pharmaceutical compositions having the compounds of the present invention as active ingredients and to their use to treat, prevent or ameliorate a range of conditions in mammals such as but not limited to inflammation of various genesis or etiology, for example rheumatoid arthritis, cardiovascular disease, inflammatory bowel disease, acute, chronic, inflammatory and neuropathic pain, dental pain and headache (such as migraine, cluster headache and tension headache) and other conditions causally related to inflammation or immune dysfunction.

The compounds of the present invention are also useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, uveitis, asthma, myocardial infarction, traumatic brain injury, spinal cord injury, neurodegenerative disorders, inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides bicycloheteroaryl compounds which are capable of modulating the activity of the $P2X_7$ receptor, in vivo. In a further aspect, the compounds of the invention are capable of antagonizing (suppressing or inhibiting) the activity of the $P2X_7$ receptor, and thereby treating those conditions, representative ones of which are causally related to aberrant $P2X_7$ activity.

The compounds of the present invention may show low toxicity, good absorption, good half-life, good solubility, low protein binding affinity, low drug-drug interaction, low inhibitory activity at the HERG channel, low QT prolongation and good metabolic stability.

Accordingly, in a first aspect of the invention, bicycloheteroaryl compounds are disclosed that are capable of capable of modulating the activity of the $P2X_7$ receptor in vivo, having a formula (I):

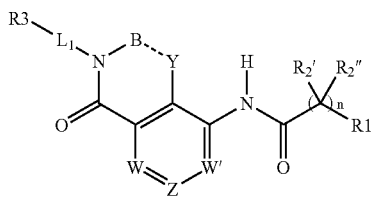

wherein

B and Y are independently selected from $CR^{2a}$ and $CR^{2a}R^{2b}$;

W, W' and Z are independently selected from $CR^4$ and N, provided that all three of W, W' and Z are not N at the same time;

$L^1$ is substituted or unsubstituted $C_1$-$C_5$ alkylene;

n is 0, 1, 2, 3 or 4;

$R^1$ is selected from substituted or unsubstituted 5-13 membered aryl and heteroaryl;

each $R^{2a}$, $R^{2b}$, $R^{2'}$ and $R^{2''}$ is independently selected from hydrogen, halo, substituted or unsubstituted $C_1$-$C_6$ alkyl; or any of $R^{2'}$ and $R^{2''}$ join together to form a cycloalkyl or cycloheteroalkyl ring of 3-7 atoms;

$R^3$ is a hydrogen bond donor group;

each $R^4$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;

or a pharmaceutically acceptable salt, solvate or prodrug thereof;

and stereoisomers, isotopic variants and tautomers thereof.

In a further embodiment, with respect to compounds of formulae I, n is 0-4.

In a further embodiment, with respect to compounds of formula I, $L^1$ is a $C_1$-$C_5$ alkylene group unsubstituted or substituted by one or more substituents selected from alkyl, oxo, aryl, hydroxyl, and hydroxyalkyl.

In a further embodiment, with respect to compounds of formula I, $L^1$ is a $C_1$-$C_5$ alkylene group substituted with two alkyl groups and wherein any two alkyl groups on the same carbon atom can join together to form a cycloalkyl or cycloheteroalkyl ring of 3-7 atoms.

In a further embodiment, with respect to compounds of formula I, $L^1$ is a $C_1$-$C_5$ alkylene group; and $R^3$ is a hydrogen bond donor group. In one embodiment, $R^3$ is —OH. In another embodiment, $R^3$ is $NH_2$. In yet another embodiment $R^3$ is —NH—$R^{3'}$ and $R^{3'}$ is alkyl, acyl, cycloalkyl or aryl.

In a further embodiment, with respect to compounds of formula I, $L^1$ is a bond, a $C_1$-$C_5$ alkylene group substituted with oxo; and $R^3$ is a hydrogen bond donor group. In one embodiment, $R^3$ is —OH. In another embodiment, $R^3$ is $NH_2$. In yet another embodiment $R^3$ is —NH—$R^{3'}$ and $R^{3'}$ is alkyl, acyl, cycloalkyl or aryl.

In a further embodiment, with respect to compounds of formula I, $L^1$ is a $C_1$-$C_5$ alkylene group and $R^3$ is a heterocycloalkyl group containg —NH—.

In a further embodiment, with respect to compounds of formula I, B and Y are independently selected from $CR^{2a}$ and $CR^{2a}R^{2b}$.

In a further embodiment, with respect to compounds of formula I, B and Y are independently selected from $CR^{2a}R^{2b}$ and the dotted bond is a single bond.

In a further embodiment, with respect to compounds of formula I, B and Y may all represent $CH_2$ and the dotted bond is a single bond.

In a further embodiment, with respect to compounds of formula I, B and Y are independently selected from $CR^{2a}$ and the dotted bond is a double bond.

In a further embodiment, with respect to compounds of formula I, B and Y may all represent CH and the dotted bond is a double bond.

In a further embodiment, with respect to compounds of formula I, n is 0, 1 or 2. In one particular embodiment, n is 1.

In another embodiment, with respect to compounds of formula I, each of $R^{2'}$ and $R^{2'}$ of the

group is H or Me. In one particular embodiment, each of $R^{2'}$ and $R^{2''}$ is H.

In a further embodiment, with respect to compounds of formula I, one of $R^{2'}$ and $R^{2''}$ of the

group may be selected from Me, Et, halo and Cl, and the other is H.

In a further embodiment, with respect to compounds of formula I, $R^1$ is selected from a 5-13 membered aryl and heteroaryl ring system, unsubstituted or substituted with one or more substituents independently selected from halo, hydroxyl, amino, cyano, sulfo, sulfanyl, sulfinyl, amido, carboxy, carbalkoxy, alkyl, substituted alkyl, alkenyl, substituted alkenyl, alkynyl, substituted alkynyl, and sulfonamide.

In a further embodiment, with respect to compounds of formula I, $R^1$ is substituted or unsubstituted aryl. In one particular embodiment, $R^1$ is substituted phenyl.

In a further embodiment, with respect to compounds of formula I, each of W and W' is N.

In a further embodiment, with respect to compounds of formula I, each of W, Z and W' is $CR^4$. In one particular embodiment, each of W, Z and W' is CH.

In a further embodiment, with respect to compounds of formula I, each of W and Z is $CR^4$, W' is $CR^5$ and $R^5$ is selected from H, alkyl, cycloalkyl or halo. In one embodiment. $R^5$ is cycloalkyl, halo or alkyl. In a particular embodiment, $R^5$ is H or halo. In a yet further particular embodiment, $R^5$ is H, cyclopropyl, Cl, F or Me.

In a further aspect, the present invention provides pharmaceutical compositions comprising a bicycloheteroaryl compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. inflammation, such as rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction, including autoimmune disorders, which method comprises administering an effective amount of one or more of the pharmaceutical compositions just described.

In yet another method of treatment aspect, this invention provides a method of treating a mammal susceptible to or afflicted with a condition that is causally related to aberrant $P2X_7$ receptor activity, and that for example, gives rise to pain responses or that relates to imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with conditions that are causally related to abnormal activity of the $P2X_7$ receptor, such as neurodegenerative diseases and disorders including, for example, Parkinson's disease, multiple sclerosis; diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and cardiovascular and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of the $P2X_7$ receptor and thus avert or treat any maladies that may be causally related thereto.

It is further an object of this invention to provide a series of compounds that can treat or alleviate maladies or symptoms of same, such as pain and inflammation, that may be causally related to the activation of the $P2X_7$ receptor.

A still further object of this invention is to provide pharmaceutical compositions that are effective in the treatment or prevention of a variety of disease states, including the diseases associated with the central nervous system, cardiovascular conditions, chronic pulmonary obstructive disease COPD), inflammatory bowel disease, rheumatoid arthritis, osteoarthritis, and other diseases where an inflammatory component is present.

Other objects and advantages will become apparent to those skilled in the art from a consideration of the ensuing detailed description.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)R$^{20}$, where R$^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR$^{21}$C(O)R$^{22}$, where R$^{21}$ is hydrogen, alkyl, cycloalkyl, cycloheteroalkyl, aryl, arylalkyl, heteroalkyl, heteroaryl, heteroarylalkyl and R$^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —N(H)O$R^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —S(O)$_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)$R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —S$R^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N($R^{36}$)$_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N($R^{36}$)$_2$ is an amino group.

"Aminocarbonyl" refers to the group —C(O)$NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}$C(O)$NR^{38}R^{38}$ where each $R^{38}$ independently hydrogen, alkyl, aryl or cycloalkyl, or where two R groups are joined to form an alkylene group.

"Aminocarbonyloxy" refers to the group —OC(O)$NR^{39}R^{39}$ where each $R^{39}$ is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NH$R^{40}$ where $R^{40}$ represents an aryl group as defined herein.

"Aryloxycarbonyl" refers to a radical —C(O)—O-aryl where aryl is as defined herein.

"Arylsulfonyl" refers to a radical —S(O)$_2R^{41}$ where $R^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O)$_2$O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$OR$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

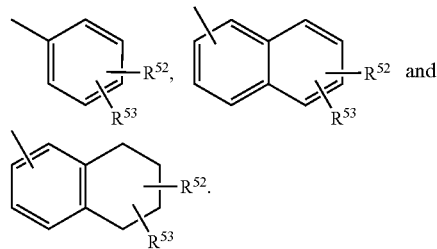

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

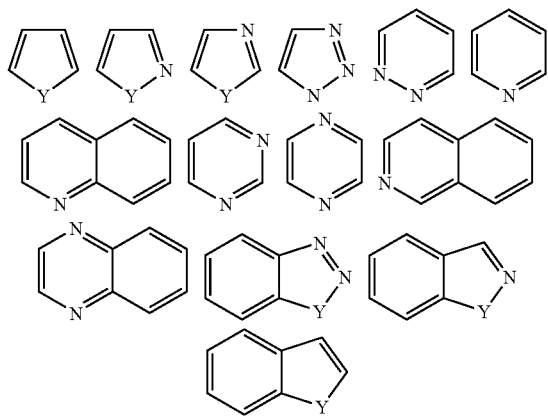

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

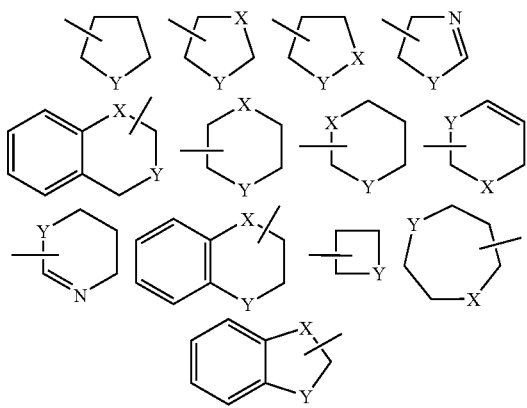

wherein each X is selected from $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

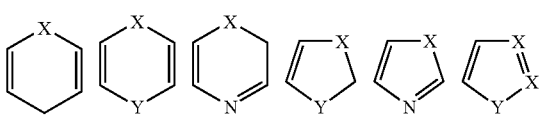

wherein each X is selected from $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

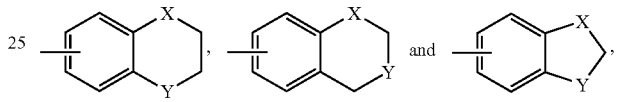

wherein each X is selected from C—$R^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on A, B, W, Y or Z of the compounds of this invention or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containg O—H, or N—H functionality. Examples of "hydrogen bond donor" groups include —OH, —$NH_2$, and —NH— $R^{59a}$ and wherein $R^{59a}$ is alkyl, acyl, cycloalkyl, aryl, or heteroaryl.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)$NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}$$_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides bicycloheteroaryl compounds useful for preventing and/or treating a broad range of conditions, associated with abnormalities in the activity of the $P2X_7$ receptor, among them, rheumatoid arthritis, Parkinson's disease, uveitis, asthma, cardiovascular conditions such as myocardial infarction, the treatment and prophylaxis of pain syndromes (acute and chronic or neuropathic), traumatic brain injury, acute spinal cord injury, neurodegenerative disorders, inflammatory bowel disease and immune dysfunctions such as autoimmune disorders or conditions, in mammals.

In a first aspect of the invention, bicycloheteroaryl compounds are disclosed that are capable of capable of modulating the activity of the $P2X_7$ receptor in vivo, having a formula (I):

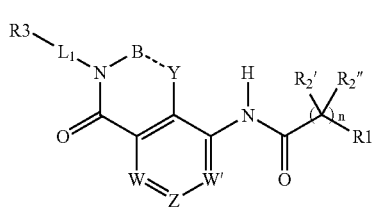

wherein

B and Y are independently selected from $CR^{2a}$ and $CR^{2a}R^{2b}$;

W, W' and Z are independently selected from $CR^4$ and N, provided that all three of W, W' and Z are not N at the same time;

$L^1$ is substituted or unsubstituted $C_1$-$C_5$ alkylene;

n is 0, 1, 2, 3 or 4;

$R^1$ is selected from substituted or unsubstituted 5-13 membered aryl and heteroaryl;

each $R^{2a}$, $R^{2b}$, $R^{2'}$ and $R^{2''}$ is independently selected from hydrogen, halo, substituted or unsubstituted $C_1$-$C_6$ alkyl; or any of $R^{2'}$ and $R^{2''}$ join together to form a cycloalkyl or cycloheteroalkyl ring of 3-7 atoms;

$R^3$ is a hydrogen bond donor group;

each $R^4$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;

or a pharmaceutically acceptable salt, solvate or prodrug thereof;

and stereoisomers, isotopic variants and tautomers thereof.

In a further embodiment, with respect to compounds of formulae I, n is 0-4.

In a further embodiment, with respect to compounds of formula I, $L^1$ is a $C_1$-$C_5$ alkylene group unsubstituted or substituted by one or more substituents selected from alkyl, aryl, hydroxyl, and hydroxyalkyl.

In a further embodiment, with respect to compounds of formula I, $L^1$ is a $C_1$-$C_5$ alkylene group substituted with two alkyl groups and wherein any two alkyl groups on the same carbon atom can join together to form a cycloalkyl or cycloheteroalkyl ring of 3-7 atoms.

In a further embodiment, with respect to compounds of formula I, $L^1$ is a $C_1$-$C_5$ alkylene group; and $R^3$ is a hydrogen bond donor group. In one embodiment, $R^3$ is —OH. In another embodiment, $R^3$ is $NH_2$. In yet another embodiment $R^3$ is —NH—$R^{3'}$ and $R^{3'}$ is alkyl, cycloalkyl or aryl.

In a further embodiment, with respect to compounds of formula I, $L^1$ is a $C_1$-$C_5$ alkylene group substituted with oxo; and $R^3$ is a hydrogen bond donor group. In one embodiment, $R^3$ is —OH. In another embodiment, $R^3$ is $NH_2$. In yet another embodiment $R^3$ is —NH—$R^{3'}$ and $R^{3'}$ is alkyl, cycloalkyl or aryl.

In a further embodiment, with respect to compounds of formula I, $L^1$ is a $C_1$-$C_5$ alkylene group; and $R^3$ is a heterocycloalkyl group containg —NH—.

In a further embodiment, with respect to compounds of formula I, B and Y are independently selected from $CR^{2a}$ and $CR^{2a}R^{2b}$.

In a further embodiment, with respect to compounds of formula I, B and Y are independently selected from $CR^{2a}R^{2b}$ and the dotted bond is a single bond.

In a further embodiment, with respect to compounds of formula I, B and Y may all represent $CH_2$ and the dotted bond is a single bond.

In a further embodiment, with respect to compounds of formula I, B and Y are independently selected from $CR^{2a}$ and the dotted bond is a double bond.

In a further embodiment, with respect to compounds of formula I, B and Y may all represent CH and the dotted bond is a double bond.

In a further embodiment, with respect to compounds of formula I, n is 0, 1 or 2. In one particular embodiment, n is 1.

In another embodiment, with respect to compounds of formula I, each of $R^{2'}$ and $R^{2''}$ of the

group is H or Me. In one particular embodiment, each of $R^{2'}$ and $R^{2''}$ is H.

In a further embodiment, with respect to compounds of formula I, one of $R^{2'}$ and $R^{2''}$ of the

group may be selected from Me, Et, halo and Cl, and the other is H.

In a further embodiment, with respect to compounds of formula I, $R^1$ is selected from a 5-13 membered aryl and heteroaryl ring system, unsubstituted or substituted with one or more substituents independently selected from halo, hydroxyl, amino, cyano, sulfo, sulfanyl, sulfinyl, amido, carboxy, carbalkoxy, alkyl, substituted alkyl, alkenyl, substituted alkenyl, alkynyl, substituted alkynyl, and sulfonamide.

In a further embodiment, with respect to compounds of formula I, $R^1$ is substituted or unsubstituted aryl. In one particular embodiment, $R^1$ is substituted phenyl.

In a further embodiment, with respect to compounds of formula I, $R^1$ is substituted or unsubstituted naphthyl.

In a further embodiment, with respect to compounds of formula I, $R^1$ is substituted or unsubstituted heteroaryl.

In a further embodiment, with respect to compounds of formula I, $R^1$ is substituted or unsubstituted pyridyl, substituted or unsubstituted quinoline, substituted or unsubstituted benzodioxole, substituted or unsubstituted benzodioxane, substituted or unsubstituted benzofuran, substituted or unsubstituted benzothiophene, and substituted or unsubstituted benzodioxepine.

In a further embodiment, with respect to compounds of formula I, each of W and W' is N.

In a further embodiment, with respect to compounds of formula I, each of W, Z and W' is $CR^4$. In one particular embodiment, each of W, Z and W' is CH.

In a further embodiment, with respect to compounds of formula I, each of W and Z is $CR^4$ W' is $CR^5$ and $R^5$ is selected from H, alkyl, cycloalkyl or halo. In one embodiment $R^5$ is halo, cycloalkyl or alkyl. In a particular embodiment, $R^5$ is H or halo. In a yet further particular embodiment, $R^5$ is H, Cl, F, cycloalkyl or Me.

In another embodiment, with respect to compounds of formulae I, the compound is according to formula I, II, III or IV:

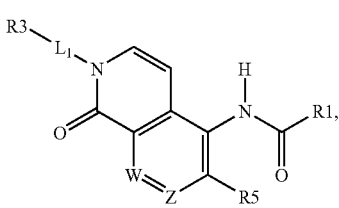

II

-continued

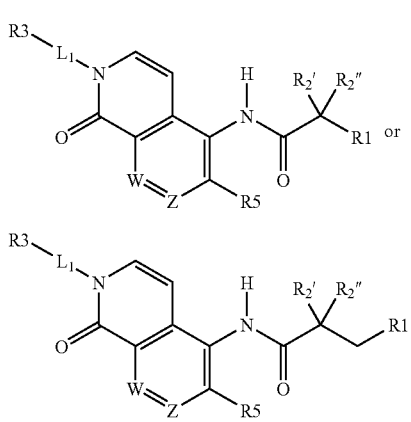

wherein
W is CR⁴; Z is CR⁴;
L¹, R¹R²', R²'', R³ and R⁴ are as described for formula I;
and R⁵ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
or a pharmaceutically acceptable salt, solvate or prodrug thereof;
and stereoisomers, isotopic variants and tautomers thereof.

In another embodiment, with respect to compounds of formulae III-IV, each of R²' and R²'' is H.

In another embodiment, with respect to compounds of formulae III-IV, R²' is halo; and R²'' is H.

In another embodiment, with respect to compounds of formulae III-IV, R²' is Cl or F; and R²'' is H.

In another embodiment, with respect to compounds of formulae III-IV, R²' is Me or Et; and R²'' is H.

In another embodiment, with respect to compounds of formulae III-IV, each of R²' and R²'' is Me.

In a more particular embodiment, with respect to compounds of formulae III-IV, R²' is Me; and R²'' is H.

In another embodiment, with respect to compounds of formulae II-IV, R¹ is substituted or unsubstituted aryl.

In another embodiment, with respect to compounds of formulae II-IV, R¹ is substituted or unsubstituted phenyl or naphthalene.

In another embodiment, with respect to compounds of formulae II-IV, R¹ is substituted or unsubstituted naphthalene.

In another embodiment, with respect to compounds of formulae II-IV, R¹ is unsubstituted naphthalene.

In another embodiment, with respect to compounds of formulae II-IV, R¹ is substituted or unsubstituted phenyl.

In another embodiment, with respect to compounds of formulae II-IV, R¹ is substituted or unsubstituted heteroaryl.

In another embodiment, with respect to compounds of formulae II-IV, R¹ is substituted or unsubstituted pyridyl, substituted or unsubstituted quinoline, substituted or unsubstituted benzodioxole, substituted or unsubstituted benzodioxane, substituted or unsubstituted benzofuran, substituted or unsubstituted benzothiophene, and substituted or unsubstituted benzodioxepine.

In another embodiment, with respect to compounds of formulae I, the compound is according to formula V, VI or VII:

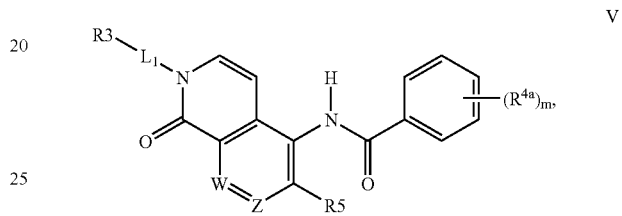

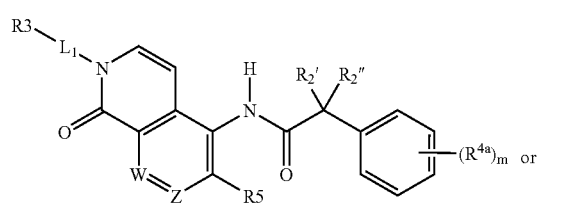

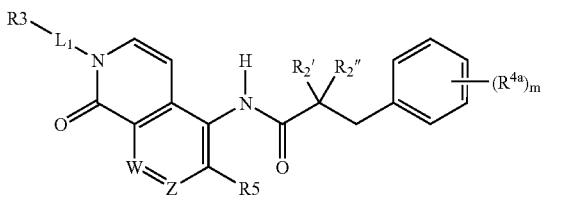

wherein
W is CR⁴; Z is CR⁴;
L¹, R¹, R²', R²'', R³ and R⁴ are as described for formula I; R⁵ is as described for formulae II-IV;
R⁴ᵃ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5;

or a pharmaceutically acceptable salt, solvate or prodrug thereof;

and stereoisomers, isotopic variants and tautomers thereof.

With respect to the compounds of the invention wherein m is 0-5 as set forth above, and at any and all locations herein, it is to be understood that when m=0, the ring is unsubstituted.

In one embodiment, with respect to compounds of formulae VI-VII, each of $R^{2'}$ and $R^{2''}$ is H.

In another embodiment, with respect to compounds of formulae VI-VII, $R^{2'}$ is halo; and $R^{2''}$ is H.

In another embodiment, with respect to compounds of formulae VI-VI,I $R^{2'}$ is Cl or F; and $R^{2''}$ is H.

In another embodiment, with respect to compounds of formulae VI-VII, $R^2$ is Me or Et; and R is H.

In another embodiment, with respect to compounds of formulae VI-VII, each of $R^{2'}$ and $R^{2''}$ is Me.

In a more particular embodiment, with respect to compounds of formulae VI-VII, $R^{2'}$ is Me; and $R^{2''}$ is H.

In another embodiment, with respect to compounds of formula I, the compound is according to formula VIII, IX or X:

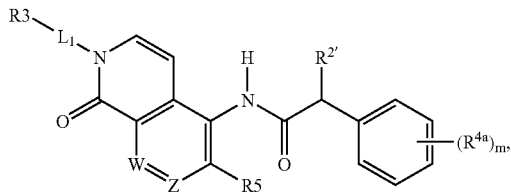

VIII

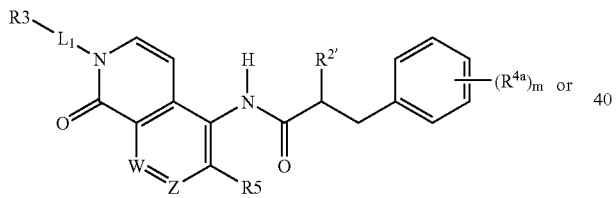

IX

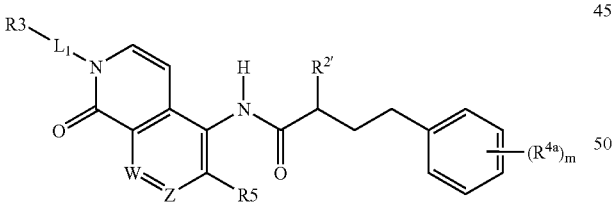

X and wherein $L^1$, $R^1$, $R^{2'}$, $R^3$ and $R^4$ are as described for formula I; $R^5$ is as described for formulae II-IV; and $R^{4a}$ and m are as described for formulae V-VII.

In one embodiment, with respect to compounds of formulae V-X, $R^{2'}$ is H or Me. In another embodiment, $R^{2'}$ is Me. In one particular embodiment, $R^{2'}$ is H.

In another embodiment, with respect to compounds of formulae V-X, m is 1, 2 or 3.

In another embodiment, with respect to compounds of formulae V-X, m is 1 or 2. In a particular embodiment m is 2.

In another embodiment, with respect to compounds of formulae V-X, each of $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, $CH=CH-CO_2H$, SOMe, $SO_2Me$, $SO_3H$, $SO_3Me$, and pyridyl.

In another embodiment, with respect to compounds of formulae I-X, $L^1$ is a $C_1$-$C_5$ alkylene group.

In another embodiment, with respect to compounds of formulae I-X, $L^1$ is a $C_1$-$C_5$ alkylene unsubstituted or substituted by one or more substituents selected from alkyl, hydroxyl, oxo and hydroxyalkyl.

In another embodiment, with respect to compounds of formulae I-X, $L^1$ is an ethylene unsubstituted or substituted by one or more substituents selected from Me, Et, i-Pr, hydroxy, and hydroxymethyl.

In another embodiment, with respect to compounds of formulae I-X, $L^1$ is a methylene unsubstituted or substituted by one or more substituents selected from Me, Et, i-Pr, and hydroxymethyl.

In another embodiment, with respect to compounds of formulae I-X, $R^3$ is a hydrogen bond donor group.

In another embodiment, with respect to compounds of formulae I-X, $R^3$ is selected from hydroxyl, amino, alkylamino, cycloalkylamino or carbamoyl.

In another embodiment, with respect to compounds of formulae I-X, the group -$L_1$-$R^3$ is selected from

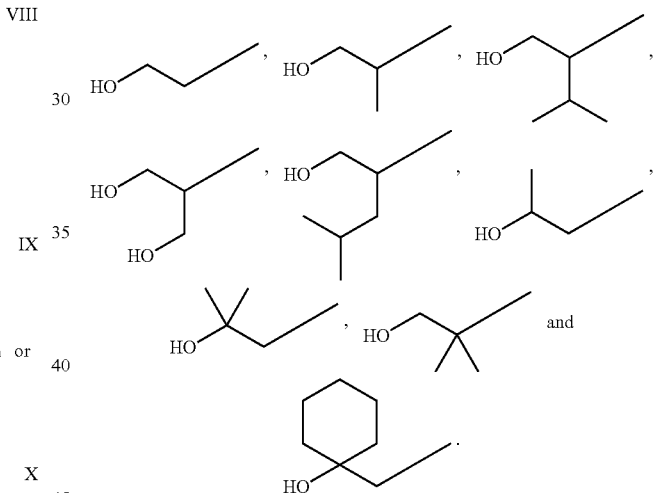

In a particular embodiment, with respect to compounds of formulae I-X, the group -$L_1$-$R^3$ is

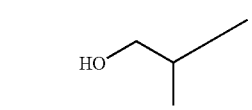

In another embodiment, with respect to compounds of formulae I-X, the group -$L_1$-$R^3$ is selected from

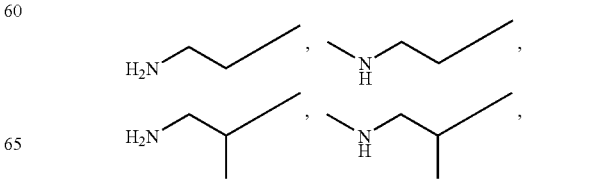

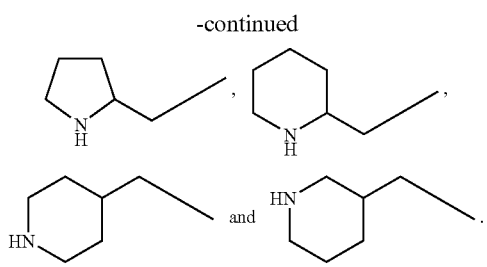
In another embodiment, with respect to compounds of formulae I-X, the group -L$_1$-R$^3$ is selected from
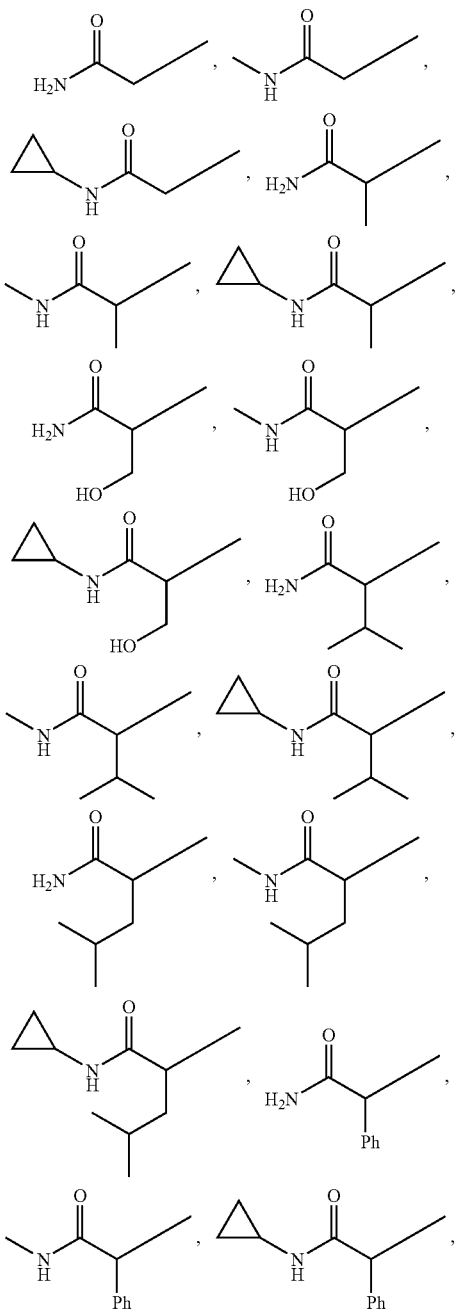
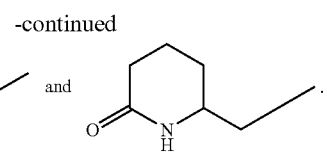
In another embodiment, with respect to compounds of formula I, the compound is according to formula XIa, XIb, XIc, XId, XIe, XIf, XIg, XIh, XIi or XIj:
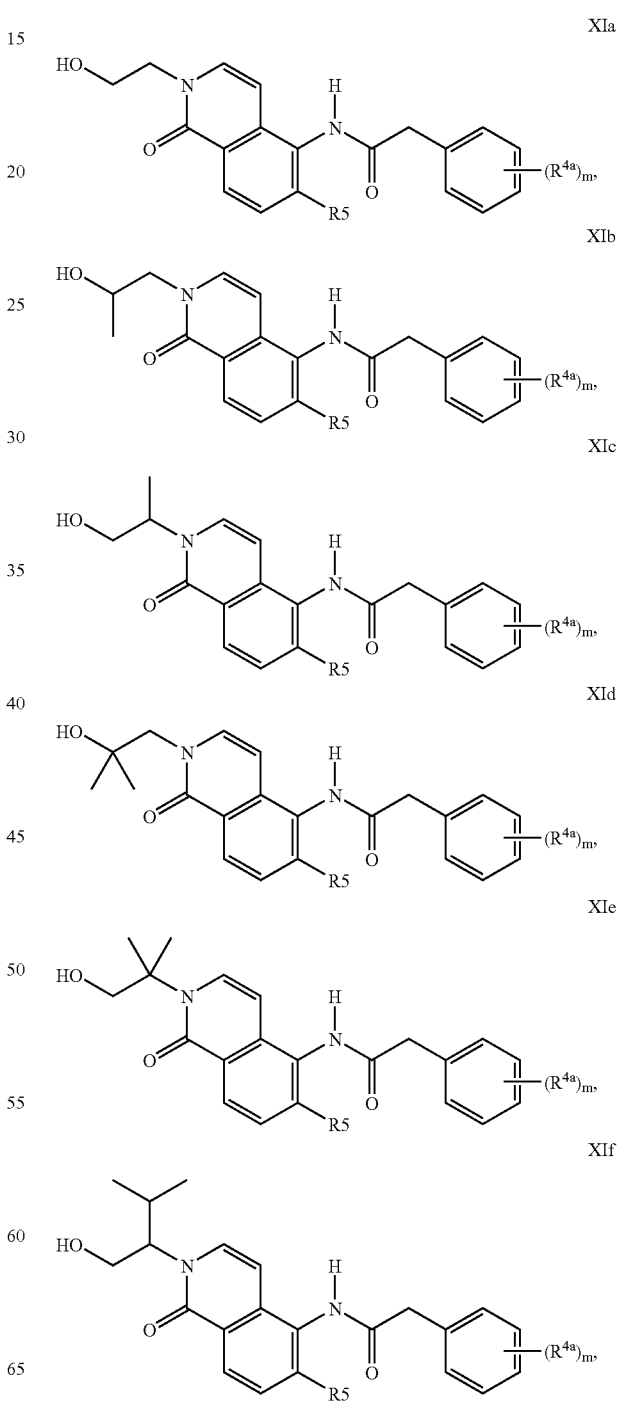

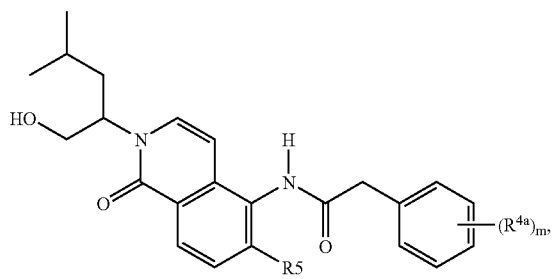
XIg

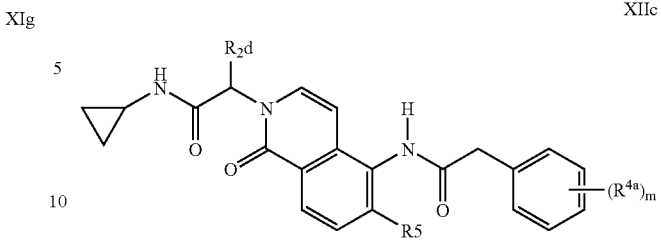
XIIc

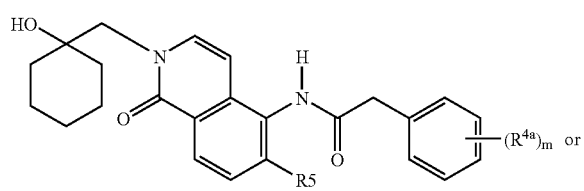
XIh and wherein $R^5$ is as described for formulae II-IV; $R^{4a}$ and m are as described for formulae V-VII; and $R^{2d}$ is selected from hydrogen, alkyl, hydroxyalkyl and substituted or unsubstituted phenyl. In one particular embodiment, $R^{2d}$ is hydrogen, methyl, i-Pr and hydroxymethyl. In another particular embodiment, $R^{2d}$ is phenyl. In another particular embodiment, $R^{2d}$ is hydrogen. In yet another particular embodiment, $R^{2d}$ is methyl.

In another embodiment, with respect to compounds of formula I, the compound is according to formula XIIIa, XIIIb, XIIIc or XIIId:

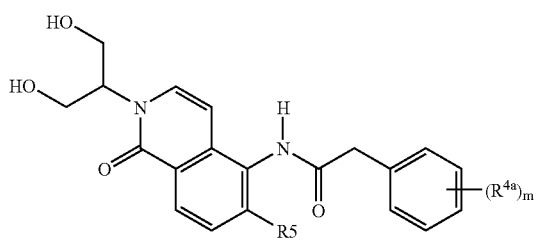
XIj

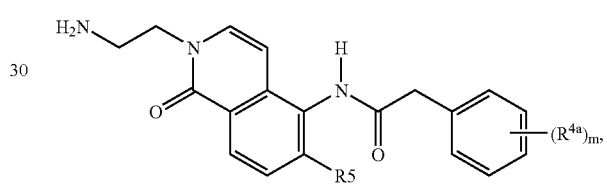
XIIIa and wherein $R^5$ is as described for formulae II-IV; and $R^{4a}$ and m are as described for formulae V-VII.

In another embodiment, with respect to compounds of formula I, the compound is according to formula XIIa, XIIIb or XIIc:

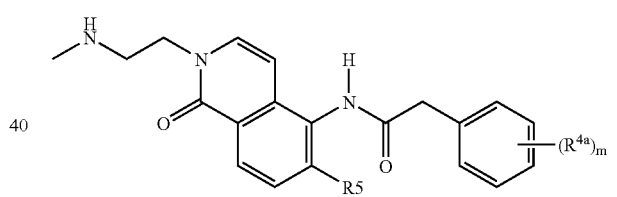
XIIIb

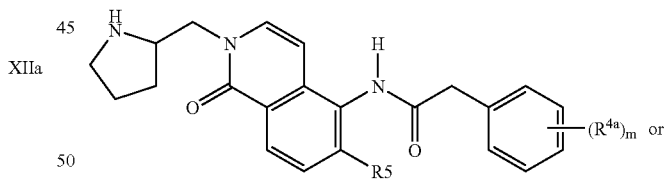
XIIIc

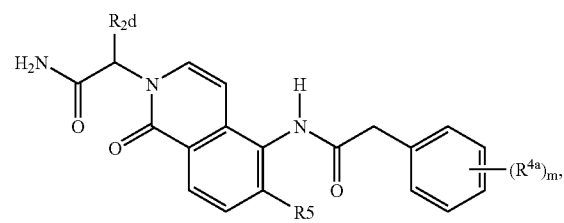
XIIa

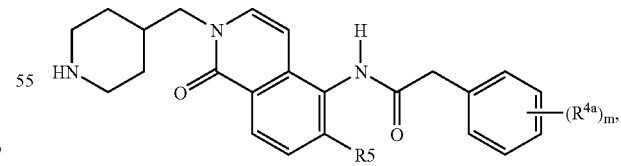
XIIId

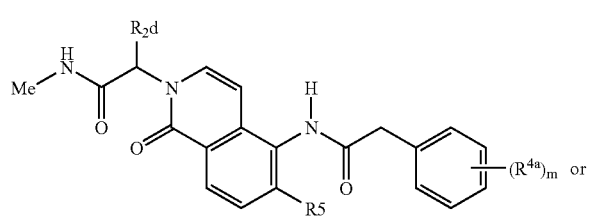
XIIb and wherein $R^5$ is as described for formulae II-IV; and $R^{4a}$ and m are as described for formulae V-VII.

In one embodiment, with respect to compounds of formulae XIa-XIIId, m is 1, 2 or 3.

In another embodiment, with respect to compounds of formulae XIa-XIIId, m is 1 or 2. In a particular embodiment m is 2.

In another embodiment, with respect to compounds of XIa-XIIId, each of $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl.

In another embodiment, with respect to compounds of V-XIIId, m is 1 and $R^{4a}$ is $CF_3$.

In another embodiment, with respect to compounds of V-XIIId, m is 2 and $R^{4a}$ is F and $CF_3$.

In another embodiment, with respect to compounds of V-XIIId, m is 2 and $R^{4a}$ is F and Cl.

In one embodiment, with respect to compounds of formulae I-X, each of W and Z is independently $CR^4$.

In one embodiment, with respect to compounds of formulae I-X, each of W and Z is independently CH.

In one embodiment, with respect to compounds of formulae I-X, W is N.

In one embodiment, with respect to compounds of formulae I-X, W is N and Z is H.

In one embodiment, with respect to compounds of formulae II-XIIId, $R^5$ is H.

In one embodiment, with respect to compounds of formulae II-XIIId, $R^5$ is selected from alkyl, substituted alkyl, cycloalkyl, substituted cycloalkyl and halo. In one particular embodiment, $R^5$ is selected from Me, cyclopropyl, Cl, F and $CF_3$.

In one embodiment, with respect to compounds of formulae II-XIIId, $R^5$ is Me.

In one embodiment, with respect to compounds of formulae II-XIIId, $R^5$ is $CF_3$.

In one embodiment, with respect to compounds of formulae II-XIIId, $R^5$ is F.

In a further embodiment with respect to compounds of formulae II-XIIId, $R^5$ is Cl.

In one embodiment, with respect to compounds of formulae II-XIIId, $R^5$ is cyclopropyl.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound—administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's *Pharmaceutical Sciences*.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the $P2X_7$ receptor. Accordingly, the compounds and pharmaceutical compositions of this invention find use as therapeutics for preventing and/or treating autoimmune, inflammatory and cardiovascular conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, multiple sclerosis; diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following schemes are presented with details as to the preparation of representative bicycloheteroaryls that have been listed hereinabove. The compounds of the invention may be prepared from known or commercially available starting materials and reagents by one skilled in the art of organic synthesis.

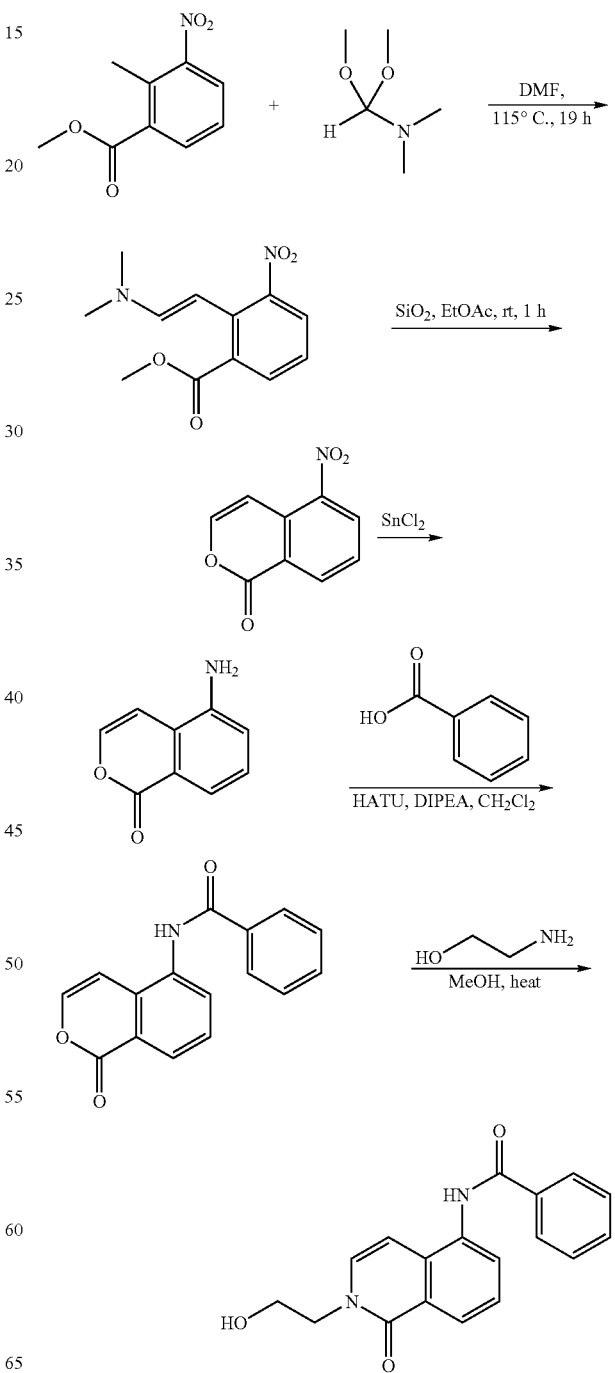

Representative Scheme 1

Representative Scheme 2
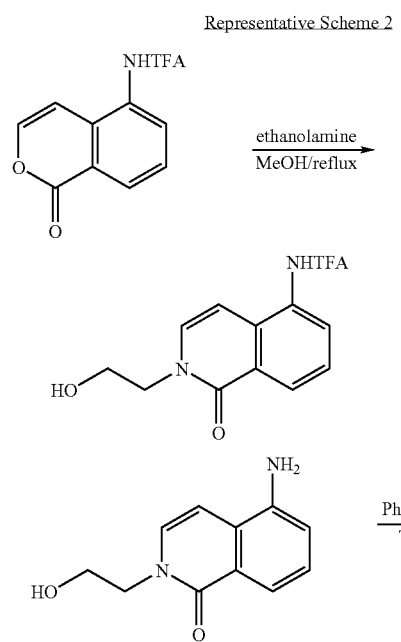
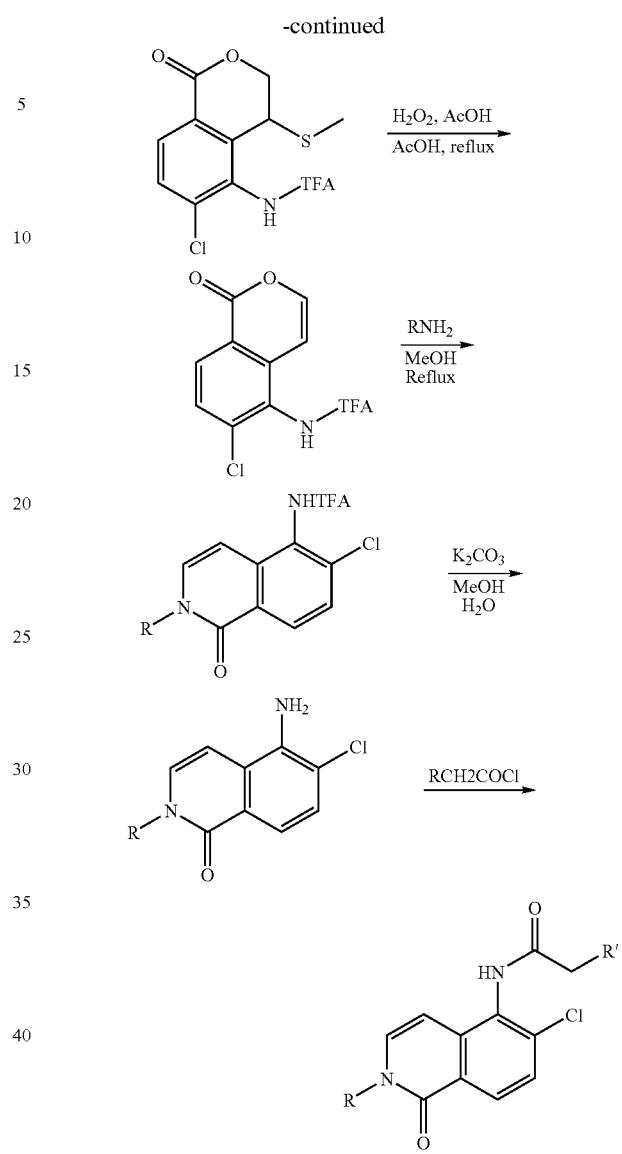
wherein R'=R¹ and R=-L-R³.
Representative Scheme 3
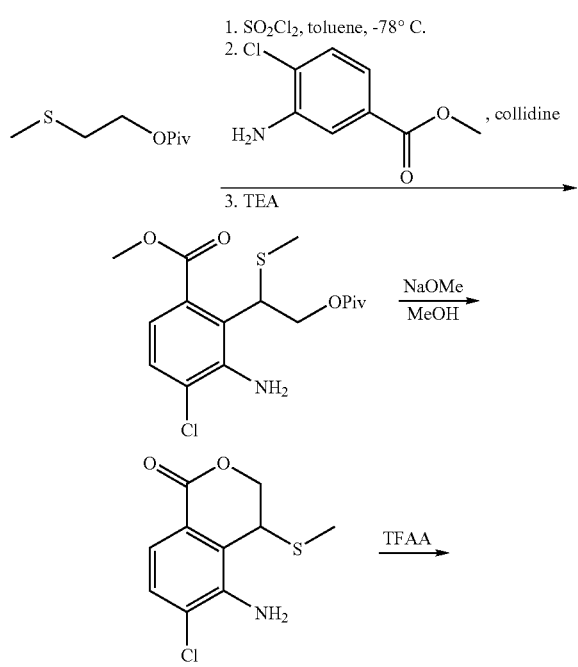
Representative Scheme 4
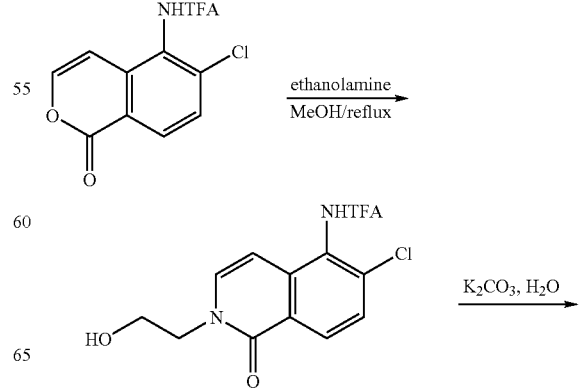

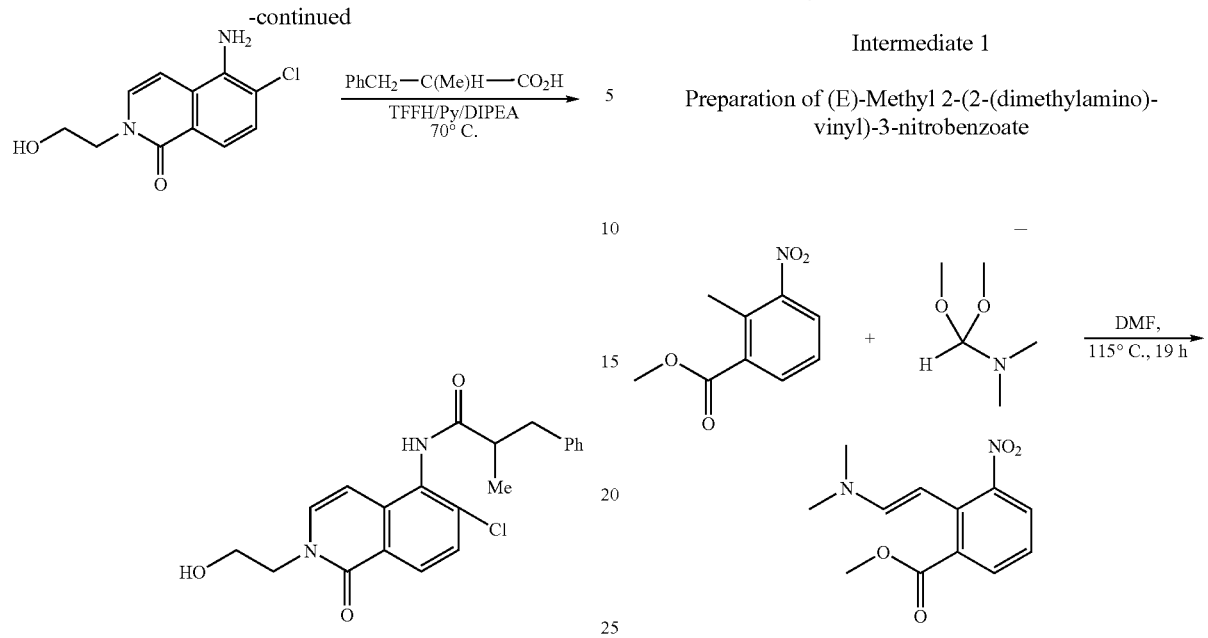
Synthesis of Intermediates
Intermediate 1
Preparation of (E)-Methyl 2-(2-(dimethylamino)-vinyl)-3-nitrobenzoate
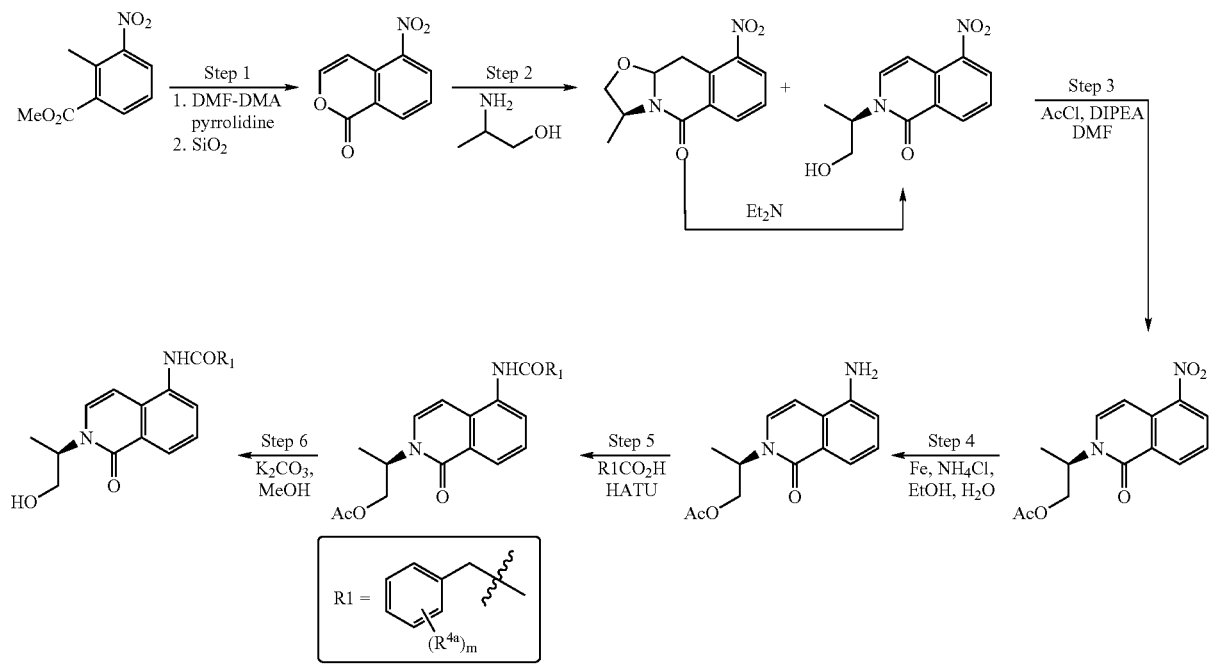

A mixture of methyl 2-methyl-3-nitrobenzoate (5.0 g, 25.6 mmol) and N,N-dimethylformamide dimethyl acetal (9.18 g, 77 mmol) in DMF (30 mL) was stirred at 115° C. for 17 h. The volatiles were removed under reduced pressure to give (E)-methyl 2-(2-(dimethylamino)-vinyl)-3-nitrobenzoate as brown oil.

$^1$H-NMR (300 MHz, CDCl$_3$) δ 7.68 (m, 2H), 7.07 (t, J=7.5 Hz 1H), 6.32 (d, J=13.5 Hz, 1H), 5.65 (d, J=13.5 Hz, 1H), 3.85 (s, 3H), 2.82 (s, 6H).

Intermediate 2

Preparation of 5-Nitro-1H-isochromen-1-one

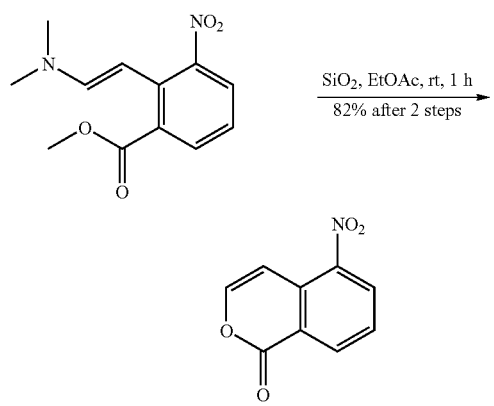

(E)-Methyl 2-(2-(dimethylamino)vinyl)-3-nitrobenzoate was dissolved in EtOAc (200 mL), and silica gel (200 g) was added. The resulting suspension was stirred at room temperature for 1 h. The EtOAc solution was filtered off. Silica gel was washed with EtOAc (2×150 mL) and the combined organics were evaporated and dried under reduced pressure to yield 5-nitro-1H-isochromen-1-one (4.0 g, 21.0 mmol, 82% after two steps) of as a brown solid.

$^1$H-NMR (300 MHz, CDCl$_3$) δ 8.62 (d, J=7.8 Hz, 1H), 8.47 (d, J=8.1 Hz, 1H), 7.65 (m, 1H), 7.42 (d, J=6.3 Hz, 1H), 7.36 (d, J=6.3 Hz, 1H). HPLC ret. time 1.72 min, 10-100% CH$_3$CN, 3.5 min gradient; ESI-MS m/z 192.1 (M+H)$^+$.

Additional information can be found in McDonald, M. C. et al. British J. Pharmacol. 2000, 130, 843, incorporated herein by reference.

Intermediate 3

Preparation of 5-Amino-1H-isochromen-1-one

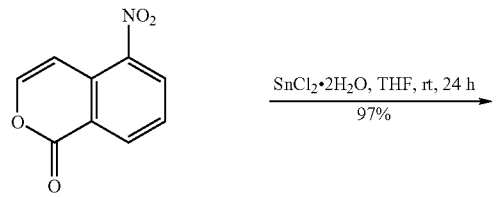

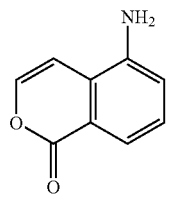

Tin(II)chloride dihydrate (41.9 g, 185.7 mmol) was added to a stirred solution of 5-nitro-1H-isochromen-1-one (7.1 g, 37.1 mmol) in anhydrous THF (120 mL). The reaction mixture was stirred at room temperature for 18 h. The resulting mixture was diluted with EtOAc (400 mL) and treated with saturated aqueous sodium bicarbonate to pH=10. Water (100 mL) was added and the layers were separated. The aqueous phase was extracted with ethyl acetate (2×150 mL) and the combined organic fractions were dried over Na$_2$SO$_4$, filtered and evaporated to yield 5-amino-1H-isochromen-1-one (5.8 g, 36.0 mmol, 97%) as a yellow solid.

$^1$H-NMR (300 MHz, CD$_3$OD) δ 7.52 (d, J=7.8 Hz, 1H), 7.32 (d, J=5.7 Hz, 1H), 7.27 (t, J=7.8 Hz, 1H), 7.07 (d, J=7.8 Hz, 1H), 6.80 (d, J=5.7 Hz, 1H). HPLC ret. time 1.16 min, 10-100% CH$_3$CN, 3.5 min gradient; ESI-MS m/z 162.3 (M+H)$^+$. Additional information can be found in Lee, B. S.; et al. *J. Org. Chem.* 2004, 69, 3319 incorporated herein by reference.

Intermediate 4

Preparation of 6-methyl-5-nitro-1H-isochromen-1-one

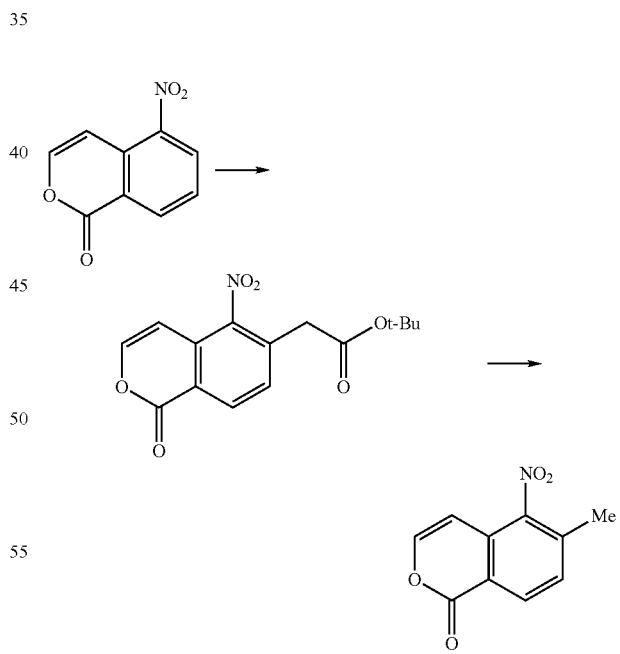

a. (E)-tert-Butyl 2-(5-nitro-1-oxo-1H-isochromen-6-yl)acetate

A round bottom flask was charged with potassium tert-butoxide (4.4 g, 0.039 mol) and N,N-dimethylformamide (30 mL, 0.4 mol) and a solution of acetic acid, chloro-, 1,1- dimethylethyl ester (2.5 mL, 0.017 mol) and 5-nitro-isochromen-1-one (3.00 g, 0.0157 mol) in N,N-dimethylformamide (5 mL, 0.06 mol) was added at −20° C. slowly over a period of 40 minutes and the reaction was stirred for another 45 minutes at the same temperature. The reaction mixture was poured into 4 ml of HCl and 80 mL of water and extracted with DCM and washed with brine and dried over $Na_2SO_4$. The solvent was removed under reduced pressure and the residue purified by flash chromatography to get the product as light thick oil. MS m/z=306.4 (M+H).

b. 6-Methyl-5-nitro-1H-isochromen-1-one

A microwave vial was charged with tert-butyl 2-(5-nitro-1-oxo-1H-isochromen-6-yl)acetate (800.0 mg, 0.002620 mol), trifluoroacetic Acid (2 mL, 0.02 mol) and subjected to microwave at 100° C. for 20 minutes. The starting material became converted into the corresponding acid. TFA was removed under reduced pressure and the residue was again taken a microwave tube and quinoline (2 mL, 0.02 mol) was added and heated at 120° C. for 20 minutes. The reaction went to completion and ethylacetate (50 mL) was added and washed with 10 mL of 6N HCl. The HCl layer was extracted with ethyl acetate (50 mL) and the combined organic layers were washed with water, brine and dried. The solvent was removed and the brown solid residue was purified by flash chromatography to yield the pure product as a white solid. MS m/z=206.4 (M+H) $^1$H-NMR (400 MHz, DMSO-d6) δ 8.29 (d, J=8.19 Hz, 1H), 7.71-7.69 (m, 2H), 6.57 (d, J=6.02 Hz, 1H), 2.45 (s, 3H).

Intermediate 5

Preparation of
6-cyclopropyl-5-nitro-1H-isochromen-1-one

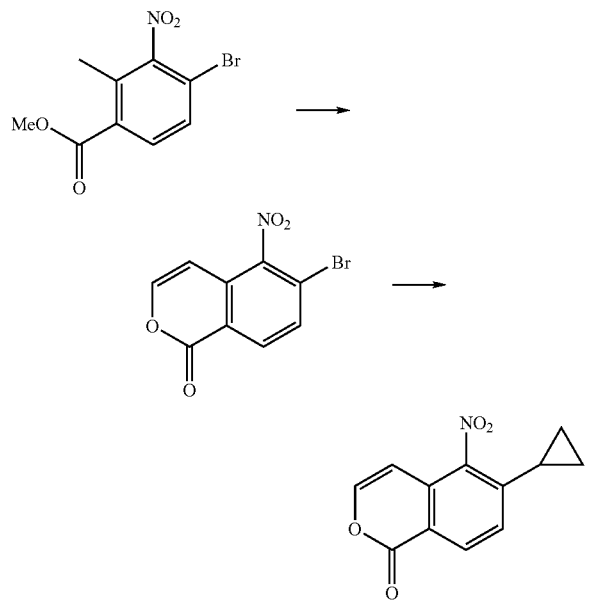

a. 6-Bromo-5-nitro-1H-isochromen-1-one

A pressure tube (150 mL) was charged with methyl 4-bromo-2-methyl-3-nitrobenzoate (2.1 g, 0.0077 mol), 1,1-dimethoxy-N,N-dimethylmethanamine (3.6 mL, 0.027 mol) and N,N-dimethylformamide (5 mL, 0.06 mol) and heated at 120° C. for 20 hours. The reaction gave multiple products. The solvent was removed and the residue was dissolved in Ethyl acetate (100 mL, 1 mol). Silica Gel (20 g, 0.3 mol) was then added and the reaction stirred at room temperature for 12 h. The reaction was filtered and the solvent removed and the residue purified by flash chromatography. MS m/z=271.2 (M+H).

b. 6-Cyclopropyl-5-nitro-1H-isochromen-1-one

A microwave vial was charged with 6-bromo-5-nitro-1H-isochromen-1-one (500.00 mg, 0.0018516 mol), cyclopropylboronic acid (206.8 mg, 0.002407 mol), palladium acetate (21 mg, 0.000092 mol), tricyclohexylphosphine (52 mg, 0.00018 mol), potassium phosphate (1376 mg, 0.006481 mol), toluene (10 mL, 0.09 mol) and water and heated at 100° C. for 30 minutes under microwaves. The rection mixture was then diluted with water and extracted with ethyl acetate. The combined organic layers were washed with brine, dried and evaporated. The resultant residue was purified by flash chromatography to obtain the product. The product was only 65% pure and was used to synthesize 6-cyclopropyl compounds of this invention without further purification. MS m/z=232.3 (M+H). $^1$H NMR (400 MHz, DMSO-d6): δ 8.22 (d, J=8.63 Hz, 1H), 7.69 (d, J=5.85 Hz, 1H), 7.33 (d, J=8.47 Hz, 1H), 651 (d, J+6.05 Hz, 1H), 1.96-1.89 (m, 1H), 1.19-1.14 (m, 2H, 0.97-0.93 (m, 2H).

Intermediate 6

Preparation of
6-chloro-5-nitro-1H-isochromen-1-one

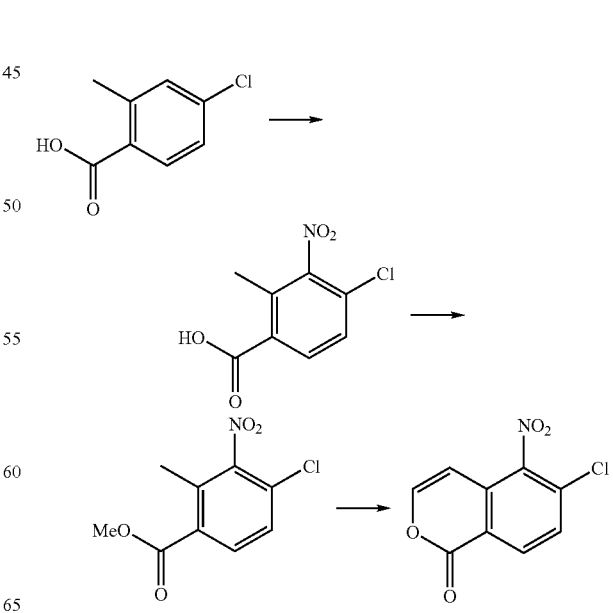

a. 4-Chloro-2-methyl-3-nitrobenzoic acid

A round bottom flask was charged with 4-chloro-2-methylbenzoic acid (200 mg, 0.001 mol) and sulfuric acid (1 mL, 0.02 mol). Fuming nitric acid (0.05 mL, 0.001 mol) was added at −20° C. and the reaction was stirred for 1 hour at 70° C. and poured into ice cold water wherein the mixture of 2- and 4-nitro compounds precipitated out. The precipitate was filtered and dissolved in ethylacetate (30 mL) and washed with saturated aqueous sodium bicarbonate solution, brine and dried over sodium sulfate. The solvent was reduced ¼ volume whereby the undesired isomer precipitated out. The precipitate was filtered and the filtrate was dried to obtain a 1:1 mixture of isomers as a white solid. MS m/z=214.5 (M−H).

b. Methyl 4-chloro-2-methyl-3-nitrobenzoate

A round bottom flask was charged with 4-chloro-2-methyl-3-nitrobenzoic acid (11.00 g, 0.05102 mol) and methanol (110 mL, 2.7 mol) and thionyl chloride (4.5 mL, 0.061 mol) was added at 0° C. and the reaction heated at 75° C. for 3 hours. The solvent was removed under reduced pressure and the residue dissolved in ethyl acetate (300 mL) and washed with aqueous sodium bicarbonate, water and brine. The organic extracts were dried over sodium sulfate and the solvent removed to recover the esters. MS m/z=230.3 (M+H).

c. 6-Chloro-5-nitro-1H-isochromen-1-one

A pressure tube was charged with methyl 4-chloro-2-methyl-3-nitrobenzoate (13 g, 57 mmol), N,N-dimethylformamide (10 mL, 200 mmol) and 1,1-dimethoxy-N,N-dimethylmethanamine (26.5 mL, 200 mmol) and the reaction heated to 120° C. for 20 h. The solvents were removed and the resultant brown residue was redissolved in ethyl acetate (600 mL, 6000 mmol) and 130-270 mesh 60A silica gel (500 g, 6000 mmol) was added and the reaction stirred with a mechanical stirrer for 8 h. The silica gel was filtered off, washed with ethyl acetate (400 mL) and the organics were removed under vacuum and the residue purified by flash chromatography (330 g, 2-50% ethyl acetate/hexane) to obtain the two isomers in 14% yields each in almost 98% purity. MS m/z=226.2 (M+H). $^1$H NMR (400 MHz; DMSO-d6) δ 8.35 (d, J=8.63 Hz, 1H), 7.95 (d, J=8.63 Hz, 1H), 7.76 (d, J=5.91 Hz, 1H), 6.61 (d, J=6.04 Hz, 1H).

Representative Synthetic Methods

Method A

Compound 65

2-(4-Chloro-3-trifluoromethyl-phenyl)-N-[2-(2-hydroxy-ethyl)-1-oxo-1,2-dihydro-isoquinolin-5-yl]-acetamide

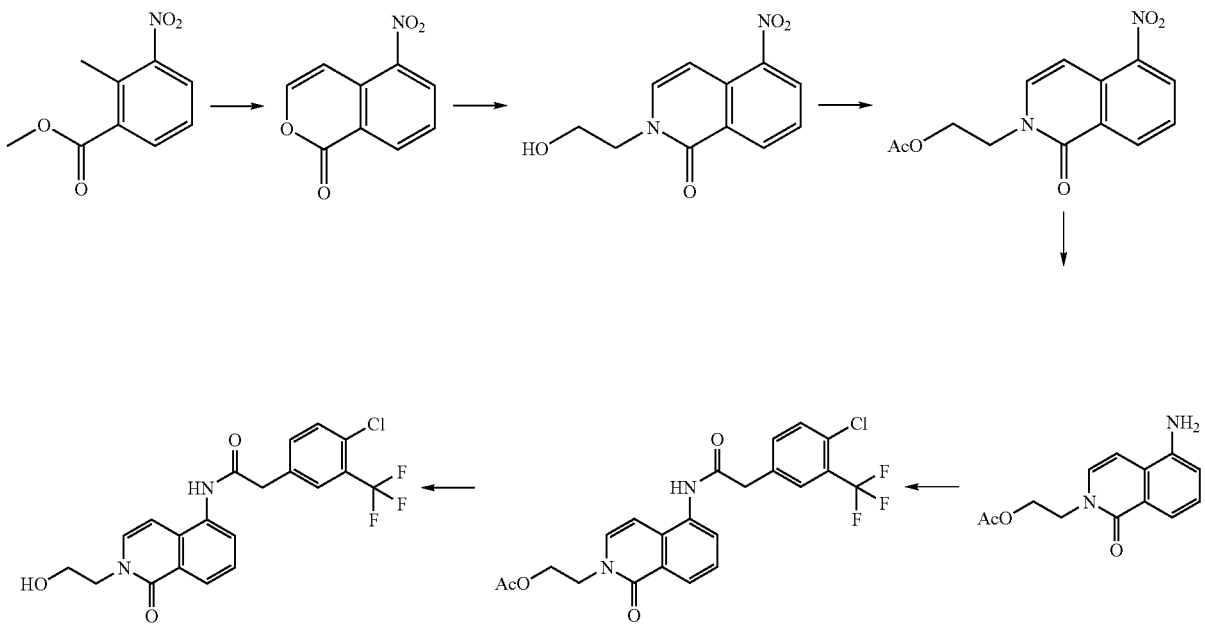

a. 5-Nitro-isochromen-1-one

Methyl 2-methyl-3-nitrobenzoate (5 g, 0.02 mol) and 1,1-dimethoxy-N,N-dimethylmethanamine (10 mL, 0.07 mol) were dissolved in N,N-dimethylformamide (30 mL, 0.4 mol). The mixture was stirred at 115° C. for 17 hours. The volatiles were removed on a rotavapor. The residue was dissolved in ethylacetate (400 mL) and then silica gel (400 g) was added. The mixture was stirred at room temperature for 3 hours. Filtered, rinsed with ethylacetate (400 mL×3). Combined filtrates were concentrated to dryness to get a brown solid (3.6 g). MS m/z=192.0 (M+1).

b. 2-(2-Hydroxyethyl)-5-nitroisoquinolin-1(2H)-one 5-nitro-isochromen-1-one (3.60 g, 0.0170 mol) was suspended in methanol (40 mL), ethanolamine (3.11 g, 0.0508 mol) was added and the reaction mixture was stirred at 70° C. for 2 h under an atmosphere of nitrogen. The mixture was cooled to room temperature and triethylamine (5 mL) was added and the reaction mixture was stirred at room temperature for 2 days. The resulting solid was filtered out (yellow solid was obtained as the desired product, 0.9 g). The filtrate was concentrated and the residue was dissolved in ethylacetate, washed by water and brine, dried over sodium sulfate. Solvent was removed to obtain product as yellow solid (1.3 g). MS m/z=235.1 (M+1).

c. 2-(5-Nitro-1-oxoisoquinolin-2(1H)-yl)ethyl acetate 2-(2-Hydroxyethyl)-5-nitroisoquinolin-1(2H)-one (2.2 g, 0.0089 mol) was dissolved in the mixture of methylene chloride (20 mL) and N,N-dimethylformamide (10 mL), N,N-diisopropylethylamine (2.33 mL, 0.0134 mol) and acetyl chloride (1.06 g, 0.0134 mol) were added and the reaction mixture was stirred at room temperature for 30 min. The volatiles were removed, and the residue was washed by water and then with diethyl ether to obtain the product as light yellow solid (2.45 g). MS m/z=277.0 (M+1).

d. 2-(5-Amino-1-oxoisoquinolin-2(1H)-yl)ethyl acetate 2-(5-Nitro-1-oxoisoquinolin-2(1H)-yl)ethyl acetate (2.45 g, 0.00842 mol) was dissolved in methanol (100 mL), palladium on charcoal (10%) was added and the reaction mixture was stirred under an atmosphere of hydrogen for 1 hour. The mixture was filtered through celite, and solvent was removed. The product was obtained as a light orange solid (1.98 g). MS m/z=246.5(M+1).

e. Acetic acid 2-5-[2-(4-chloro-3-trifluoromethyl-phenyl)-acetylamino]-1-oxo-1H-isoquinolin-2-yl-ethyl ester The solution of 2-(4-chloro-3-(trifluoromethyl)phenyl) acetic acid (131 mg, 0.000548 mol) in thionyl chloride (5 mL) was stirred at 60° C. for 1 hour. Thionyl chloride was removed, and residue was dissolved in tetrahydrofuran (5 mL). 2-(5-Amino-1-oxoisoquinolin-2(1H)-yl)ethyl acetate (100.0 mg, 0.0003655 mol) and N,N-diisopropylethylamine (95.5 μL, 0.000548 mol) were added and the reaction mixture was stirred at room temperature for 1 hour. The volatiles were removed, the residue was dissolved in ethylacetate, washed with water, dilute HCl and brine, and purified by column. The product was obtained as a beige solid (65 mg). MS m/z=467.4 (M+1). $^1$H NMR (DMSO-d6) δ 10.11(s, 1 H), 8.08(d, J=8.0 Hz, 1 H), 7.90(s, 1 H), 7.84(d, J=7.0 Hz, 1 H), 7.75-7.65 (m, 2 H), 7.55-7.42(m, 2 H), 6.69(d, J=7.6 Hz, 1 H), 4.33(t, J=5.1 Hz, 2 H), 4.20(t, J=5.1 Hz, 2 H), 3.92(s, 2 H), 1.96(s, 3 H).

f. 2-(4-Chloro-3-(trifluoromethyl)phenyl)-N-(1,2-dihydro-2-(2-hydroxyethyl)-1-oxoisoquinolin-5-yl) acetamide Acetic acid 2-5-[2-(4-chloro-3-trifluoromethyl-phenyl)-acetylamino]-1-oxo-1H-isoquinolin-2-yl-ethyl ester (55.0 mg, 0.000111 mol) was dissolved in methanol (5 mL) and aqueous 2N sodium hydroxide solution (5 mL) was added and the reaction mixture was stirred at room temperature for 1 hour. Methanol was removed, and solid thus formed was filtered out, washed with water and dried in a vacuum oven. The product was obtained as a beige solid (45 mg). MS m/z=425.2 (M+1). $^1$H NMR (DMSO-d6) δ 10.10(s, 1 H), 8.08(d, J=7.9 Hz, 1 H), 7.89(s, 1 H), 7.82(d, J=7.6 Hz, 1 H), 7.78-7.62 (m, 2 H), 7.55-7.40(m, 2 H), 6.65(d, J=7.5 Hz, 1 H), 4.89(s, 1 H), 4.02(t, J=5.2 Hz, 2 H), 3.92(s, 2 H), 3.67(t, J=5.2 Hz, 2 H).

Method B

Compound 81

2-(4-Chloro-3-trifluoromethyl-phenyl)-N-[2-(2-hydroxy-1-hydroxymethyl-ethyl)-1-oxo-1,2-dihydro-isoquinolin-5-yl]-acetamide

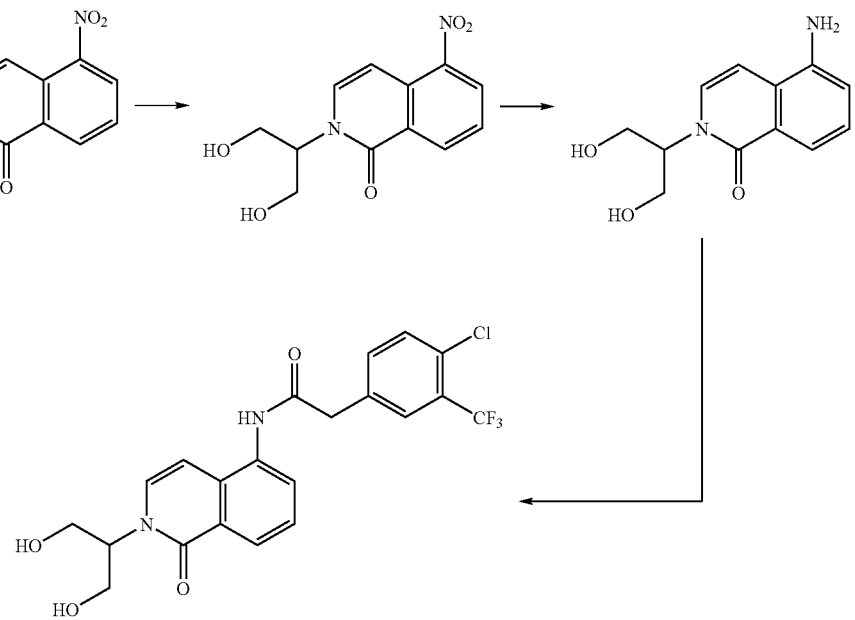

a. 2-(1,3-Dihydroxypropan-2-yl)-5-nitroisoquinolin-1(2H)-one 5-nitro-isochromen-1-one (4.2 g, 0.022 mol) and Serinol (2.0 g, 0.022 mol) were refluxed in methanol (40 mL, 1 mol) for 1 hour. TLC showed that all of the starting material was consumed. Triethylamine (5 mL, 0.04 mol) was added to the mixture and the reaction mixture was refluxed overnight. The volatiles were removed via rotovapor, and the residue was purified by flash column chromatography (40 g of silica gel, 0-50% EtOAc/Hexane), and gave a green yellow solid. MS m/z=264.7 (M+1).

b. 5-Amino-2-(1,3-dihydroxypropan-2-yl)isoquinolin-1(2H)-one 2-(1,3-dihydroxypropan-2-yl)-5-nitroisoquinolin-1(2H)-one (1.2 g, 0.0045 mol) was stirred with palladium 10% wt. on calcium carbonate (0.1 g, 0.0005 mol) in methanol (100 mL, 2 mol) under hydrogen (balloon) over 1 hr at room temperature. The catalyst was filtered, the filtrate was concentrated to dryness gave light green oil. MS m/z=235.0 (M+1).

c. 2-(4-Chloro-3-(trifluoromethyl)phenyl)-N-(2-(1,3-dihydroxypropan-2-yl)-1-oxo-1, 2-dihydroisoquinolin-5-yl)acetamide To a solution of 5-amino-2-(1,3-dihydroxypropan-2-yl)isoquinolin-1(2H)-one (100.0 mg, 0.0004055 mol) in N,N-dimethylformamide (8 mL, 0.1 mol) was added 2-(4-chloro-3-(trifluoromethyl)phenyl)acetic acid (378.0 mg, 0.001584 mol), N,N,N',N'-tetramethyl-O-(7-azabenzotriazol-1-yl)uronium hexafluorophosphate (448.0 mg, 0.001178 mol) and N,N-diisopropylethylamine (600.0 μL, 0.003445 mol). The reaction mixture was stirred for 16 hours at 50° C. After most of the DMF was rotovaped, MeOH (20 mL) and 2N NaOH (5 mL) were added to the residue. The solution was stirred for 1 hour at room temperature. MeOH was rotovaped and EtOAc (100 mL) was added, and the resultant solution was then washed with water (2×100 mL), Sat. NaHCO₃, H₂O, and brine. The EtOAc layer was dried by MgSO₄ and was rotovaped. The resultant solution was washed with DCM and then purified with silica-gel. The final product was obtained as a solid. MS m/z=455.1 (M+1). $^1$H NMR (400 MHz; DMSO-d6) δ 10.09(s, 1 H), 8.09(d, J=8.0 Hz, 1 H), 7.89(s, 1 H), 7.80(d, J=7.6 Hz, 1 H), 7.75-7.65(m, 2 H), 7.55-7.40(m, 2 H), 6.63(d, J=7.6 Hz, 1 H), 4.98-4.85(m, 3 H), 3.92(s, 2 H), 3.85-3.65 (m, 4 H).

Method C

Compound 232

2-(4-Chloro-3-trifluoromethyl-phenyl)-N-(1-oxo-2-(S)-1-pyrrolidin-2-ylmethyl-1,2-dihydro-isoquinolin-5-yl)-acetamide

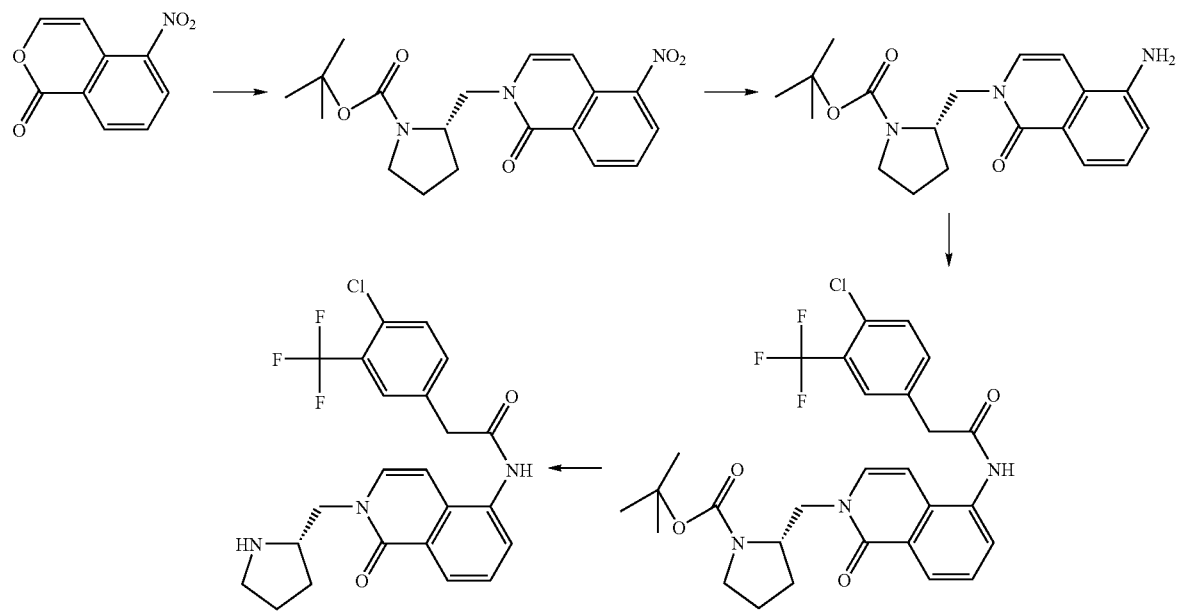

a. (S)-tert-Butyl 2-((5-nitro-1-oxoisoquinolin-2(1H)-yl)methyl)pyrrolidine-1-carboxylate Into a round bottom flask was combined 5-nitro-isochromen-1-one (3.50 g, 0.0165 mol), (S)-tert-butyl 2-(aminomethyl)pyrrolidine-1-carboxylate (4.12 g, 0.0206 mol) and methanol (100.0 mL, 2.469 mol). The mixture was heated at reflux for 2 hours. The mixture was allowed to cool and the volatiles were removed under reduced pressure. The crude oil was chromatographed using a methylene chloride:methanol (0-10%) gradient. The combined pure fractions were reduced in vacuo to yield the title compound as a yellow solid.

b. (S)-tert-Butyl 2-((5-amino-1-oxoisoquinolin-2(1H)-yl)methyl)pyrrolidine-1-carboxylate Into a round bottom flask was combined (S)-tert-butyl 2-((5-nitro-1-oxoisoquinolin-2(1H)-yl)methyl)pyrrolidine-1-carboxylate (1.54 g, 0.00412 mol) palladium on C (0.04 g, 0.0004 mol) and methanol (60 mL, 1 mol). The flask was purged and evacuated three times with hydrogen. The mixture was allowed to stir at room temperature under 1 atm for three hours. The mixture was filtered over a bed of celite and the filtrate was reduced in vacuo to yield a light brown oil which was purified by column chromatography on silica gel using a methylene chloride:methanol (0-10%) gradient. The combined pure fractions were reduced in vacuo to yield a tan solid.

c. (S)-tert-Butyl 2-((5-(2-(4-chloro-3-(trifluoromethyl)phenyl)acetamido)-1-oxoisoquinolin-2(1H)-yl)methyl)pyrrolidine-1-carboxylate To a solution of (S)-tert-butyl 2-((5-amino-1-oxoisoquinolin-2(1H)-yl)methyl)pyrrolidine-1-carboxylate (248.0 mg, 0.0006860 mol) in N,N-dimethylformamide (10 mL, 0.1 mol) was added 2-(4-chloro-2-(trifluoromethyl)phenyl)acetic acid (350.0 mg, 0.001467 mol), N,N,N',N'-tetramethyl-O-(7-azabenzotriazol-1-yl)uronium hexafluorophosphate (530.0 mg, 0.001394 mol) and N,N-diisopropylethylamine (488.0 µL, 0.002802 mol). The reaction mixture was stirred for 16 hours at 50° C. LC/MS was checked, and revealed that the reaction was completed. EtOAc (100 ML) was added and the resulting solution was washed by water (2×100 mL), Sat. NaHCO$_3$, H$_2$O and brine. The EtOAc layer was dried with MgSO$_4$ and was rotovaped. The yellow residue was purified by silica-gel column.

d. 2-(4-Chloro-3-(trifluoromethyl)phenyl)-N-(1,2-dihydro-1-oxo-2-(((S)-pyrrolidin-2-yl)methyl)isoquinolin-5-yl)acetamide Into a 20 ml reaction vessel was combined (S)-tert-butyl 2-((5-(2-(4-chloro-3-(trifluoromethyl)phenyl)acetamido)-1-oxoisoquinolin-2(1H)-yl)methyl)pyrrolidine-1-carboxylate (20.0 mg, 0.0000355 mol) and 1,4-dioxane (5 mL, 0.06 mol). Hydrogen chloride (0.016 g, 0.00044 mol) as a 2.0M solution in ether was added dropwise. The reaction was allowed to stir overnight. A white preciptate had formed and was filtered, washed with ether, and dried. The product was dissolved in diethylamine and DMSO (1 mL) and was purified by HPLC using a Phenomenex AXIA packed C18 column (100×21.2 10 micron) at pH 10. The combined pure fractions were reduced in vacuo to yield the title compound as a white solid. LC/MS M+H=464.2.

$^1$H-NMR (400MHz, DMSO-d6) δ 10.21 (s, 1H), 8.98 (d, 1H, J=93.24 Hz), 8.10 (d, 1H, J=8.03 Hz), 7.90 (s, 1H), 7.85 (dd, 1H, J=7.85 Hz), 7.73-7.68 (m, 2H), 7.60 (d, 1H, J=7.67 Hz), 7.50 (t, 1H, J=7.96 Hz), 6.76 (d, 1H, J=7.65 Hz), 4.36-4.22 (m, 2H), 3.94 (s, 2H), 3.80 (br 's', 1H), 3.29-3.24 (m, 1H), 3.12-3.06 (m, 1H), 2.15-2.07 (m, 1H), 1.99-1.86 (m, 2H), 1.74-1.64 (m, 1H).

Method D

Compound 235

2-(4-Chloro-3-trifluoromethyl-phenyl)-N-[2-(2-methylamino-ethyl)-1-oxo-1, 2-dihydro-isoquinolin-5-yl]-acetamide

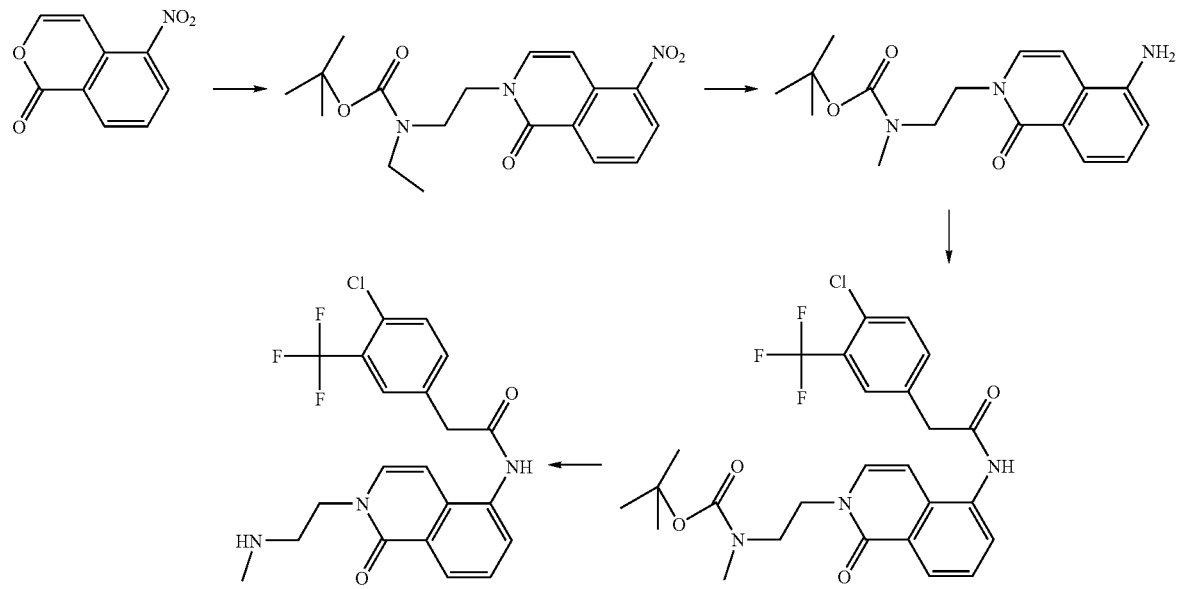

a. tert-Butyl methyl 2-(5-nitro-1-oxoisoquinolin-2(1H)-yl)ethylcarbamate

Into a round bottom flask was combined 5-nitro-isochromen-1-one (5.00 g, 0.0235 mol), tert-butyl 2-aminoethylmethylcarbamate (7.18 g, 0.0412 mol) N,N-diisopropylethylamine (4.92 mL, 0.0282 mol) and methanol (150 mL, 3.7 mol). The mixture was heated at reflux for 3 hours. The contents were allowed to cool, reduced in vacuo, and taken up in methylene chloride (250 ml) and washed with equal parts water and brine. The organic layer was separated, dried over sodium sulfate and reduced in vacuo. The mixture was purified by column chromatography using a methanol:methylene chloride (0-5%) gradient. The combined pure fractions were reduced in vacuo to yield the title compound as an orange solid.

b. tert-Butyl 2-(5-amino-1-oxoisoquinolin-2(1H)-yl)ethyl(methyl)carbamate

Into a 500 ml round bottom flask was combined tert-butyl methyl 2-(5-nitro-1-oxoisoquinolin-2(1H)-yl)ethylcarbamate (4.25 g, 0.0122 mol), methanol, and palladium on C (0.1 g, 0.001 mol). The flask was purged and evacuated with hydrogen 3 times. The mixture was stirred at room temperature under hydrogen (1 atm). The flask was evacuated and the contents filtered over celite. The filtrate was reduced in vacuo to yield an orange oil. The oil was purified by column chromatography using a methanol:methylene chloride (0-5%) gradient. The combined pure fractions were reduced in vacuo to yield the title compound as a light orange solid.

c. (2-5-[2-(4-Chloro-3-trifluoromethyl-phenyl)-acetylamino]-1-oxo-1H-isoquinolin-2-yl-ethyl)-methyl-carbamic acid-tert-butyl ester Into a 20 ml reaction vessel was combined tert-butyl 2-(5-amino-1-oxoisoquinolin-2(1H)-yl)ethyl(methyl)carbamate (150 mg, 0.00045 mol) 2-(4-chloro-3-trifluoromethyl)phenyl)-acetic acid (0.214 g, 0.000898 mol) N,N,N',N'-tetramethyl-O-(7-azabenzotriazol-1-yl)uronium hexafluorophosphate (427 mg, 0.00112 mol) N,N-diisopropylethylamine (391 μL, 0.00224 mol), and N,N-dimethylformamide (0.03 mL, 0.0004 mol). The mixture was heated at at 50° C. for two hours, allowed to cool and poured into sat. sodium bicarbonate (200 ml). The mixture was extracted with methylene chloride (3×100 ml). The combined extracts were dried over sodium sulfate and reduced in vacuo. The mixture was purified by reverse phase prep HPLC using an acetonitrile:water gradient at pH 10. The combined pure fractions were reduced in vacuo to yield the compound as an off white solid.

d. 2-(4-Chloro-3-trifluoromethyl-phenyl)-N-[2-(2-methylamino-ethyl)-1-oxo-1,2-dihydro-isoquinolin-5-yl]-acetamide hydrochloride Into a 20 ml reaction vessel was combined (2-5-[2-(4-chloro-3-trifluoromethyl-phenyl)-acetylamino]-1-oxo-1H-isoquinolin-2-yl-ethyl)-methyl-carbamic acid-tert-butyl ester (126 mg, 0.000234 mol) and 1,4-dioxane (5 mL, 0.06 mol). Hydrogen chloride (20 mg, 0.00054 mol) as a 2.0M solution in ether was added dropwise. The reaction was allowed to stir overnight. A white precipitate had formed and was filtered, washed with ether, and dried to give the title compound. LC/MS M+H=438.2.

$^1$H-NMR (400MHz, DMSO-d6) δ 10.22 (s, 1H), 8.64 (br 's', 1H), 8.09 (d, 1H, J=8.14 Hz), 7.90 (s, 1H), 7.83 (d, 1H, J=7.76 Hz), 7.73-7.68 (m, 2H), 7.51-7.47 (m, 2H), 6.74 (d, 1H, 7.57 Hz), 4.26 (t, 2H, J=5.74 Hz), 3.94 (s, 2H), 3.31-3.25 (m, 2H), 2.57 (t, 3H, J=5.28)

Method E

Compound 236

(S)-2-{5-[2-(3,4-Dichloro-phenyl)-acetylamino]-1-oxo-1H-isoquinolin-2-yl}-propionamide

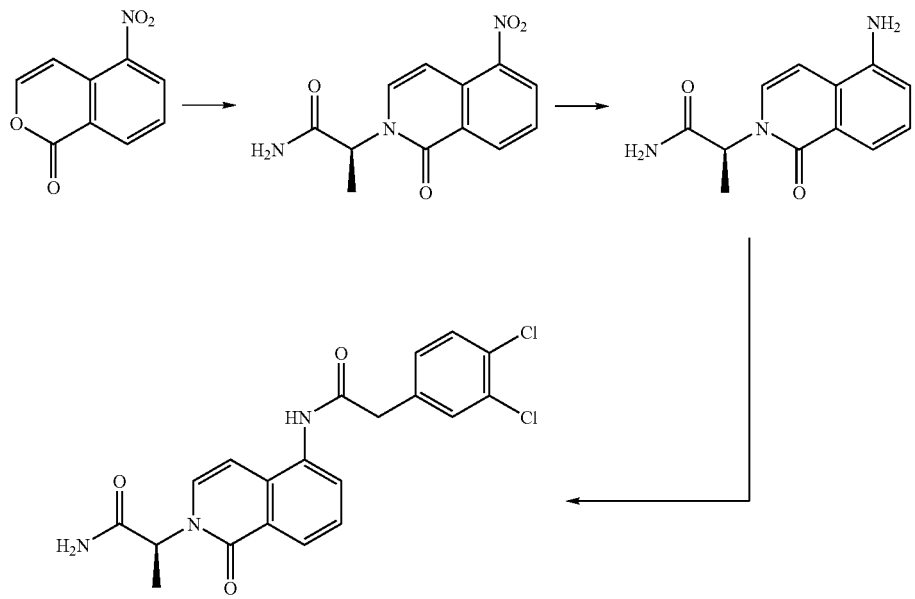

a. (S)-2-(5-Nitro-1-oxoisoquinolin-2(1H)-yl)propanamide

To a solution of 5-nitro-isochromen-1-one (1.5 g, 0.0078 mol) in methanol (20 mL, 0.4 mol) was added triethylamine (2 mL, 0.02 mol) and (S)-2-aminopropanamide hydrobromide (1.6 g, 0.0094 mol) and the resulting mixture was heated at 50° C. overnight. The reaction mixture was cooled to room temperature wherein the product precipitated out. The precipitate was filtered and dried to yield the pure product as a yellow solid. MS m/z=262.2 (M+H).

b. (S)-2-(5-Amino-1-oxoisoquinolin-2(1H)-yl)propanamide

To a solution of (S)-2-(5-nitro-1-oxoisoquinolin-2(1H)-yl)propanamide (1.3 g, 0.0050 mol) in methanol (40 mL, 1 mol) and dichloromethane (5 mL) was added palladium on charcoal (0.2 g, 0.001 mol) and stirred under hydrogen (1 atm) for 2 h. The reaction mixture was filtered over celite and the filtrate removed under reduced pressure to yield the pure product as an off white solid. MS m/z=232.5 (M+H).

c. (S)-2-(5-(2-(3,4-Dichlorophenyl)acetamido)-1-oxoisoquinolin-2(1H)-yl)propanamide To a stirred solution of 3,4-dichlorophenyl acetic acid (0.12 g, 0.00056 mol), N,N,N',N'-tetramethyl-O-(7-azabenzotriazol-1-yl)uronium hexafluorophosphate (0.3 g, 0.0009 mol) and N,N-diisopropylethylamine (0.2 mL, 0.0009 mol) in N,N-dimethylformamide (5 mL, 0.06 mol) was added (S)-2-(5-amino-1-oxoisoquinolin-2(1H)-yl)propanamide (0.10 g, 0.00043 mol). The reaction was stirred for 16 h at room temperature. The reaction was quenched with water, extracted with dichloromethane, washed with 2N HCl, saturated sodium bicarbonate solution, brine and dried over sodium sulfate. The solvent was removed under reduced pressure and the residue was purified by flash chromatography (12 g, 0-10% MeOH/DCM) to yield the product as a white solid. MS m/z=419.2 (M+H). $^1$H NMR (400 MHz; DMSO-d6) δ 10.08 (s, 1H), 8.07 (d, J=8.42 Hz, 1H), 7.82 (d, J=8.42 Hz, 1H) 7.66-7.61 (m, 3H), 7.48-7.43 (m, 2H), 7.38 (d, J=9.08 Hz, 1H), 7.23 (bs, 1H), 6.67 (d, J=8.42 Hz, 1H), 5.50-5.45 (q, J=7.24 Hz, 1H), 3.82 (s, 2H), 1.54 (d, J=7.50 Hz, 3H).

Method F

Compound 237

(S)-2-{5-[2-(4-Chloro-2-trifluoromethyl-phenyl)-acetylamino]-1-oxo-1H-isoquinolin-2-yl}-propionamide

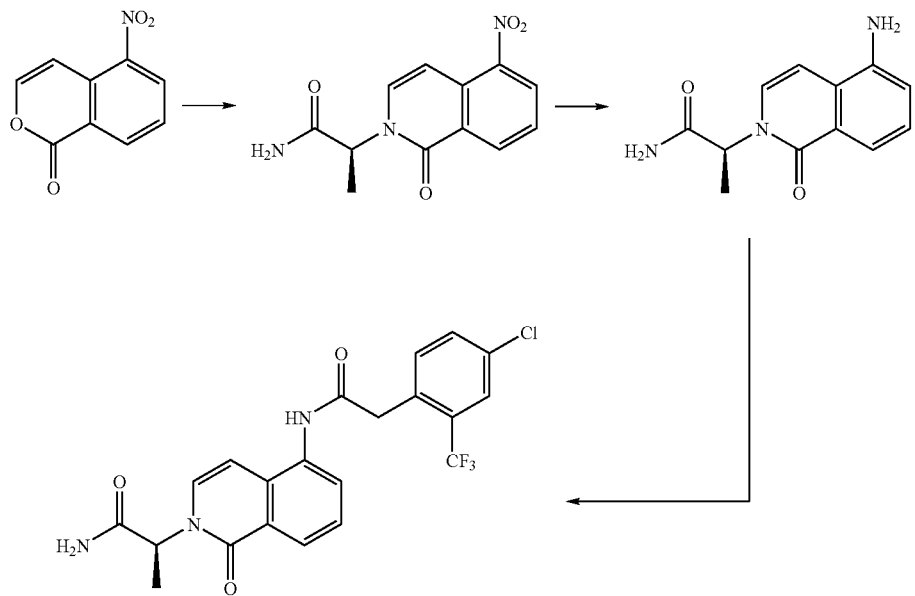

a. (S)-2-(5-Nitro-1-oxoisoquinolin-2(1H)-yl)propanamide

A round bottom flask was charged with 5-nitro-isochromen-1-one (1.5 g, 0.0078 mol), methanol (20 mL, 0.4 mol), triethylamine (2 mL, 0.02 mol) and (S)-2-aminopropanamide hydrobromide (1.6 g, 0.0094 mol) and the reaction was heated at 50° C. overnight. The reaction mixture was cooled to room temperature wherein the product precipitated out. The precipitate was filtered and dried to yield the pure product as a yellow solid. MS m/z=262.2 (M+H).

b. (S)-2-(5-Amino-1-oxoisoquinolin-2(1H)-yl)propanamide

A round bottom flask was charged with (S)-2-(5-nitro-1-oxoisoquinolin-2(1H)-yl)propanamide (1.3 g, 0.0050 mol), methanol (40 mL, 1 mol), dichloromethane (5 mL) and palladium on charcoal (0.2 g, 0.001 mol) were added and the mixture was stirred under hydrogen (1 atm) for 2 h. The reaction mixture was filtered over celite and the solvent removed under reduced pressure to yield the pure product as an off white solid. MS m/z=232.5 (M+H).

c. (S)-2-(5-(2-(4-Chloro-2-(trifluoromethyl)phenyl)acetamido)-1-oxoisoquinolin-2(1H)-yl)propanamide A round bottom flask was charged with 2-(4-chloro-2-(trifluoromethyl)phenyl)acetic acid (0.13 g, 0.00056 mol), N,N,N',N'-tetramethyl-O-(7-azabenzotriazol-1-yl)uronium hexafluorophosphate (0.3 g, 0.0009 mol), N,N-diisopropylethylamine (0.2 mL, 0.0009 mol), N,N-dimethylformamide (5 mL, 0.06 mol) and (S)-2-(5-amino-1-oxoisoquinolin-2(1H)-yl)propanamide (0.1 g, 0.0004 mol), and the reaction was stirred for 16 h at room temperature. The reaction was quenched with water and extracted with dichloromethane, washed with 2N HCl, saturated sodium bicarbonate solution, brine and dried over sodium sulfate. The solvent was removed under reduced pressure and the residue purified by flash chromatography (12 g, 0-10% MeOH/DCM) to yield the product as a white solid. MS m/z=452.4 (M+H). $^1$H NMR (400 MHz; DMSO-d6) δ 10.11 (s, 1H), 8.07 (d, J=8.80 Hz, 1H), 7.79-7.76 (m, 3H) 7.64-7.60 (m, 2H), 7.49 (d, J=8.08 Hz, 1H), 7.45 (t, J=7.7 Hz, 1H), 7.23 (bs, 1H), 6.71 (d, J=7.77 Hz, 1H), 5.50-5.45 (q, J=7.24 Hz, 1H), 4.06 (s, 2H), 1.55 (d, J=7.54 Hz, 3H).

Method G

Compound 238

(R)-2-{5-[2-(4-Chloro-3-trifluoromethyl-phenyl)-acetylamino]-1-oxo-1H-isoquinolin-2-yl}-propionamide a. (R)-2-(5-Nitro-1-oxoisoquinolin-2(1H)-yl)propanamide

A round bottom flask was charged with 5-nitro-isochromen-1-one (2 g, 0.01 mol), methanol (40 mL, 1 mol), (R)-2-aminopropanamide hydrochloride (2.0 g, 0.016 mol) and triethylamine (2.6 mL, 0.019 mol) and stirred at 52° C. for 3 hours. The product (yellow solid) precipitated out which was filtered and carried on to the next reaction without any further purification. MS m/z=262.3 (M+H).

b. (R)-2-(5-Amino-1-oxoisoquinolin-2(1H)-yl)propanamide

A round bottom flask was charged with (R)-2-(5-nitro-1-oxoisoquinolin-2(1H)-yl)propanamide (5.0 g, 0.018 mol), palladium on charcoal (10%) (0.3 g, 0.003 mol) and methanol (200 mL, 5 mol) and ethylacetate (80 mL). The reaction mixture was stirred under hydrogen (1 atm) at room temperature for 40 minutes. The mixture was filtered over celite, the solvent was removed to yield the product as a light yellow solid. MS m/z=232.3 (M+H).

c. (R)-2-(5-(2-(4-Chloro-3-(trifluoromethyl)phenyl)acetamido)-1-oxoisoquinolin-2(1H) -yl)propanamide A round bottom flask was charged with 2-(4-chloro-3-(trifluoromethyl)phenyl)acetic acid (0.13 g, 0.00056 mol), N,N,N',N'-tetramethyl-O-(7-azabenzotriazol-1-yl)uronium hexafluorophosphate (0.3 g, 0.0009 mol), N,N-diisopropylethylamine (0.2 mL, 0.0009 mol), N,N-dimethylformamide (3 mL, 0.04 mol) and (R)-2-(5-amino-1-oxoisoquinolin-2(1H)-yl)propanamide (0.1 g, 0.0004 mol). The reaction was

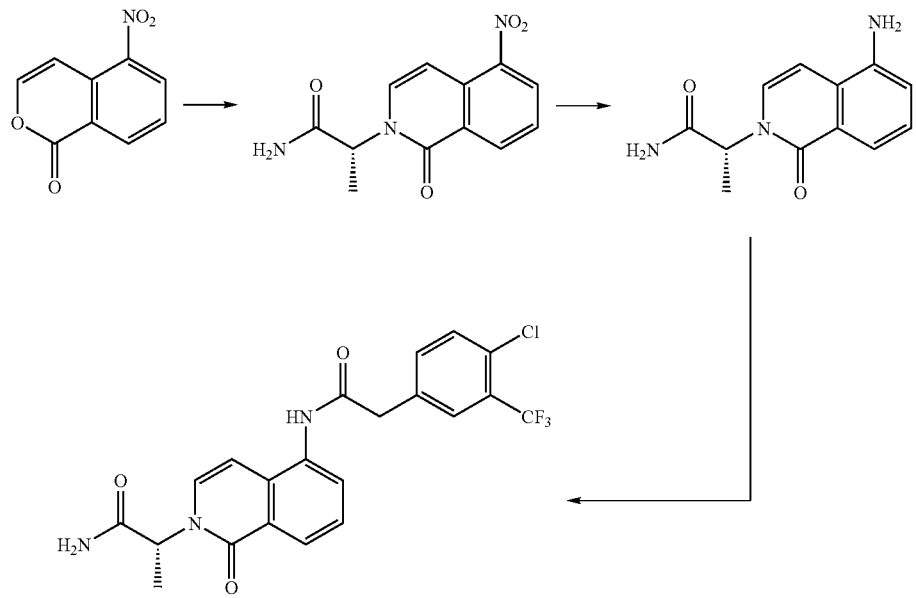

stirred at room temperature for 16 h. The solvent was removed under reduced pressure and the residue purified by flash chromatography (12 g, 0-10% MeOH/DCM) to get the product as white solid. MS m/z=451.8(M+H). $^1$H NMR (400 MHz; DMSO-d6) δ 10.10 (s, 1H), 8.07(d, J=8.42 Hz, 1H), 7.89 (s, 1H), 7.82 (d, J=8.47 Hz, 1H) 7.73-7.68 (m, 2H), 7.63 (s, 1H), 7.46 (d, J=7.57 Hz, 2H), 7.23 (bs, 1H), 6.68 (d, J=8.02 Hz, 1H), 5.50-5.45 (q, J=7.24 Hz, 1H), 3.92 (s, 2H), 1.54 (d, J=7.66 Hz, 3H).

Method H

Compound 249

2-{5-[2-(4-Chloro-3-trifluoromethyl-phenyl)-acetylamino]-1-oxo-1H-isoquinolin-2-yl}-acetamide charcoal (0.1 g, 0.001 mol) was added and the reaction was stirred under hydrogen atmosphere (1 atm) for 1 hour. The reaction mixture was filtered and the solvent removed under reduced pressure and the residue purified by flash chromatography (40 g, 0-10% MeOH/DCM) to yield the product as an off white solid. MS m/z=218.3 (M+H).

c. N-(2-(2-Amino-2-oxoethyl)-1-oxo-1,2-dihydroisoquinolin-5-yl)-2-(4-chloro-3-(trifluoromethyl)phenyl)acetamide A round bottom flask was charged with 2-(4-chloro-3-(trifluoromethyl)phenyl)acetic acid (170 mg, 0.00072 mol),

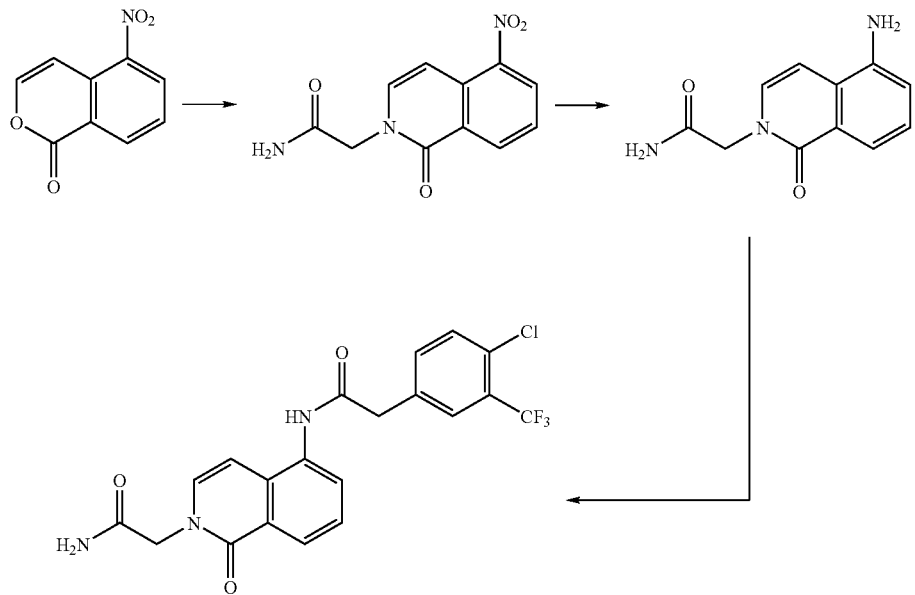

a. 2-(5-Nitro-1-oxoisoquinolin-2(1H)-yl)acetamide

A round bottom flask was charged with 5-nitro-isochromen-1-one (2.5 g, 0.013 mol), methanol (50 mL, 1 mol), glycinamide hydrochloride (3.0 g, 0.027 mol) and triethylaluminum (4.4 mL, 0.033 mol) and heated at 85° C. for 3 hours. The solvent was removed under reduced pressure to get the product as a yellow solid. MS m/z=248.2 (M+H).

b. 2-(5-Amino-1-oxoisoquinolin-2(1H)-yl)acetamide

A round bottom flask was charged with 2-(5-nitro-1-oxoisoquinolin-2(1H)-yl)acetamide (0.98 g, 0.0040 mol), methanol (200 mL, 4 mol) and palladium, 10% weight on N,N,N',N'-tetramethyl-O-(7-azabenzotriazol-1-yl)uronium hexafluorophosphate (400 mg, 0.001 mol), N,N-diisopropylethylamine (0.2 mL, 0.001 mol), N,N-dimethylformamide (2 mL, 0.03 mol) and 2-(5-amino-1-oxoisoquinolin-2(1H)-yl)acetamide (120 mg, 0.00055 mol). The reaction was stirred for 16 h at room temperature and the solvent was removed and the residue purified by preparative HPLC (reverse phase) to yield the product as a white powder. MS m/z=437.8 (M+1). $^1$H NMR (400 MHz; DMSO-d6) δ 10.09 (s, 1H), 8.04 (d, J=8.07 Hz, 1H), 7.89 (bs, 1H), 7.83 (d, J=8.07 Hz, 1H), 7.73-7.70 (m, 2H), 7.63 (bs, 1H), 7.46 (t, J=8.0 Hz, 1H), 7.42 (d, J=7.76 Hz, 1H) 7.19 (bs, 1H), 6.64 (d, J=7.70 Hz, 1H), 4.56 (s, 2H), 3.92 (s, 2H).

Method J

Compound 250

(S)-2-{5-[2-(4-Chloro-3-trifluoromethyl-phenyl)-acetylamino]-1-oxo-1H-isoquinolin-2-yl}-3-hydroxy-propionamide vaccum and the reaction was stirred under an atmosphere of hydrogen (1 atm) with the aid of a balloon. The reaction was stirred for 45 minutes, in which time the reaction was complete. The reaction was filtered and the solvent removed under reduced pressure to yield the pure product as a light yellow solid. MS m/z=248.3 (M+H).

b. (S)-2-(5-Amino-1-oxoisoquinolin-2(1H)-yl)-3-hydroxypropanamide

A round bottom flask (250 mL) was charged with (S)-3-hydroxy-2-(5-nitro-1-oxoisoquinolin-2(1H)-yl)propanamide (0.2 g, 0.0007 mol) and methanol (20 mL, 0.5 mol) and palladium, 10% weight on charcoal (0.02 g, 0.0001 mol) was added and the flask was evacuated of air with the aid of c. (S)-2-5-[2-(4-Chloro-3-trifluoromethyl-phenyl)-acetylamino]-1-oxo-1 H-isoquinolin-2-yl-3-hydroxy-propionamide A round bottom flask was charged with 2-(4-chloro-3-(trifluoromethyl)phenyl)acetic acid (0.12 g, 0.00052 mol),

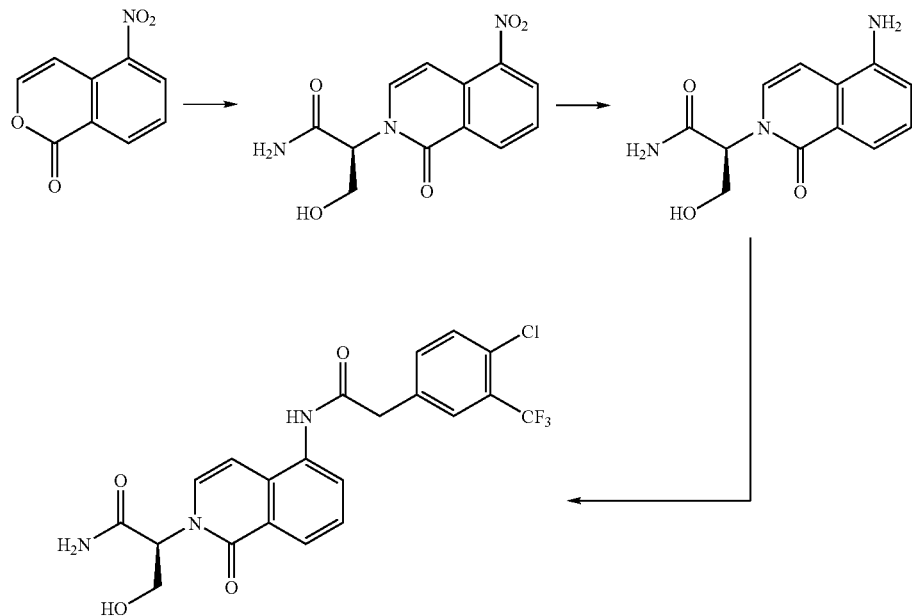

a. (S)-3-Hydroxy-2-(5-nitro-1-oxoisoquinolin-2(1H)-yl)propanamide

A round bottom flask was charged with 5-nitro-isochromen-1-one (2 g, 0.01 mol), methanol (40 mL, 1 mol), (S)-2-amino-3-hydroxypropanamide hydrochloride (2.2 g, 0.016 mol) and triethylamine (2.55 mL, 0.0183 mol) and stirred at 52° C. overnight. The product precipitated out and was filtered and dried to yield the pure product as a yellow solid. MS m/z=278.3 (M+H).

N,N,N',N'-tetramethyl-O-(7-azabenzotriazol-1-yl)uronium hexafluorophosphate (0.3 g, 0.0008 mol), N,N-diisopropylethylamine (0.1 mL, 0.0008 mol) and(S)-2-(5-amino-1-oxoisoquinolin-2(1H)-yl)-3-hydroxypropanamide (0.1 g, 0.0004 mol). The reaction was stirred for 16 h at room temperature and the solvent was removed and the residue purified by preparative HPLC (reverse phase) to yield the product as a white powder. MS m/z=468.3(M+H). $^1$H NMR (400 MHz; DMSO-d6) δ10.09 (s, 1H), 8.07 (d, J=8.34 Hz, 1H), 7.89 (bs, 1H), 7.81 (d, J=7.78 Hz, 1H), 7.73-7.66 (m, 3H), 7.53 (d, J=8.21 Hz, 1H), 7.44 (t, J=7.88 Hz, 1H), 7.30 (bs, 1H), 6.64 (d, J=7.88 Hz, 1H), 5.50 (t, J=6.69 Hz, 1H), 5.16 (t, J=5.48 Hz, 1H), 3.98-3.96 (m, 2H), 3.92 (s, 2H).

Method K

Compound 252

(R)-2-{5-[2-(4-Chloro-phenyl)-propionylamino]-1-oxo-1H-isoquinolin-2-yl}-3-hydroxy-propionamide by the reaction became homogeneous. The reaction was then heated at 70° C. overnight. The solvent was removed and the residue purified by flash chromatography (120 g, 0-10% MeOH/DCM) to yield the product as a yellow solid. MS m/z=293.5 (M+H).

b. (R)-Methyl 3-(tert-butyldimethylsilyloxy)-2-(5-nitro-1-oxoisoquinolin-2(1H)-yl)propanoate A round bottom flask was charged with (R)-methyl 3-hydroxy-2-(5-nitro-1-oxoisoquinolin-2(1H)-yl)propanoate (4

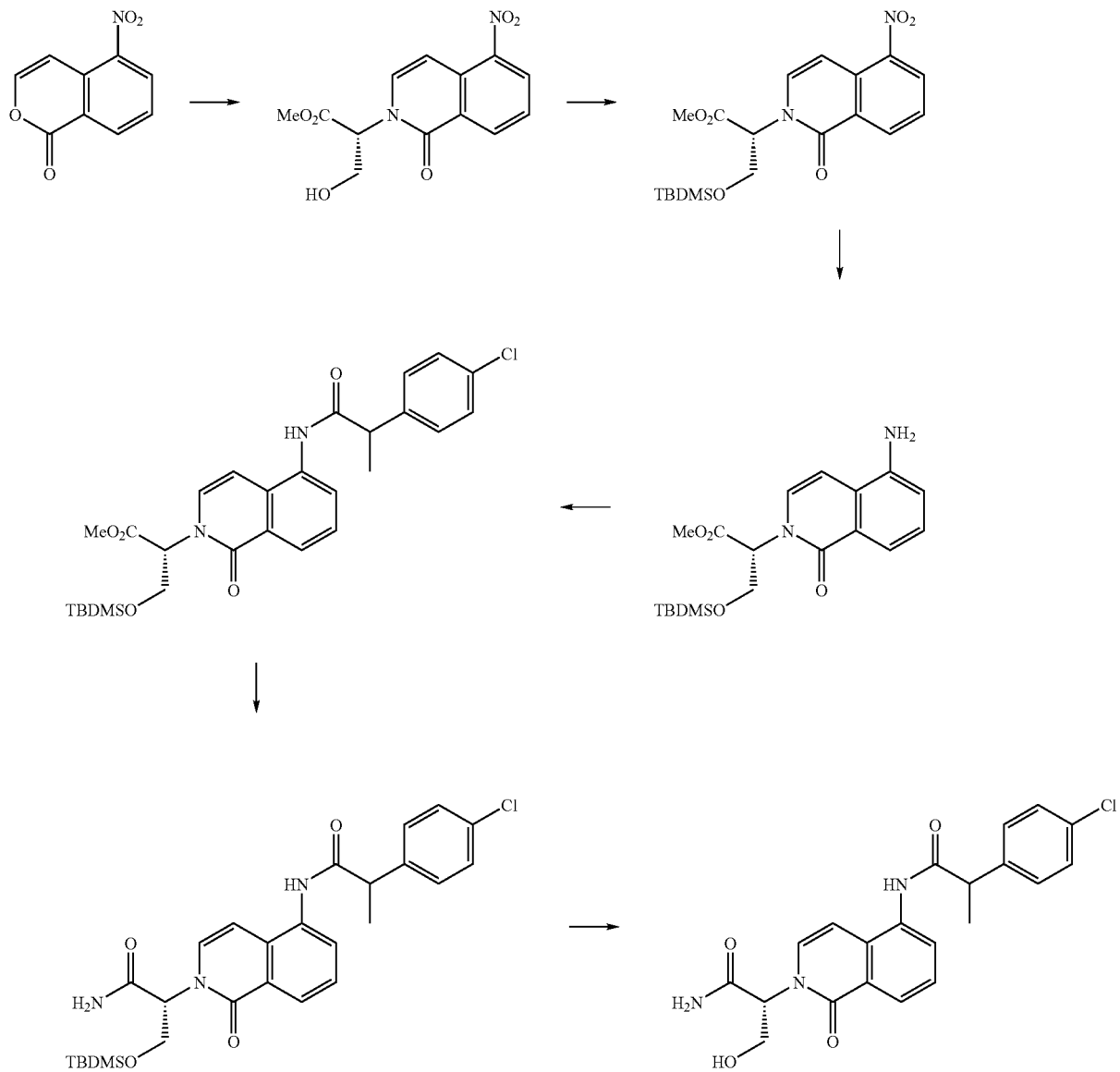

a. (R)-Methyl 3-hydroxy-2-(5-nitro-1-oxoisoquinolin-2(1H)-yl)propanoate

A round bottom flask was charged with 5-nitro-isochromen-1-one (10 g, 0.05 mol), methanol (200 mL, 5 mol), triethylamine (18 mL, 0.13 mol) and (R)-methyl 2-amino-3-hydroxypropanoate hydrochloride (9.8 g, 0.063 mol) where g, 0.01 mol) and methylene chloride (40 mL, 0.5 mol) and 1H-imidazole (1.6 g, 0.023 mol) and tert-butyldimethylsilyl chloride (2.3 g, 0.015 mol) were added at 0° C. and the reaction allowed to warm to room temperature and stirred for 16 h. The reaction mixture was quenched with water and extracted with methylene chloride. Solvent was removed under reduced pressure to yield pure product. MS m/z=407.5 (M+H).

c. (R)-Methyl 2-(5-amino-1-oxoisoquinolin-2(1H)-yl)-3-(tert-butyldimethylsilyloxy)propanoate A round bottom flask was charged with (R)-methyl 3-(tert-butyldimethylsilyloxy)-2-(5-nitro-1-oxoisoquinolin-2(1H)-yl)propanoate (5.5 g, 0.014 mol), methanol (100 mL, 2 mol); palladium, 10% weight on charcoal (0.3 g, 0.003 mol) was added and the reaction stirred under hydrogen atmosphere (1 atm) for 2 h. The reaction was filtered over celite and the solvent removed under reduced pressure and the residue purified by flash chromatography (40 g, 0-10% MeOH/DCM) to yield the product as a yellow sticky mass. MS m/z=377.5 (M+H).

d. (2R)-Methyl 3-(tert-butyldimethylsilyloxy)-2-(5-(2-(4-chlorophenyl)propanamido)-1-oxoisoquinolin-2(1H)-yl)propanoate A round bottom flask was charged with (R)-methyl 2-(5-amino-1-oxoisoquinolin-2(1H)-yl)-3-(tert-butyldimethylsilyloxy)propanoate (500 mg, 0.001 mol), N,N-dimethylformamide (2 mL, 0.03 mol), N,N-diisopropylethylamine (0.5 mL, 0.003 mol), N,N,N',N'-tetramethyl-O-(7-azabenzotriazol-1-yl)uronium hexafluorophosphate (1 g, 0.003 mol) and 2-(4-chlorophenyl)propanoic acid (340 mg, 0.0018 mol) and the reaction stirred at room temperature overnight then for another 12 h. The solvent was removed and the residue purified by flash chromatography to yield the product as a white solid. MS m/z=545.4 (M+H).

e. (2R)-3-(tert-Butyldimethylsilyloxy)-2-(5-(2-(4-chlorophenyl)propanamido)-1-oxoisoquinolin-2(1H)-yl)-propanamide A round bottom flask was charged with (2R)-methyl 3-(tert-butyldimethylsilyloxy)-2-(5-(2-(4-dichlorophenyl)propanamido)-1-oxoisoquinolin-2(1H)-yl)propanoate (200 mg, 0.00032 mol) and 5 mL of ammonia in methanol (2M) and the reaction heated in a sealed tube to 70° C. over night. The reaction was only partially complete. The solvent was removed and the residue purified by flash chromatography to yield the product as a light yellow oil. MS m/z=529.2 (M+H).

f. N-(2-((R)-1-Amino-3-hydroxy-1-oxopropan-2-yl)-1-oxo-1,2-dihydroisoquinolin-5-yl)-2-(4-chlorophenyl)-propanamide A mixture of (2R)-3-(tert-butyldimethylsilyloxy)-2-(5-(2-(4-dichlorophenyl)propanamido)-1-oxoisoquinolin-2(1H)-yl)propanamide (60 mg, 0.0001 mol), tetrahydrofuran (3 mL, 0.04 mol) and tetra-n-butylammonium fluoride (0.037 mL, 0.00012 mol) was stirred at room temperature for 30 minutes during which time the reaction was complete. The solvent was removed under reduced pressure and the residue purified by preparative HPLC (reverse phase) to yield the product as a white solid. MS m/z=414.3 (M+H). $^1$H NMR (400 MHz; DMSO-d6) δ 9.98 (s, 1H), 8.06 (d, J=8.0 Hz, 1H), 7.73 (t, J=7.81 Hz, 1H), 7.65 (s, 1H), 7.49(m, 6H), 7.29 (s, 1H), 6.46-6.43 (dd, J=4.61&3.42 Hz, (t, J=6.03 Hz, 1H), 5.15 (s, 1H), 4.06-4.01 (q, J=6.64 Hz, 1H), 3.98-3.96 (m, 2H), 1.45 (d, J=7.14 Hz, 3H).

Method L

Compound 257

2-(4-Chloro-3-trifluoromethyl-phenyl)-N-(1-oxo-2-piperidin-4-ylmethyl-1,2-dihydro-isoquinolin-5-yl)-acetamide

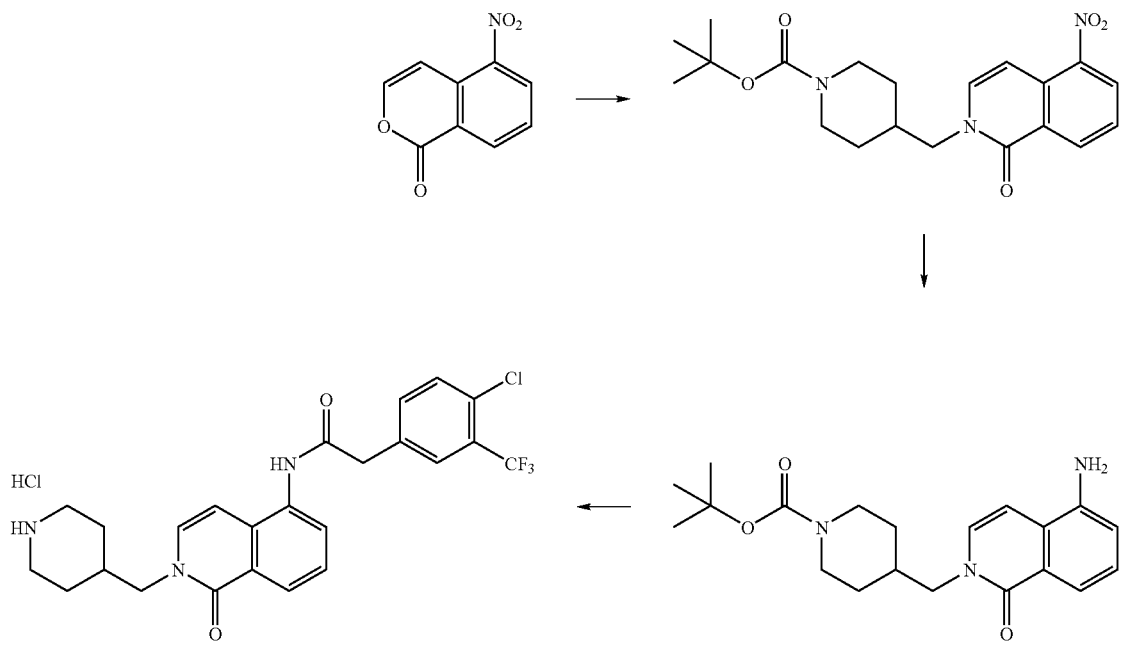

a. 4-(5-Nitro-1-oxo-1H-isoquinolin-2-ylmethyl)-piperidine-1-carboxylic acid-tert-butyl ester Into a round bottom flask was combined 5-nitro-isochromen-1-one (2.0 g, 0.0094 mol), tert-butyl 4-(aminomethyl) piperidine-1-carboxylate hydrochloride (4.7 g, 0.019 mol) and methanol (80 mL, 2 mol). The mixture was heated at reflux for 1.5 hours. The mixture was cooled to room temperature and was stirred overnight. LC-MS showed the starting material was completely consumed. Volatiles were removed and the resulting oil was purified by silical gel in a methanol:methylene chloride (0-10%) gradient. Fractions containing the desired product, as determined by TLC and LC-MS, were combined and concentrated to yield a yellow solid (3.22 g). MS m/z=388.1 (M+1).

b. tert-Butyl 4-((5-amino-1-oxoisoquinolin-2(1H)-yl)methyl)pipieridine-1-carboxylate Into a round bottom flask was combined 4-(5-nitro-1-oxo-1H-isoquinolin-2-ylmethyl)-piperidine-1-carboxylic acid -tert-butyl ester (3.22 g, 0.00790 mol), palladium on C (0.48 g, 0.0045 mol) and methanol (100 mL, 2 mol). The reaction mixture was stirred under hydrogen balloon at room temperature for 1 hr. The mixture was filtered over celite, MeOH was removed and the product was obtained as a solid (2.68 g). m/z=357.9 (M+1).

c. 2-(4-Chloro-3-(trifluoromethyl)phenyl)-N-(1-oxo-2-(piperidin-4-ylmethyl)-1, 2-dihydroisoquinolin-5-yl)acetamide hydrochloride To a solution of tert-butyl 4-((5-amino-1-oxoisoquinolin-2(1H)-yl)methyl)piperidine-1-carboxylate (100.0 mg, 0.0002658 mol) in N,N-dimethylformamide (5 mL, 0.06 mol) were added 2-(4-chloro-3-(trifluoromethyl)phenyl)acetic acid (143.0 mg, 0.0005994 mol), N,N,N',N'-tetramethyl-O-(7-azabenzotriazol-1-yl)uronium hexafluorophosphate (360.0 mg, 0.0009468 mol) and N,N-diisopropylethylamine (305.0 µL, 0.001751 mol). The reaction mixture was stirred for 16 hours at 50° C. LC/MS was checked and the reaction was complete. EtOAc (100 mL) was added and the mixture was washed with water (2×100 mL), Sat. NaHCO$_3$, H$_2$O, and brine. The EtOAc layer was dried by MgSO$_4$ and was rotovaped. The yellow residue was purified by silica-gel column, and a pure Boc protected product was obtained. To a solution of the Boc-protected product in 2 mL of dioxane was added 2M HCl in EtOEt (15 mL). The mixture was then stirred for 2 hours at room temperature to yield the final compound as a light colored solid (65.3 mg). MS m/z=478.2 (M+1). $^1$H NMR (400 MHz; DMSO-d6) δ 10.25(s, 1 H), 8.83(s, 1 H), 8.08 (d, J=7.5 Hz, 1 H), 7.91(s, 1 H), 7.82(d, J=6.9 Hz, 1 H), 7.72(bs, 2 H), 7.55-7.40 (m, 2 H), 6.71(d, J=6.8 Hz, 1 H), 4.20-3.80(m, 4 H), 3.28-3.15(m, 2 H), 2.90-2.70(m, 2 H), 2.10(bs 1 H), 1.80-1.60 (m, 2 H), 1.52-1.35(m, 2 H).

Method M

Compound 258

N-[2-(3-Amino-2-chloromethyl-propyl)-1-oxo-1,2-dihydro-isoquinolin-5-yl]-2-(4-chloro-3-trifluoromethyl-phenyl)-acetamide

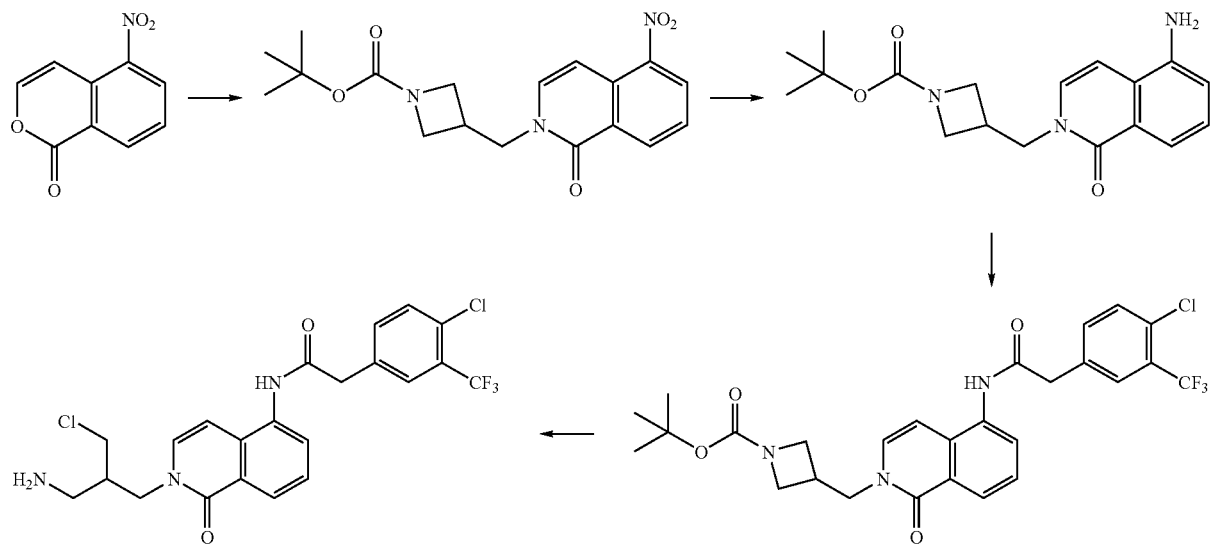

a. tert-Butyl 3-((5-nitro-1-oxoisoquinolin-2(1H)-yl)methyl)azetidine-1-carboxylate Into a round bottom flask was combined 5-nitro-isochromen-1-one (0.5 g, 0.002 mol), tert-butyl 3-(aminomethyl) azetidine-1-carboxylate (0.975 g, 0.00523 mol), methanol (15 mL, 0.37 mol), and the mixture was heated at reflux for 2 hours. The mixture was cooled to room temperature. LC-MS showed that the starting material was completely consumed. Volatiles were removed and the resulting oil was purified by silica-gel twice in a methanol:methylene chloride (0-10%) gradient and in a EtoAc:Hexane(30-80%). A light yellow solid was obtained (0.56 g). m/z=360.0 (M+1).

b. 3-(5-Amino-1-oxo-1H-isoquinolin-2-ylmethyl)-azetidine-1-carboxylic acid-tert-butyl ester Into a round bottom flask was combined tert-butyl 3-((5-nitro-1-oxoisoquinolin-2(1H)-yl)methyl)azetidine-1-carboxylate (0.56 g, 0.0015 mol), palladium on C (0.16 g, 0.0015 mol) and methanol (50 mL, 1 mol). The reaction mixture was stirred under hydrogen balloon at room temperature overnight. The mixture was filtered over celite, MeOH was removed and purified by silica-gel column twice (DCM: MeOH and EtOAc:Hexane). A white solid was obtained (190 mg). MS m/z=330.0 (M+1).

c. N-(2-(3-Amino-2-(chloromethyl)propyl)-1-oxo-1, 2-dihydroisoquinolin-5-yl)-2-(4-chloro-3-(trifluoromethyl)phenyl)acetamide To a solution of 3-(5-amino-1-oxo-1H-isoquinolin-2-ylmethyl)-azetidine-1-carboxylic acid-tert-butyl ester (96.0 mg, 0.000277 mol) in N,N-dimethylformamide (5 mL, 0.06 mol) is added 2-(4-chloro-3-(trifluoromethyl)phenyl)acetic acid (150.0 mg, 0.0006287 mol), N,N,N',N'-tetramethyl-O-(7-azabenzotriazol-1-yl)uronium hexafluorophosphate (230.0 mg, 0.0006049 mol) and N,N-diisopropylethylamine (215 µL, 0.00123 mol). The reaction mixture was stirred for 16 hours at 50° C. LC/MS was checked, and the reaction was found to be complete. EtOAc (100 mL) was added, and the mixture was washed with water (2×100 mL), Sat. NaHCO₃, H₂O, and brine. The EtOAc layer was dried with MgSO₄ and was rotovaped. The yellow residue was purified by silica-gel column to yield the pure Boc protected product.

To a solution of the Boc-protected product in 2 mL dioxane was added 2M HCl in EtOEt (15 mL) and stirred for 2 hours at room temperature to obtain the title product which was purified by HPLC. MS m/z=487.2 (M+1). ¹H NMR (400 MHz; DMSO-d6) δ 10.15(s, 1 H), 8.08(d, J=8.0 Hz, 1 H), 7.90(s, 1 H), 7.84(d, J=7.5 Hz, 1 H), 7.75-7.65(m, 2 H), 7.55-7.42(m, 2 H), 6.73(d, J=7.6 Hz, 1 H), 5.30-4.30(bs, 2H), 4.08(dd, J=13.4, 7.3 Hz, 1 H), 3.97(dd, J=13.5, 6.6 Hz, 1 H), 3.93(s, 2 H), 3.80(dd, J=11.2, 4.8 Hz, 1H), 3.73(dd, J=11.2, 5.1 Hz, 1 H), 2.67(d, J=6.0 Hz, 2 H), 2.45-2.30 (m, 1 H).

Method N

Compound 267

(R)-2-{5-[2-(4-Chloro-3-trifluoromethyl-phenyl)-propionylamino]-1-oxo-1H-isoquinolin-2-yl}-propionamide

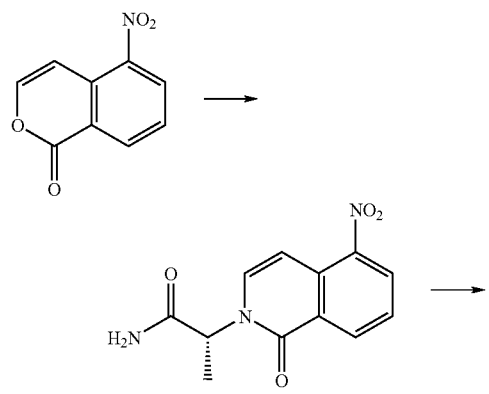

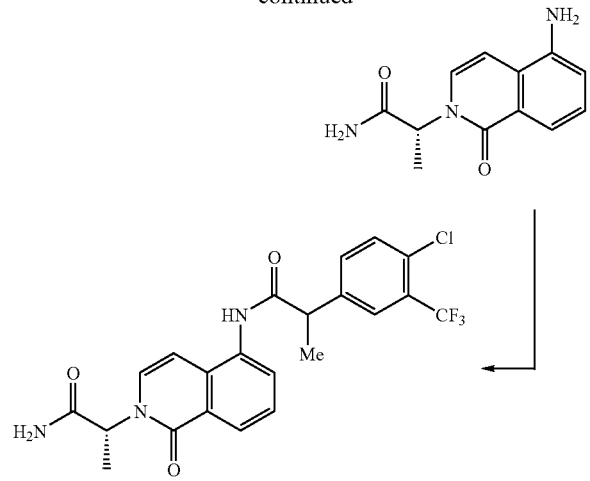

a. (R)-2-(5-Nitro-1-oxoisoquinolin-2(1H)-yl)propanamide

To a solution of 5-nitro-isochromen-1-one (2 g, 0.01 mol) in methanol (40 mL, 1 mol) was added (R)-2-aminopropanamide hydrochloride (2.0 g, 0.016 mol) and triethylamine (2.6 mL, 0.019 mol) and stirred at 52° C. for 3 hr. The product (yellow solid) precipitated out and was filtered and carried on to the next reaction. MS m/z=262.1 (M+1).

b. (R)-2-(5-Amino-1-oxoisoquinolin-2(1H)-yl)propanamide

Into a round bottom flask was combined (R)-2-(5-nitro-1-oxoisoquinolin-2(1H)-yl)propanamide (5.0 g, 0.018 mol), palladium on C (0.3 g, 0.003 mol) and methanol (200 mL, 5 mol) (about 80 mL EtOAc was added to dissolve the reactants). The reaction mixture was stirred under hydrogen balloon at room temperature for 40 min. The mixture was filtered over celite, MeOH was removed and a solid was obtained (4.02 g). MS m/z=232.4 (M+1).

c. N-(2-((R)-1-Amino-1-oxopropan-2-yl)-1-oxo-1,2-dihydroisoquinolin-5-yl)-2-(4-chloro-3-(trifluoromethyl)phenyl)propanamide To a solution of (R)-2-(5-amino-1-oxoisoquinolin-2(1H)-yl)propanamide (183.1 mg, 0.0007522 mol) in N,N-dimethylformamide (6 mL, 0.08 mol) was added 2-(4-chloro-3-(trifluoromethyl)phenyl)propanoic acid (110.0 mg, 0.0004137 mol), N,N,N',N'-tetramethyl-O-(7-azabenzotriazol-1-yl)uronium hexafluorophosphate (360 mg, 0.00095 mol) and N,N-diisopropylethylamine (305 µL, 0.00175 mol). The reaction mixture was stirred at 50° C. overnight. LC/MS was checked, and the reaction was complete. In the work up, EtOAc (100 mL) was added to the reaction solution, and the solution was washed with water (2×100 mL), Sat. NaHCO₃, H₂O, and brine. The mixture was dried with MgSO₄ and was rotovaped. The residue was purified by HPLC. The product was recovered as a solid. MS m/z=466.1 (M+1). ¹H NMR (400 MHz; DMSO-d6) δ 10.08(s, 1 H), 8.07(d, J=7.9 Hz, 1 H), 7.92(s, 1 H), 7.80-70(m, 3 H), 7.63(s, 1 H), 7.50-7.40(m, 2 H), 7.23 (s, 1 H), 6.51(dd, J=7.6, 4.8 Hz, 1 H), 5.47(q, J=7.2 Hz, 1 H), 4.16(q, J=7.0 Hz, 1 H), 1.58-1.45(m, 6H).

Method O

Compound 270

(R)-2-{5-[2-(3,4-Dichloro-phenyl)-propionylamino]-1-oxo-1H-isoquinolin-2-yl}-3-hydroxy-N-methyl-propionamide

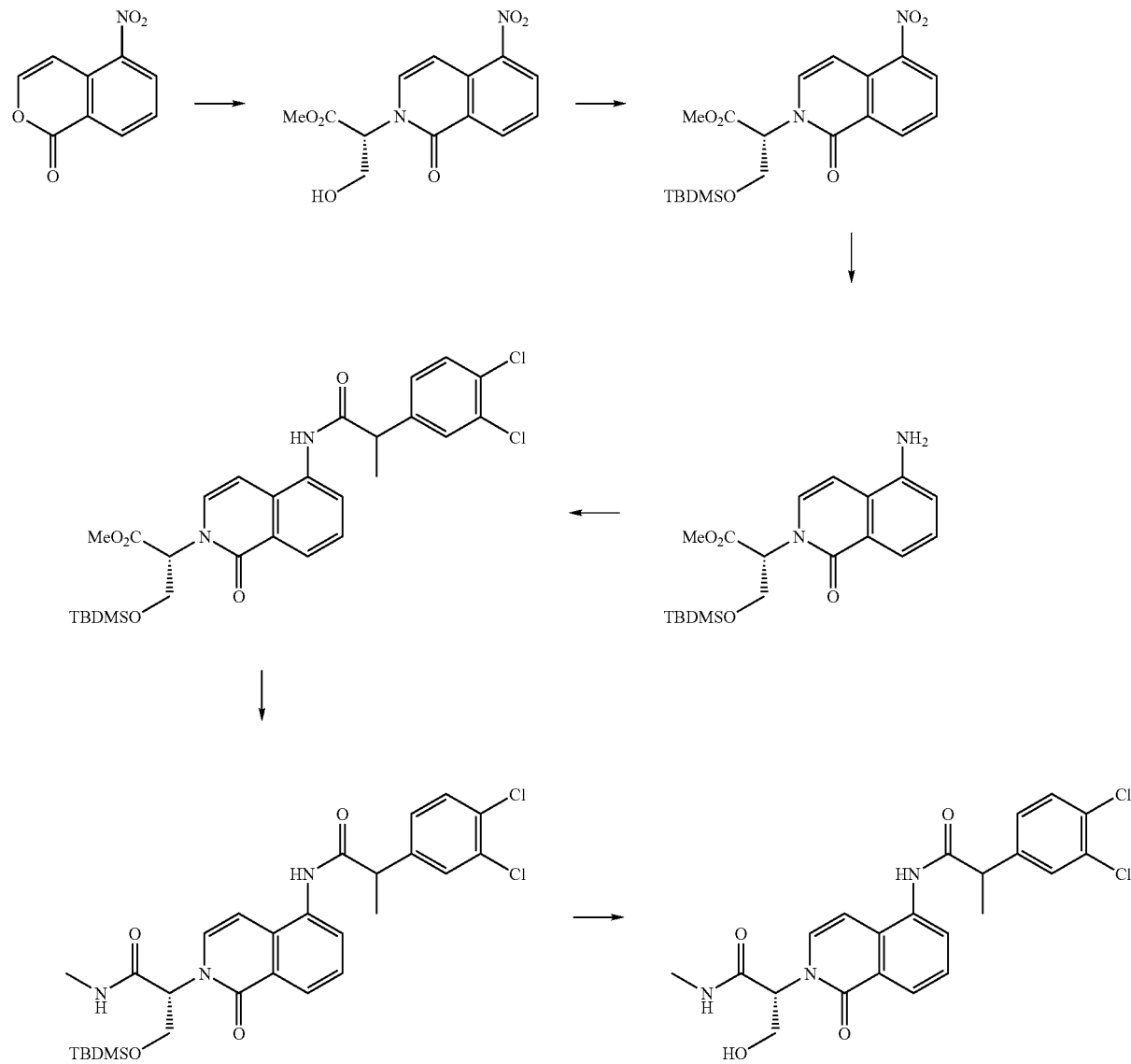

a. (R)-Methyl 3-hydroxy-2-(5-nitro-1-oxoisoquinolin-2(1H)-yl)propanoate

A round bottom flask was charged with 5-nitro-isochromen-1-one (10 g, 0.05 mol), methanol (200 mL, 5 mol), triethylamine (18 mL, 0.13 mol) and (R)-methyl 2-amino-3-hydroxypropanoate hydrochloride (9.8 g, 0.063 mol) where by the reaction became homogeneous. The reaction was then heated at 70° C. overnight. The solvent was removed and the residue purified by flash chromatography (120 g silica gel, 0-10% MeOH/DCM) to obtain the product as a yellow solid. MS m/z=293.5 (M+H).

b. (R)-Methyl 3-(tert-butyldimethylsilyloxy)-2-(5-nitro-1-oxoisoquinolin-2(1H)-yl)propanoate A round bottom flask was charged with (R)-methyl 3-hydroxy-2-(5-nitro-1-oxoisoquinolin-2(1H)-yl)propanoate (4 g, 0.01 mol), methylene chloride (40 mL, 0.5 mol) and 1H-imidazole (1.6 g, 0.023 mol) and tert-butyldimethylsilyl chloride (2.3 g, 0.015 mol) were added at 0° C. and the reaction allowed to warm to room temperature and stirred for 16 h. The reaction mixture was quenched with water and extracted with methylene chloride. Solvent was removed under reduced pressure to recover the pure product as an orange solid. MS m/z=407.5 (M+H).

c. (R)-Methyl 2-(5-amino-1-oxoisoquinolin-2(1H)-yl)-3-(tert-butyldimethylsilyloxy)propanoate A round bottom flask was charged with (R)-methyl 3-(tert-butyldimethylsilyloxy)-2-(5-nitro-1-oxoisoquinolin-2(1H)-yl)propanoate (5.5 g, 0.014 mol), methanol (100 mL, 2 mol)

and palladium, 10% weight on charcoal (0.3 g, 0.003 mol) was added and the reaction stirred under hydrogen atmosphere (1 atm) for 2 h. The reaction was filtered over celite, the solvent was removed under reduced pressure and the residue purified by flash chromatography (40 g silica gel, 0-10% MeOH/DCM) to yield the product as a yellow sticky mass. MS m/z=377.5 (M+H).

d. (2R)-Methyl 3-(tert-butyldimethylsilyloxy)-2-(5-(2-(3,4-dichlorophenyl)propanamido)-1-oxoisoquinolin-2-(1H)-yl)propanoate A round bottom flask was charged with (R)-methyl 2-(5-amino-1-oxoisoquinolin-2(1H)-yl)-3-(tert-butyldimethylsilyloxy)propanoate (300 mg, 0.0008 mol), 2-(3,4-dichlorophenyl)propanoic acid (200 mg, 0.00092 mol), N,N,N',N'-tetramethyl-O-(7-azabenzotriazol-1-yl)uronium hexafluorophosphate (600 mg, 0.002 mol), N,N-diisopropylethylamine (0.3 mL, 0.002 mol) and N,N-dimethylformamide (2 mL, 0.03 mol) and the reaction stirred at room temperature over night. The reaction did not go to completion. The solvent was removed and the residue was purified flash chromatography to obtain the product as a solid. MS m/z=578.3 (M+H).

e. (2R)-3-(tert-Butyldimethylsilyloxy)-2-(5-(2-(3,4-dichlorophenyl)propanamido)-1-oxoisoquinolin-2-(1H)-yl)-N-methylpropanamide A mixture of (2R)-methyl 3-(tert-butyldimethylsilyloxy)-2-(5-(2-(3,4-dichlorophenyl)propanamido)-1-oxoisoquinolin-2(1H)-yl)propanoate (200 mg, 0.0003 mol), 5 mL of methylamine and tetrahydrofuran (2M) was heated in a sealed tube to 70° C. overnight. The reaction was only partially complete. The solvent was removed and the residue purified by flash chromatography to obtain the product as a light yellow oil. MS m/z=577.4 (M+H).

f. (2R)-2-(5-(2-(3,4-Dichlorophenyl)propanamido)-1-oxoisoquinolin-2(1H)-yl)-3-hydroxy-N-methylpropanamide A round bottom flask was charged with (2R)-3-(tert-butyldimethylsilyloxy)-2-(5-(2-(3,4-dichlorophenyl)propanamido)-1-oxoisoquinolin-2(1H)-yl)-N-methylpropanamide (60 mg, 0.0001 mol), tetrahydrofuran (3 mL, 0.04 mol) and tetra-n-butylammonium fluoride (0.037 mL, 0.00012 mol) and the reaction stirred at room temperature for 30 minutes during which time the reaction was complete. The solvent was removed under reduced pressure and the residue purified by preparative HPLC (reverse phase) to yield the product as a white solid. MS m/z=463.3 (M+H). $^1$H NMR (400 MHz; DMSO-d6) δ 10.02 (s, 1H), 8.12 (m, 1H), 8.06 (d, J=8.26 Hz, 1H), 7.74 (t, J=7.29 Hz, 1H), 7.68 (d, J=1.82 Hz, 1H), 7.64 (d, J=8.43 Hz, 1H), 7.51 (dd, J=7.97&3.17 Hz, 1H), 7.46-7.42 (m, 2H), 6.37 (dd, J=5.04&2.04 Hz, 1H), 5.47 (t, J=6.94 Hz, 1H), 5.15-5.13 (m, 1H), 4.05 (q, J=7.24 Hz, 1H), 3.95-3.92 (m, 2H), 2.57 (d, J=4.25 Hz, 3H), 1.47 (d, J=7.22 Hz, 3H).

Method P

Compound 273

(R)-2-(4-Chloro-phenyl)-N-[(R)-2-(1-hydroxymethyl-2-methyl-propyl)-1-oxo-1, 2-dihydro-isoquinolin-5-yl]-propionamide

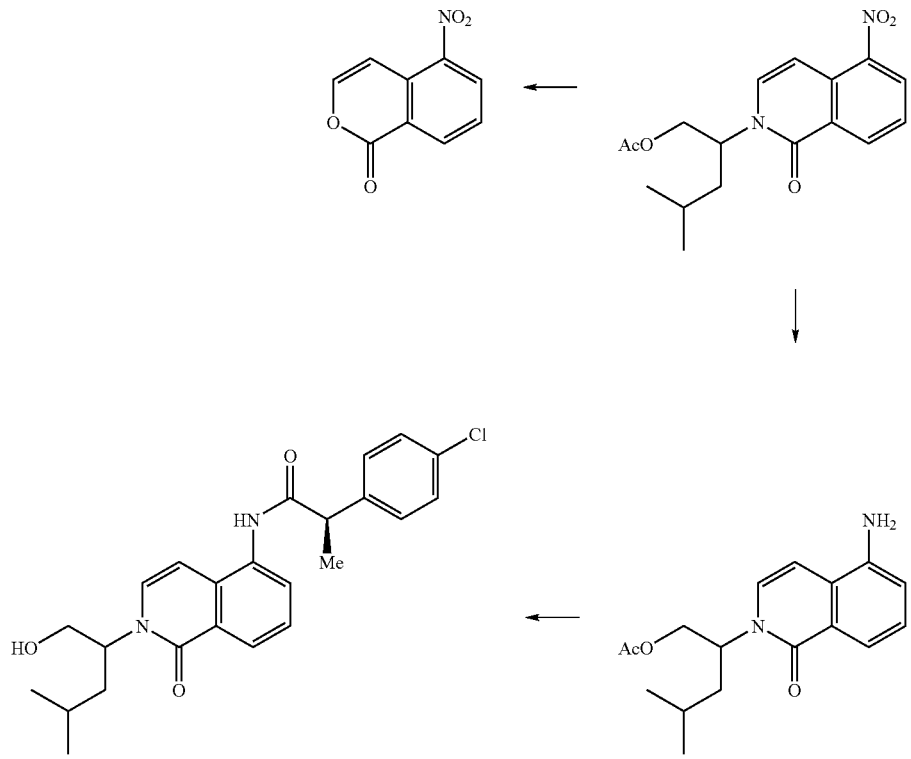

a. (R)-4-Methyl-2-(5-nitro-1-oxoisoquinolin-2(1H)-yl)pentyl acetate

Into a round bottom flask was combined 5-nitro-isochromen-1-one (5.50 g, 0.0259 mol), (R)-2-amino-4-methylpentan-1-ol (6.07 g, 0.0518 mol) and methanol (160 mL, 4.1 mol). The mixture was heated at reflux for 3 hours. The mixture was allowed to cool, reduced in vacuo and dried on high vacuum for approximately 1 hour. methylene chloride (200 mL, 3 mol) and acetyl chloride (4.1 g, 0.052 mol) were added and the mixture was heated at 50° C. for 3 hours. The resulting solution was reduced in vacuo and purified. The mixture was purified by column chromatography using a methanol:methylene chloride (0-3%) gradient. The combined pure fractions were reduced in vacuo to yield the title compound as a dark yellow solid which was taken to the next step without further purification.

b. (R)-2-(5-Amino-1-oxoisoquinolin-2(1H)-yl)-4-methylpentyl acetate

Into a round bottom flask was combined (R)-4-methyl-2-(5-nitro-1-oxoisoquinolin-2(1H)-yl)pentyl acetate (3.00 g, 0.00903 mol), palladium on C (0.1 g, 0.0009 mol), and methanol (170 mL, 4.1 mol). The reaction mixture was stirred under hydrogen at room temperature and was monitored for progress. At 40 minutes, the reaction was completed by the absence of any starting material in the LC-MS analysis. The mixture was filtered twice using a DryDisk system to remove the catalyst. Volatiles were removed under vacuum and the mixture was purified by column chromatography using an ethyl acetate:hexanes (0-100%) gradient. The combined pure fractions were reduced in vacuo to yield the title compound as a yellow oil.

c. (R)-2-(4-Chloro-phenyl)-N-[2-((R)-1-hydroxymethyl-3-methyl-butyl)-1-oxo-1,2-dihydro-isoquinolin-5-yl]-propionamide Into a 20 ml reaction vial reaction vial was combined (R)-2-(5-amino-1-oxoisoquinolin-2(1H)-yl)-4-methylpentyl acetate (0.23 g, 0.00076 mol), (R)-2-(4-chlorophenyl)propanoic acid (0.175 g, 0.000949 mol) N,N,N',N'-tetramethyl-O-(7-azabenzotriazol-1-yl)uronium hexafluorophosphate (0.58 g, 0.0015 mol) N,N-diisopropylethylamine (0.26 mL, 0.0015 mol), and N,N-dimethylformamide (4 mL, 0.06 mol). The mixture was heated at 50° C. for 3 hours and allowed to cool to room temperature. The mixture was poured on to saturated sodium bicarbonate (200 ml) and extracted with ethyl acetate (3×100 ml). The combined extracts were dried over sodium sulfate and reduced in vacuo to yield a light brown oil. The oil was taken up in methanol (10 ml) and 2N NaOH (10 ml) was added. The mixture was allowed to stir overnight. The volatiles were removed and the mixture was extracted with methylene chloride (2×20 ml). The combined extracts were reduced in vacuo and the mixture was purified by reversed phase prep HPLC using an acetonitrile: water gradient at pH 10. The combined pure fractions were reduced in vacuo to yield the title compound as yellow solid.

$^1$H-NMR (400MHz, DMSO-d6) δ 9.97 (s, 1H), 8.07 (d, 1H, J=7.93 Hz), 7.23 (d, 1H, J=7.67 Hz), 7.48-7.41 (m, 6H), 6.47 (t, 1H, J=7.57 Hz), 4.81 (m, 1H), 4.63 (br 's', 1H), 4.03 (q, 1H, J=6.95 Hz), 3.83-3.77 (m, 1H), 3.72-3.66 (m, 1H), 2.16-2.10 (m, 1H), 1.45 (dd, 3H, J=7.03 Hz), 1.03 (d, 3H, J=6.45 Hz), 0.66 (d, 3H, J=6.67 Hz).

Method Q

Compound 276

(R)-2-{5-[(S)-2-(4-Chloro-phenyl)-propionylamino]-1-oxo-1H-isoquinolin-2-yl}-3,N-dimethyl-butyramide

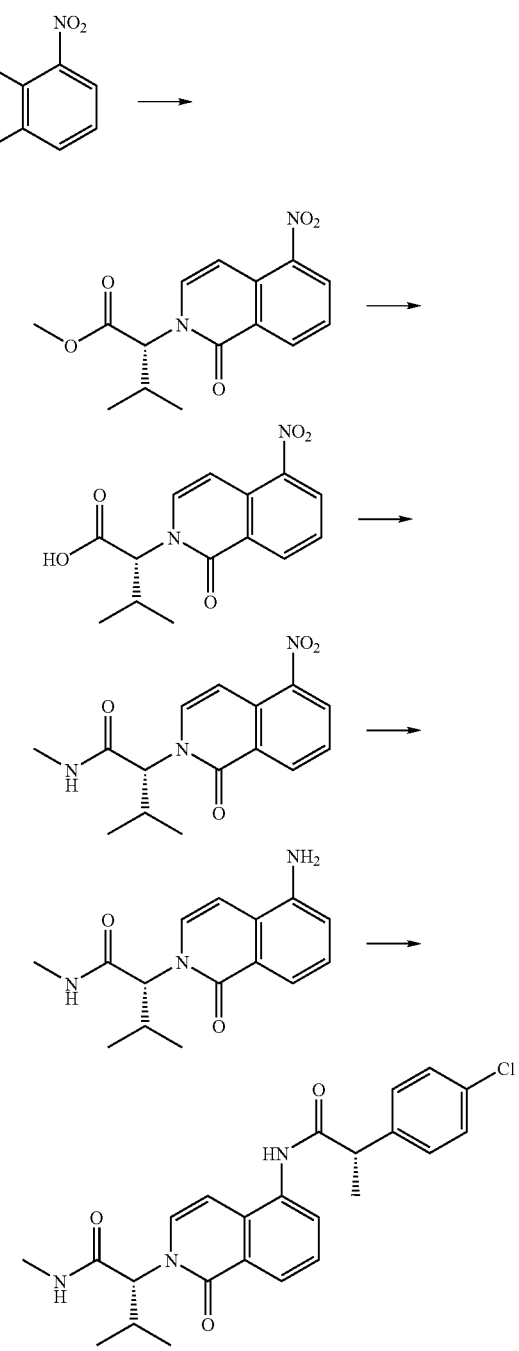

a. (R)-Methyl 3-methyl-2-(5-nitro-1-oxoisoquinolin-2(1H)-yl)butanoate

5-Nitro-isochromen-1-one (5 g, 0.03 mol) and D-Valine methyl ester hydrochloride (5 g, 0.03 mol) were refluxed in methanol (40 mL, 1 mol) with triethylamine (5 g, 0.05 mol) for 2 hours. The volatiles were removed via rotovapor, and the residue was purified via flash column chromatography (40 g of silica gel, 0-30% EtOAc/Hexane) to give a brown oil. MS m/z 305.2 (M+H).

b. (R)-3-Methyl-2-(5-nitro-1-oxoisoquinolin-2(1H)-yl)butanoic acid (R)-Methyl 3-methyl-2-(5-nitro-1-oxoisoquinolin-2(1H)-yl)butanoate (0.6 g, 0.002 mol) was stirred with lithium hydroxide (0.09 g, 0.004 mol) in tert-butyl alcohol (4 mL, 0.04 mol) and water (2 mL, 0.1 mol) at 0° C. for 3 hours. 1 N HCl was added until pH<7 and then the reaction mixture was extracted with CH$_2$Cl$_2$ (40 mL×3). The organic layers were dried over MgSO$_4$, filtered, purified via flash chromatography (12 g silica gel, 0-50% EtOAc/Hexane) to give a yellow oil. MS m/z 291.0 (M+H)+ c. (R)-3,N-Dimethyl-2-(5-nitro-1-oxo-1H-isoquinolin-2-yl)-butyramide (R)-3-Methyl-2-(5-nitro-1-oxoisoquinolin-2(1H)-yl)butanoic acid (2 g, 0.007 mol), methylamine (7 mL, 0.01 mol), 1-hydroxybenzotriazole hydrate (2 g, 0.01 mol), N-(3-dimethylaminopropyl)-N'-ethylcarbodiimide hydrochloride (3 g, 0.01 mol), N,N-diisopropylethylamine (4 g, 0.03 mol) were stirred in methylene chloride (20 mL, 0.3 mol) at room temperature for 16 hours. The reaction mixture was diluted with CH$_2$Cl$_2$ (200 mL), washed with sat. NaHCO$_3$, dried over MgSO$_4$, filtered, purified via flash chromatoraphy (40 g of silica gel, 0-50% EtOAc/Hexane) to yield a yellow solid. m/z 304.2 (M+H)+.

d. (R)-2-(5-Amino-1-oxoisoquinolin-2(1H)-yl)-N,3-dimethylbutanamide (R)-3,N-Dimethyl-2-(5-nitro-1-oxo-1H-isoquinolin-2-yl)-butyramide (1.4 g, 0.0045 mol) was stirred with palladium 10% wt. on calcium carbonate (1.4 g, 0.00068 mol) in methanol (100 mL, 2 mol) under hydrogen (balloon) over 1 h at room temperature. The catalyst was filtered, the filtrate was concentrated to dryness to give a yellow solid. MS m/z 273.9 (M+H)+.

e. (R)-2-(5-((S)-2-(4-Chlorophenyl)propanamido)-1-oxoisoquinolin-2(1H)-yl)-N,3-dimethylbutanamide (R)-2-(5-Amino-1-oxoisoquinolin-2(1H)-yl)-N,3-dimethylbutanamide (0.2 g, 0.0007 mol), (S)-2-(4-chlorophenyl) propanoic acid (0.16 g, 0.00088 mol), N,N,N',N'-tetramethyl-O-(7-azabenzotriazol-1-yl)uronium hexafluorophosphate (0.56 g, 0.0015 mol), N,N-diisopropylethylamine (0.4 g, 0.003 mol) were stirred in methylene chloride (3 mL, 0.05 mol) and N,N-dimethylformamide (1 mL, 0.01 mol) at room temperature over a weekend. The reaction mixture was diluted with CH$_2$Cl$_2$ (100 mL), washed with NaHCO$_3$ (20 mL×3), dried over Na$_2$SO$_4$, purified via flash chromatography (12 g of silica gel, 0-90% EtOAc/Hexane), and then prep. HPLC yielded a white solid. $^1$H NMRδ (CDCl$_3$) δ: 9.23 (d, J=8.1 Hz, 1H), 8.00 (t, J=7.5 Hz, 1H), 7.52-7.36 (m, 6H), 7.04 (br, 1H), 6.17 (br, 1H), 6.03-6.00 (m, 1H), 5.07 (d, J=11.4 Hz, 1H), 3.82 (q, J=7.0 Hz, 1H), 2.76 (d, J=4.8 Hz, 3H), 2.56-2.48 (m, 1H), 1.65 (dd, J=1.8, 7.1 Hz, 3H), 1.06 (d, J=6.4 Hz, 3H), 0.75 (dd, J=2.6, 6.6 Hz, 3H). MS m/z 440.0 (M+H)+.

Method R

Compound 278

(S)—N-[2-((R)-Carbamoyl-phenyl-methyl)-1-oxo-1,2-dihydro-isoquinolin-5-yl]-2-(3, 4-dichloro-phenyl)-propionamide

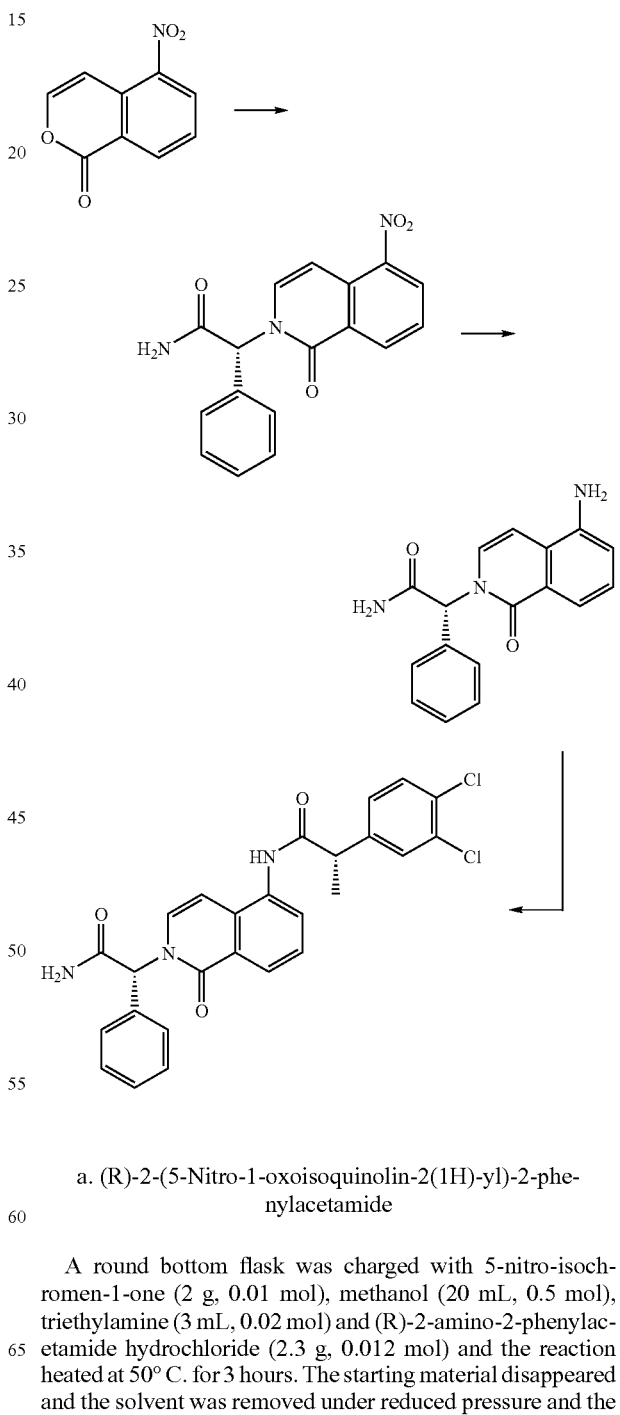

a. (R)-2-(5-Nitro-1-oxoisoquinolin-2(1H)-yl)-2-phenylacetamide

A round bottom flask was charged with 5-nitro-isochromen-1-one (2 g, 0.01 mol), methanol (20 mL, 0.5 mol), triethylamine (3 mL, 0.02 mol) and (R)-2-amino-2-phenylacetamide hydrochloride (2.3 g, 0.012 mol) and the reaction heated at 50° C. for 3 hours. The starting material disappeared and the solvent was removed under reduced pressure and the residue purified by flash chromatography (40 g silica gel, 0-10% MeOH/DCM) to yield the product as a brown solid. MS m/z=324.3 (M+H).

b. (R)-2-(5-Amino-1-oxoisoquinolin-2(1H)-yl)-2-phenylacetamide

A round bottom flask was charged with (R)-2-(5-nitro-1-oxoisoquinolin-2(1H)-yl)-2-phenylacetamide (2.3 g, 0.0071 mol), methanol (30 mL, 0.7 mol) and palladium, 10% weight on charcoal (110 mg, 0.00090 mol) was added and the flask is evacuated of air and stirred under hydrogen atmosphere (1 atm) for 1.5 hours. The reaction mixture was filtered over celite and the solvent removed under pressure. The residue was purified by flash chromatography (40 g silica gel, 0-10% MeOH/DCM) to obtain the product as a light yellow solid. MS m/z=294.5(M+H).

c. (S)—N-(2-((R)-2-Amino-2-oxo-1-phenylethyl)-1-oxo-1,2-dihydroisoquinolin-5-yl)-2-(3,4-dichlorophenyl)-propanamide A round bottom flask was charged with (R)-2-(5-amino-1-oxoisoquinolin-2(1H)-yl)-2-phenylacetamide (120 mg, 0.00041 mol), N,N-dimethylformamide (1.5 mL, 0.019 mol), N,N-diisopropylethylamine (0.1 mL, 0.0008 mol), N,N,N',N'-tetramethyl-O-(7-azabenzotriazol-1-yl)uronium hexafluorophosphate (0.3 g, 0.0008 mol) and (S)-2-(3,4-dichlorophenyl)propanoic acid (0.11 g, 0.00049 mol) and the reaction stirred at room temperature overnight. The solvent was removed and the residue purified by flash chromatography and again by preparative HPLC (reverse phase) to obtain the product as a white solid. MS m/z=495.2 (M+H). $^1$H NMR (400 MHz; DMSO-d6) δ 9.98 (s, 1H), 8.13-8.11 (d, J=8.37 Hz, 1H), 8.03 (s, 1H), 7.74-7.72 (d, J=7.90 Hz, 1H), 7.64-7.63 (d, J=2.06 Hz, 1H), 7.61-7.59 (d, J=7.94 Hz, 1H), 7.55 (s, 1H), 7.50-7.33 (m, 6H), 7.00-6.98 (d, J=8.02 Hz, 1H), 6.74 (s, 1H), 6.39-6.37 (d, J=8.02 Hz, 1H), 4.02-3.96 (q, J=7.01 Hz, 1H), 1.45-1.43 (d, J=7.55 Hz, 3H).

Method S

Compound 279

(S)—N-[2-((R)-Carbamoyl-phenyl-methyl)-1-oxo-1,2-dihydro-isoquinolin-5-yl]-2-(4-chloro-phenyl)-propionamide

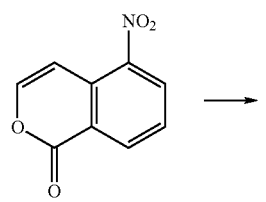

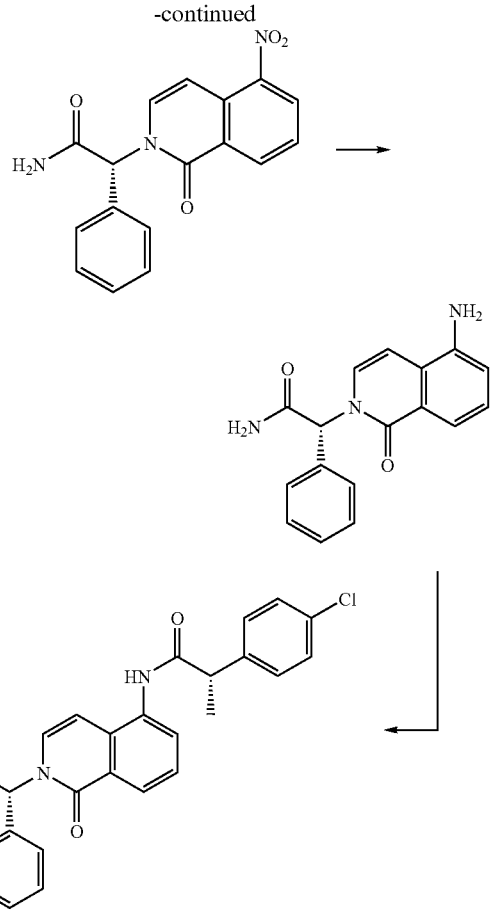

a. (R)-2-(5-Nitro-1-oxoisoquinolin-2(1H)-yl)-2-phenylacetamide

A round bottom flask was charged with 5-nitro-isochromen-1-one (2 g, 0.01 mol), methanol (20 mL, 0.5 mol), triethylamine (3 mL, 0.02 mol) and (R)-2-amino-2-phenylacetamide hydrochloride (2.3 g, 0.012 mol) and the reaction heated at 50° C. for 3 hours. The starting material disappeared and the solvent was removed under reduced pressure and the residue purified by flash chromatography (40 g silica gel, 0-10% MeOH/DCM) to obtain the product as a brown solid. MS m/z=324.3 (M+H).

b. (R)-2-(5-Amino-1-oxoisoquinolin-2(1H)-yl)-2-phenylacetamide

A round bottom flask was charged with (R)-2-(5-nitro-1-oxoisoquinolin-2(1H)-yl)-2-phenylacetamide (2.3 g, 0.0071 mol), methanol (30 mL, 0.7 mol) palladium, 10% weight on charcoal (110 mg, 0.00090 mol) was added and the flask was evacuated of air and stirred under hydrogen atmosphere (1 atm) for 1.5 h. The reaction mixture was filtered over celite and the solvent removed under pressure. The residue was purified by flash chromatography (40 g silica, 0-10% MeOH/DCM) to obtain the product as a light yellow solid. MS m/z=294.5 (M+H).

c. (S)—N-(2-((R)-2-Amino-2-oxo-1-phenylethyl)-1-oxo-1,2-dihydroisoquinolin-5-yl)-2-(4-chlorophenyl)-propanamide A mixture of (R)-2-(5-amino-1-oxoisoquinolin-2(1H)-yl)-2-phenylacetamide (120 mg, 0.00041 mol), N,N-dimethylformamide (1.5 mL, 0.019 mol), N,N-diisopropylethylamine (0.1 mL, 0.0008 mol), N,N,N',N'-tetramethyl-O-(7-azabenzotriazol-1-yl)uronium hexafluorophosphate (0.3 g, 0.0008 mol) and (S)-2-(4-chlorophenyl)propanoic acid (0.091 g, 0.00049 mol) was allowed to stir over night at room temperature. The solvent was removed and the residue purified by flash chromatography (12 g silica gel, 0-10% MeOH/DCM) and again by preparative HPLC (reverse phase) to obtain the product as an off white solid. MS m/z=460.3 (M+H). $^1$H NMR (400 MHz; DMSO-d6) δ 9.95 (s, 1H), 8.13-8.11 (d, J=7.99 Hz, 1H), 8.02 (s, 1H), 7.74-7.72 (d, J=7.60 Hz, 1H), 7.71-7.69 (d, J=8.03 Hz, 1H), 7.55 (s, 1H), 7.50-7.32 (m, 10H), 6.99-6.97 (dd, J=7.89&1.86 Hz, 1H), 6.74 (s, 1H), 6.39-6.37 (d, J=8.02 Hz, 1H), 4.00-3.94 (q, J=6.97 Hz, 1H), 1.44-1.41 (d, J=7.11 Hz, 3H).

Method T

Compound 281

(R)-2-{5-[(S)-2-(4-Chloro-phenyl)-propionylamino]-1-oxo-1H-isoquinolin-2-yl}-N-cyclopropyl-3-methyl-butyramide

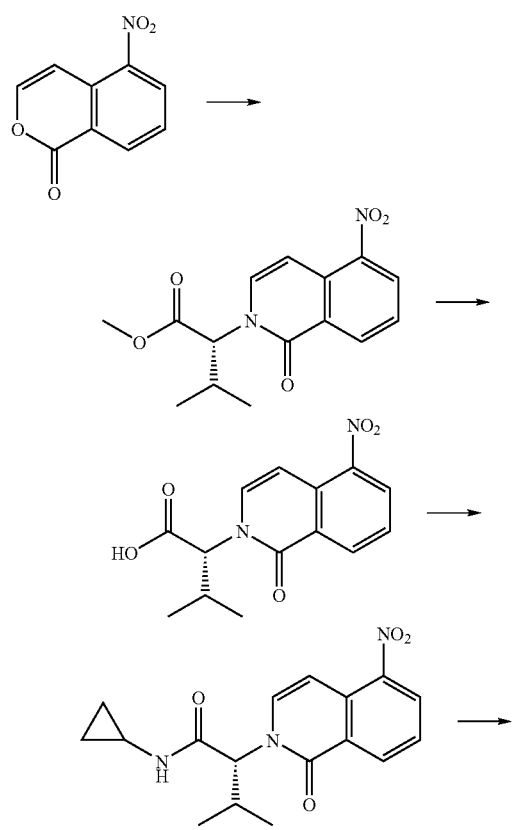

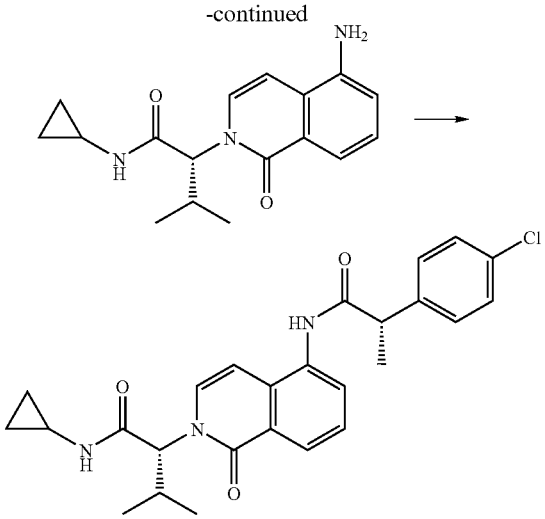

a. (R)-Methyl 3-methyl-2-(5-nitro-1-oxoisoquinolin-2(1H)-yl)butanoate 5-nitro-isochromen-1-one (5 g, 0.03 mol) and D-Valine methyl ester hydrochloride (5 g, 0.03 mol) were refluxed in methanol (40 mL, 1 mol) with triethylamine (5 g, 0.05 mol) for 2 hours. The volatiles were removed via rotovapor, and the residue was purified via flash column chromatography (40 g of silica gel, 0-30% EtOAc/Hexane) to yield a brown oil. MS m/z 305.2 (M+H)+.

b. (R)-3-Methyl-2-(5-nitro-1-oxoisoquinolin-2(1H)-yl)butanoic acid (R)-Methyl 3-methyl-2-(5-nitro-1-oxoisoquinolin-2(1H)-yl)butanoate (0.6 g, 0.002 mol) was stirred with lithium hydroxide (0.09 g, 0.004 mol) in tert-butyl alcohol (4 mL, 0.04 mol) and water (2 mL, 0.1 mol) at 0° C. for 3 hours. 1 N HCl was added until pH<7 and then reaction mixture was extracted with CH$_2$Cl$_2$ (40 mL×3). The organic layers were dried over MgSO$_4$, filtered, purified via flash chromatography (12 g of silica gel, 0-50% EtOAc/Hexane) and the product was recovered as a yellow oil. MS m/z 291.0 (M+H)+.

c. (R)-N-Cyclopropyl-3-methyl-2-(5-nitro-1-oxoisoquinolin-2(1H)-yl)butanamide (R)-3-Methyl-2-(5-nitro-1-oxoisoquinolin-2(1H)-yl)butanoic acid (4 g, 0.01 mol), 1-hydroxybenzotriazole hydrate (2.5 g, 0.016 mol), N-(3-dimethylaminopropyl)-N'-ethylcarbodiimide hydrochloride (3.2 g, 0.016 mol), cyclopropylamine (0.91 g, 0.016 mol) were stirred in methylene chloride (100 mL, 2 mol) at room temperature for 16 hours. The reaction mixture was diluted with CH$_2$Cl$_2$ (200 mL), washed with sat. NaHCO$_3$, dried over MgSO$_4$, filtered, purified via flash chromatography (40 g of silica gel, 0-50% EtOAc/Hexane) and gave a yellow solid. MS m/z 330.3 (M+H)+.

d. (R)-2-(5-Amino-1-oxoisoquinolin-2(1H)-yl)-N-cyclopropyl-3-methylbutanamide (R)-N-Cyclopropyl-3-methyl-2-(5-nitro-1-oxoisoquinolin-2(1H)-yl)butanamide (1.3 g, 0.0039 mol) was stirred with palladium 10% wt. on calcium carbonate (0.2 g, 0.0001 mol)

in methanol (60 mL, 1 mol) under hydrogen (balloon) for 1 h at room temperature. The catalyst was filtered and the filtrate was concentrated to dryness to give a brown oil. MS m/z 301.1 (M+H)+.

e. (R)-2-(5-((S)-2-(4-Chlorophenyl)propanamido)-1-oxoisoquinolin-2(1H)-yl)-N-cyclopropyl-3-methylbutanamide (R)-2-(5-Amino-1-oxoisoquinolin-2(1H)-yl)-N-cyclopropyl-3-methylbutanamide (0.2 g, 0.0007 mol), (S)-2-(4-chlorophenyl)propanoic acid (0.16 g, 0.00088 mol), N,N,N',N'-tetramethyl-O-(7-azabenzotriazol-1-yl)uronium hexafluorophosphate (0.56 g, 0.0015 mol), N,N-diisopropylethylamine (0.4 g, 0.003 mol) were stirred in N,N-dimethylformamide (3 mL, 0.04 mol) at room temperature over a weekend. The reaction mixture was diluted with CH$_2$Cl$_2$ (100 mL), washed with NaHCO$_3$ (20 mL×3), dried over Na$_2$SO$_4$, purified via flash chromatography (12 g of silica gel, 0-90% EtOAc/Hexane), and then prep. HPLC gave a white solid. $^1$H NMR δ (CDCl$_3$) δ: 8.22 (d, J=8.0 Hz, 1H), 8.00 (t, J=7.4 Hz, 1H), 7.52-7.37 (m, 6H), 7.14 (br, 1H), 6.35 (br, 1H), 6.06-6.03 (m, 1H), 5.01 (d, J=11.3 Hz, 1H), 3.82 (q, J=7.2 Hz, 1H), 2.65-2.61 (m, 1H), 2.52-2.32 (m, 1H), 1.64 (d, J=11.1 Hz, 3H), 1.06 (d, J=6.4 Hz, 3H), 0.90-0.67 (m 5H) 0.51-0.41 (m, 2H). MS m/z 465.8 (M+H)+.

Method U

Compound 284

(R)-2-{5-[(R)-2-(4-Chloro-phenyl)-propionylamino]-1-oxo-1H-isoquinolin-2-yl}-3-methyl-butyramide

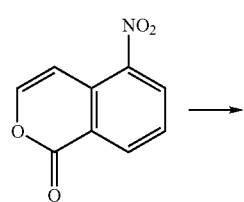

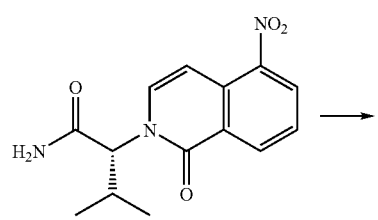

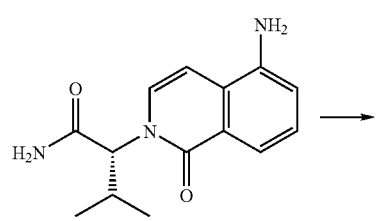

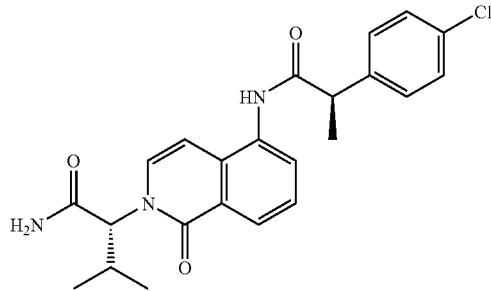

a. (R)-2-(5-Amino-1-oxoisoquinolin-2(1H)-yl)-3-methylbutanamide

5-Nitro-isochromen-1-one (2 g, 0.01 mol) and H-D-Val-NH$_2$HCl (1.9 g, 0.012 mol) were refluxed in methanol (40 mL, 1 mol) with triethylamine (5 g, 0.05 mol) for 2 hours. The volatiles were removed via rotovapor, and the residue was purified via flash column chromatography (40 g of silica gel, 0-30% EtOAc/Hexane) to give a yellow solid. MS m/z 290.2 (M+H)+.

b. (R)-2-(5-Amino-1-oxoisoquinolin-2(1H)-yl)-3-methylbutanamide (R)-2-(5-Amino-1-oxoisoquinolin-2(1H)-yl)-3-methylbutanamide (1.38 g, 0.00477 mol) was stirred with palladium 10% wt. on calcium carbonate (0.2 g, 0.0001 mol) in methanol (60 mL, 1 mol) under hydrogen (balloon) over 1 h at room temperature. The catalyst was filtered, the filtrate was concentrated to dryness to give a brown solid. m/z 260.2 (M+H)+.

c. (R)-2-(5-((R)-2-(4-Chlorophenyl)propanamido)-1-oxoisoquinolin-2(1H)-yl)-3-methylbutanamide (R)-2-(5-Amino-1-oxoisoquinolin-2(1H)-yl)-3-methylbutanamide (0.2 g, 0.0007 mol), (R)-2-(4-chlorophenyl)propanoic acid (0.16 g, 0.00088 mol) N,N,N',N'-tetramethyl-O-(7-azabenzotriazol-1-yl)uronium hexafluorophosphate (0.33 g, 0.00088 mol), N,N-diisopropylethylamine (0.4 g, 0.003 mol) were stirred in N,N-dimethylformamide (3 mL, 0.04 mol) at room temperature over a weekend. The reaction mixture was diluted with CH$_2$Cl$_2$ (100 mL), washed with NaHCO$_3$ (20 mL×3), dried over Na$_2$SO$_4$, purified via flash chromatography (12 g of silica gel, 0-90% EtOAc/Hexane) and then prep. HPLC gave a white solid. $^1$H NMR δ (CDCl$_3$) δ: 8.24 (d, J=8.1 Hz, 1H), 7.99 (t, J=7.2 Hz, 1H), 7.53-7.33 (m, 6H), 7.07 (br, 1H), 6.26 (br, 1H), 6.06-6.03 (m, 1H), 5.31 (br, 1H), 5.14 (d, J=11.4 Hz, 1H), 3.82 (q, J=7.2 Hz, 1H), 2.55-2.48 (m, 1H), 1.62 (d, J=11.1 Hz, 3H), 1.13 (d, J=6.4 Hz, 3H), 0.76 (dd, J=2.1, 6.6 Hz, 3H). MS m/z 426.2 (M+H)+.

Method V

Compound 308

(R)-2-{5-[(S)-2-(4-Chloro-phenyl)-propionylamino]-1-oxo-1H-isoquinolin-2-yl}-N-cyclopropyl-propionamide

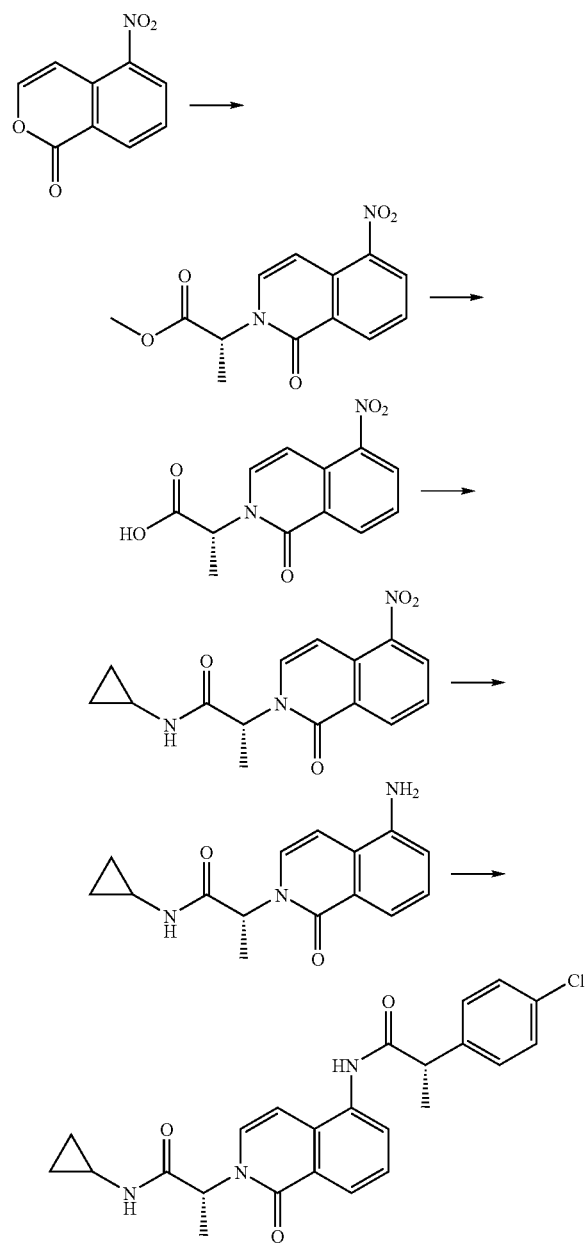

a. (R)-Methyl 2-(5-nitro-1-oxoisoquinolin-2(1H)-yl)propanoate

5-Nitro-isochromen-1-one (5 g, 0.03 mol) and D-alanine methyl ester (4 g, 0.04 mol) were refluxed in methanol (40 mL, 1 mol) for 2 hours. The volatiles were removed via rotovapor, and the residue was purified via flash column chromatography (330 g of silica gel, 0-50% EtOAc/Hexane) to give a yellow solid. MS m/z 277.2 (M+H)+.

b. (R)-2-(5-Nitro-1-oxoisoquinolin-2(1H)-yl)propanoic acid (R)-Methyl 2-(5-nitro-1-oxoisoquinolin-2(1H)-yl)propanoate (5.2 g, 0.019 mol) and lithium iodide (10 g, 0.08 mol) were refluxed in ethyl acetate (200 mL, 2 mol) for 64 hours. The solid was filtered, and the filtrate was concentrated and gave a brown solid.

MS m/z 264.1 (M+H)+.

c. (R)-N-Cyclopropyl-2-(5-nitro-1-oxoisoquinolin-2(1H)-yl)propanamide (R)-2-(5-Nitro-1-oxoisoquinolin-2(1H)-yl)propanoic acid (3 g, 0.01 mol), 1-hydroxybenzotriazole hydrate (2.1 g, 0.014 mol), N-(3-dimethylaminopropyl)-N'-ethylcarbodiimide hydrochloride (2.6 g, 0.014 mol), N,N-diisopropylethylamine (4 g, 0.03 mol) were stirred in methylene chloride (100 mL, 2 mol) at room temperature for 16 hours. The reaction mixture was diluted with $CH_2Cl_2$ (200 mL), washed with sat. $NaHCO_3$, dried over $MgSO_4$, filtered, purified via flash chromatography (40 g of silica gel, 0-50% EtOAc/Hexane) and gave a yellow solid. MS m/z 302.3 (M+H)+.

d. (R)-2-(5-Amino-1-oxoisoquinolin-2(1H)-yl)-N-cyclopropylpropanamide (R)-N-Cyclopropyl-2-(5-nitro-1-oxoisoquinolin-2(1H)-yl)propanamide (0.6 g, 0.002 mol) was stirred with palladium 10% wt. on calcium carbonate (0.1 g, 0.00005 mol) in methanol (30 mL, 0.7 mol) under hydrogen (balloon) over 1 h at room temperature. The catalyst was filtered, the filtrate was concentrated to dryness gave a brown solid. MS m/z 271.7 (M+H)+.

e. (S)-2-(4-Chlorophenyl)-N-(2-((R)-1-(cyclopropylamino)-1-oxopropan-2-yl)-1-oxo-1,2-dihydroisoquinolin-5-yl)propanamide (R)-2-(5-Amino-1-oxoisoquinolin-2(1H)-yl)-N-cyclopropylpropanamide (0.2 g, 0.0007 mol), (S)-2-(4-chlorophenyl)propanoic acid (0.16 g, 0.00088 mol), N,N,N',N'-tetramethyl-O-(7-azabenzotriazol-1-yl)uronium hexafluorophosphate (0.33 g, 0.00088 mol), N,N-diisopropylethylamine (0.4 g, 0.003 mol) were stirred in N,N-dimethylformamide (3 mL, 0.04 mol) at room temperature over a weekend. The reaction mixture was diluted with $CH_2Cl_2$ (100 mL), washed with $NaHCO_3$ (20 mL×3), dried over $Na_2SO_4$, purified via flash chromatography (12 g of silica gel, 0-90% EtOAc/Hexane) and then prep. HPLC gave a white solid. $^1H$ NMR δ ($CDCl_3$) δ: 8.23 (d, J=8.5 Hz, 1H), 7.95 (d, J=7.9 Hz, 1H), 7.52-7.39 (m, 5H), 7.22 (d, J=7.6 Hz, 1H), 7.09 (br, 1H), 6.44 (br, 1H), 6.06-6.03 (m, 1H), 5.58 (q, J=7.0 Hz, 1H), 3.83 (q, J=6.7 Hz, 1H), 2.63 (br, 1H), 1.64 (d, J=7.2 Hz, 3H), 1.56 (d, J=5.2 Hz, 3H), 0.78-0.67 (m, 2H), 0.51-0.40 (m, 2H). MS m/z 438.3 (M+H)+.

85

Method W

Compound 315

(S)—N-{2-[Carbamoyl-(4-chloro-phenyl)-methyl]-1-oxo-1,2-dihydro-isoquinolin-5-yl}-2-(4-chloro-phenyl)-propionamide

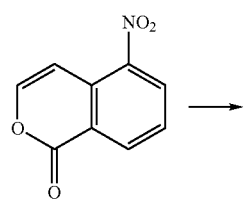

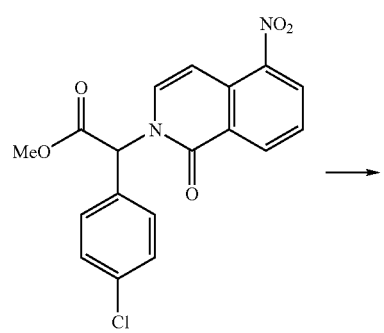

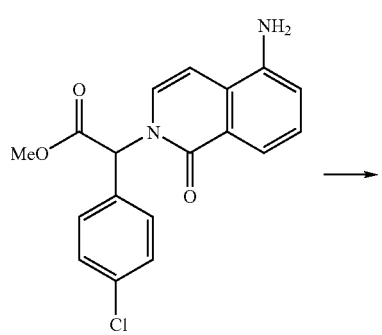

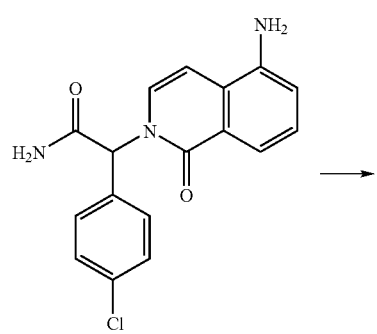

-continued

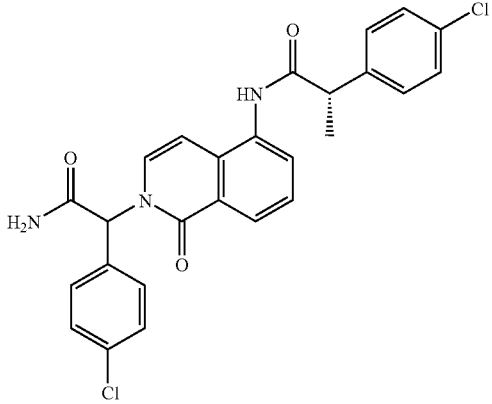

a. Methyl 2-(4-chlorophenyl)-2-(5-nitro-1-oxoiso-quinolin-2(1H)-yl)acetate

A round bottom flask was charged with 5-nitro-isochromen-1-one (2.5 g, 0.013 mol), methanol (40 mL, 1 mol), triethylamine (4 mL, 0.03 mol) and methyl 2-amino-2-(4-chlorophenyl)acetate hydrochloride (4.0 g, 0.017 mol) and the reaction heated at 50° C. for 4 hours. The solvent was removed and the residue purified by flash chromatography (40 g silica gel, 0-10% MOH/DCM) to yield the product as a yellow solid. MS m/z=373.3 (M+H).

b. Methyl 2-(5-amino-1-oxoisoquinolin-2(1H)-yl)-2-(4-chlorophenyl)acetate

A round bottom flask was charged with methyl 2-(4-chlorophenyl)-2-(5-nitro-1-oxoisoquinolin-2(1H)-yl)acetate (4.2 g, 0.011 mol) ethanol (60 mL, 1 mol) and ammonium chloride (6 g, 0.1 mol) in water (60 mL, 3 mol) was added and the reaction heated at 80° C. and iron (2 g, 0.04 mol) was added in four portions 5 minutes apart. The reaction was heated for another 1 h at that temperature and cooled to room temperature and poured into 200 ml dichloromethane and extracted. The solvent was removed to obtain the product as a light brown solid. MS m/z=343.0 (M+H).

c. 2-(5-Amino-1-oxoisoquinolin-2(1H)-yl)-2-(4-chlorophenyl)acetamide

A pressure tube was charged with methyl 2-(5-amino-1-oxoisoquinolin-2(1H)-yl)-2-(4-chlorophenyl)acetate (1.35 g, 0.00394 mol) and ammonia in methanol (7 mL, 2M solution) was added and the reaction heated at 70° C. for 16 hours. The reaction mixture was cooled to room temperature and checked for completion. The reaction was only 20% complete. Further heating of the reaction for another 6 hours did not seem to help in the progress of the reaction. The solvent was removed and the residue was purified by flash chromatography to obtain the product as a light yellow solid. MS m/z=328.2 (M+H).

d. (2S)-N-(2-(2-Amino-1-(4-chlorophenyl)-2-oxoethyl)-1-oxo-1,2-dihydroisoquinolin-5-yl)-2-(4-chlorophenyl)propanamide A round bottom flask was charged with 2-(5-amino-1-oxoisoquinolin-2(1H)-yl)-2-(4-chlorophenyl)acetamide (100 mg, 0.3 mmol), N,N-dimethylformamide (1 mL, 10 mmol), N,N-diisopropylethylamine (0.1 mL, 0.6 mmol), N,N,N',N'-tetramethyl-O-(7-azabenzotriazol-1-yl)uronium hexafluorophosphate (200 mg, 0.6 mmol) and (S)-2-(4-chlorophenyl)propanoic acid (68 mg, 0.37 mmol) and the reaction stirred at room temperature over night. The solvent was removed and the residue purified by flash chromatography (12 g silica gel, 0-10% MeOH/DCM) followed by preparative HPLC (reverse phase) to obtain the product as an off white solid. MS m/z=477.1 (M+H). $^1$H NMR (400 MHz; DMSO-d6) δ 9.97 (s, 1H), 8.12-8.10 (d, J=8.18 Hz, 1H), 8.03 (s, 1H), 7.75-7.70 (dd, J=8.18&5.63 Hz, 1H), 7.59 (s, 1H), 7.501-7.34 (m, 9H), 7.03-7.00 (d, J=8.01 Hz, 1H), 6.71 (s, 1H), 6.40-6.38 (d, J=8.27 Hz, 1H), 4.00-3.94 (q, J=6.97 Hz, 1H), 1.44-1.41 (d, J=7.11 Hz, 3H).

Method X

Compound 316

(R)-2-{6-Chloro-1-oxo-5-[2-(4-trifluoromethyl-phenyl)-acetylamino]-1H-isoquinolin-2-yl}-propionamide

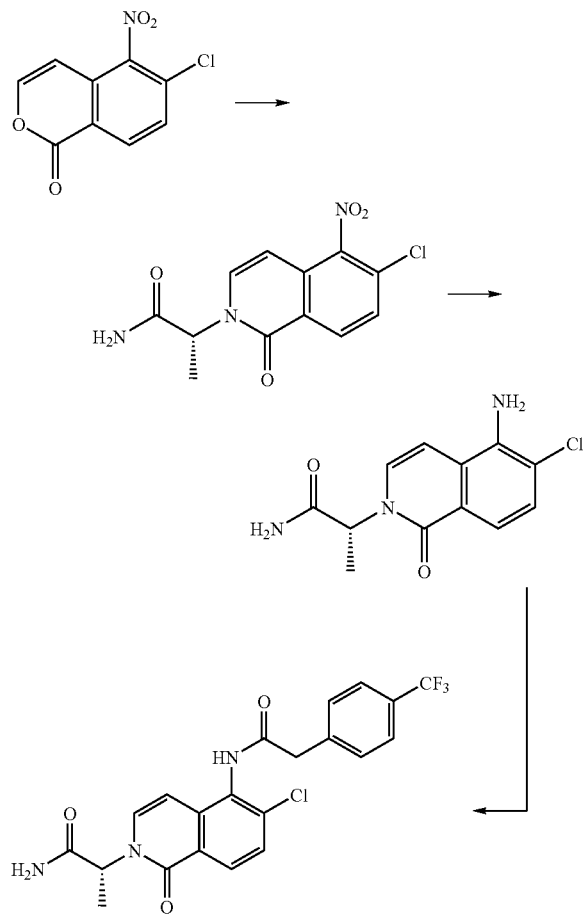

a. (R)-2-(6-Chloro-5-nitro-1-oxoisoquinolin-2(1H)-yl)propanamide

A round bottom flask was charged with 6-chloro-5-nitro-1H-isochromen-1-one (950 mg, 0.0042 mol), methanol (30 mL, 0.7 mol), triethylamine (0.64 mL, 0.0046 mol) and (R)-2-aminopropanamide hydrochloride (0.58 g, 0.0046 mol) and the reaction heated to 55° C. overnight. The reaction went to 90% completion. The solvent was removed and the residue purified by flash chromatography (40 g silica gel, 0-10% MeOH/DCM) to obtain the pure product as a light yellow solid. MS m/z=296.4 (M+H).

b. (R)-2-(5-Amino-6-chloro-1-oxoisoquinolin-2 (1H)-yl)propanamide

A round bottom flask was charged with (R)-2-(6-chloro-5-nitro-1-oxoisoquinolin-2(1H)-yl)propanamide (120 mg, 0.00040 mol), ethanol (4 mL, 0.07 mol) and ammonium chloride (200 mg, 0.004 mol) in water (4 mL, 0.2 mol) was added and the reaction heated at 85° C. and iron (90 mg, 0.002 mol) was added in two portions 5 minutes apart. The reaction was stirred at that temperature for 30 minutes and ethylacetate was added and decanted. The solvent was removed to get the product as yellow solid. MS m/z=266.2 (M+H).

c. (R)-2-(6-Chloro-1-oxo-5-(2-(4-(trifluoromethyl) phenyl)acetamido)isoquinolin-2(1H)-yl)propanamide A round bottom flask was charged with (R)-2-(5-amino-6-chloro-1-oxoisoquinolin-2(1H)-yl)propanamide (50 mg, 0.0002 mol), N,N-dimethylformamide (1 mL, 0.01 mol), N,N-diisopropylethylamine (60 µL, 0.0004 mol), N,N,N',N'-tetramethyl-O-(7-azabenzotriazol-1-yl)uronium hexafluorophosphate (100 mg, 0.0004 mol) and 2-(4-(trifluoromethyl)phenyl)acetic acid (46 mg, 0.00022 mol) and the reaction stirred at room temperature overnight. The reaction was only 60% complete. Stirring for an additional 6 hours did not improve the reaction. The solvent was removed and the residue purified by preparative HPLC (reverse phase) to obtain the product as an off white solid. MS m/z=452.2 (M+H). $^1$H NMR (400 MHz; DMF) δ 10.41 (s, 1H), 8.34 (d, J=8.71 Hz, 1H), 7.93 (d, J=8.22 Hz, 1H), 7.84 (d, J=10.96 Hz, 1H), 7.80 (t, J=9.13 Hz, 1H), 7.68 (d, J=8.53 Hz, 1H), 7.44 (bs, 1H), 6.62 (d, J=7.89 Hz, 1H), 5.67-5.61 (q, J=7.24 Hz, 1H), 4.09 (s, 2H), 1.72 (d, J=7.50 Hz, 3H).

Method Y

Compound 322

(R)-2-{5-[(S)-2-(4-Chloro-phenyl)-propionylamino]-1-oxo-1H-isoquinolin-2-yl}-propionic acid

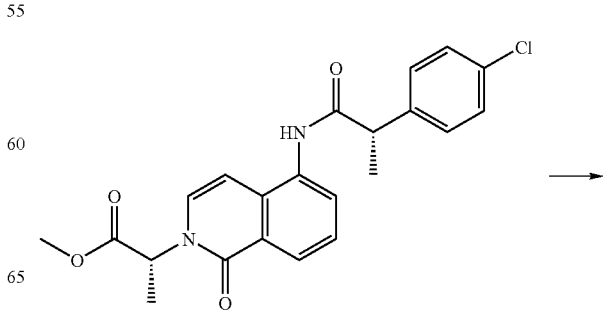

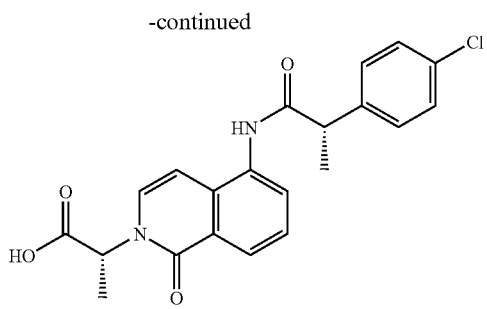

a. (R)-2-(5-((S)-2-(4-Chlorophenyl)propanamido)-1-oxoisoquinolin-2(1H)-yl)propanoic acid (R)-Methyl 2-(5-((S)-2-(4-chlorophenyl)propanamido)-1-oxoisoquinolin-2(1H)-yl)propanoate (0.23 g, 0.00050 mol) was stirred with lithium hydroxide (0.03 g, 0.001 mol) in tert-butyl alcohol (4 mL, 0.04 mol) and water (2 mL, 0.1 mol) at 0° C. for 1 hour. 1 N HCl was added until pH<7 and the reaction mixture was extracted with $CH_2Cl_2$ (40 mL×3). The organic layers were dried over $MgSO_4$, filtered, purified via flash chromatography (12 g of silica gel, 0-50% EtOAc/Hexane) and gave a light yellow solid. $^1H$ NMR δ ($CDCl_3$) δ: 8.05-8.01 (m, 1H), 7.89-7.62 (m, 2H), 7.38-7.29 (m, 5H), 6.89-6.80 (m, 1H), 6.04-5.94 (m, 1H), 5348-5.39 (m, 1H), 3.86 (d, J=6.6 Hz, 1H), 3.03-2.88 (m, 6H). MS m/z 399.0 (M+H)+.

Method Z

Compound 323

(R)-2-{5-[(S)-2-(4-Chloro-phenyl)-propionylamino]-1-oxo-1H-isoquinolin-2-yl}-3-methyl-butyric acid

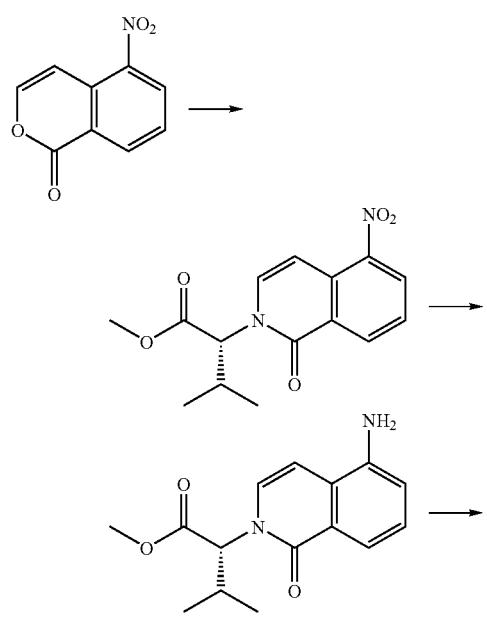

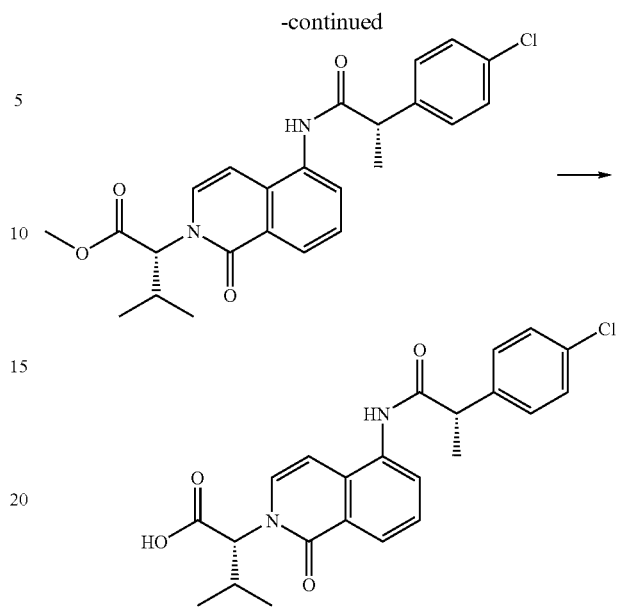

a. (R)-Methyl 3-methyl-2-(5-nitro-1-oxoisoquinolin-2(1H)-yl)butanoate

5-Nitro-isochromen-1-one (5 g, 0.03 mol) and D-Valine methyl ester hydrochloride (5 g, 0.03 mol) were refluxed in methanol (40 mL, 1 mol) with triethylamine (5 g, 0.05 mol) for 2 hours. The volatiles were removed via rotovapor, and the residue was purified via flash column chromatography (40 g silica gel, 0-30% EtOAc/Hexane) and gave a brown oil. MS m/z 305.2 (M+H)+.

b. (R)-Methyl 2-(5-amino-1-oxoisoquinolin-2(1H)-yl)-3-methylbutanoate (R)-methyl 3-methyl-2-(5-nitro-1-oxoisoquinolin-2(1H)-yl)butanoate (2.8 g, 0.0091 mol) was stirred with palladium 10% wt. on calcium carbonate (0.23 g, 0.00011 mol) in methanol (40 mL, 1 mol) under hydrogen (balloon) over 1 h at room temperature. The catalyst was filtered, the filtrate was concentrated to dryness and yielded a yellow oil. MS m/z 274.8 (M+H)+.

c. (R)-Methyl 2-(5-((S)-2-(4-chlorophenyl)propanamido)-1-oxoisoquinolin-2(1H)-yl)-3-methylbutanoate (R)-Methyl 2-(5-amino-1-oxoisoquinolin-2(1H)-yl)-3-methylbutanoate (0.3 g, 0.001 mol), (S)-2-(4-chlorophenyl)propanoic acid (0.4 g, 0.002 mol), N,N,N',N'-tetramethyl-O-(7-azabenzotriazol-1-yl)uronium hexafluorophosphate (0.8 g, 0.002 mol), N,N-diisopropylethylamine (0.6 g, 0.004 mol) were stirred in N,N-dimethylformamide (3 mL, 0.04 mol) at room temperature over a weekend. The reaction mixture was diluted with $CH_2Cl_2$ (100 mL), washed with $NaHCO_3$ (20 mL×3), dried over $Na_2SO_4$, purified via flash chromatography (12 g of silica gel, 0-90% EtOAc/Hexane) and then prep. HPLC gave a light yellow oil. MS m/z 441.3 (M+H)+.

d. (R)-2-(5-((S)-2-(4-Chlorophenyl)propanamido)-1-oxoisoquinolin-2(1H)-yl)-3-methylbutanoic acid (R)-methyl 2-(5-((S)-2-(4-chlorophenyl)propanamido)-1-oxoisoquinolin-2(1H)-yl)-3-methylbutanoate (0.43 g, 0.00088 mol) was stirred with lithium hydroxide (0.05 g, 0.002 mol) in tert-butyl alcohol (6 mL, 0.06 mol) and water (3 mL, 0.2 mol) at 0° C. for 1 hour. 1 N HCl was added until pH<7 and then reaction mixture was extracted with $CH_2Cl_2$ (40 mL×3). The organic layers were dried over $MgSO_4$, filtered, purified via flash chromatography (12 g of silica gel, 0-50% EtOAc/Hexane) and gave a light yellow solid. $^1H$ NMR δ ($CDCl_3$) δ: 8.17 (br, 1H), 7.86 (br, 1H), 7.52-7.29 (m, 6H), 7.03 (br, 1H), 6.09-6.05 (m, 1H), 5.00-4.87 (m, 1H), 3.87-3.82 (m, 1H), 2.70-2.60 (m, 1H), 1.64 (d, J=7.0 Hz, 3H), 1.14 (d, J=6.5 Hz, 3H), 0.78 (d, J=6.4 Hz, 3H). MS m/z 427.1 (M+H)+.

Method AA1

Compound 333

2-(3,4-Dichloro-phenyl)-N-[2-((R)-2-hydroxy-1-methyl-ethyl)-1-oxo-1,2-dihydro-isoquinolin-5-yl]-acetamide lent of N,N-Diisopropylamine were added and the reaction was left to stir overnight at room temperature. After analysis showed that less than 50% of the starting material was consumed, 4 more equivalents of acetyl chloride and 2 equivalents of N,N-diisopropylethylamine were added and the reaction temperature raised to 40° C. The reaction was allowed to stir for 4 more hours. LC-MS analysis showed the presence of approximately 5% of unreacted material. The flask was cooled to room temperature and reduced in vacuo. The dark yellow residue was taken up in 300 ml ethyl acetate and washed 3 times with 50 ml water. Saturated sodium chloride solution was added to remove any emulsion formed between the layers. Most of the desired product stayed in the organic layer although a minimal amount was in the aqueous layer. The organic layer was dried with sodium sulfate and reduced in vacuo to produce a brownish-yellow oil which was purified via flash chromatography using a 120 g normal phase silica column and an Ethyl acetate:Hexane gradient (0-60%). The pure fractions were collected and volatiles were removed under reduced pressure to give a yellow oil. M+1=291.0 $^1H$-NMR (400 MHz, DMSO-d6) δ 8.63 (dq, 1H), 8.48 (dd, 1H), 7.83 (d, 1H, J=8.02 Hz), 7.69 (t, 1H, J=8.02 Hz), 7.09 (dd, 1H, J=8.02 Hz), 5.32-5.22 (m, 1H), 4.33 (d, 2H, J=6.26 Hz), 1.93 (s, 3H), 1.40 (d, 3H, J=7.11 Hz).

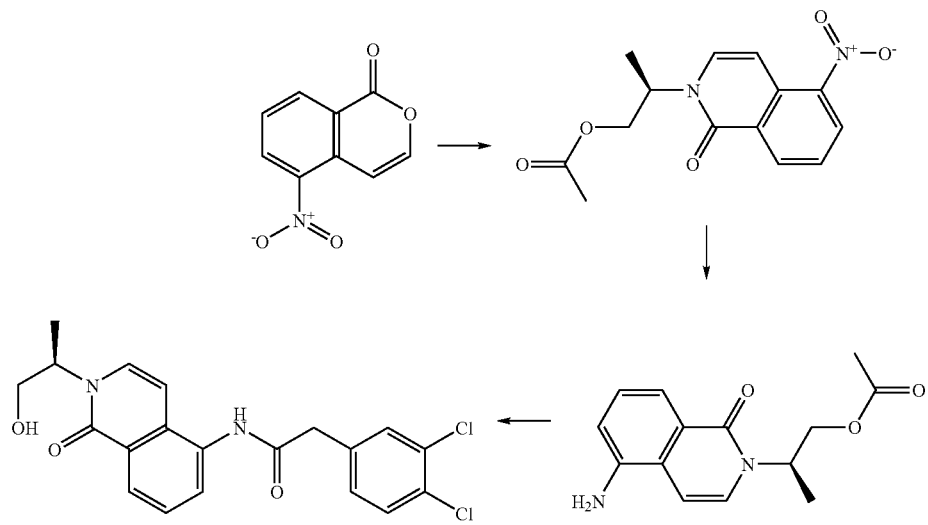

a. (R)-2-(5-Nitro-1-oxoisoquinolin-2(1H)-yl)propyl acetate

A mixture of 5-nitro-isochromen-1-one (6.81 g, 0.0320 mol), (2R)-2-Aminopropan-1-ol (5.0 mL, 0.064 mol) and methanol (210 mL, 5.1 mol) was heated at reflux for 1 hour. 10 ml of Triethylamine was added and the reaction temperature was lowered to 60° C. and stirred at this temperature for 3 hours. LC-MS analysis showed the starting material was consumed. The reaction mixture was reduced in vacuo and the reaction flask was placed under high vacuum for 1 hour. The black residue was taken up in a mixture of methylene chloride (200 mL, 2 mol) and N,N-dimethylformamide (7.6 mL, 0.098 mol). Acetyl chloride (9.1 mL, 0.13 mol) and N,N-diisopropylethylamine (14 mL, 0.078 mol) were added and the reaction was allowed to stir at 40° C. for 5 hours. LC-MS analysis showed that the reaction did not go to completion. Two equivalents of acetyl chloride and 1 equivab. (R)-2-(5-Amino-1-oxoisoquinolin-2(1H)-yl)propyl acetate To a suspension of (R)-2-(5-nitro-1-oxoisoquinolin-2 (1H)-yl)propyl acetate (5.34 g, 0.0184 mol) in ethanol (100 mL, 2 mol) was added ammonium chloride (9.840 g, 0.1840 mol) in water (100 mL, 6 mol). The reaction heated at 85° C. and iron (4.11 g, 0.0736 mol) was added in four portions 3 minutes apart. The reaction started turning dark and became completely brown. After 2 hours, the flask was removed from the oil bath and 150 ml of ethyl acetate was added in the flask. The organic layer was decanted and the aqueous layer was extracted again with ethyl acetate. The combined organic layers were dried over sodium sulfate and concentrated under reduced pressure to give a bright yellow oil.

M+1=261.1 ¹H-NMR (400 MHz, DMSO-d6) δ 7.43 (d, 1H, J=7.81 Hz), 7.38 (d, 1H, J=7.82 Hz), 7.16 (t, 1H, J=7.85 Hz), 6.85 (dd, 1H, J=7.92 Hz), 7.78 (d, 1H, J=7.80 Hz), 5.67 (s, 2H), 5.30-5.21 (m, 1H), 4.29 (d, 2H, J=6.50 Hz), 1.91 (s, 3H), 1.34 (d, 3H, J=7.08 Hz).

c. (R)-2-(3,4-Dichlorophenyl)-N-(2-(1-hydroxypropan-2-yl)-1-oxo-1,2-dihydroisoquinolin-5-yl)acetamide To a solution of (R)-2-(5-amino-1-oxoisoquinolin-2(1H)-yl)propyl acetate (100 mg, 0.0004 mol) in methylene chloride (2 mL, 0.03 mol) was added 3,4-dichlorophenyl acetic acid (120 mg, 0.00058 mol), N,N,N',N'-tetramethyl-O-(7-azabenzotriazol-1-yl)uronium hexafluorophosphate (360 mg, 0.00096 mol) and N,N-diisopropylethylamine (300 μL, 0.002 mol). The reaction mixture was stirred overnight at room temperature. The mixture was then purified by column chromatography using an ethyl acetate:hexane (0-40%) gradient. The combined pure fractions were reduced in vacuo and taken up in methanol (3 mL, 0.07 mol), potassium carbonate (200 mg, 0.001 mol) and a few drops of water were added, and the mixture was stirred at room temperature for one hour. This was followed by purification using column chromatography (ethyl acetate:hexane, 0-100%) thus producing the title compound.

¹H-NMR (400 MHz, DMSO-d6) δ 10.06 (s, 1H), 8.08 (d, 1H, J=8.03 Hz), 7.79 (d, 1H, J=7.84 Hz), 7.65 (d, 1H, J=1.87 Hz), 7.62 (d, 1H, J=8.21 Hz), 7.52 (d, 1H, J=7.82 Hz), 7.44 (t, 1H, J=7.95 Hz), 7.38 (dd, 1H, J=8.34 Hz), 6.64 (d, 1H, J=7.89 Hz), 5.08-5.00 (m, 1H), 4.93 (t, 1H, J=5.41 Hz), 3.81 (s, 2H), 3.69-3.57 (m, 2H), 1.29 (d, 3H, J=7.00 Hz).

Method AA2

Compound 330

2-(4-Chloro-3-fluorophenyl)-N-[2-((R)-2-hydroxy-1-methyl-ethyl)-1-oxo-1, 2-dihydro-isoquinolin-5-yl]-acetamide

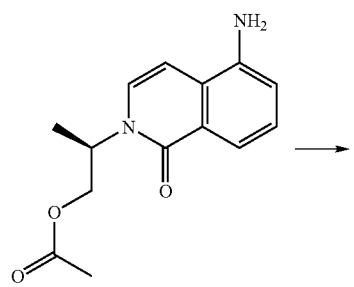

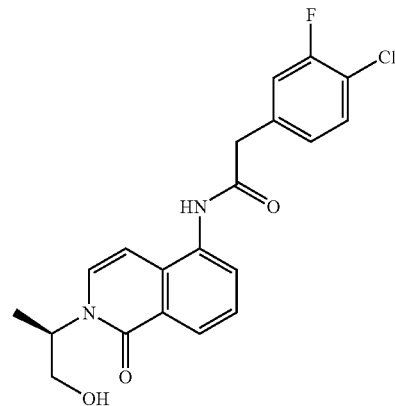

a. (R)-2-(4-Chloro-3-fluorophenyl)-N-(2-(1-hydroxypropan-2-yl)-1-oxo-1,2-dihydroisoquinolin-5-yl) acetamide To a solution of (R)-2-(5-amino-1-oxoisoquinolin-2(1H)-yl)propyl acetate (800 mg, 0.003 mol) in methylene chloride (20 mL, 0.2 mol) was added 2-(4-chloro-3-fluorophenyl)acetic acid (870 mg, 0.0046 mol), N,N,N',N'-tetramethyl-O-(7-azabenzotriazol-1-yl)uronium hexafluorophosphate (2900 mg, 0.0077 mol) and N,N-diisopropylethylamine (3000 μL, 0.02 mol). The reaction mixture was stirred overnight at room temperature and then concentrated. methanol (20 mL, 0.6 mol) and potassium carbonate (1000 mg, 0.009 mol) were added and the mixture was allowed to stir at room temperature for one hour. Volatiles were removed and the residue was taken up in methylene chloride (100 ml). The mixture was washed with aqueous NaHCO₃ (150 ml), brine (150 ml) and water (200 ml). The layers were separated and the organics dried over Na₂SO₄ and concentrated under reduced pressure. The mixture was then purified by flash chromatography (Ethyl acetate: Hexanes, 0-40%). The combined pure fractions were reduced in vacuo to yield the title compound as a yellow solid. M+1=389.1

¹H-NMR (400 MHz, DMSO-d6) δ 10.06 (s, 1H), 8.08 (d, 1H, J=7.98 Hz), 7.79 (dd, 1H, J=7.94 Hz), 7.57 (t, 1H, J=8.15 Hz), 7.52 (d, 1H, J=7.85 Hz), 7.46-7.41 (m, 2H), 7.25 (dd, 1H, J=8.25 Hz), 6.64 (d, 1H), 5.08-5.00 (m, 1H), 4.93 (t, 1H, J=5.38 Hz), 3.82 (s, 2H), 3.69-3.57 (m, 2H), 1.29 (d, 3H, J=7.04 Hz).

Method AB

Compound 344

(R)-2-{6-Methoxy-1-oxo-5-[2-(4-trifluoromethyl-phenyl)-acetylamino]-1H-isoquinolin-2-yl}-propionamide

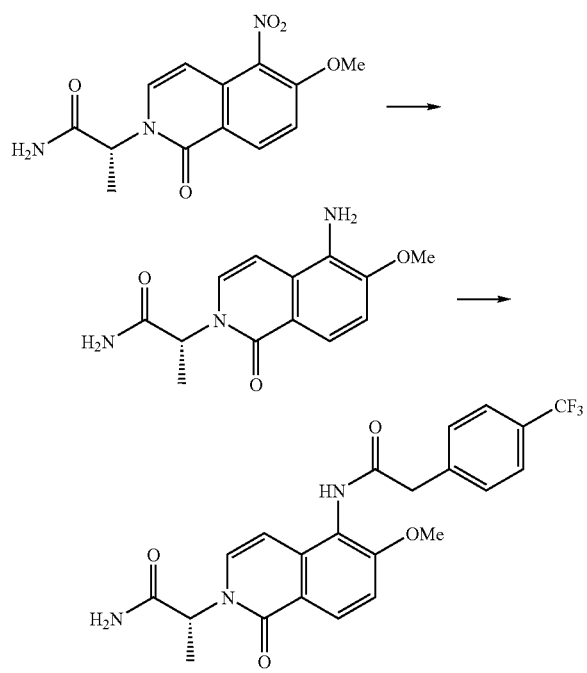

a. (R)-2-(5-Amino-6-methoxy-1-oxoisoquinolin-2(1H)-yl)propanamide

A mixture of (R)-2-(6-methoxy-5-nitro-1-oxoisoquinolin-2(1H)-yl)propanamide (200 mg, 0.0007 mol), methanol (20 mL, 0.5 mol) and palladium, 10% weight on charcoal (21 mg, 0.00017 mol) was stirred under hydrogen (1 atm) for 3 h. The reaction mixture was filtered over celite and the solvent removed to obtain the product as a brown solid. MS m/z=263.3 (M+H).

b. (R)-2-(6-Methoxy-1-oxo-5-(2-(4-(trifluoromethyl)phenyl)acetamido)isoquinolin-2(1H)-yl)propanamide A mixture of (R)-2-(5-amino-6-methoxy-1-oxoisoquinolin-2(1H)-yl)propanamide (98.34 mg, 0.0003764 mol), 2-(4-(trifluoromethyl)phenyl)acetic acid (115.2 mg, 0.0005646 mol), N,N-diisopropylethylamine (163.9 μL, 0.0009409 mol), N,N,N',N'-tetramethyl-O-(7-azabenzotriazol-1-yl)uronium hexafluorophosphate (357.8 mg, 0.0009409 mol) and N,N-dimethylformamide (2 mL, 0.02 mol) was stirred at room temperature overnight. The reaction was only 40% complete. The solvent was removed and the residue purified by preparative HPLC (reverse phase) to obtain the pure product as a light yellow solid. MS m/z=448.3 (M+H). $^1$H NMR (400 MHz; DMSO-d6) δ 9.71 (s, 1H), 8.17 (d, J=8.87 Hz, 1H), 7.74 (d, J=7.76 Hz, 2H), 7.62 (d, J=7.76 Hz, 2H), 7.34-7.29 (m, 2H), 7.20 (s, 1H), 6.28 (d, J=8.48 Hz, 1H), 5.45 (q, J=7.07 Hz, 1H), 3.90 (s, 3H), 3.84 (s, 2H), 1.49 (d, J=7.39 Hz, 3H).

Method AC

Compound 345

(S)-2-{6-Chloro-1-oxo-5-[2-(4-trifluoromethyl-phenyl)-acetylamino]-1H-isoquinolin-2-yl}-propionamide

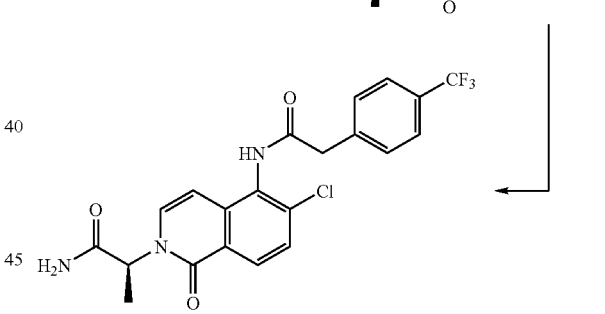

a. (S)-2-(6-Chloro-5-nitro-1-oxoisoquinolin-2(1H)-yl)propanamide

A mixture of 6-chloro-5-nitro-1H-isochromen-1-one (230 mg, 0.00102 mol), (S)-2-aminopropanamide hydrochloride (127 mg, 0.00102 mol), triethylamine (142 μL, 0.00102 mol) and methanol (20 mL, 0.5 mol) was stirred at 60° C. for 3 hours. The solvent was removed and the residue purified by flash chromatography to obtain the product as a yellow solid. MS m/z=262.3 (M+H).

b. (S)-2-(5-Amino-6-chloro-1-oxoisoquinolin-2(1H)-yl)propanamide

A mixture of (S)-2-(6-chloro-5-nitro-1-oxoisoquinolin-2(1H)-yl)propanamide (201 mg, 0.000679 mol), ethanol (10 mL, 0.2 mol), ammonium chloride (363.03 mg, 0.0067868 mol) and water (10 mL, 0.6 mol) was heated at 85° C. and iron (152 mg, 0.00271 mol) was added in three portions 2 minutes apart. The reaction was stirred at that temperature for 1 hour and poured into dichloromethane (150 mL) and the layers were separated. The organic layer was washed with brine, dried over sodium sulfate and the solvent removed under reduced pressure to obtain the pure product as a light yellow solid. MS m/z=232.5 (M+H).

c. (S)-2-(6-Chloro-1-oxo-5-(2-(4-(trifluoromethyl) phenyl)acetamido)isoquinolin-2(1H)-yl)propanamide A mixture of (S)-2-(5-amino-6-chloro-1-oxoisoquinolin-2 (1H)-yl)propanamide (100.0 mg, 0.0003764 mol), 2-(4-(trifluoromethyl)phenyl)acetic acid (115.2 mg, 0.0005646 mol), N,N-diisopropylethylamine (163.9 µL, 0.0009409 mol), N,N,N',N'-tetramethyl-O-(7-azabenzotriazol-1-yl)uronium hexafluorophosphate (357.8 mg, 0.0009409 mol) and N,N-dimethylfonnamide (2 mL, 0.02 mol) was stirred at 60° C. for 3 days. The reaction was only about 40% complete. The solvent was removed and the residue purified by preparative HPLC (reverse phase) to obtain the product as light yellow solid. MS m/z=452.1 (M+H). $^1$H NMR (400 MHz; DMSO-d6) δ10.21 (s, 1H), 8.15 (d, J=8.68 Hz, 1H), 7.74 (d, J=7.76 Hz, 2H), 7.66-7.58 (m, 4H), 7.49 (d, J=7.95 Hz, 1H), 7.25 (s, 1H), 6.43 (d, J=7.50 Hz, 1H), 5.47-5.42 (q, J=7.07 Hz, 1H), 3.90 (s, 2H), 1.53 (d, J=7.39 Hz, 3H).

Method AD

Compound 369

2-(4-Chloro-3-trifluoromethyl-phenyl)-N-[2-(2-hydroxy-1,1-dimethyl-ethyl)-1-oxo-1, 2-dihydro-isoquinolin-5-yl]-acetamide in a mixture of methylene chloride (20 mL, 0.3 mol) and N,N-dimethylformamide (0.85 mL, 0.011 mol). Acetyl chloride (1.0 mL, 0.014 mol) and N,N-diisopropylethylamine (1.5 mL, 0.0088 mol) were added. The mixture was allowed to stir at 40° C. for 5 hours. The flask was cooled to room temperature and solvents were removed in vacuo. The residue was taken up in Ethyl acetate and washed twice with aqueous NaHCO$_3$. The organic layer was dried with Sodium sulfate and concentrated under reduced pressure. The residue was purified by column chromatography using an Ethyl acetate: Hexane (0-100%) gradient to obtain the desired product. M+1=263.2 b. 2-(5-Amino-1-oxoisoquinolin-2(1H)-yl)-2-methylpropyl acetate

To a suspension of 2-methyl-2-(5-nitro-1-oxoisoquinolin-2(1H)-yl)propyl acetate (1.28 g, 0.00441 mol) in Ethanol (20 mL, 0.4 mol) was added ammonium chloride (2.359 g, 0.04410 mol) in water (20 mL) and the reaction heated to 85° C. and iron (0.985 g, 0.0176 mol) was added in four portions 3 minutes apart. The reaction started turning dark and became completely brown. The reaction was heated for 2 hours and the reaction was removed from the oil bath. 150 ml of dichloromethane was added in the flask and the mixture was transferred to an Erlenmeyer flask, leaving most of the iron in the reaction flask. The layers were separated and the organic layer was washed twice with brine. The combined organic layers were dried over sodium sulfate and the solvent removed under reduced pressure to give a bright yellow oil.

M+1=275.0 $^1$H-NMR (400 MHz, DMSO-d6) δ 7.83 (d, 1H, J=8.13 Hz), 7.26-7.21 (m, 2H), 6.94 (dd, 1H, J=7.71 Hz), 6.42 (d, 1H, J=8.11 Hz), 4.73 (s, 2H), 4.30 (bs, 2H), 1.95 (s, 3H), 1.70 (s, 6H).

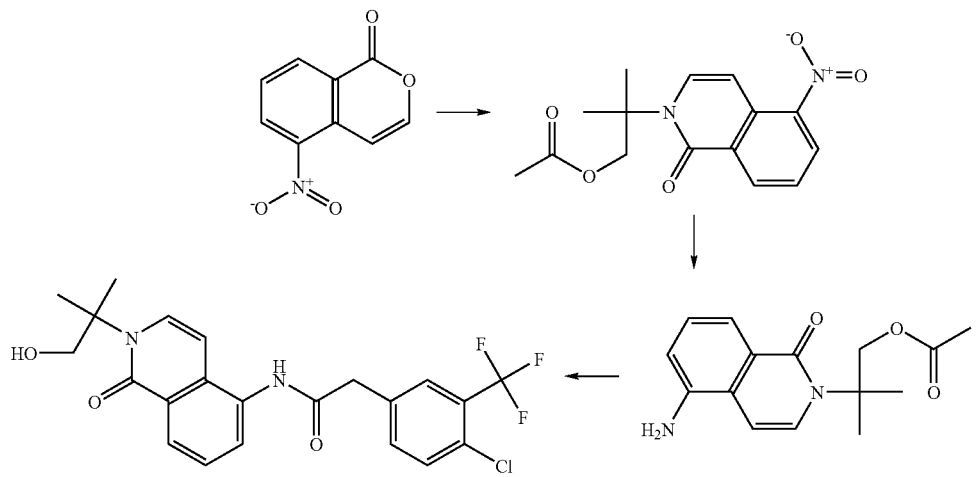

a. 2-Methyl-2-(5-nitro-1-oxoisoquinolin-2(1H)-yl) propyl acetate

A mixture of 5-nitro-isochromen-1-one (1.02 g, 0.00480 mol), 2-amino-2-methyl-1-propanol (0.921 mL, 0.00960 mol) and methanol (23 mL, 0.58 mol) and triethylamine (2 mL, 0.01 mol) was stirred overnight at 80° C. LC-MS analysis showed the formation of the desired product. Volatiles were removed under reduced pressure and the residue was taken up c. 2-(4-Chloro-3-(trifluoromethyl)phenyl)-N-(2-(1-hydroxy-2-methylpropan-2-yl)-1-oxo-1,2-dihydroisoquinolin-5-yl)acetamide To a solution of 2-(5-amino-1-oxoisoquinolin-2(1H)-yl)-2-methylpropyl acetate (90.0 mg, 0.000328 mol) in methylene chloride (2 mL, 0.03 mol) were added 2-(4-chloro-3-(trifluoromethyl)phenyl)acetic acid (120 mg, 0.00049 mol), N,N,N',N'-tetramethyl-O-(7-azabenzotriazol-1-yl)uronium hexafluorophosphate (310 mg, 0.00082 mol) and N,N-diisopropylethylamine (300 μL, 0.002 mol). The reaction mixture was stirred overnight at room temperature. The mixture was then purified by HPLC. The combined pure fractions were concentrated in vacuo and taken up in methanol (2 mL, 0.06 mol). Potassium carbonate (136 mg, 0.000984 mol) was added and the mixture was stirred at room temperature for one hour. This was followed by purification using HPLC thus producing the title compound. $^1$H-NMR (400 MHz, DMSO-d6) δ 10.06 (s, 1H), 8.06 (d, 1H, J=8.09 Hz), 7.88 (d, 1H, J=1.06 Hz), 7.77 (dd, 1H, J=7.79 Hz), 7.73-7.67 (m, 2H), 7.51 (d, 1H, J=8.16 Hz), 7.40 (t, 1H, J=7.91 Hz), 6.56 (d, 1H, J=8.14 Hz), 4.99 (t, 1H, J=5.64 Hz), 3.91 (s, 2H), 3.88 (d, 2H, J=5.69 Hz), 1.57 (s, 6H).

Method AE1

Compound 377

N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide b. (R)-2-(6-Chloro-5-nitro-1-oxoisoquinolin-2(1H)-yl)propyl acetate A mixture of (R)-6-chloro-2-(1-hydroxypropan-2-yl)-5-nitroisoquinolin-1(2H)-one (750.0 mg, 0.002653 mol), acetic anhydride (0.325 mL, 0.00345 mol), pyridine (0.322 mL, 0.00398 mol) and methylene chloride (20 mL, 0.3 mol) was heated at 45° C. over night. The solvent was removed under reduced pressure and dried to get pure product as thick yellow oil. MS m/z=325.4 (M+H). $^1$H NMR (400 MHz; DMSO) δ 8.42 (d, J=8.61 Hz, 1H), 7.47 (d, J=8.61 Hz, 1H), 7.23 (d, J=8.6 Hz, 1H), 6.29 (d, J=8.03 Hz, 1H), 5.34-5.29 (m, 1H), 4.28-4.20 (m, 2H), 1.94 (s, 3H), 1.40 (d, J=6.96 Hz, 3H).

c. (R)-2-(5-Amino-6-chloro-1-oxoisoquinolin-2(1H)-yl)propyl acetate

A round bottom flask was charged with (R)-2-(6-chloro-5-nitro-1-oxoisoquinolin-2(1H)-yl)propyl acetate (160.0 mg, 0.0004927 mol) and ethanol (7 mL, 0.1 mol) and the reaction heated at 85° C. Ammonium chloride (264 mg, 0.00493 mol) in water (7 mL, 0.4 mol) was then added followed by the addition of iron (110 mg, 0.0020 mol) in two portions. The

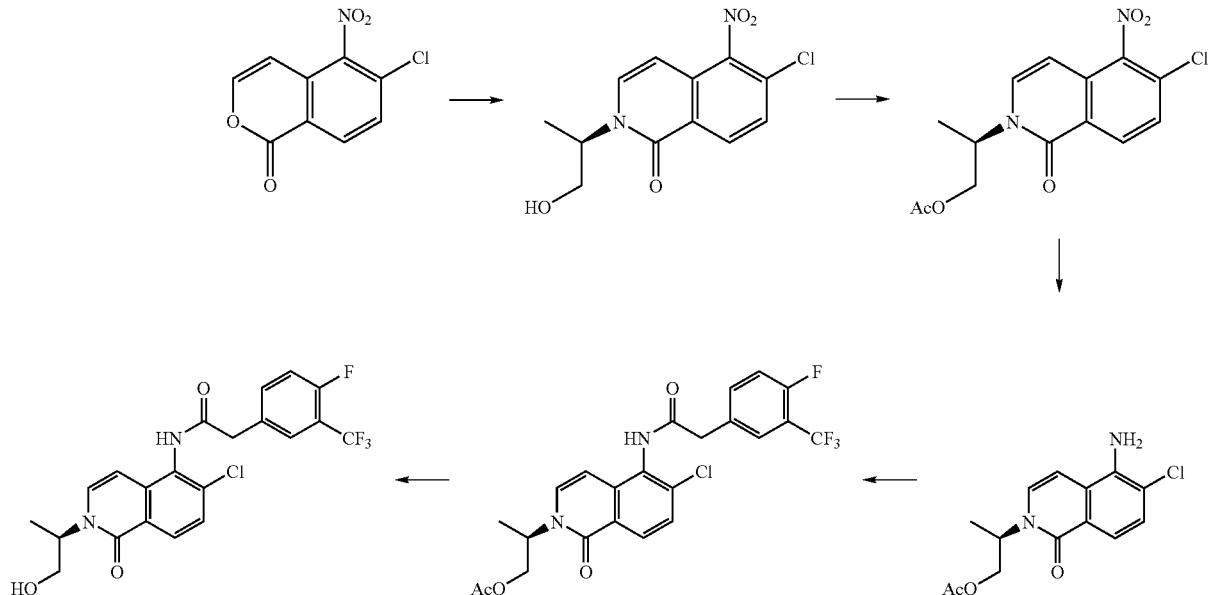

a. (R)-6-Chloro-2-(1-hydroxypropan-2-yl)-5-nitroisoquinolin-1(2H)-one

A microwave vial was charged with 6-chloro-5-nitro-1H-isochromen-1-one (80.0 mg, 0.000355 mol), (2R)-2-aminopropan-1-ol (29 mg, 0.00039 mol), triethylamine (0.15 mL, 0.0011 mol) and methanol (4 mL, 0.1 mol) and subjected to microwaves at 100° C. for 30 minutes. The reaction went to completion with 10% of cyclized product in addition to the required product. The solvent was removed and the residue purified by flash chromatography to obtain the product as a light yellow solid. MS m/z=283.2 (M+H). $^1$H NMR (400 MHz; DMSO-d6) δ 8.43 (d, J=8.86 Hz, 1H), 7.80 (d, J=8.86 Hz, 1H), 7.75 (d, J=7.98 Hz, 1H), 6.36 (d, J=7.09 Hz, 1H), 5.03-4.86 (m, 2H), 3.63-3.52 (m, 2H), 1.30 (d, J=7.0 Hz, 3H).

reaction was heated at that temperature for another hour. The reaction mixture was poured into dichloromethane (60 mL) and extracted. The extracts were washed with brine, dried over sodium sulfate and the solvent removed under reduced pressure to obtain the product as a colorless solid. MS m/z=295.5 (M+H).

d. (R)-2-(6-Chloro-5-(2-(4-fluoro-3-(trifluoromethyl)phenyl)acetamido)-1-oxoisoquinolin-2(1H)-yl)propyl acetate A reaction vial was charged with (R)-2-(5-amino-6-chloro-1-oxoisoquinolin-2(1H)-yl)propyl acetate (210 mg, 0.00071 mol), 2-(4-fluoro-3-(trifluoromethyl)phenyl)acetic acid (300 mg, 0.001 mol), N,N,N',N'-tetramethyl-O-(7-azabenzotriazol-1-yl)uronium hexafluorophosphate (600 mg, 0.002 mol), N,N-diisopropylethylamine (600 μL, 0.003 mol) and the reaction was stirred at 50° C. for 5 days. At this point, the reaction was only 50% complete. The solvent was removed and the residue purified by flash chromatography to obtain the product as a light yellow oil. MS m/z=499.3 (M+H).

e. (R)-N-(6-Chloro-2-(1-hydroxypropan-2-yl)-1-oxo-1,2-dihydroisoquinolin-5-yl)-2-(4-fluoro-3-(trifluoromethyl)phenyl)acetamide A round bottom flask was charged with (R)-2-(6-chloro-5-(2-(4-fluoro-3-(trifluoromethyl)phenyl)acetamido)-1-oxoisoquinolin-2(1H)-yl)propyl acetate (250 mg, 0.00050 mol), potassium carbonate (100 mg, 0.00075 mol) and methanol (8 mL, 0.2 mol) and 2 drops of water. The reaction was stirred at room temperature for 30 minutes. The reaction mixture was filtered, washed with methanol. The solvent was removed and the residue purified by preparative HPLC (reverse phase) to obtain the product as an off white solid (about 150 mg). MS m/z=457.4 (M+1). $^1$H NMR (400 MHz; DMSO) δ 10.17 (s, 1H), 8.16 (d, J=8.85 Hz, 1H), 7.82 (d, J=7.76 Hz, 1H), 7.72-7.74 (m, 1H), 7.59 (d, J=8.84 Hz, 1H), 7.54-7.49 (m, 2H), 6.42 (d, J=7.50 Hz, 1H), 5.03-4.93 (m, 2H), 3.90 (s, 2H), 3.66-3.56 (m, 2H), 1.28 (d, J=7.63 Hz, 3H).

Method AE2

Compound 375

N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide

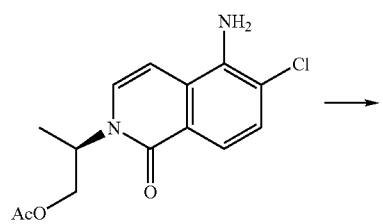

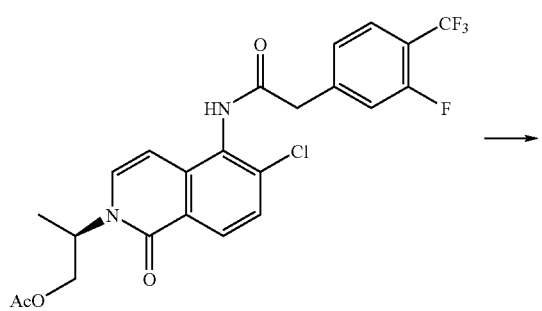

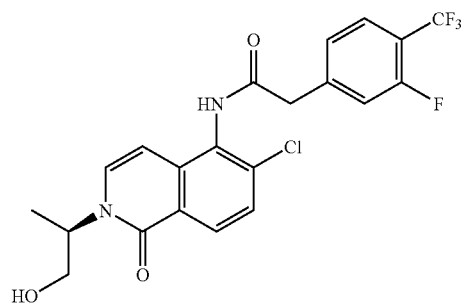

a. (R)-2-(6-Chloro-5-(2-(3-fluoro-4-(trifluoromethyl)phenyl)acetamido)-1-oxoisoquinolin-2(1H)-yl)propyl acetate A vial was charged with (R)-2-(5-amino-6-chloro-1-oxoisoquinolin-2(1H)-yl)propyl acetate (160 mg, 0.00054 mol), methylene chloride (10 mL, 0.2 mol), 2-(3-fluoro-4-(trifluoromethyl)phenyl)acetic acid (145 mg, 0.000651 mol), N,N,N',N'-tetramethyl-O-(7-azabenzotriazol-1-yl)uronium hexafluorophosphate (413 mg, 0.00108 mol), and N,N-diisopropylethylamine (0.189 mL, 0.00108 mol), and was stirred at 40° C. for 2 days. The reaction was only 50% complete. The solvent was removed and the residue purified by flash chromatography (0-75% ethylacetate/hexane) to obtain the product as a colorless oil. MS m/z=499.3 (M+H)

b. (R)-N-(6-Chloro-2-(1-hydroxypropan-2-yl)-1-oxo-1,2-dihydroisoquinolin-5-yl)-2-(3-fluoro-4-(trifluoromethyl)phenyl)acetamide A round bottom flask was charged with (R)-2-(6-chloro-5-(2-(3-fluoro-4-(trifluoromethyl)phenyl)acetamido)-1-oxoisoquinolin-2(1H)-yl)propyl acetate (1.200 g, 0.002406 mol), potassium carbonate (0.997 g, 0.00722 mol) and methanol (20 mL, 0.5 mol) and 2 drops of water. The reaction was stirred at room temperature for 1 hour in which time the reaction was complete. The reaction mixture was filtered over Na$_2$SO$_4$ and washed repeatedly with methanol. The solvent was removed under reduced pressure and the residue purified by flash chromatography to obtain the product as a white solid. MS m/z=457.3 (M+H). $^1$H NMR (400 MHz, DMSO-d$_6$): δ 10.20 (s, 1H), 8.17 (d, J=8.54 Hz, 1H), 7.79 (t, J=8.21 Hz, 1H), 7.60 (d, J=8.87 Hz, 1H), 7.56-7.51 (m, 2H), 7.45 (d, J=8.54 Hz, 1H), 6.44 (d, J=7.90 Hz, 1H), 5.03-4.99 (m, 1H), 4.94 (t, J=5.21 Hz, 1H), 3.94 (s, 2H), 3.68-3.56 (m, 2H), 1.28 (d, J=7.51 Hz, 3H).

Method AF1

Compound 384

N-[6-Cyclopropyl-2-((R)-2-hydroxy-1-methyl-ethyl)-1-oxo-1,2-dihydro-isoquinolin-5-yl]-2-(3-fluoro-4-trifluoromethyl-phenyl)-acetamide

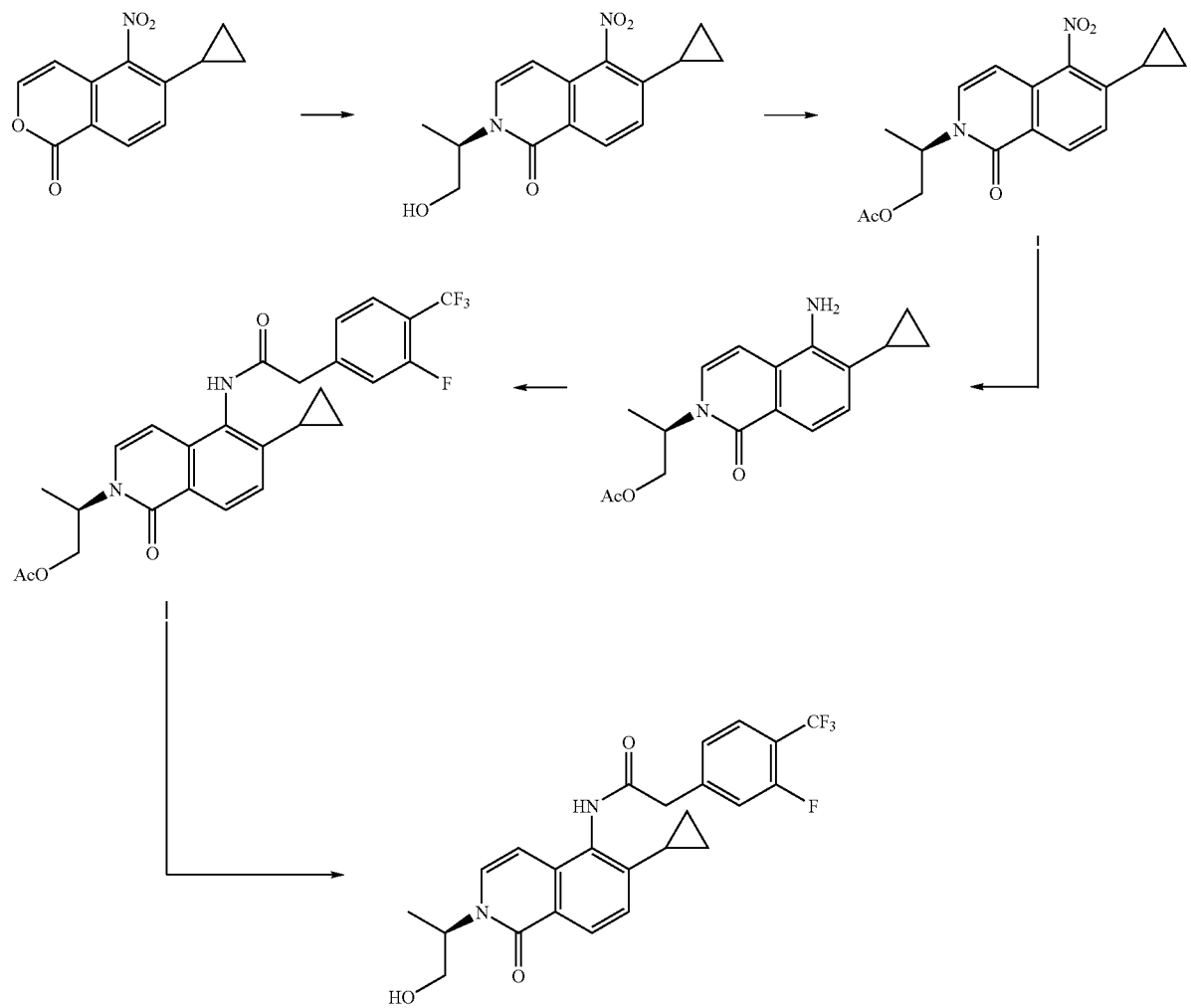

a. (R)-2-(6-Cyclopropyl-5-nitro-1-oxoisoquinolin-2(1H)-yl)propyl acetate

A round bottom flask was charged with (R)-6-cyclopropyl-2-(1-hydroxypropan-2-yl)-5-nitroisoquinolin-1(2H)-one (30 mg, 0.0001 mol), acetic anhydride (0.015 mL, 0.00016 mol), pyridine (0.015 mL, 0.00019 mol) and methylene chloride (4 mL, 0.06 mol) and the reaction stirred at room temperature over night. The solvent was then removed and the product was taken to the next step without purification. MS m/z=331.5 (M+H).

b. (R)-2-(5-Amino-6-cyclopropyl-1-oxoisoquinolin-2(1H)-yl)propyl acetate

A round bottom flask was charged with (R)-2-(6-cyclopropyl-5-nitro-1-oxoisoquinolin-2(1H)-yl)propyl acetate (28 mg, 0.000085 mol), ethanol (10 mL, 0.2 mol) and palladium, 10% weight on charcoal (1.0 mg, 0.0000085 mol) was added and the flask was evacuated of any air and flushed with hydrogen two times and the reaction was stirred at room temperature under hydrogen (1 atm) for 2 hours. The reaction was filtered over celite and the solvent removed to obtain the product. MS m/z=301.2 (M+H).

c. (R)-2-(6-Cyclopropyl-5-(2-(3-fluoro-4-(trifluoromethyl)phenyl)acetamido)-1-oxoisoquinolin-2(1H)-yl)propyl acetate A reaction vial was charged with (R)-2-(5-amino-6-cyclopropyl-1-oxoisoquinolin-2(1H)-yl)propyl acetate (23.0 mg, 0.0000766 mol), 2-(3-fluoro-4-(trifluoromethyl)phenyl)acetic acid (26 mg, 0.00011 mol), N,N,N',N'-tetramethyl-O-(7-azabenzotriazol-1-yl)uronium hexafluorophosphate (73 mg, 0.00019 mol), N,N-diisopropylethylamine (33 µL, 0.00019 mol) and methylene chloride (2 mL, 0.03 mol) and the reaction stirred at 40° C. over night. The solvent was removed and the residue purified by flash chromatography (0-70% ethylacetate) to obtain the product as light yellow solid. MS m/z=505.3 (M+H).

d. (R)-N-(6-Cyclopropyl-2-(1-hydroxypropan-2-yl)-1-oxo-1,2-dihydroisoquinolin-5-yl)-2-(3-fluoro-4-(trifluoromethyl)phenyl)acetamide A round bottom flask was charged with (R)-2-(6-cyclopropyl-5-(2-(3-fluoro-4-(trifluoromethyl)phenyl)acetamido)-1-oxoisoquinolin-2(1H)-yl)propyl acetate (23 mg, 0.000046 mol), potassium carbonate (9.4 mg, 0.000068 mol) and methanol (2 mL, 0.05 mol) and 2 drops of water and the reaction was stirred for 30 minutes. The reaction mixture was then filtered over celite and the solvent removed under reduced pressure. The residue was then purified by preparative HPLC (reverse phase) to get the product as a sticky mass. MS m/z=463.5 (M+H). $^1$H NMR (400 MHz; Acetone-d) δ 9.02 (s, 1H), 8.03 (d, J=8.15 Hz, 1H), 7.61 (t, J=7.52 Hz, 1H), 7.42 (d, J=5.01 Hz, 1H), 7.39 (s, 1H), 7.24 (d, J=7.52 Hz, 1H), 6.91 (d, J=8.15 Hz, 1H), 6.36 (d, J=8.15 Hz, 1H), 4.99-4.97 (m, 1H), 3.93 (s, 2H), 3.68-3.64 (m, 2H), 2.04-1.94 (m, 1H), 1.24 (d, J=7.32 Hz, 3H), 0.81-0.77 (m, 2H), 0.60-0.56 (m, 2H).

Method AF2

Compound 393

N-[6-Methyl-2-((R)-2-hydroxy-1-methyl-ethyl)-1-oxo-1,2-dihydro-isoquinolin-5-yl]-2-(3-fluoro-4-trifluoromethyl-phenyl)-acetamide

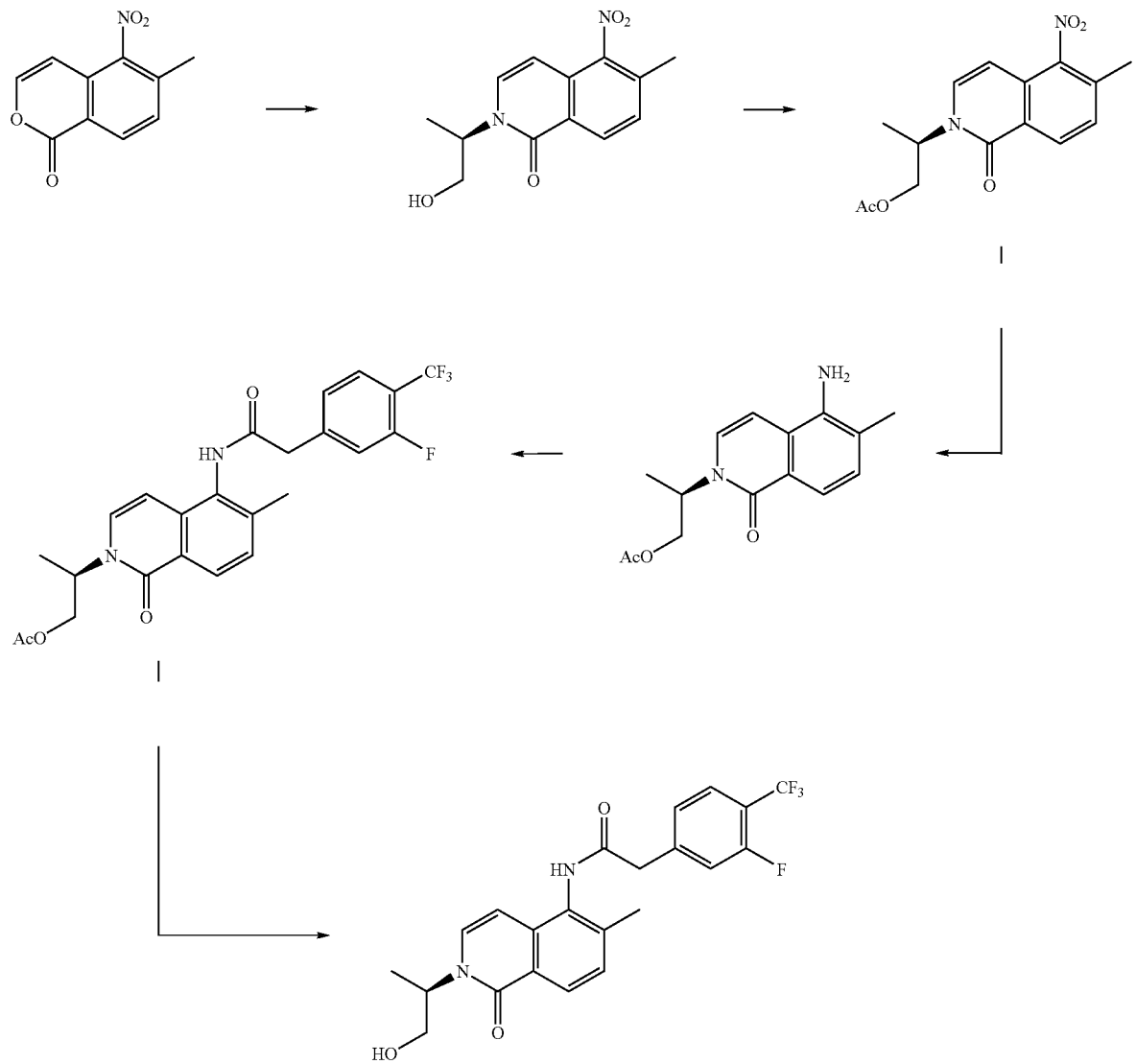

a. (R)-2-(1-Hydroxypropan-2-yl)-6-methyl-5-nitroisoquinolin-1(2H)-one

A round bottom flask was charged with 6-methyl-5-nitro-1H-isochromen-1-one (260.00 mg, 0.0012673 mol), (2R)-2-aminopropan-1-ol (143 mg, 0.00190 mol), triethylamine (1.6 mL, 0.011 mol) and methanol (5 mL, 0.1 mol) and the reaction was heated at 80° C. overnight. The solvent was removed and the residue purified by flash chromatography to obtain the product as a light yellow solid, as well as the cyclized acetal as a yellow solid. The cyclized accetal was then taken in methanol and triethylamine (2 mL) was added and heated in microwave for 1 hour at 110° C. to get the uncyclized product. MS m/z=263.4 (M+H).

b. (R)-2-(6-Methyl-5-nitro-1-oxoisoquinolin-2(1H)-yl)propyl acetate

A mixture of (R)-2-(1-hydroxypropan-2-yl)-6-methyl-5-nitroisoquinolin-1(2H)-one (100.0 mg, 0.0003813 mol), pyridine (0.062 mL, 0.00076 mol), acetic anhydride (0.0432 mL, 0.000458 mol) and methylene chloride (5 mL, 0.08 mol) was stirred at room temperature overnight. The reaction went to completion and the solvent was removed under reduced pressure, and the resulting product was dried in vacuum (yellow oil) and was used in the next reaction without any purification. MS m/z=305.4 (M+H).

c. (R)-2-(5-amino-6-methyl-1-oxoisoquinolin-2(1H)-yl)propyl acetate

A round bottom flask was charged with (R)-2-(6-methyl-5-nitro-1-oxoisoquinolin-2(1H)-yl)propyl acetate (110.0 mg, 0.0003615 mol), ethanol (10 mL, 0.2 mol) and the reaction heated at 85° C. and ammonium chloride (193.4 mg, 0.003615 mol) in water (2 mL, 0.1 mol) was added followed by iron (80.7 mg, 0.00144 mol) in two portions and continued to heat for 30 minutes. The reaction went to completion and was poured into DCM (50 mL) and extracted. The removal of the solvent under reduced pressure gave the pure product as an oil. MS m/z=275.4 (M+H).

d. (R)-2-(5-(2-(3-Fluoro-4-(trifluoromethyl)phenyl) acetamido)-6-methyl-1-oxoisoquinolin-2(1H)-yl) propyl acetate A round bottom flask was charged with (R)-2-(5-amino-6-methyl-1-oxoisoquinolin-2(1H)-yl)propyl acetate (175 mg, 0.000638 mol), 2-(3-fluoro-4-(trifluoromethyl)phenyl)acetic acid (210 mg, 0.00096 mol), N,N,N',N'-tetramethyl-O-(7-azabenzotriazol-1-yl)uronium hexafluorophosphate (610 mg, 0.0016 mol), N,N-diisopropylethylamine (0.28 mL, 0.0016 mol) and N,N-dimethylformamide (8 mL, 0.1 mol) and the reaction stirred at 45° C. for 24 hours. The reaction did not go to completion. The reaction was then quenched with water and extracted with ethyl acetate, washed with NaHCO$_3$, brine and dried. The solvent was removed under reduced pressure and the residue purified by flash chromatography to obtain the product as a light yellow oil. MS m/z=479.3 (M+H)

e. (R)-2-(3-Fluoro-4-(trifluoromethyl)phenyl)-N-(2-(1-hydroxypropan-2-yl)-6-methyl-1-oxo-1,2-dihydroisoquinolin-5-yl)acetamide A round bottom flask was charged with (R)-2-(5-(2-(3-fluoro-4-(trifluoromethyl)phenyl)acetamido)-6-methyl-1-oxoisoquinolin-2(1H)-yl)propyl acetate (300.00 mg, 6.2704E-4 mol), potassium carbonate (260 mg, 0.0019 mol), methanol (20 mL, 0.4 mol) and 2 drops of water. The reaction was stirred at room temperature for 20 minutes. The solvent was removed and the reaction mixture was extracted with ethyl acetate and the solvent was removed to obtain the product as a light yellow solid. MS m/z=437.5 (M+H). $^1$H NMR (400 MHz, DMSO-d$_6$): δ 9.91 (s, 1H), 8.07 (d, J=8.45 Hz, 1H), 7.79 (t, J=7.85 Hz, 1H), 7.53 (d, J=12.68 Hz, 1H), 7.45 (d, J=7.85 Hz, 2H), 7.37 (d, J=8.45 Hz, 1H), 6.44 (d, J=7.66 Hz, 1H), 5.05-5.00 (m, 1H), 4.93 (t, J=5.66 Hz, 1H), 3.92 (s, 2H), 3.67-3.51 (m, 2H), 2.22 (s, 3H), 1.28 (d, J=7.51 Hz, 3H).

Method AG

Compound 385

2-(2-Fluoro-3-trifluoromethyl-phenyl)-N-[2-(2-hydroxy-ethyl)-6-(2-hydroxy-ethylamino)-1-oxo-1,2-dihydro-isoquinolin-5-yl]-acetamide

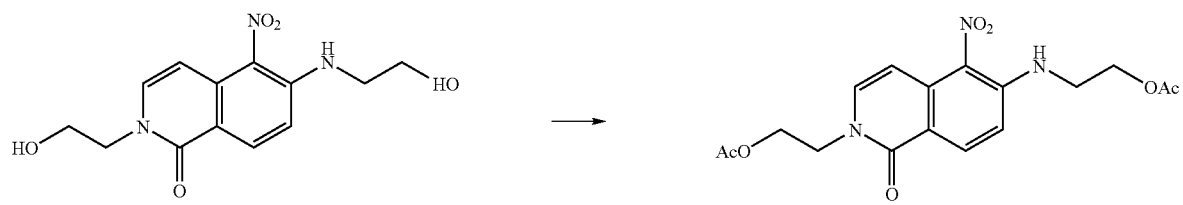

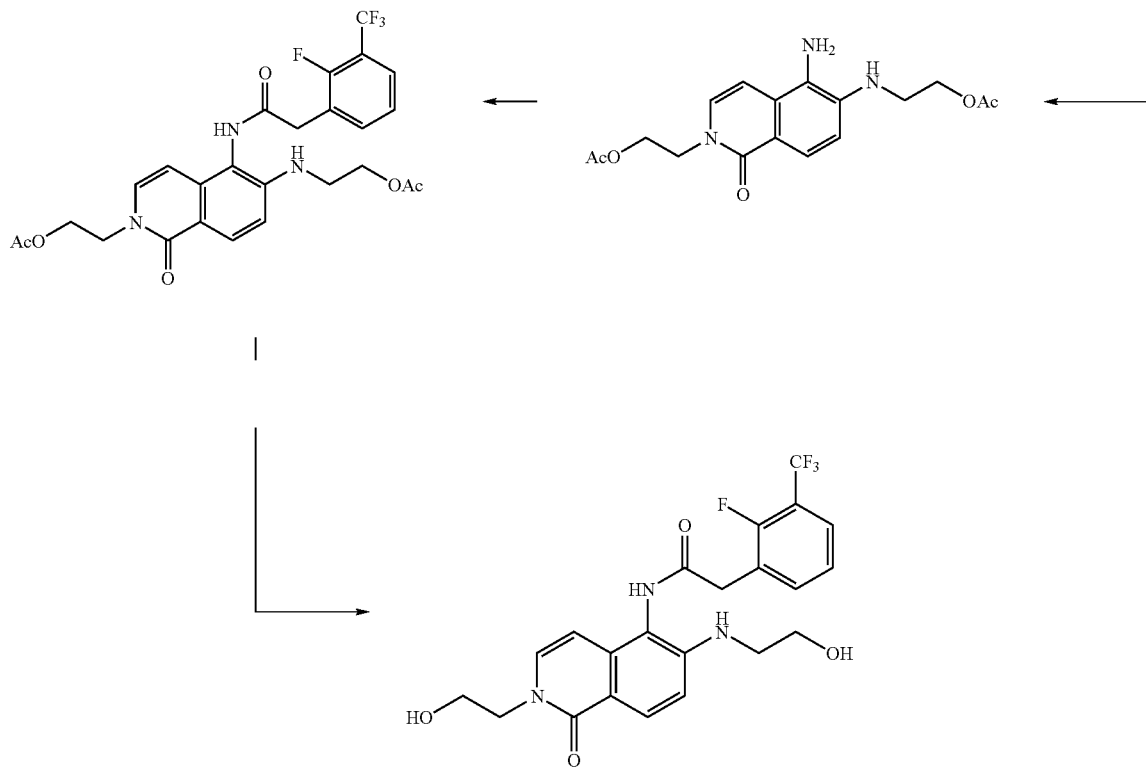

a. 2-(2-(2-Acetoxyethyl)-5-nitro-1-oxo-1,2-dihydroisoquinolin-6-ylamino)ethyl acetate A round bottom flask was charged with 2-(2-hydroxyethyl)-6-(2-hydroxyethylamino)-5-nitroisoquinolin-1(2H)-one (300.0 mg, 0.0010 mol), acetic anhydride (0.24 mL, 0.0026 mol), pyridine (0.33 mL, 0.0041 mol) and methylene chloride (10 mL, 0.2 mol) and the reaction heated at 45° C. overnight. The reaction went to completion and the solvent was removed to get the product which was used in the next reaction without further purification. MS m/z=378.2 (M+H).

b. Acetic acid 2-[6-(2-acetoxy-ethylamino)-5-amino-1-oxo-1H-isoquinolin-2-yl]-ethyl ester A mixture of 2-(2-(2-acetoxyethyl)-5-nitro-1-oxo-1,2-dihydroisoquinolin-6-ylamino)ethyl acetate (350 mg, 0.00093 mol), ethanol (20 mL, 0.3 mol), ammonium chloride (496.1 mg, 0.009275 mol) and water (10 mL, 0.6 mol) was added at 85° C. Iron (207 mg, 0.00371 mol) was added in two portions five minutes apart and the reaction was stirred at that temperature for 1 hour. The reaction mixture was then poured into methylene chloride (100 mL) and the layers were separated and the organic layer was washed with brine and dried over sodium sulfate. The solvent was removed under reduced pressure and used for the next reaction without purification. MS m/z=348.5 (M+H).

c. 2-(2-Acetoxyethyl)-5-(2-(2-fluoro-3-(trifluoromethyl)phenyl)acetamido)-1-oxo-1,2-dihydroisoquinolin-6-ylamino)ethyl acetate A reaction vial was charged with acetic acid 2-[6-(2-acetoxy-ethylamino)-5-amino-1-oxo-1H-isoquinolin-2-yl]-ethyl ester (100.00 mg, 0.00028788 mol), 2-(2-fluoro-3-(trifluoromethyl)phenyl)acetic acid (76.74 mg, 0.0003454 mol), N,N,N',N'-tetramethyl-O-(7-azabenzotriazol-1-yl)uronium hexafluorophosphate (274 mg, 0.000720 mol), N,N-diisopropylethylamine (0.125 mL, 0.000720 mol) and methylene chloride (3 mL, 0.05 mol) and the reaction heated at 40° C. for 5 h. The solvent was removed and the residue purified by flash chromatography to obtain the product as an off white solid. MS m/z=552.3 (M+H).

d. 2-(2-Fluoro-3-(trifluoromethyl)phenyl)-N-(2-(2-hydroxyethyl)-6-(2-hydroxyethylamino)-1-oxo-1,2-dihydroisoquinolin-5-yl)acetamide A round bottom flask was charged with 2-(2-(2-acetoxyethyl)-5-(2-(2-fluoro-3-(trifluoromethyl)phenyl)acetamido)-1-oxo-1,2-dihydroisoquinolin-6-ylamino)ethyl acetate (120 mg, 0.00022 mol), potassium carbonate (45 mg, 0.00033 mol) and methanol (3 mL, 0.07 mol) and 2 drops of water was added and the reaction stirred at room temperature for 30 minutes and was filtered over sodium sulfate and the solvent removed and the residue purified by flash chromatography to get the product as white solid. MS m/z=468.4 (M+H). $^1$H NMR (400 MHz) δ 9.45 (s, 1H), 7.98 (d, J=8.95 Hz, 1H), 7.79 (t, J=7.45 Hz, 1H), 7.70 (t, J=7.09 Hz, 1H), 7.40 (t, J=7.83 Hz, 1H), 7.22 (d, J=7.83 Hz, 1H), 6.91 (d, J=9.08 Hz, 1H), 6.16 (d, J=7.73 Hz, 1H), 5.64 (t, J=5.72 Hz, 1H), 4.84 (t, J=5.33 Hz, 1H), 4.76 (t, J=5.48 Hz, 1H), 3.96 (s, 2H), 3.91 (t, J=5.27 Hz, 2H), 3.62-3.53 (m, 4H), 3.27 (q, J=6.15 Hz, 2H).

Method AH

Compound 386

N-[6-Chloro-2-(2-hydroxy-ethyl)-1-oxo-1,2-dihydro-isoquinolin-5-yl]-2-(4-fluoro-3-trifluoromethyl-phenyl)-acetamide 4-nitro compounds precipitated out. The precipitate was filtered and dissolved in ethylacetate (30 mL) and washed with saturated aqueous sodium bicarbonate solution, brine and dried over sodium sulfate. The solvent was reduced ¼ volume, and the undesired isomer precipitated out. The precipitate was filtered and the filtrate was dried to obtain a 1:1 mixture of isomers as a white solid. MS m/z=214.5 (M–H).

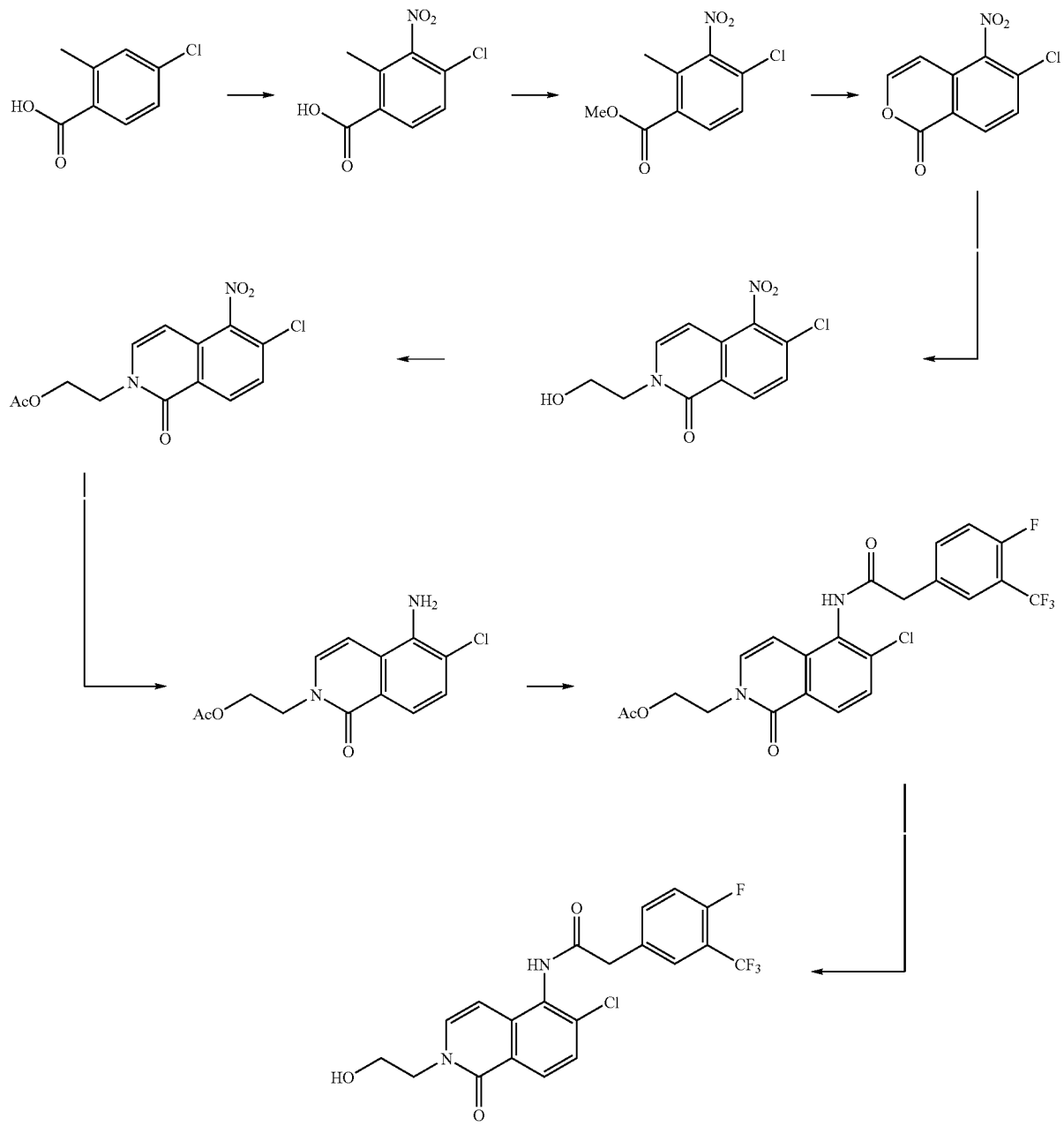

a. 4-Chloro-2-methyl-3-nitrobenzoic acid

A round bottom flask was charged with 4-chloro-2-methylbenzoic acid (200 mg, 0.001 mol) and sulfuric acid (1 mL, 0.02 mol) and fuming nitric acid (0.05 mL, 0.001 mol) was added at −20° C. and the reaction stirred for 1 hour at 70° C. and poured into ice cold water wherein the mixture of 2- and b. Methyl 4-chloro-2-methyl-3-nitrobenzoate A round bottom flask was charged with 4-chloro-2-methyl-3-nitrobenzoic acid (11.00 g, 0.05102 mol) and methanol (110 mL, 2.7 mol) and thionyl chloride (4.5 mL, 0.061 mol) was added at 0° C. and the reaction heated at 75° C. for 3 hours. The solvent was removed under reduced pressure and the residue dissolved in ethyl acetate (300 mL) and washed with aqueous sodium bicarbonate, water and brine. The combined organic extracts were dried over sodium sulfate and the solvent removed to obtain the esters. MS m/z=230.3 (M+H).

c. 6-Chloro-5-nitro-1H-isochromen-1-one

A pressure tube was-charged with methyl 4-chloro-2-methyl-3-nitrobenzoate (13 g, 57 mmol) in N,N-dimethylformamide (10 mL, 200 mmol) was added 1,1-dimethoxy-N,N-dimethylmethanamine (26.5 mL, 200 mmol) and the reaction heated to 120° C. for 20 h. The solvents were removed and the resultant brown residue was redissolved in ethyl acetate (600 mL, 6000 mmol) and 130-270 mesh 60A silica gel (500 g, 6000 mmol) was added and the reaction stirred with a mechanical stirrer for 8 h. The silica gel was filtered off, washed with ethyl acetate (400 mL) and the organics were removed under vacuum and the residue purified by flash chromatography (330 g silica gel, 2-50% ethyl acetate/hexane) to obtain the two isomers in 14% yields each in almost 98% purity. MS m/z=226.2 (M+H). $^1$H NMR (400 MHz; DMSO) δ 8.35 (d, J=8.63 Hz, 1H), 7.95 (d, J=8.63 Hz, 1H), 7.76 (d, J=5.91 Hz, 1H), 6.61 (d, J=6.04 Hz, 1H).

d. 6-Chloro-2-(2-hydroxyethyl)-5-nitroisoquinolin-1(2H)-one

A microwave vial was charged with 6-chloro-5-nitro-1H-isochromen-1-one (1.0 g, 0.00443 mol), ethanolamine (0.401 mL, 0.00665 mol), triethylamine (1.24 mL, 0.00886 mol) and methanol (30 mL, 0.7 mol) and the reaction was subjected to microwave at 100° C. for 1 hour. The reaction was complete in the sense that all the starting material was consumed but the major product formed was the chloro displacement with the amine. The solvent was removed and the residue purified by flash chromatography to obtain the product as a yellow solid. MS m/z=269.4 (M+H). $^1$H NMR (400 MHz; CDCl$_3$) δ 8.41 (d, J=8.56 Hz, 1H), 7.52 (d, J=8.56 Hz, 1H), 7.33 (d, J=8.4 Hz, 1H), 6.31 (d, J=8.56 Hz, 1H), 4.17 (t, J=44.88 Hz, 2H), 3.99 (t, J=5.11 Hz, 2H), 2.55 (bs, 1H).

e. 2-(6-Chloro-5-nitro-1-oxoisoquinolin-2(1H)-yl) ethyl acetate

A round bottom flask was charged with 6-chloro-2-(2-hydroxyethyl)-5-nitroisoquinolin-1(2H)-one (400.0 mg, 0.00149 mol), acetic anhydride (0.21 mL, 0.0022 mol), pyridine (0.18 mL, 0.0022 mol) and methylene chloride (20 mL, 0.2 mol) and the reaction stirred at room temperature overnight. The solvent was removed to obtain the product as a yellow solid. MS m/z=311.3 (M+H).

f. 2-(5-Amino-6-chloro-1-oxoisoquinolin-2(1H)-yl) ethyl acetate

A round bottom flask was charged with 2-(6-chloro-5-nitro-1-oxoisoquinolin-2(1H)-yl)ethyl acetate (450.00 mg, 0.0014484 mol), ethanol (20 mL, 0.3 mol) and ammonium chloride (774.8 mg, 0.01448 mol) in water (10 mL, 0.6 mol) was added at 85° C. followed by iron (324 mg, 0.00579 mol) in two portions. The reaction was stirred at that temperature for 45 minutes and then poured into methylene chloride (200 mL) and extracted. The solvent was removed to give the pure product as a light yellow solid. MS m/z=281.3 (M+H)

g. 2-(6-Chloro-5-(2-(4-fluoro-3-(trifluoromethyl) phenyl)acetamido)-1-oxoisoquinolin-2(1H)-yl)ethyl acetate A reaction vial was charged with 2-(5-amino-6-chloro-1-oxoisoquinolin-2(1H)-yl)ethyl acetate (60.0 mg, 0.000214 mol), 2-(4-fluoro-3-(trifluoromethyl)phenyl)acetic acid (57.0 mg, 0.000256 mol), N,N,N',N'-tetramethyl-O-(7-azabenzotriazol-1-yl)uronium hexafluorophosphate (203 mg, 0.000534 mol), N,N-diisopropylethylamine (0.093 mL, 0.00053 mol) and methylene chloride (3 mL, 0.05 mol) and the reaction stirred at 45° C. for 4 days. The reaction did not go to completion and a polar by product started increasing and so the reaction was stopped and solvent removed and the residue purified by flash chromatography to obtain the product as a light yellow solid. MS m/z=485.2 (M+H)

h. N-(6-Chloro-2-(2-hydroxyethyl)-1-oxo-1,2-dihydroisoquinolin-5-yl)-2-(4-fluoro-3-(trifluoromethyl) phenyl)acetamide A round bottom flask was charged with 2-(6-chloro-5-(2-(4-fluoro-3-(trifluoromethyl)phenyl)acetamido)-1-oxoisoquinolin-2(1H)-yl)ethyl acetate (80.0 mg, 0.000165 mol), potassium carbonate (34.2 mg, 0.000248 mol), methanol and 2 drops of water and the reaction stirred for 20 minutes at room temperature. The reaction was then filtered over sodium sulfate and celite and washed with methanol. The solvent was removed and the residue purified by preparative HPLC (reverse phase) to obtain the product as a pale yellow solid. MS m/z=443.3 (M+H) $^1$H NMR (400 MHz; DMSO-d6) δ 10.18 (s, 1H), 8.15 (d, J=8.81 Hz, 1H), 7.82 (d, J=6.7 Hz, 1H), 7.77-7.74 (m, 1H), 7.59 (d, J=8.81 Hz, 1H), 7.52 (t, J=9.52 Hz, 1H), 7.46 (d, J=7.40 Hz, 1H), 6.40 (d, J=7.59 Hz, 1H), 4.88 (t, J=5.0 Hz, 1H), 4.00 (t, J=5.55 Hz, 2H), 3.89 (s, 2H), 3.65 (q, J=5.55 Hz, 2H).

Method AJ

Compound 388

N-[2-(2-Acetylamino-ethyl)-1-oxo-1,2-dihydro-isoquinolin-5-yl]-2-(4-chloro-3-fluoro-phenyl)-acetamide

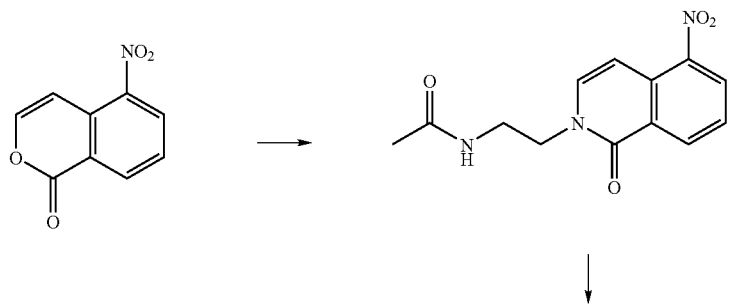

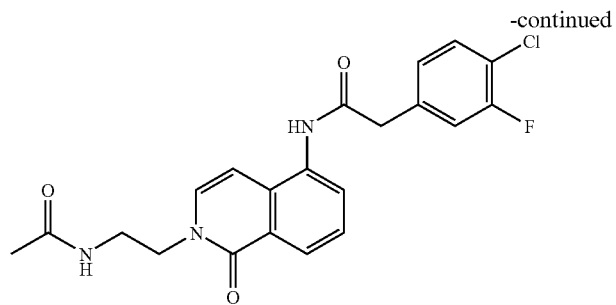
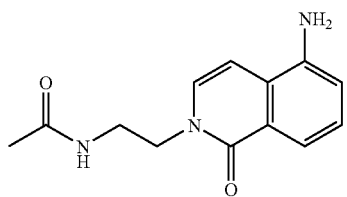

a. N-(2-(5-Nitro-1oxoisoquinolin-2(1H)-yl)ethyl) acetamide

Into a round bottom flask was combined 5-nitro-isochromen-1-one (5.00 g, 0.0235 mol), N-Acetylethylenediamine (7.21 g, 0.0706 mol) and methanol (150 mL, 3.7 mol). The mixture was heated at reflux for 1.5 hours. The mixture was cooled to room temperature and was stirred overnight. LC-MS showed that the starting material was completely consumed. Volatiles were removed and the resulting oil was purified in a methanol:methylene chloride (0-10%) gradient. Fractions containing the desired product, as determined by TLC and LC-MS, were combined and concentrated to produce a yellow solid.

b. N-(2-(5-Amino-1-oxoisoquinolin-2(1 H)-yl)ethyl) acetamide

Into a round bottom flask was combined N-(2-(5-nitro-1-oxoisoquinolin-2(1H)-yl)ethyl)acetamide (3.27 g, 0.0119 mol), palladium on C (1.6 g, 0.015 mol) and ethanol (250 mL, 4.2 mol). The reaction mixture was stirred under hydrogen at room temperature overnight. The mixture was filtered over celite, volatiles were removed under vacuum producing the title compound as a yellow solid. The compound was taken to the next step without further purification.

c. N-(2-(2-Acetamidoethyl)-1-oxo-1,2-dihydroisoquinolin-5-yl)-2-(4-chloro-3-fluorophenyl)acetamide Into a 20 ml reaction vial was combined N-(2-(5-amino-1-oxoisoquinolin-2(1H)-yl)ethyl)acetamide (20 mg, 0.00008 mol), 2-(4-chloro-3-fluorophenyl)acetic acid (30.55 mg, 0.0001620 mol), N,N,N',N'-tetramethyl-O-(7-azabenzotriazol-1-yl)uronium hexafluorophosphate (72.66 mg, 0.0001911 mol) N,N-diisopropylethylamine (61.6 µL, 0.000353 mol), and N,N-dimethylformamide (1 mL, 0.02 mol). The mixture was heated at 50° C. for two hours, allowed to cool and poured onto sat sodium bicarbonate (200 ml). The mixture was extraced with methylene chloride (3×100 ml). The combined extracts were dried over sodium sulfate and reduced in vacuo. The mixture was purified by reverse phase prep HPLC using an acetonitrile:water gradient at pH 10. The combined pure fractions were reduced in vacuo to yield the compound as an off white solid.

$^1$H-NMR (400 MHz, DMSO-d6) δ 10.06 (s, 1H), 8.07 (d, 1H, J=8.01 Hz), 7.96 (t, 1H, J=5.89 Hz), 7.83 (dd, 1H, J=7.84 Hz), 7.56 (t, 1H, J=8.13 Hz), 7.47-7.41 (m, 2H), 7.36 (d, 1H, J=7.66 Hz), 7.24 (dd, 1H, J=8.37 Hz), 6.36 (d, 1H, J=7.63 Hz), 3.98 (t, 2H, J=5.93 Hz), 3.82 (s, 2H), 3.39-3.35 (m, 2H), 1.75 (s, 3H).

Method AK

Compound 401

N-[6-Methyl-2-((R)-2-hydroxy-1-methyl-ethyl)-1-oxo-1,2,3,4-tetrahydro-isoquinolin-5-yl]-2-(3-fluoro-4-trifluoromethyl-phenyl)-acetamide

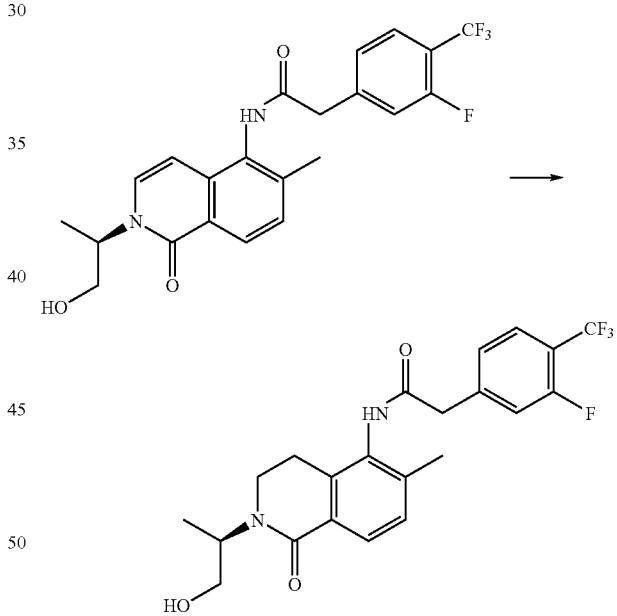

a. (R)-2-(3-Fluoro-4-(trifluoromethyl)phenyl)-N-(2-(1-hydroxypropan-2-yl)-6-methyl-1-oxo-1,2,3,4-tetrahydroisoquinoline-5-yl)acetamide A round bottom flask was charged with (R)-2-(3-fluoro-4-(trifluoromethyl)phenyl)-N-(2-(1-hydroxypropan-2-yl)-6-methyl-1-oxo-1,2-dihydroisoquinolin-5-yl)acetamide (50.0 mg, 0.000114 mol), ethanol (6 mL, 0.1 mol) and palladium, 10% weight on charcoal (1.4 mg, 0.000011 mol) was added and the flask was evacuated and flushes with hydrogen. The evacuation and flushing was repeated two times and the reaction was stirred under an atmosphere of hydrogen (balloon)

over night. The reaction mixture was then filtered over cellite and solvent removed under reduced pressure. The residue was then purified by flash chromatography to get the product as white solid.

MS m/z=439.5 (M+H). 1H NMR (400 MHz, DMSO-d6): δ 9.70 (s, 1H), 7.78 (t, J=7.75 Hz, 1H), 7.71 (d, J=8.00 Hz, 1H), 7.49 (d, J=12.25 Hz, 1H), 7.41 (d, J=8.50 Hz, 1H), 7.22 (d, J=8.25 Hz, 1H), 4.73 (t, J=5.73 Hz, 1H), 4.69-4.63 (m, 1H), 3.85 (s, 2H), 3.48-3.38 (m, 2H), 2.73-2.61 (m, 2H), 2.17 (s, 3H), 2.02-1.98 (m, 1H), 1.42-1.39 (m, 1H), 1.06 (d, J=6.90 Hz, 3H).

EXAMPLE 1

The $P2X_7$ receptor is strongly expressed in macrophage-derived cell lines, including, but not limited to, J774 (mouse macrophage line, American Type Culture Collection (ATCC), Rockville, Md., ATCC TIB-67), P388 (mouse cell line, ATCC CCL-46), P815 (mouse mast cell mastocytoma-derived line, ATCC TIB-64), THP-1 (Human monocyte-derived cell line, ATCC TIB202) and U937 (human cell line derived from histiocytic lymphoma, induceable to monocyte differentiation, ATCC CRL-1593.2) and in isolated macrophage cultures. Human or non-human animal macrophages are isolated using the procedure noted below.

The $P2Z/P2X_7$ receptor can be characterized by measuring channel opening, for instance ion flux, and/or by assessing pore formation, including by monitoring dye uptake or cell lysis in cells naturally expressing this receptor. Compounds such as ATP, 2' and 3'-(O)-(4-benzoyl benzoyl) ATP (BzATP) effect the formation of pores in the plasma membrane of these cells, particularly at low extracellular divalent ion concentrations (Buisman et al, Proc. Natl. Acad. Sci. USA 85:7988 (1988); Zambon et al, Cell. Immunol 156:458 (1994); Hickman et al Blood 84:2452 (1994)). Large molecular size dyes, including propidium dye YO-PRO-1, can be seen entering macrophage-derived cell lines during cell recordings (Hickman et al, Blood 84:2452 (1994); Wiley et al, Br J Pharmacol 112:946 (1994); Steinberg et al, J Biol Chem 262:8884 (1987)). Ethidium bromide (a fluorescent DNA probe) can also be monitored, where an increase in the fluorescence of intracellular DNA-bound ethidium bromide is observed. Expression of recombinant rat or human $rP2X_7$ in cells, including HEK293 cells, and in *Xenopus* oocytes demonstrates influx and pore formation by whole cell recordings and YO-PRO-1 fluorescence (Suprenant et al, Science 272:735 (1996); Rassendren et al, J Biol Chem 272:5482 (1997)).

The compounds of the invention may be tested for antagonist activity at the $P2X_7$ receptor. Tests to be performed include and are selected from: (i) electrophysiological experiments; (ii) YO-PRO1 fluorescence; (iii) ethidium bromide fluorescence; and (iv) IL-1β release from stimulated macrophages, including as described below. Compounds can be tested in vivo in animal models including for inflammation models (e.g. paw edema model, collagen-induced arthritis, EAE model of MS).

Isolation of Human Macrophages

Monocyte-derived human or non-human animal macrophage cultures are prepared as described by Blanchard et al (Blanchard et al, J Cell Biochem 57:452 (1995); Blanchard et al, J Immunol 147:2579 (1991)). Briefly, monocytes are isolated from leukocyte concentrates obtained from a healthy volunteer. Leukocytes are suspended in RPMI 1460 medium (Life Techologies, Inc.) with 20% serum (human for human cells), 2 mM glutamine, 5 mM HEPES, and 100 µg/ml streptomycin. Cells are allowed to adhere to culture flasks for 1-2 h, after which nonadherent cells are washed away. Adherent cells are cultured for 7-14 d in this medium plus interferon-γ (human for human cells) (1000 units/ml). Macrophages are recovered from the culture flask by pipetting with cold phosphate-buffered saline and plated onto glass coverslips for electrophysiological or other experiments carried out 12-24 h later.

EXAMPLE 2

Electrophysiological Experiments

Whole cell recordings are made using the EPC9 patch-clamp amplifier and Pulse acquisition programs (HEKA, Lambrecht, Germany). Whole-cell recordings are obtained from cells, e.g. J774A.1 cells (American Type Culture Collection, Rockville, Md., ATCC TIB-67)); agonists are applied for periods of 1 to 3 s by a fast-flow U-tube delivery system [E. M. Fenwick, A. Marty, E. Neher, J. Physiol, (London) 331, 577 (1982)]. The internal pipette solution is 140 mM cesium-aspartate or potassium-aspartate, 20 mM NaCl, 10 mM EGTA, and 5 mM Hepes; normal external solution is 145 mM NaCl, 2 mM KCl, 2 mM $CaCl_2$, 1 mM $MgCl_2$, 10 mM Hepes, and 12 mM glucose. Low divalent external solution is nominally magnesium-free with 0.3 mM $CaCl_2$. Concentration-response curves are constructed in low divalent solution by recording currents in response to 1 s applications of agonist at 8 min intervals with normal external solution present for 6 min before each application. This protocol is necessary to prevent the development of sustained inward currents.

Reversal potentials ($E_{rev}$) are obtained by application of ATP (300 µM) or BzATP (30 µM)(controls), or the compound being tested, while the membrane is held at various potentials or by application of voltage ramps from −120 to 30 or 50 mV. Permeability ratios are calculated from $E_{rev}$ by first computing α ($=P_{Na}/P_K$, where P is permeability) for internal (i) and external (o) concentrations $[Na]_i$=20 mM, $[Na]_o$=145 mM, $[K]_o$=0 mM, and $[K]_i$=140 mM from α=([145/exp($E_{rev}$FIRT)]−20)/140 (where F is the Faraday, R is the gas constant, and T is the absolute temperature). Other $P_x/P_{Na}$ values, when $[X]_o$=145 mM, $[Na]_i$=20 mM, $[K]_i$=140 mM, and $[Na]_o$=$[K]_o$=$[X]_i$=0 mM, are computed from $P_x/P_{Na}$=[(exp) $E_{rev}$F/RT)] (20+140α))/145. In order of size, X is cesium, methylamine, tris(hydroxymethyl)-aminomethane, tetraethylammonium, and N-methyl-D-glucamine. The internal solution also contains 10 mM EGTA and 5 mM Hepes. External solutions also contain 10 mM glucose and normal or low concentrations of divalent cations; pH is maintained at 7.3 with HCl, histidine, or Hepes as required, and the osmolarity of all solutions is 295 to 315.

EXAMPLE 3

YO-PRO1 Fluorescence

The Photonics Imaging (IDEA) system for microscopic fluorescence measurements (Photonics, Planegg, Germany) is used. Coverslips are placed at the stage of a Zeiss Axiovert 100 or equivalent inverted microscope and viewed under oil immersion with a 40× Fluor objective. YO-PRO-1 (10 µM; Molecular Probes, Eugene, Oreg.) is added to the superfusion fluid during electrophysiological recordings 3 to 6 min before switching to low divalent solution and washed out upon switching back to normal divalent solution, after which the fluorescent lamp is turned on and cells are examined with a fluorescein isothiocyanate filter. YO-PRO1 fluorescence is measured using 491/509 nm excitation/emission wavelengths. Images are obtained at 5-20 s intervals during continuous superfusion (2 ml/min) with YO-PRO1 and varying concentrations of control ATP, BzATP or compound to be tested. For each experiment, the time course of YO-PRO1 fluorescence obtained for 10-20 individual cells and then averaged to obtain the mean fluorescence signal. Results were expressed as mean signal at 3 min for $rP2X_7$, and the signal at 10 min is used for $P2X_7$ and human macrophage cells. All experiments are carried out at room temperature.

EXAMPLE 4

Ethidium Bromide

Compounds of the invention are tested for antagonist activity at the $P2X_7$ receptor by monitoring Ethidium Bromide entering $P2X_7$ receptor-expressing cells on pore formation. The test is performed in 96-well flat bottomed microtitre plates, the wells being filled with 250 μl of test solution comprising 200 μl of a suspension of $P2X_7$- expressing cells (e.g. THP-1 cells, J774 cells, etc.) ($2.5 \times 10^6$ cells/ml) containing $10^{-4}$ M ethidium bromide, 25 μl of a high potassium buffer solution containing $10^{-5}$ M BzATP, and 25 μl of a high potassium buffer solution containing test compound. The plate is covered with a plastic sheet and incubated at 37° C. for one hour. The plate is then read in a Perkin-Elmer fluorescent plate reader, excitation 520 nm, emission 595 nm, slit widths: Ex 15 nm, EM 20 nm. For the purposes of comparison, BzATP (a $P2X_7$ receptor agonist) and pyridoxal 5-phosphate (a $P2X_7$ receptor agonist) are used separately in the test as controls. From the readings obtained, a $IC_{50}$ figure is calculated for each test compound. This figure is the negative logarithm of the concentration of test compound necessary to reduce the BzATP agonist activity by 50%.

EXAMPLE 5

IL-1β Release

This Example demonstrates the testing of the compounds of this invention for efficacy as inhibitors of $P2X_7$-mediated release of IL-1β from human macrophages activated by the Alzheimer's beta amyloid peptide 1-42.

Cell Isolation

Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (generally, 5 to 6 washes). Monocytes are then purified from the PBMCs by negative selection using a monocyte isolation kit (Miltenyi Biotec, Inc.) that contains antibodies to non-monocytic cells, running the cells over a magnetic column to remove antibody-bound cells, and collecting the flow through volume of monocytes. Monocytes are washed once with wash buffer and seeded at 100,000 cells per well in 100 μl serum-free RPMI 1640 in 96-well plates and incubated for 1 Hour at 37° C. in a 5% $CO_2$/95% humidified tissue culture incubator. After 1 Hour, the medium is replaced with 100 μl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing Regimen

The next day, the culture medium is replaced with 100 μl fresh complete culture medium in the absence or presence of human beta amyloid 1-42 peptide (5 μM) and incubated at 37° C. in a 5% $CO_2$/95% humidified tissue culture incubator for 5 hours. Medium is then removed and discarded. Each well is washed once with Hanks buffered saline (HBSS) containing 1 mM $CaCl_2$ followed by the addition of 80 μl of HBSS/$CaCl_2$-inhibiting compound of the present invention (10× stock in HBSS/$CaCl_2$ for a final concentration of 23 nM and 206 nM) and incubated 15 minutes in the tissue culture incubator followed by the addition of either 10 μl of HBSS/$CaCl_2$ or 10 μl of benzoyl ATP (BZATP; 3 mM stock in HBSS/$CaCl_2$ for a 300 μM final concentration) and incubated for a further 30 minutes in the tissue culture incubator. Medium is then removed to new 96-well plates for storage at −70° C. until the IL-1β content was quantitated by ELISA (from R&D Systems). The cells are washed once with HBSS/$CaCl_2$ followed by lysing the cells with 100 μl ice cold lysis buffer (100 mM Tris, pH 7.6, 1% Triton X-100, and 1 tablet per 30 ml Complete™ protease inhibitor from Roche Biochemicals, Inc). Cell lysates are stored at −70° C. until the IL-1β is quantitated by ELISA.

EXAMPLE 6

In Vivo Animal Models

A. This example illustrates the efficacy of the compounds of this invention in the treatment of multiple sclerosis. As described herein, experimental autoimmune encephalomyelitis (EAE) model is used to show such an efficacy. The following procedures are employed in this model.

Animals

SJL/J female mice, 8 wks. old, are obtained from Jackson Laboratories.

Antigens

Myelin Proteolipid Protein (PLP 139-151) (HSLGK-WLGHPDKF) (Cat # H-2478) is obtained from BACHEM, Bioscience, Inc., 3700 Horizon Dr., King of Prussia, Pa. 19406, 1-610-239-0300 (phone), 1-610-239-0800 (fax).

Complete Freund's Adjuvant H37 Ra [1 mg/ml Mycobacterium Tuberculosis H37 Ra] is obtained from Difco 1-800-521-0851 (Cat # 3114-60-5, 6×10 ml).

*Mycobacterium* Tuberculosis is also obtained from Difco, 1-800-521-0851 (Cat # 3114-33-8, 6.times.100 mg).

*Pertussis* Toxin

*Bordetella Pertussis*, (Lyophilized powder containing PBS and lactose) is obtained from List Biological Laboratories, 1-408-866-6363 (Product #180, 50 ug).

Induction of EAE in Mice

PLP139-151 peptide is dissolved in $H_2O$:PBS (1:1) solution to a concentration 7.5 mg/10 ml (for 75 μg PLP per group) and emulsified with an equal volume of CFA supplemented with 40 mg/10 ml heated-killed mycobacterium tuberculosis H37Ra. Mice are injected s.c. with 0.2 ml of peptide emulsion in the abdominal flank (0.1 ml on each side). On the same day and 72 hours later, mice are injected i.v. with 100% of 35 ng and 50 ng of *Bordetella Pertussis* toxin in saline respectively.

Clinical Assessment
STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE
Clinical Courses of EAE
Acute phase: First clinical episode (Day 10-18)
Remission: Phase of clinical improvement following a clinical episode; characterized by a reduction (>=one grade) in clinical score for at least two days after the peak score of acute phase or a disease relapse.
Relapse: Increase of at least one grade in clinical score for at least two days after remission has been attained.

The animals treated with the compounds of this invention generally would be expected to show improvements in clinical scores.

B. This Example illustrates a protocol for determining the efficacy of the compounds of the present invention for the treatment of stroke using an animal model.

Male Sprague Dawley rats (Charles River) weighing 280-320 g are given free access to food and water and acclimatized for a minimum of 4 days before use in experiments. All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.

Surgical Procedure

A temporalis muscle probe is placed into the right temporalis muscle and "brain" temperature" is monitored. A midline neck incision is made in the upper thorax of the rat. Careful dissection, isolation and retraction of the sternomastoideus, digastricus, and sternohyoideus muscles is made to expose the right common, internal and external carotid arteries. The right common carotid artery is isolated with a 5-0 silk suture. During surgery the suture is released allowing reperfusion every 2-4 minutes. The right external carotid and superior thyroid arteries are also isolated and the superior thyroid is cauterized, while the external carotid is ligated distally with a 5-0 silk suture. Another 5-0 silk suture is loosely tied around the external carotid artery. The occipital artery is isolated, ligated and incised. The internal carotid is isolated.

With the common and external carotid arteries immobilized, an aneurysm clip is placed onto the internal carotid artery. A small incision is made at the distal end of the external carotid. A 3-0 nylon suture coated with poly-L-lysine is then inserted into the external carotid and up into the common carotid artery. The loosely tied 5-0 silk suture around the external carotid is now gently tightened around the filament. The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing <300 gm, 19 mm for rats weighing 0.300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture. The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%. The neck incision is reopened to expose the external carotid artery. The restoration of blood flow is accomplished by completely withdrawing the intraluminal suture from the carotid arteries. The incision is then closed with 3-0 silk in an interrupted stitch.

Compound Administration

Five groups of 15 animals are subjected to the above methodology. Compounds are infused (I.V.) at various doses (dose response) over different time period's post MCAo. A predetermined concentration is infused over a pre-selected time period beginning at various intervals post MCAo. Vehicle-treated controls receive an infusion of normally 0.9 ml/hr. A positive control compound is run at the same time.

Neurological Tests

Prior to surgery, 2 hours following the onset of ischaemia and 24 hours after ischaemia a battery of neurological tests are performed. The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation. The rats respond to a gentle lateral push with a finger behind the shoulders. A normal rat would resist such a push, whereas a rat with an infarction will not. The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

C. This Example illustrates the anti-inflammatory activity of the compounds of this invention using a model of 2,4-dinitrobenzenesulfonic acid (DNBS) induced distal colitis (a model of inflammatory bowel disease).

Test Substance and Dosing Pattern

A compound of this invention is dissolved in vehicle of 2% Tween 80 in distilled water for oral administration at a dose of 50 mg/kg or dissolved in vehicle of 2% Tween 80 and 0.9% NaCl for intraperitoneal injection at 30 mg/kg. The dose is given once daily for 7 consecutive days. Dosing volume is 10 ml/kg. DNBS was challenged 2 hours after dosing on the second day.

Animals

In these studies, male Wistar, Long Evans rats provided by animal breeding center of MDS Panlabs Taiwan, Ltd. and Balb/cByJ derived male mice (weighing 20±2 gms), provided by National Laboratory Animals Breeding Research center (NALBRC, Taiwan), may be used. Space allocation of 6 animals may be 45×23×15 cm. Animals are housed in APEC® cages (Allentown Caging, Allentown, N.J. 08501, USA) in a positive pressure isolator (NuAire®, Mode: Nu-605, airflow velocity 50±5 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water is granted. All aspects of this work including housing, experimentation and disposal of animals would be performed in general accordance with the International Guiding Principles for Biomedical Research Involving Animals (CIOMS Publication No. ISBN 92 90360194, 1985).

Chemicals

DNBS is obtained from TCI, Tokyo, Japan, ethanol is from Merck, Germany and Sulfasalazine is purchased from Sigma, USA.

Equipment

Electriconic scale (Tanita, model 1140, Japan), Electriconic scale (Sartorius, R160P, Germany), Glass syringe (2 ml, Mitsuba, Japan), Rat oral needle, Hypodermic needle (25 G.times.1" TOP Corporation, Japan), Stainless Scissors (Klappenclear, Germany), Stainless Forceps (Klappenclear, Germany).

Method

Groups of 3 Wistar derived male rats weighing 180±20 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instillated into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon is removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW×100%. The "Net" increase in ratio of Vehicle-control+DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

D. This Example illustrates the anti-inflammatory activity of the present compounds using a model of carrageenan induced paw edema (a model of inflammation, carrageenan).

Test Substance and Dosing Pattern

A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.

Animals

Animals are conditioned in accordance with the procedures set forth in the previous Example.

Chemicals

Carrageenan is obtained from TCI, Japan; Pyrogen free saline is from Astar, Taiwan; and Aspirin is purchased from ICN BioMedicals, USA.

Equipment

Glass syringe (1 ml and 2 ml Mitsuba, Japan), Hypodermic needle 24 G×1" (Top Corporation, Japan), Plethysmometer #7150 (UGO Basile, Italy), and Water cell 25 mm Diameter, #7157 (UGO Basile, Italy).

Method

Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. #7150) with water cell (25 mm diameter, Cat. #7157). Reduction of hind paw edema by 30 percent or more (30%) indicated significant acute anti-inflammatory activity.

E. This Example illustrates the anti-inflammatory activity of the present compounds using a model of Balb/c mice subjected to monoclonal antibody (mAb) type II collagen induced arthritis.

Test Substance and Dosing Pattern

A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen was injected. Dosing volume is 20 ml/kg.

Animals

Animals are conditioned in accordance with the procedures set forth in the previous Example.

Chemicals

Lipopolysaccharide is obtained from Sigma, USA; Indomethacin is from Sigma, USA; Arthrogen-CIA.™M. Monoclonal Antibodies D8, F10, DI-2G and A2 are obtained from IBL, Japan; Phosphated-Buffer Saline is purchased from Sigma, USA; and Tween 80 is from Wako, Japan.

Equipment

Plethysmometer (Ugo Basile, Italy) and Water Cell (Ugo Basile, Italy).

Method

Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mabs in a total of 4 mg/mouse at day 0, and followed by intravenous 25 μg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administrated once daily for 3 consecutive days. A plethysmometer (Ugo Basile Cat #7150) with water cell (12 mm diameter) is used for the measurement of increase in volume of the two hind paws at day 0, 5, 7, 10, 14, and 17. The percent inhibition of increase in volume is calculated by the following formula:

$$\text{Inhibition (\%): } [1-(T_n-T_0)/(C_n-C_0)] \times 100$$

Where:

Co (Cn): volume of day 0 (day n) in vehicle control

To (Tn): volume of day 0 (day n) in test compound-treated group

The reduction of both of two hind paws edema by more than 30% is considered significant.

EXAMPLE 7

Neuropathic Pain Model

This example illustrates the analgesic activity of the compounds of this invention using a Sciatic Nerve ligation model of mononeuropathic pain Test System Adult male Sprague Dawley (SD) rats weighing 250-300 gm (Charles River Laboratories, San Diego, Calif.) are used. The animal room is lighted artificially at a 12-hr light-dark cycle (from 7:00 A.M. to 7:00 P.M) with water and food supply ad libitum. Animals are allocated randomly into groups.

Model Induction

Sciatic Nerve Ligation (SNL, Seltzer's Model):

Under anesthesia with pentobarbital (50 mg/kg, i.p.) and aseptic techniques, the selective nerve injury is created by tightly ligating the selective portion of the common sciatic nerve according to the method of Seltzer (1990). Briefly, the high-thigh level of the left sciatic nerve is exposed after skin incision and blunt separation of muscles at a site near the trochanter just distal to the point at which the posterior biceps semitendious nerve nerve branches from the common sciatic nerve. The nerve is then fixed in this position with fine forceps by pinching the epineurium on its dorsal aspect, taking care not to press the nerve against underlying structures. An 8-0 silicon-treated silk suture is inserted into the nerve with a 3/8 curved, reversed-cutting mini-needle, and tightly ligated so that the dorsal 1/3-1/2 of the nerve is trapped in the ligature. The muscles are sutured in layers, and the skin closed with wound clips. Animals are then returned to their home cages. Rats exhibiting postoperative neurological deficits or poor grooming are excluded from the experiments.

Equipment

The following equipment is used in the current studies: von Frey filament set (Touch-test Sensory Evaluator, North Coast Medical Inc., Morgan Hill, Calif.).

Statistical Methods:

Within each experiment mean, standard error of the mean (SEM) and statistical significance are calculated using the average, standard error of the mean and unpaired, two-tailed t-Test functions, respectively, using Microsoft Excel®. Statistical significance of effects observed between individual experiments is determined, using Prism (GraphPad Software Inc., San Diego, Calif.) for the one-way or two-way analysis of variance (ANOVA) function. Statistical analyses are performed with a confidence limit of 0.95 and a significance level of 0.05.

EXAMPLE 8

Pore Formation

THP-1 cells (ATCC Cat # 285-IF-100) are plated in 96 well plates at a concentration of 200,000 cells per well and allowed to differentiate in RPMI-1640 media (ATCC Cat # 30-2001) containing 10% FBS, 100 IU/mL penicillin, 100 ug/mL streptomycin, 100 ng/mL LPS and 100 ng/mL IFN-γ for 16 hours. Following differentiation, the cells are pretreated with the compound of interest at the appropriate concentration for 30 minutes in RPMI-1640 media containing 100 IU/mL penicillin, 100 ug/mL streptomycin. The pretreatment media is then replaced with assay buffer (20 mM HEPES, 10 mM d-glucose, 118 mM NMDG, 5 mM KCl, 0.4 mM $CaCl_2$) containing 5 uM Yo-Pro 1 (Molecular Probes Cat # Y3603) and the compound of interest at the appropriate concentration and the cells are incubated for an additional 10 minutes. 2',3'-O-(4-benzoylbenzoyl)-adenosine 5'-triphosphate (Sigma Aldrich Cat# B6396) is then added to a final concentration of 40 uM and fluorescence readings measured at 491/509 excitation/emission every minute for 50 minutes using a Tecan Safire plate reader. During this time temperature is maintained at of 37° C. Background adjusted fluorescence levels between drug treated and non-treated cells are used to calculate the percent inhibition.

EXAMPLE 9

IL-1β Release Assay

THP-1 cells (ATCC Cat # 285-IF-100) are plated in 96 well plates at a concentration of 200,000 cells per well and allowed to differentiate in RPMI-1640 media (ATCC Cat # 30-2001) containing 10% FBS, 100 IU/mL penicillin, 100 ug/mL streptomycin, 100 ng/mL LPS and 100 ng/mL IFN-γ for 16 hours. Following differentiation, the cells are treated for an additional 2 hours in RPMI-1640 media containing 100 IU/mL penicillin, 100 ug/mL streptomycin and fresh LPS at 100 ng/mL. The cells are then pretreated for 30 minutes with the compound of interest at the appropriate concentration in RPMI media containing 100 IU/mL penicillin, 100 ug/mL streptomycin. Following the pretreatment 2',3'-O-(4-benzoylbenzoyl)-adenosine 5'-triphosphate (Sigma Aldrich Cat # B6396) is added to a final concentration of 250 uM and the cells are incubated for an additional 45 minutes. 30 uL of cell supernatant is then collected and IL-1β levels determined via ELISA (R&D systems Cat. # HSLB50) according to manufacturer's recommendations using the Tecan Safire plate reader. Background adjusted IL-1β levels of drug treated and non-treated cells are used to calculate the percent inhibition.

The synthetic and biological examples described in this application are offered to illustrate this invention and are not to be construed in any way as limiting the scope of this invention. In the examples, all temperatures are in degrees Celsius (unless otherwise indicated). The compounds that have been prepared in accordance with the invention along with their biological activity data are presented in following Tables. The syntheses of these representative compounds are carried out in accordance with the methods set forth above.

Exemplary Compounds of the Invention

The following compounds have been or can be prepared according to the synthetic methods described above. For the purpose of Table 1 below, activity of each compound, which can be determined using the IL-1β assay method described in Example 9, is expressed as follows:

"+" compound exhibited 0-25% inhibition at 0.3 μM concentration

"++" compound exhibited 26-50% inhibition at 0.3 μM concentration

"+++" compound exhibited 51-75% inhibition at 0.3 µM concentration

"++++" compound exhibited 76% or greater inhibition at 0.3 µM concentration

"*" compound exhibited 0-25% inhibition at 0.1 µM concentration

"**" compound exhibited 26-50% inhibition at 0.1 µM concentration

"***" compound exhibited 51-75% inhibition at 0.1 µM concentration

"****" compound exhibited 76% or greater inhibition at 0.1 µM concentration

Compounds with a percent inhibition represented by "++++" or "****" are of interest.

With respect to the Mass Spectrometry (MS) data presented below, "∆" he observation of a possible Na ion adduct.

TABLE 1

IL-1β % Inhibition of Exemplary Compounds

| ID | Structure | MW | MS (Obs) | IL-1β % Inhib. @ 0.3 or 0.1 µM |
|---|---|---|---|---|
| 1 | 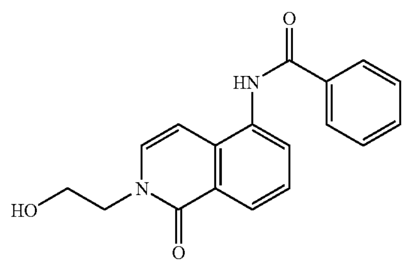 | 308.34 | 309.00 | + |
| 2 | 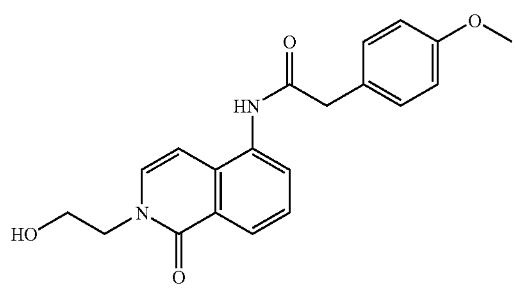 | 352.39 | 353.10 | + |
| 3 | 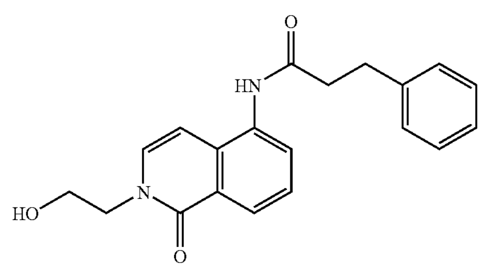 | 336.39 | 337.50 | +++ |
| 4 | 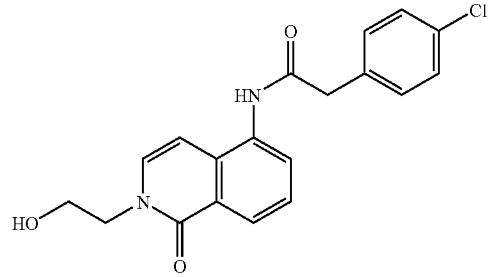 | 356.81 | 356.90 | ++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 5 | 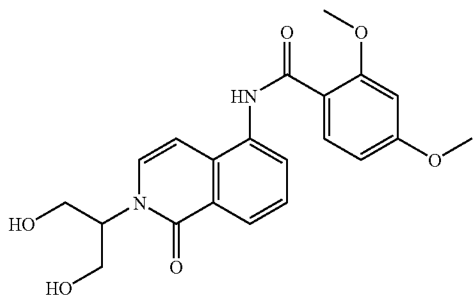 | 398.41 | 399.30 | + |
| 6 | 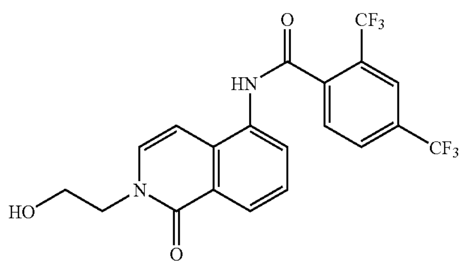 | 444.33 | 445.00 | ++ |
| 7 | 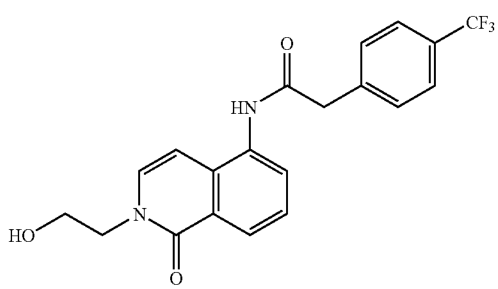 | 390.36 | 391.40 | ++ |
| 8 | 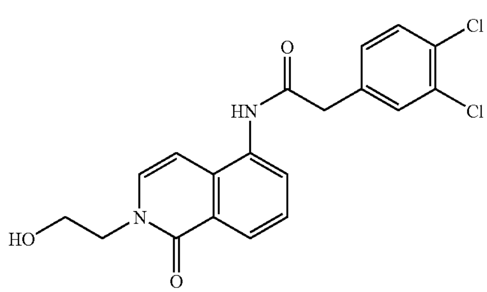 | 391.25 | 392.80 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 9 | 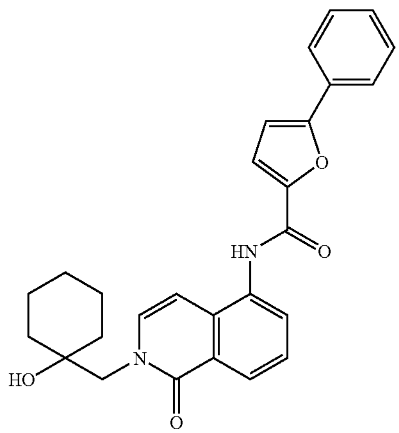 | 442.51 | 443.44 | * |
| 10 | 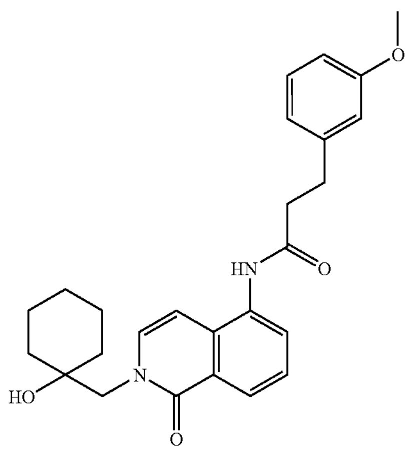 | 434.53 | 435.57 | * |
| 11 | 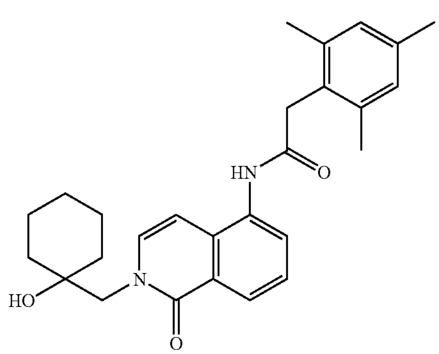 | 432.56 | 433.52 | |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 12 | | 418.53 | | 49.50 |
| 13 | | 440.92 | 441.35 | |
| 14 | | 420.51 | 421.39 | |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 15 | 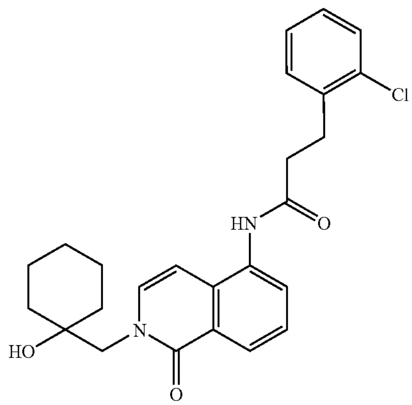 | 438.95 | 439.55 | |
| 16 | 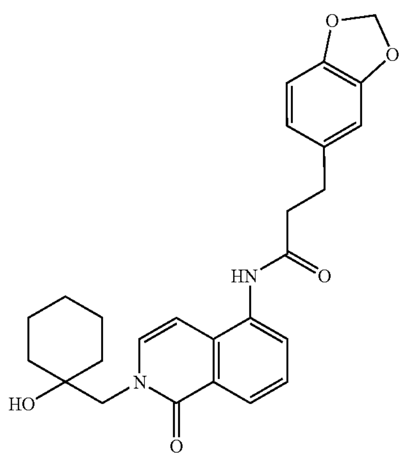 | 448.52 | 449.45 | |
| 17 | 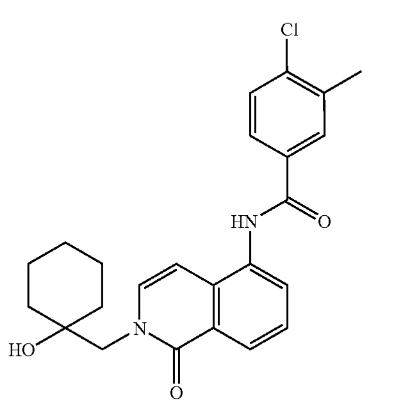 | 424.93 | 425.12 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 18 | 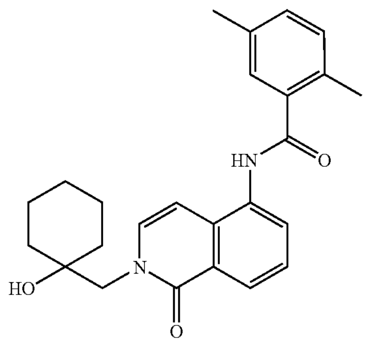 | 404.51 | 405.51 | |
| 19 | 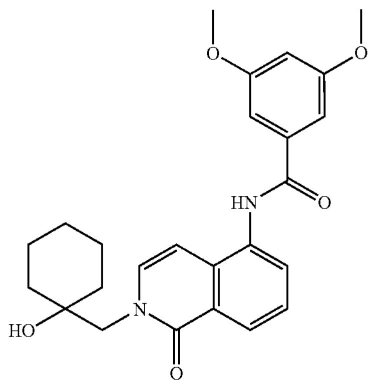 | 436.51 | 437.55 | * |
| 20 | 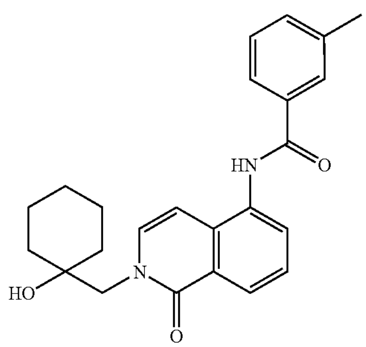 | 390.48 | 391.38 | * |
| 21 | 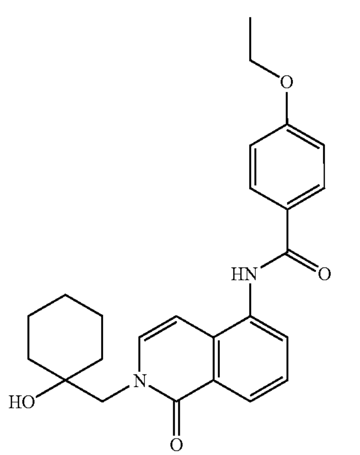 | 420.51 | 421.38 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 22 | 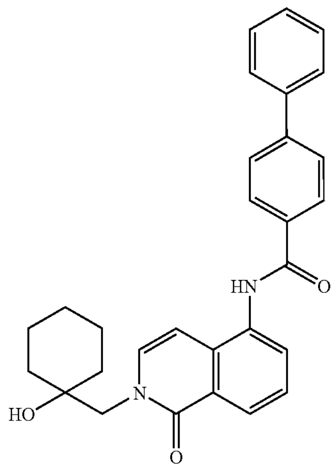 | 452.55 | 453.34 | * |
| 23 | 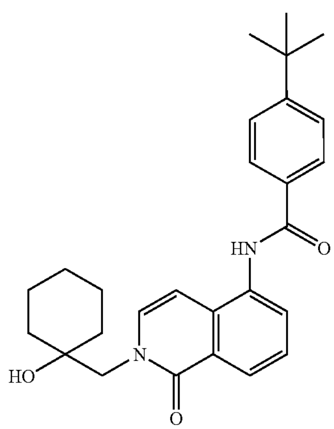 | 432.56 | 433.53 | * |
| 24 | 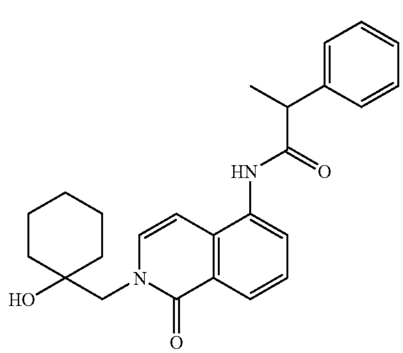 | 404.51 | 405.52 | ** |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 25 | 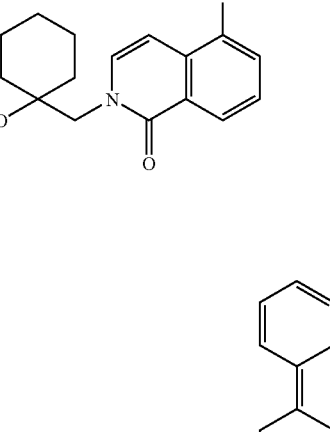 | 434.53 | 435.60 | + |
| 26 | 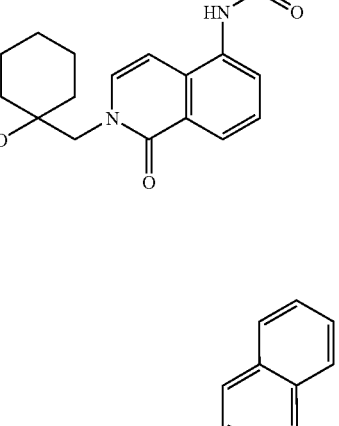 | 440.54 | 441.47 | + |
| 27 | 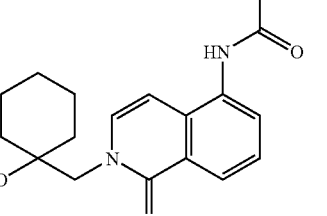 | 426.51 | 427.41 | + |

TABLE 1-continued
IL-1β % Inhibition of Exemplary Compounds
| ID | Structure | MW | MS (Obs) | IL-1β % Inhib. @ 0.3 or 0.1 μM |
|----|-----------|-----|----------|-------------------------------|
| 28 | 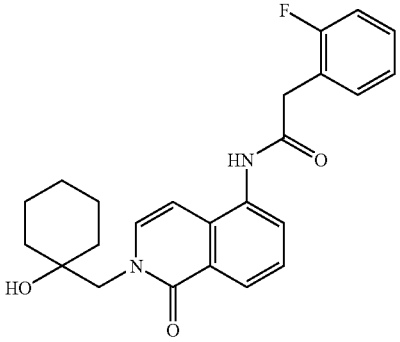 | 408.47 | 409.50 | + |
| 29 | 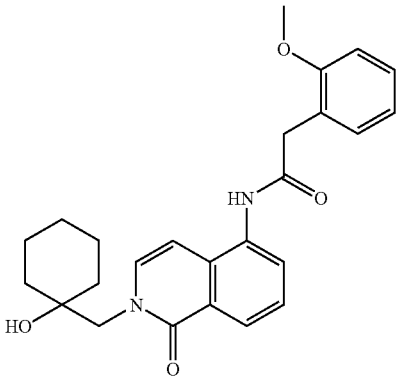 | 420.51 | 421.39 | ++ |
| 30 | 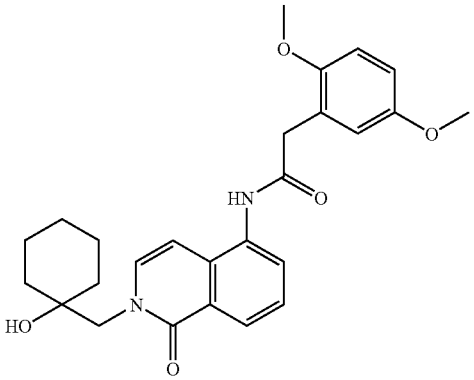 | 450.53 | 451.39 | + |
| 31 | 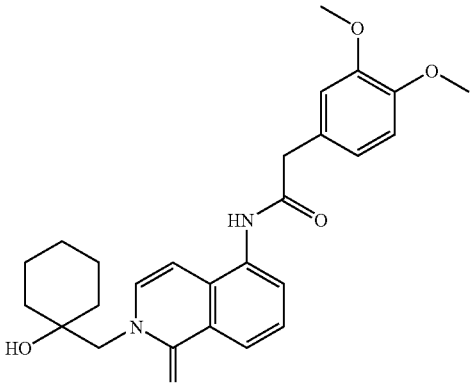 | 450.53 | 451.39 | + |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 32 | 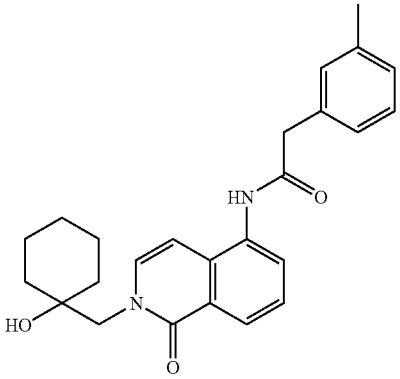 | 404.51 | 405.52 | + |
| 33 | 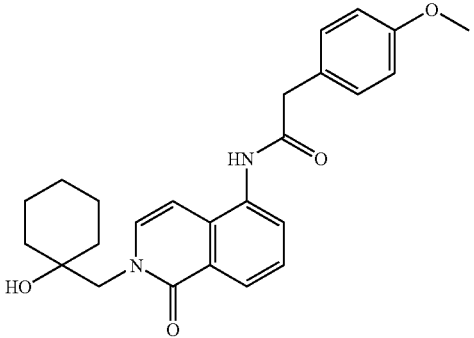 | 420.51 | 421.40 | + |
| 34 | 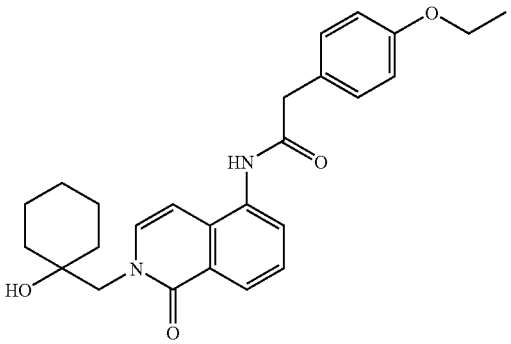 | 434.53 | 435.62 | + |
| 35 | 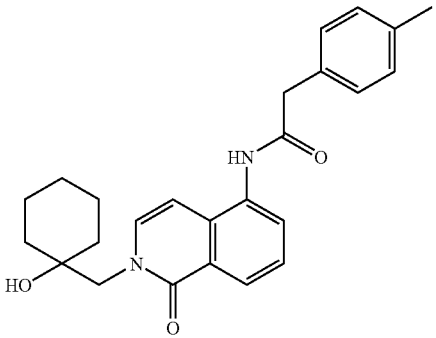 | 404.51 | 405.55 | ++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 36 | 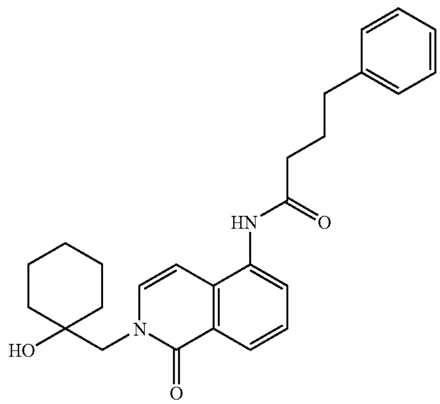 | 418.53 | 419.51 | ++ |
| 37 | 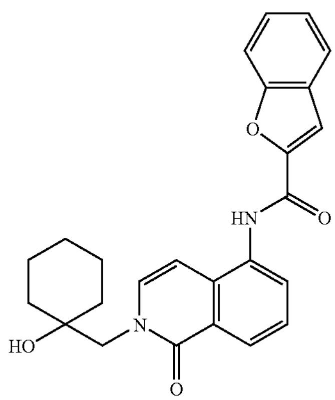 | 416.47 | 417.4 | + |
| 38 | 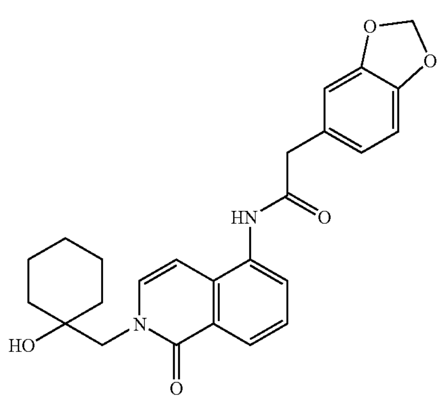 | 434.49 | 435.56 | + |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 39 | 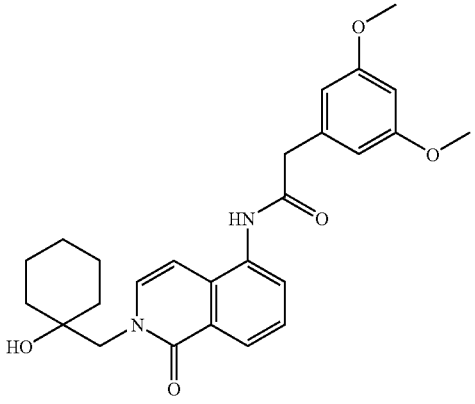 | 450.53 | 451.38 | + |
| 40 | 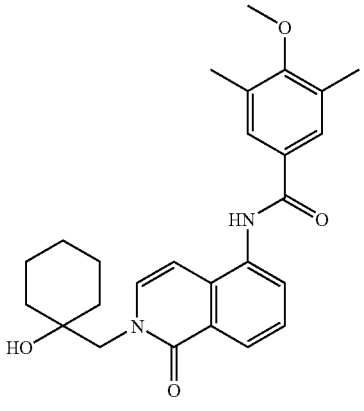 | 434.53 | 435.61 | + |
| 41 | 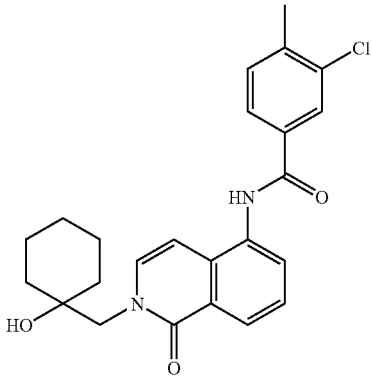 | 424.93 | 425.14 | |

US 7,816,371 B2
151                                                                                                          152
TABLE 1-continued
IL-1β % Inhibition of Exemplary Compounds
| ID | Structure | MW | MS (Obs) | IL-1β % Inhib. @ 0.3 or 0.1 μM |
|----|-----------|-----|----------|-------------------------------|
| 42 | 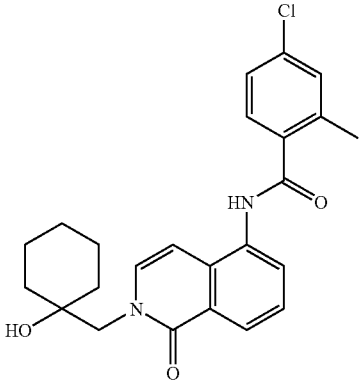 | 424.93 | 425.2 | |
| 43 | 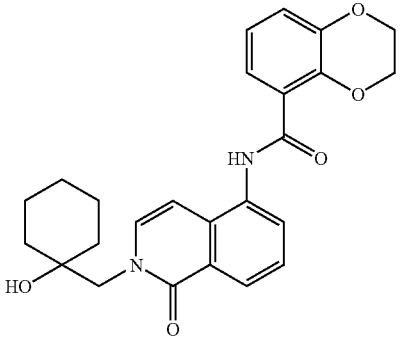 | 434.49 | 435.54 | |
| 44 | 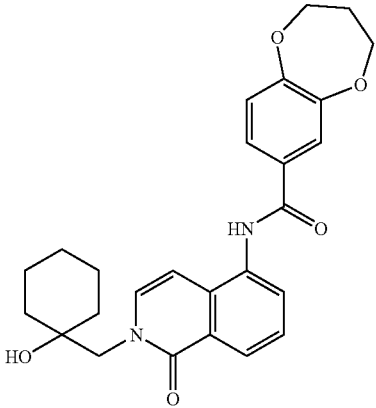 | 448.52 | 449.43 | |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 45 | | 446.57 | 447.47 | |
| 46 | | 418.53 | 419.51 | |
| 47 | | 450.53 | 451.19 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 48 | 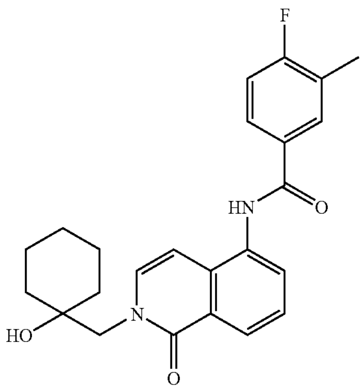 | 408.47 | 409.33 | + |
| 49 | 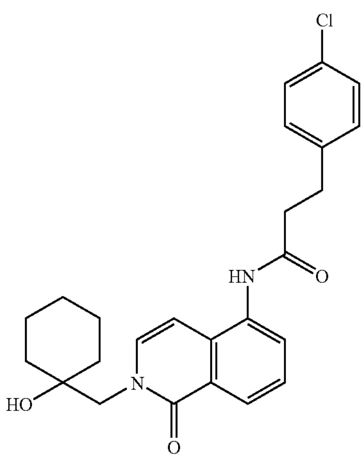 | 438.95 | 439.20 | + |
| 50 | 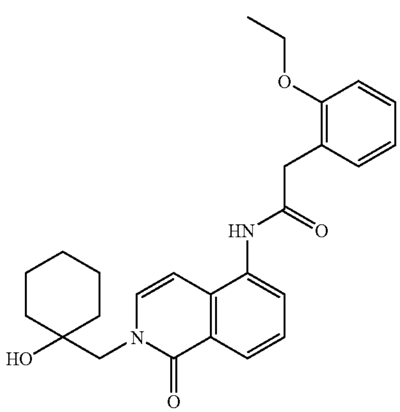 | 434.53 | 435.30 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 51 | 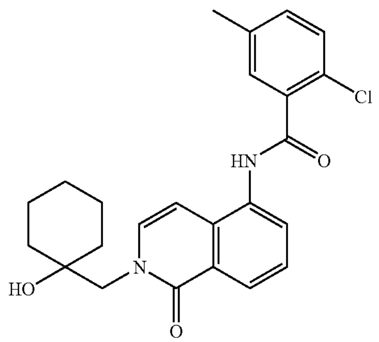 | 429.93 | 425.11 | + |
| 52 | 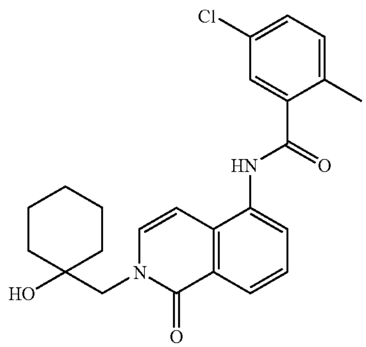 | 424.93 | 425.10 | + |
| 53 | 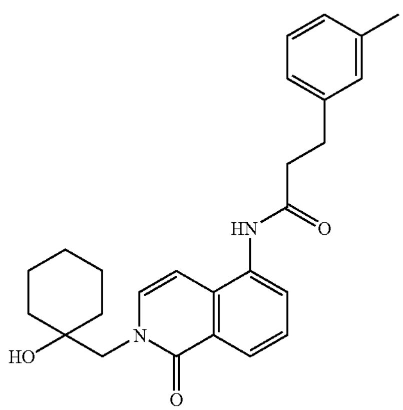 | 418.53 | 419.40 | + |
| 54 | 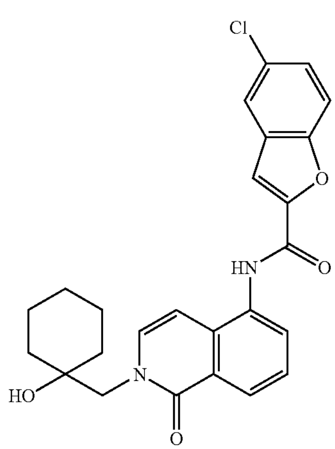 | 450.92 | 451.14 | ++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 55 | 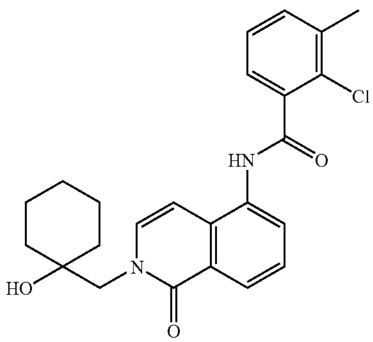 | 424.93 | 425.11 | + |
| 56 | 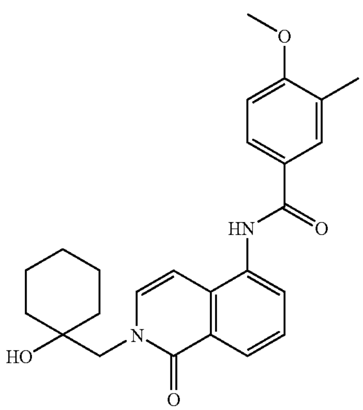 | 420.51 | 421.19 | + |
| 57 | 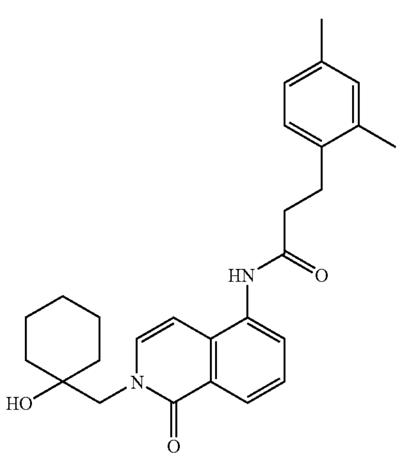 | 432.56 | 433.49 | |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 58 | 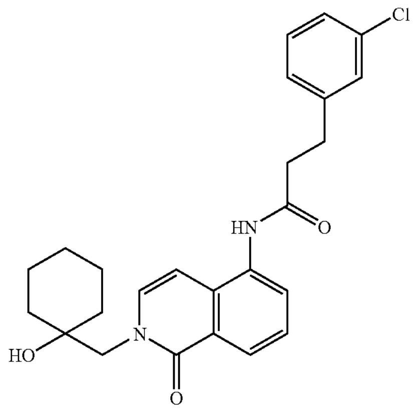 | 438.95 | 439.56 | ++ |
| 59 | 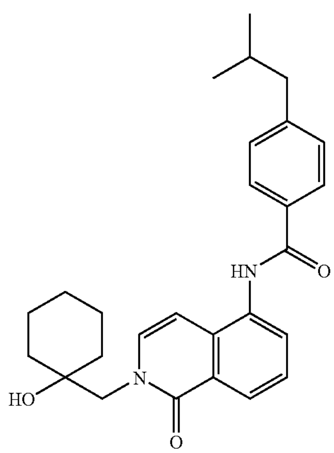 | 432.56 | 433.56 | ++ |
| 60 | 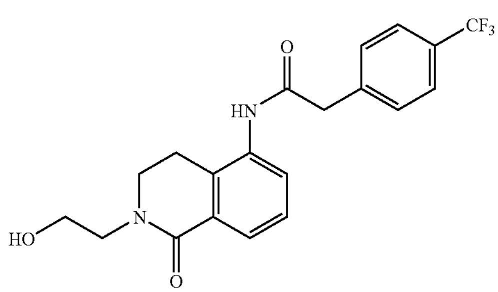 | 392.38 | 393.20 | ++ |
| 61 | 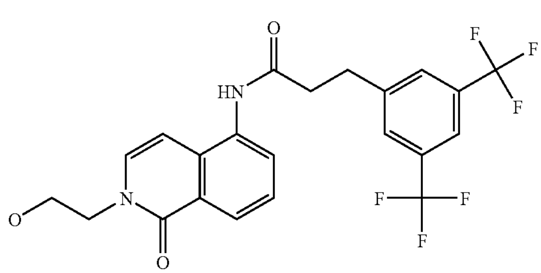 | 472.38 | 473.40 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 62 | 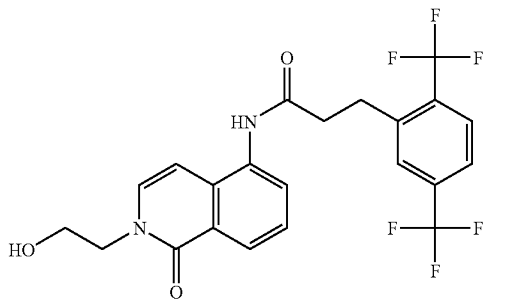 | 472.38 | 473.00 | ++++ |
| 63 | 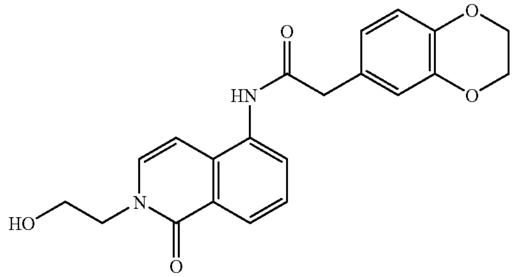 | 380.40 | 381.20 | + |
| 64 | 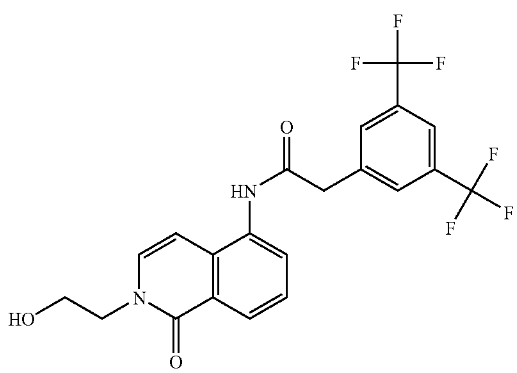 | 458.36 | 459.00 | +++ |
| 65 | 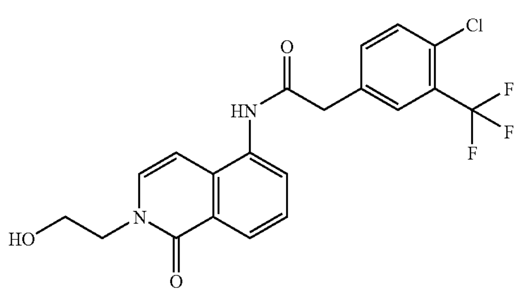 | 424.80 | 425.20 | ++++ |
| 66 | 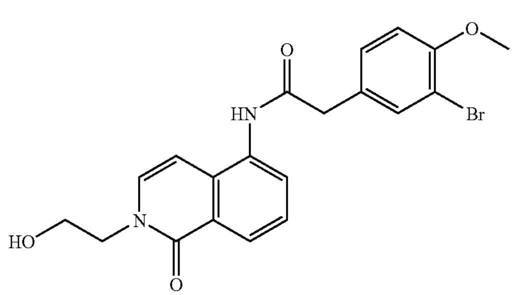 | 431.28 | 432.70 | ++++ |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 67 | | 424.80 | 424.80 | + |
| 68 | | 424.80 | 425.30 | ++ |
| 69 | | 391.25 | 391.00 | ++++ |
| 70 | | 458.36 | 459.00 | ++ |

TABLE 1-continued

IL-1β % Inhibition of Exemplary Compounds

| ID | Structure | MW | MS (Obs) | IL-1β % Inhib. @ 0.3 or 0.1 μM |
|----|-----------|------|---------|-------------------------------|
| 71 | 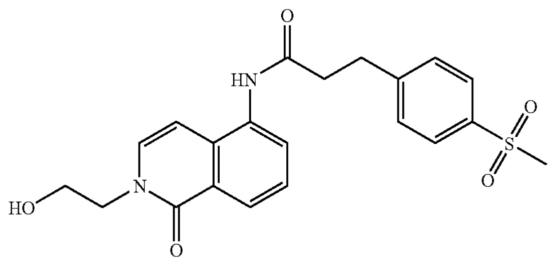 | 414.48 | 415.20 | + |
| 72 | 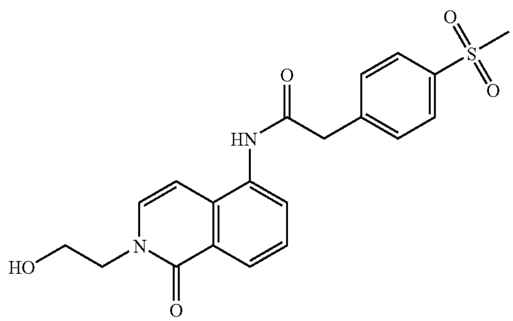 | 400.45 | 401.20 | + |
| 73 | 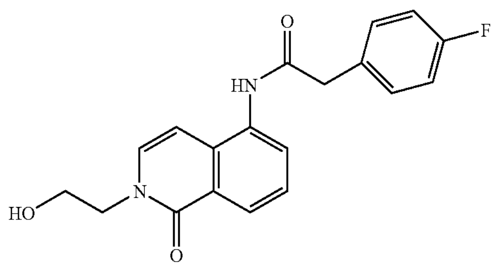 | 340.35 | 341.00 | ++ |
| 74 | 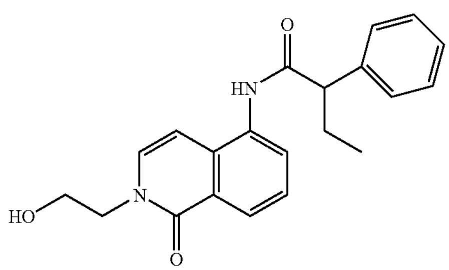 | 350.42 | 351.10 | + |
| 75 | 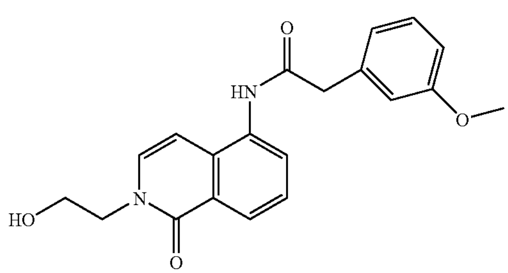 | 352.39 | 352.80 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 76 | 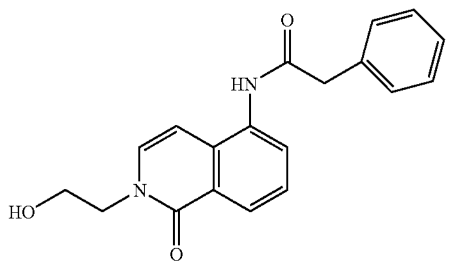 | 322.36 | 323.20 | + |
| 77 | 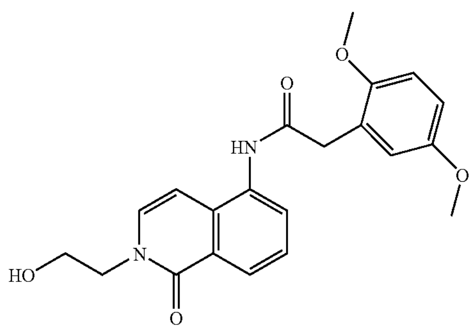 | 382.41 | 383.00 | + |
| 78 | 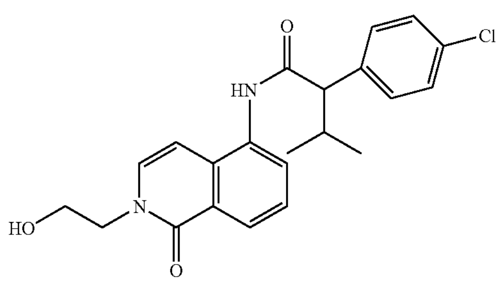 | 398.89 | 399.30 | + |
| 79 | 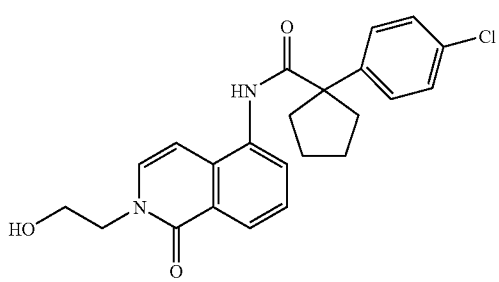 | 410.90 | 411.20 | + |

TABLE 1-continued

IL-1β % Inhibition of Exemplary Compounds

| ID | Structure | MW | MS (Obs) | IL-1β % Inhib. @ 0.3 or 0.1 μM |
|----|-----------|------|----------|--------------------------------|
| 80 | 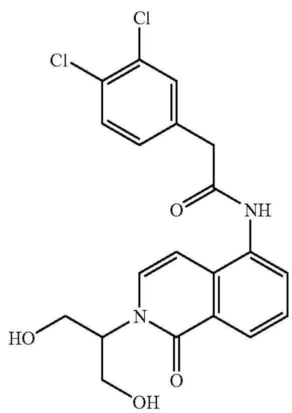 | 421.28 | 421.20 | ++++ |
| 81 | 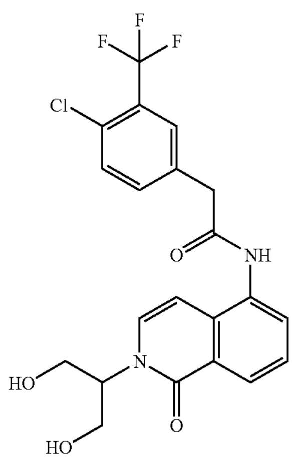 | 454.83 | 455.10 | ++++ |
| 82 | 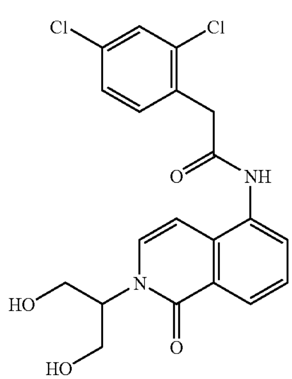 | 421.28 | 420.80 | +++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 83 | 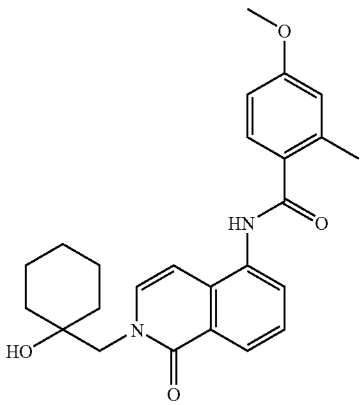 | 420.51 | 421.38 | * |
| 84 | 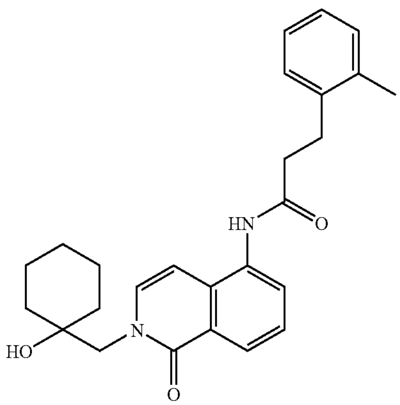 | 418.53 | 419.49 | * |
| 85 | 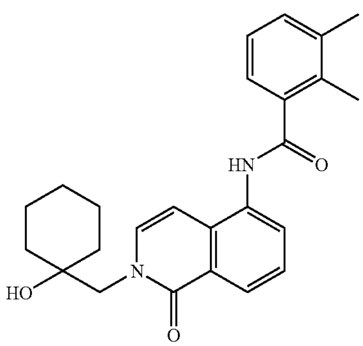 | 404.51 | 405.56 | * |
| 86 | 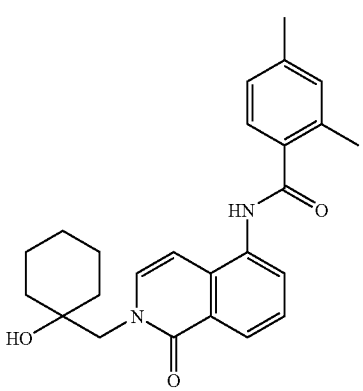 | 404.51 | 405.56 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 87 | 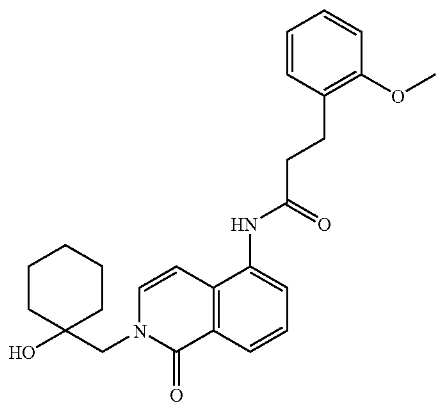 | 434.53 | 435.57 | * |
| 88 | 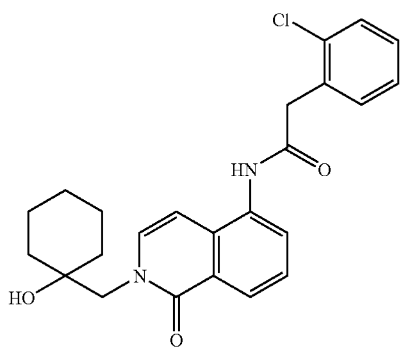 | 424.93 | 425.16 | * |
| 89 | 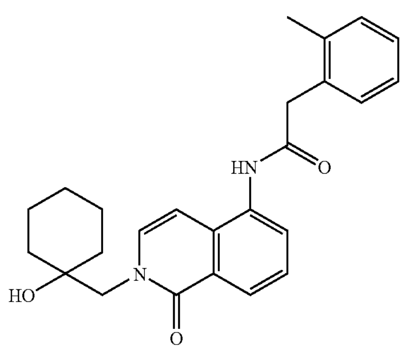 | 404.51 | 405.54 | * |
| 90 | 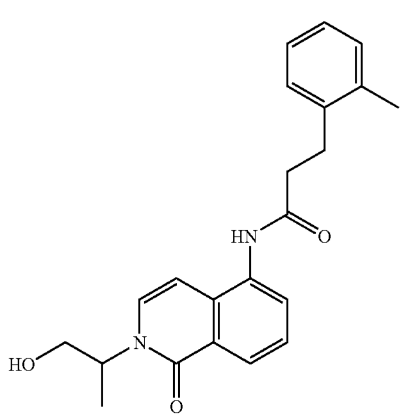 | 364.44 | 365.41 | ** |

TABLE 1-continued

| IL-1β % Inhibition of Exemplary Compounds | | | | |
|---|---|---|---|---|
| ID | Structure | MW | MS (Obs) | IL-1β % Inhib. @ 0.3 or 0.1 μM |
| 91 | | 380.44 | 381.35 | * |
| 92 | | 386.83 | 387.18 | * |
| 93 | | 366.41 | 367.35 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 94 | 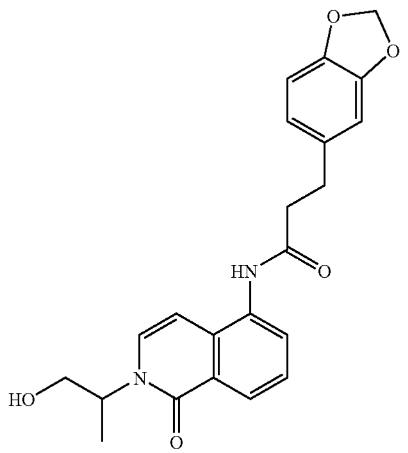 | 394.42 | 395.28 | * |
| 95 | 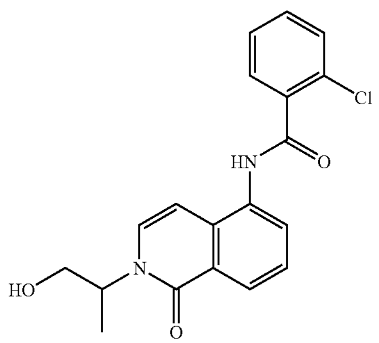 | 356.81 | 357.47 | * |
| 96 | 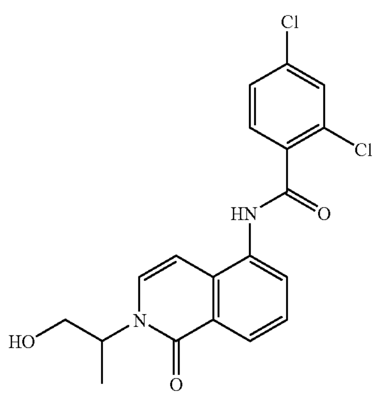 | 391.25 | 391.29 | * |
| 97 | 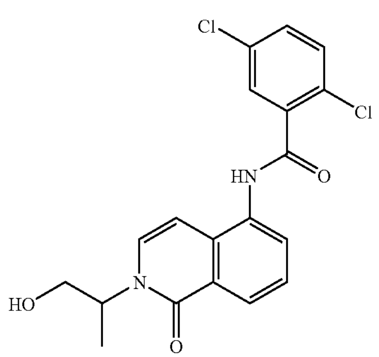 | 391.25 | 391.30 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 98 | 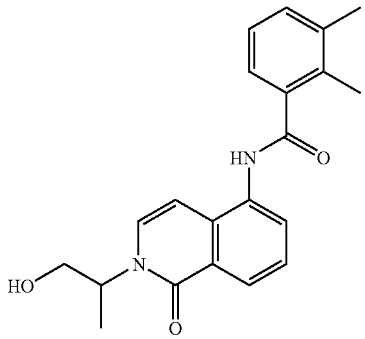 | 350.42 | 351.47 | * |
| 99 | 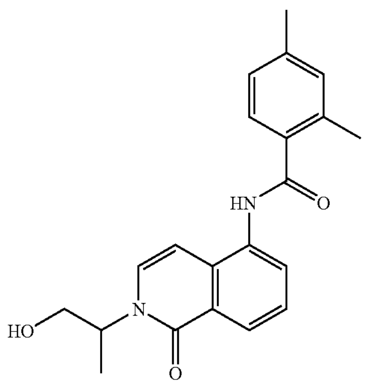 | 350.42 | 351.48 | * |
| 100 | 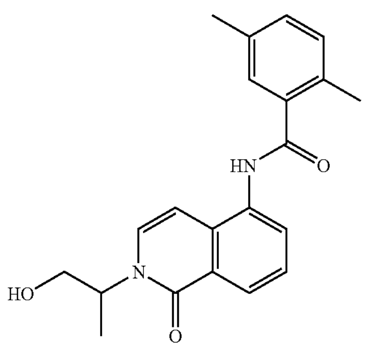 | 350.42 | 351.47 | * |
| 101 | 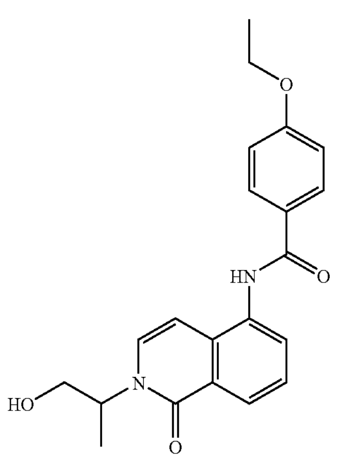 | 366.41 | 367.23 | * |

TABLE 1-continued
IL-1β % Inhibition of Exemplary Compounds
| ID | Structure | MW | MS (Obs) | IL-1β % Inhib. @ 0.3 or 0.1 μM |
|----|-----------|------|----------|-------------------------------|
| 102 | 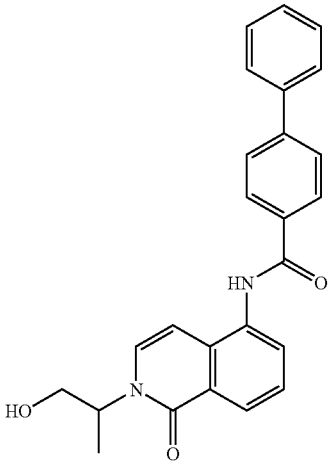 | 398.46 | 399.20 | * |
| 103 | 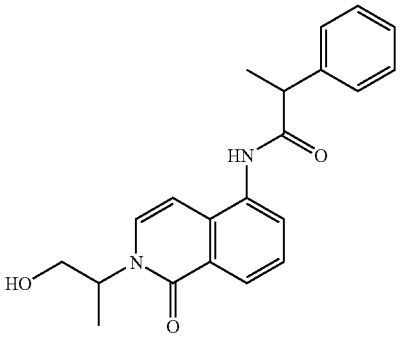 | 350.42 | 351.31 | * |
| 104 | 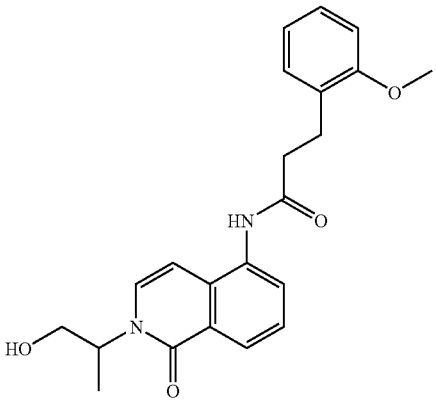 | 380.44 | 381.33 | * |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 105 | | 380.44 | 381.48 | * |
| 106 | | 372.42 | 373.30 | * |
| 107 | | 366.41 | 367.32 | * |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 108 | | 396.44 | 397.29 | * |
| 109 | | 396.44 | 397.30 | * |
| 110 | | 366.41 | 367.34 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 111 | 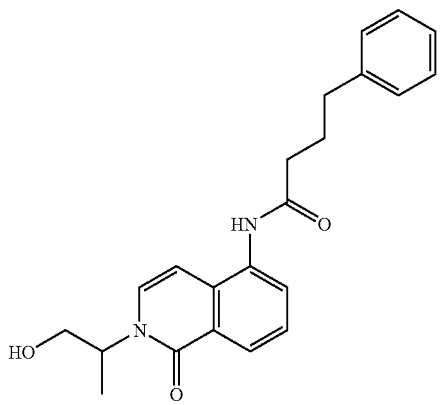 | 364.44 | 365.41 | * |
| 112 | 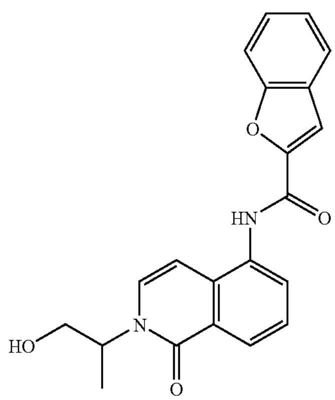 | 362.38 | 363.31 | * |
| 113 | 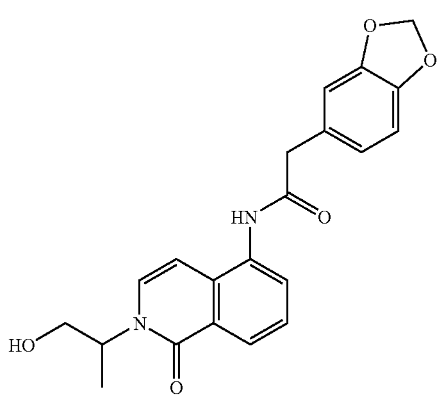 | 380.40 | 381.31 | * |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 114 | | 396.44 | 397.14 | * |
| 115 | | 370.83 | 371.12 | * |
| 116 | | 380.40 | 381.30 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 117 | 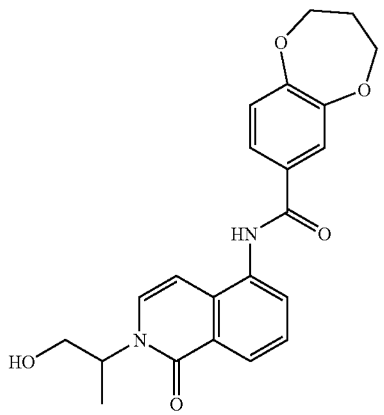 | 394.42 | 395.27 | * |
| 118 | 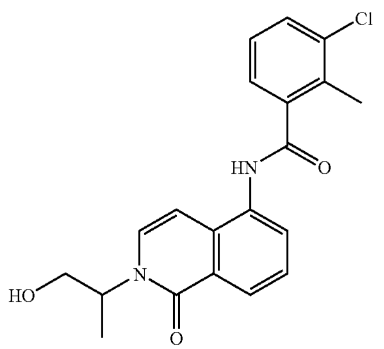 | 370.83 | 371.11 | ** |
| 119 | 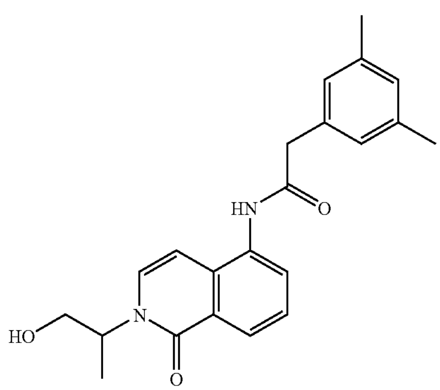 | 364.44 | 365.36 | * |
| 120 | 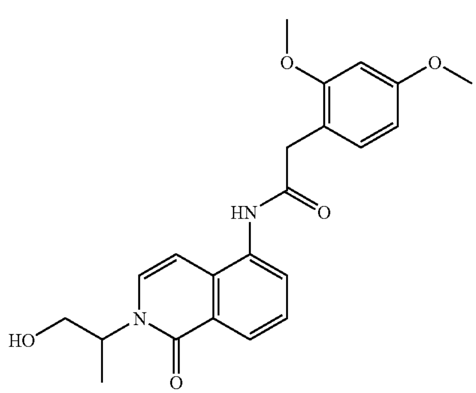 | 396.44 | 397.29 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 121 | 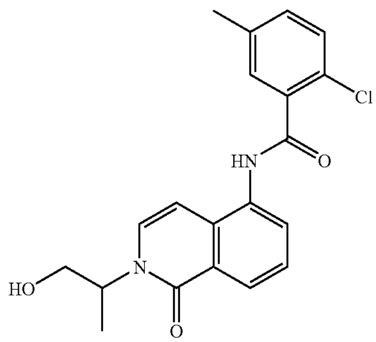 | 370.83 | 371.12 | * |
| 122 | 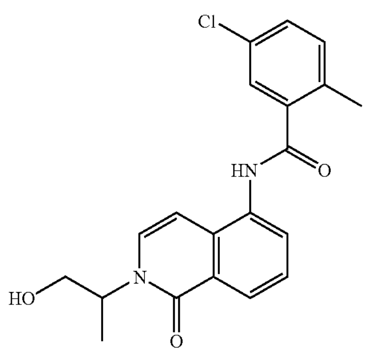 | 370.83 | 371.11 | * |
| 123 | 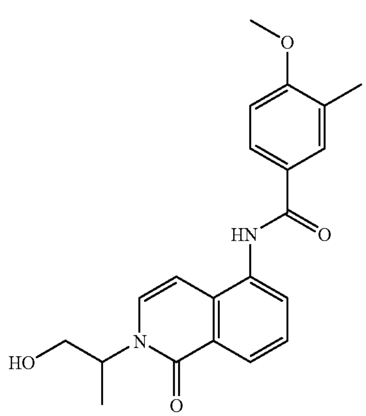 | 366.41 | 367.32 | * |

TABLE 1-continued

IL-1β % Inhibition of Exemplary Compounds

| ID | Structure | MW | MS (Obs) | IL-1β % Inhib. @ 0.3 or 0.1 μM |
|----|-----------|-----|----------|-------------------------------|
| 124 | 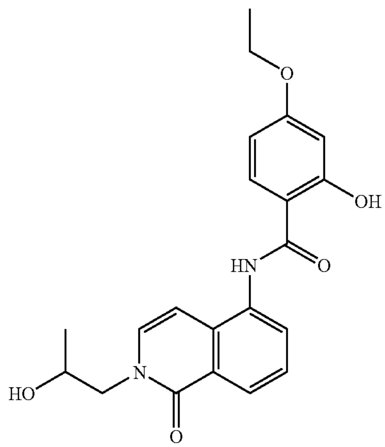 | 382.41 | 383.43 | * |
| 125 | 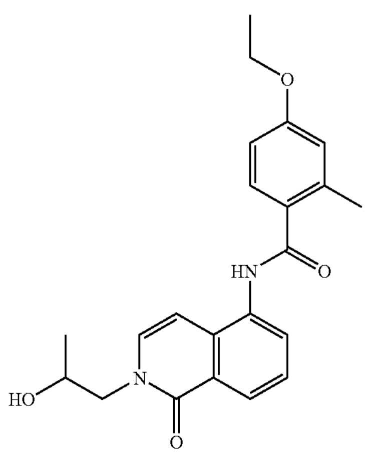 | 366.41 | 367.28 | * |
| 126 | 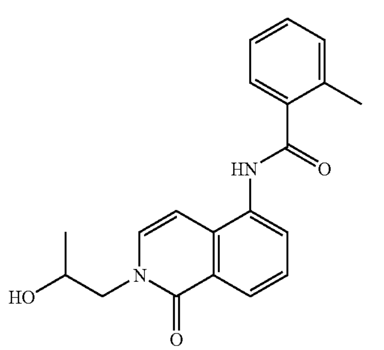 | 364.44 | 365.42 | ** |

TABLE 1-continued

IL-1β % Inhibition of Exemplary Compounds

| ID | Structure | MW | MS (Obs) | IL-1β % Inhib. @ 0.3 or 0.1 μM |
|----|-----------|------|----------|-------------------------------|
| 127 | 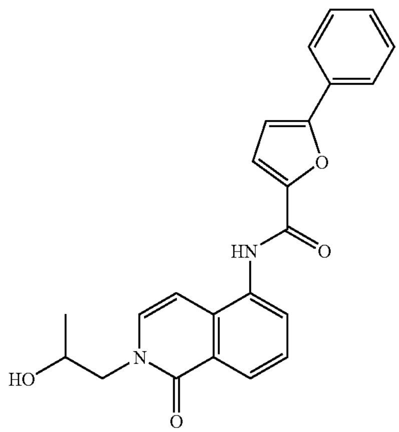 | 388.42 | 389.23 | * |
| 128 | 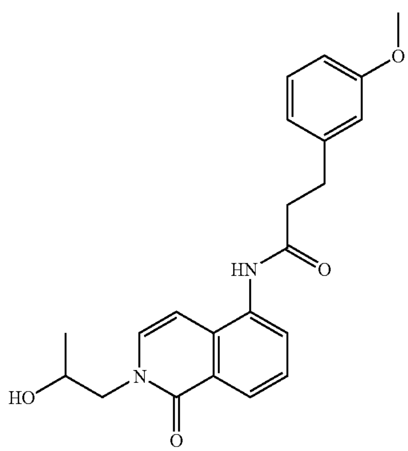 | 380.44 | 381.33 | * |
| 129 | 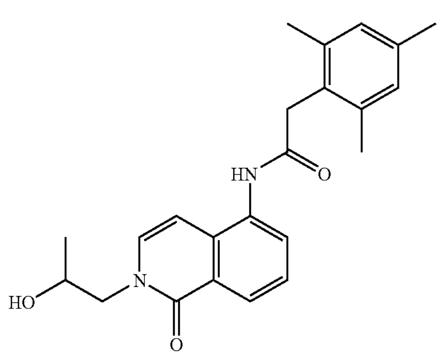 | 378.47 | 379.47 | * |

TABLE 1-continued

IL-1β % Inhibition of Exemplary Compounds

| ID | Structure | MW | MS (Obs) | IL-1β % Inhib. @ 0.3 or 0.1 μM |
|----|-----------|-----|----------|-------------------------------|
| 130 | 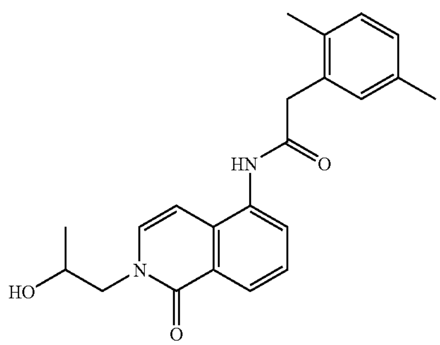 | 364.44 | 365.37 | ** |
| 131 | 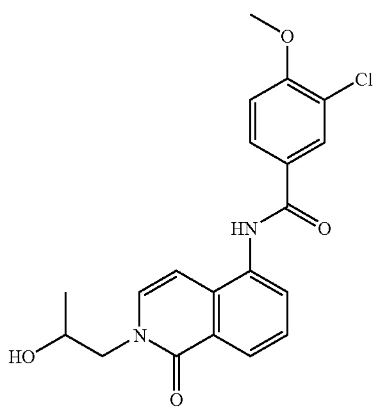 | 386.83 | 387.17 | * |
| 132 | 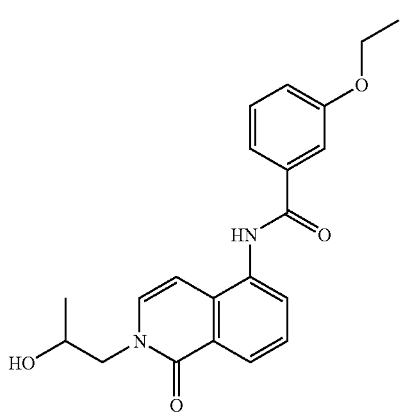 | 366.41 | 367.35 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 133 | 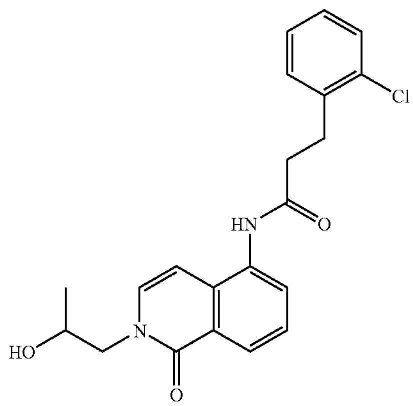 | 384.86 | 385.49 | ** |
| 134 | 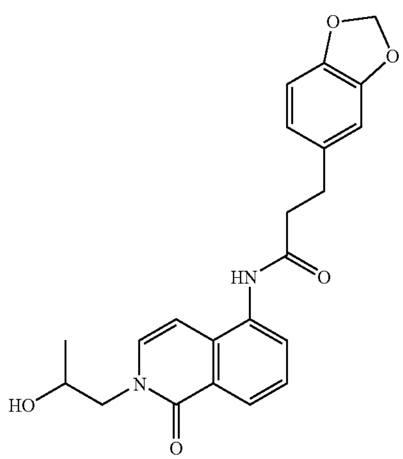 | 394.42 | 395.28 | * |
| 135 | 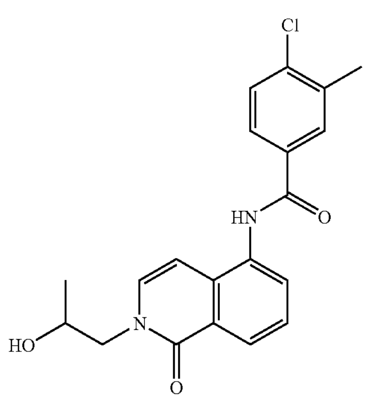 | 370.83 | 371.10 | * |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 136 | 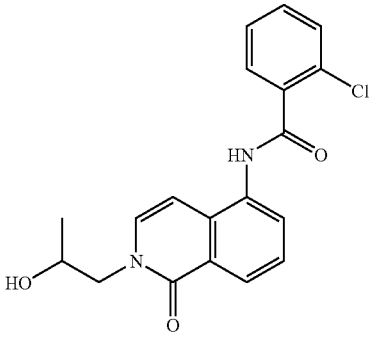 | 356.81 | 357.46 | * |
| 137 | 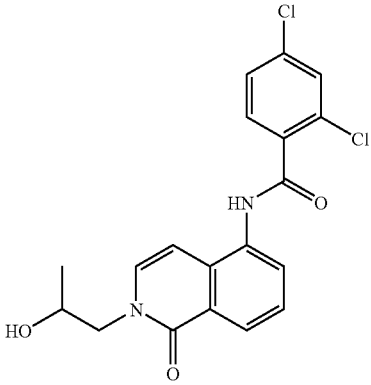 | 391.25 | 391.31 | * |
| 138 | 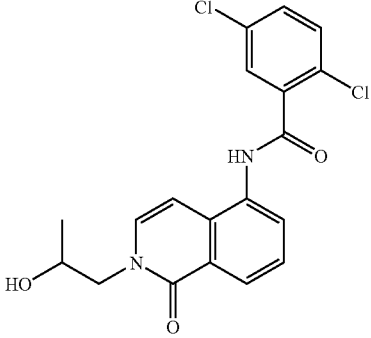 | 391.25 | 391.27 | * |
| 139 | 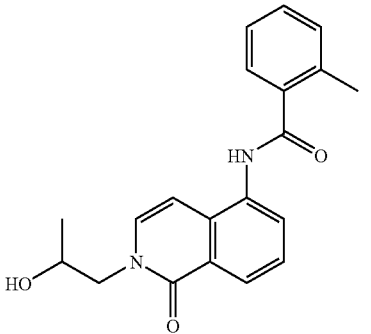 | 336.39 | 337.45 | ** |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 140 | 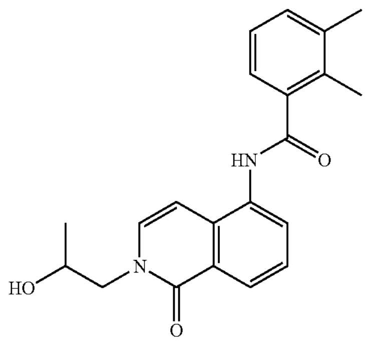 | 350.42 | 351.49 | * |
| 141 | 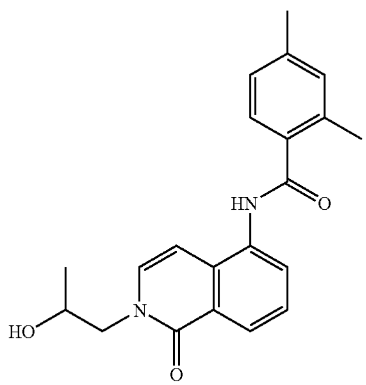 | 350.42 | 351.49 | * |
| 142 | 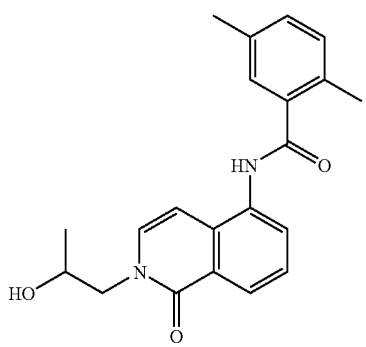 | 350.42 | 351.48 | * |
| 143 | 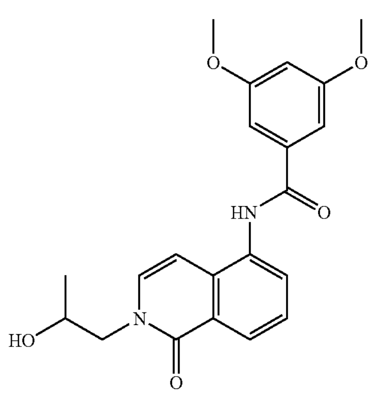 | 382.41 | 383.39 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 144 | 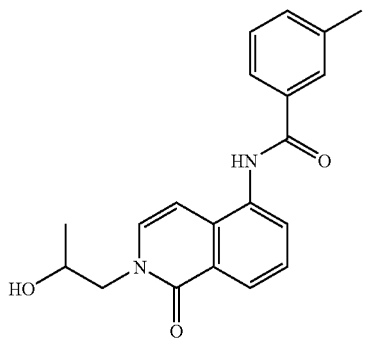 | 336.39 | 337.41 | * |
| 145 | 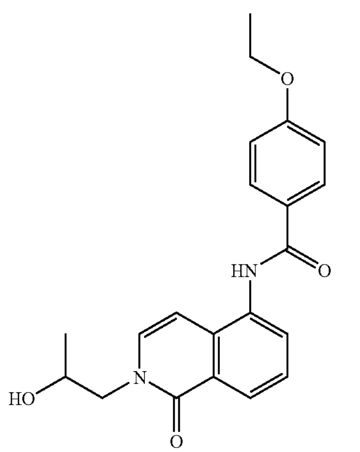 | 366.41 | 367.34 | * |
| 146 | 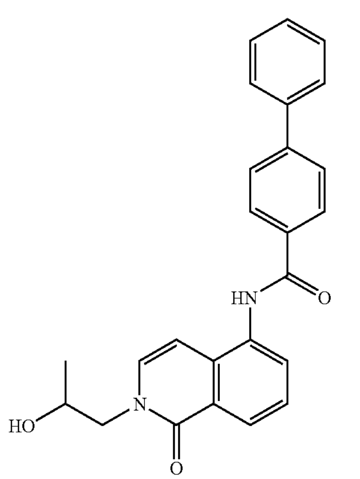 | 398.46 | 399.18 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 147 | 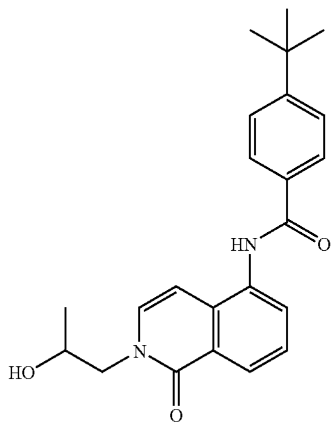 | 378.47 | 379.34 | * |
| 148 | 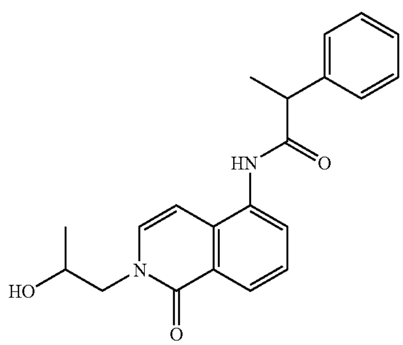 | 350.42 | 351.31 | * |
| 149 | 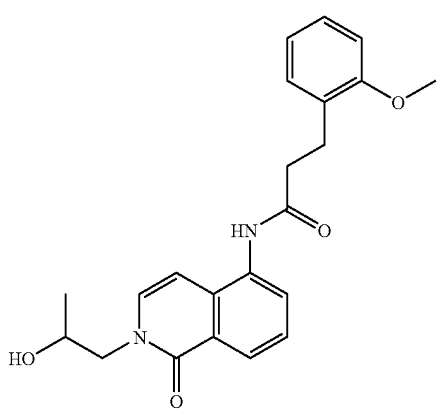 | 380.44 | 381.32 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 150 | 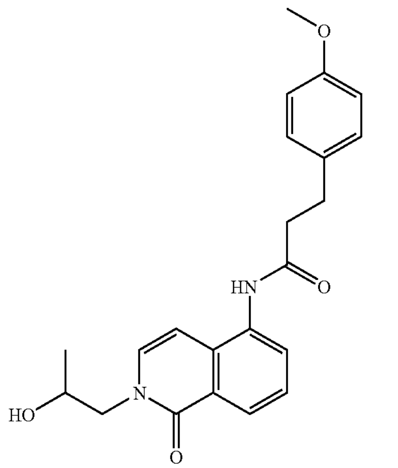 | 380.44 | 381.47 | ** |
| 151 | 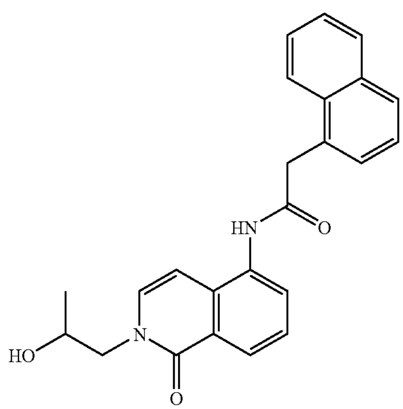 | 386.45 | 387.27 | * |
| 152 | 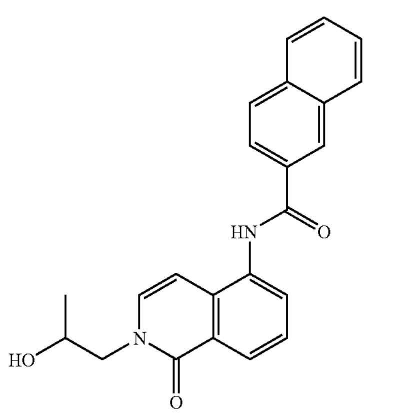 | 372.42 | 373.32 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 153 | 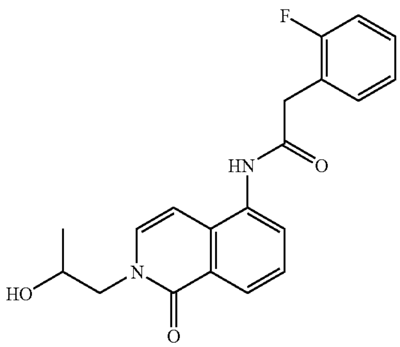 | 354.38 | 355.40 | * |
| 154 | 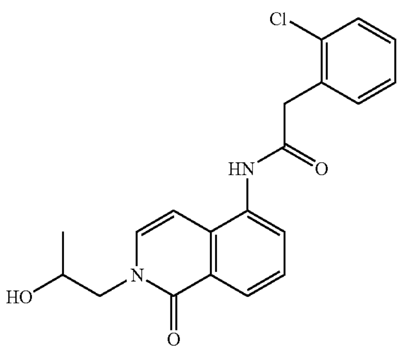 | 370.83 | 371.05 | * |
| 155 | 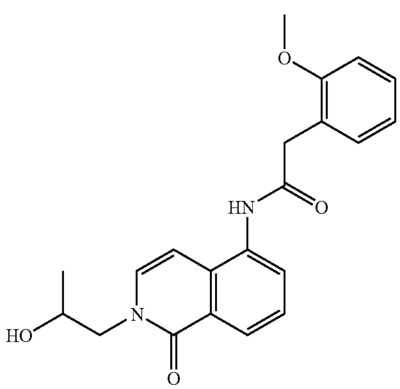 | 366.41 | 367.34 | * |
| 156 | 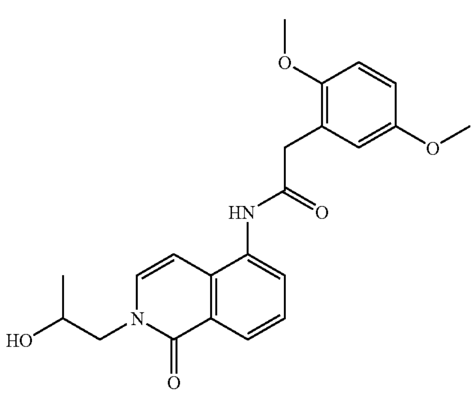 | 396.44 | 397.30 | ** |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 157 | 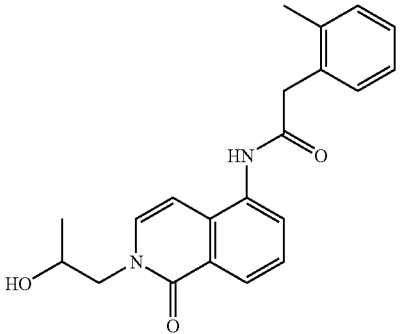 | 350.42 | 351.47 | * |
| 158 | 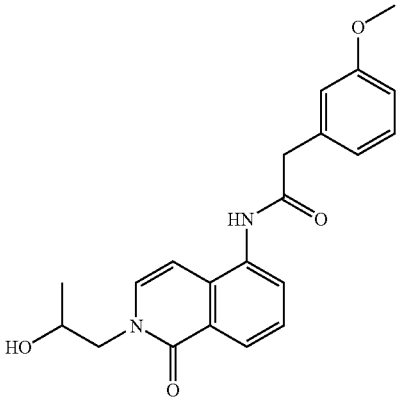 | 366.41 | 367.32 | * |
| 159 | 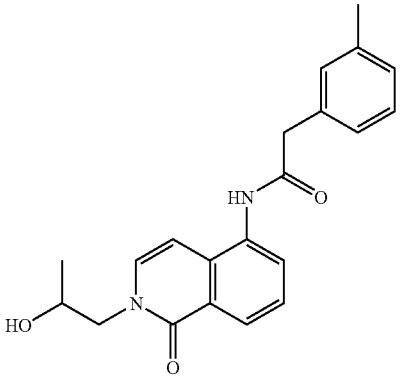 | 350.42 | 351.45 | * |
| 160 | 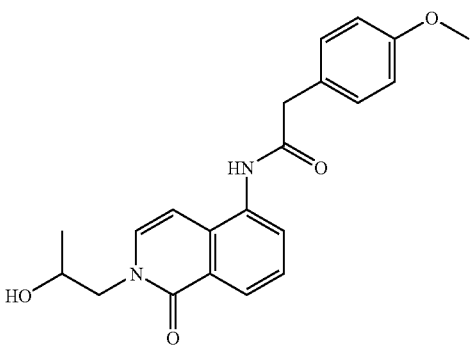 | 366.41 | 367.30 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 161 | 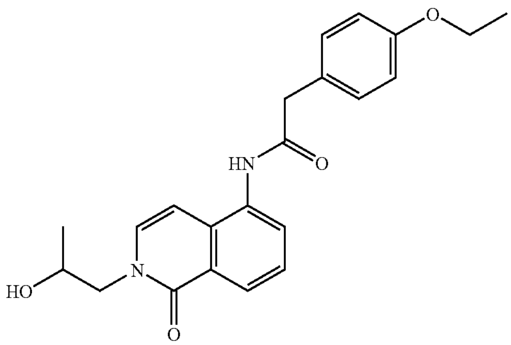 | 380.44 | 381.46 | * |
| 162 | 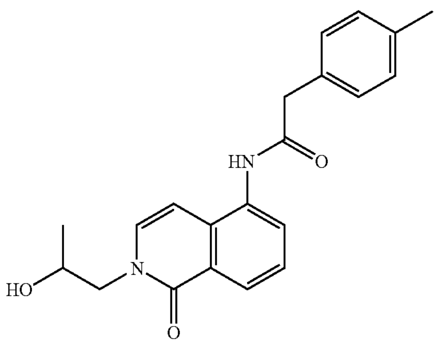 | 350.42 | 351.46 | * |
| 163 | 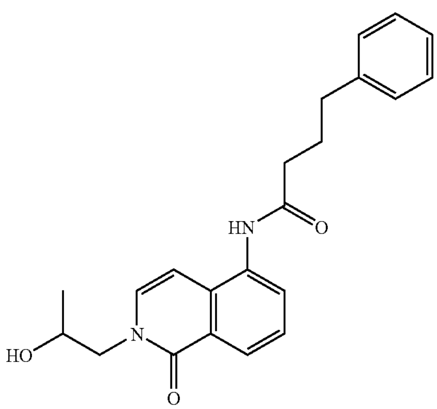 | 364.44 | 365.41 | * |
| 164 | 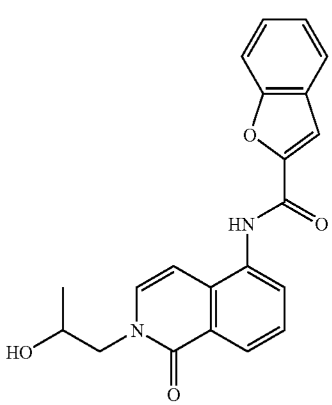 | 362.38 | 363.30 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 165 | 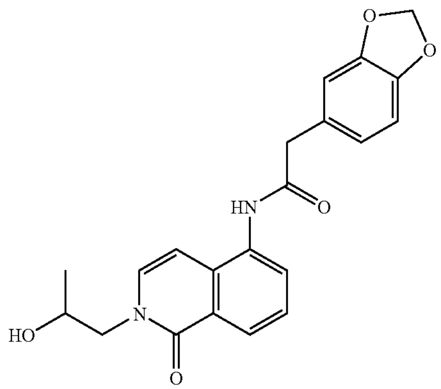 | 380.40 | 381.46 | * |
| 166 | 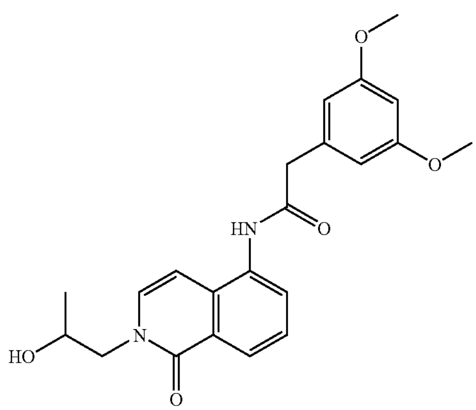 | 396.44 | 397.29 | * |
| 167 | 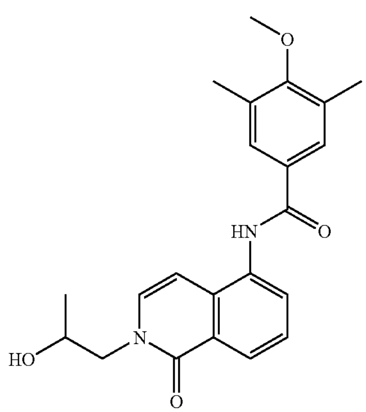 | 380.44 | 381.47 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 168 | 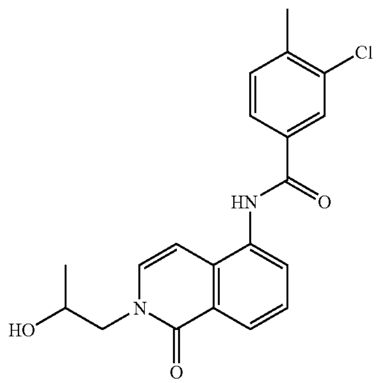 | 370.83 | 371.08 | * |
| 169 | 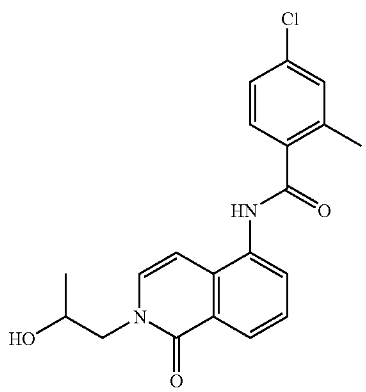 | 370.83 | 371.12 | * |
| 170 | 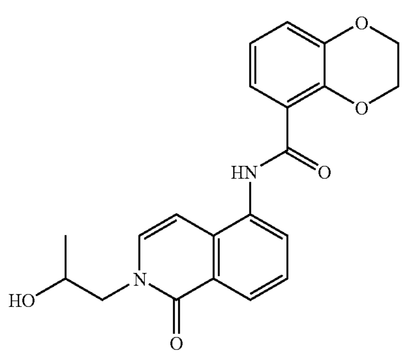 | 380.40 | 381.46 | ** |
| 171 | 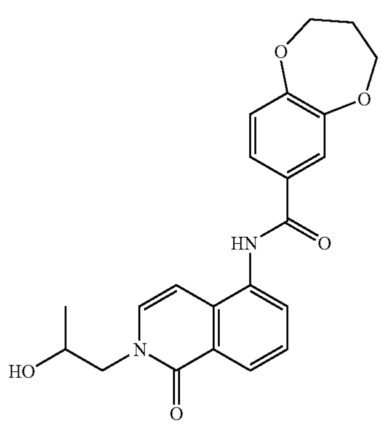 | 394.42 | 395.27 | * |

TABLE 1-continued

IL-1β % Inhibition of Exemplary Compounds

| ID | Structure | MW | MS (Obs) | IL-1β % Inhib. @ 0.3 or 0.1 μM |
|----|-----------|-----|----------|-------------------------------|
| 172 | 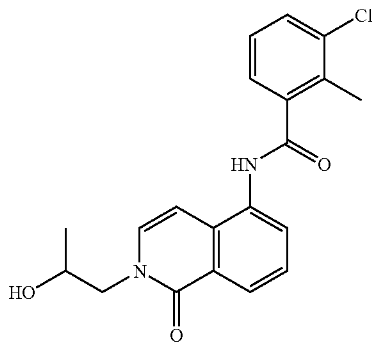 | 370.83 | 371.07 | *** |
| 173 | 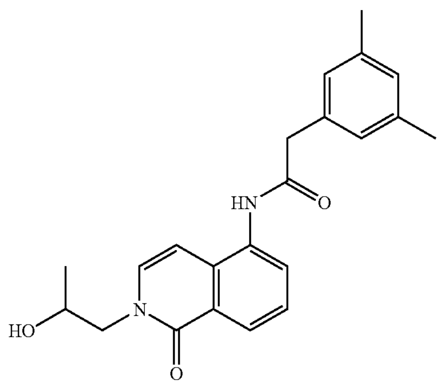 | 364.44 | 365.38 | ** |
| 174 | 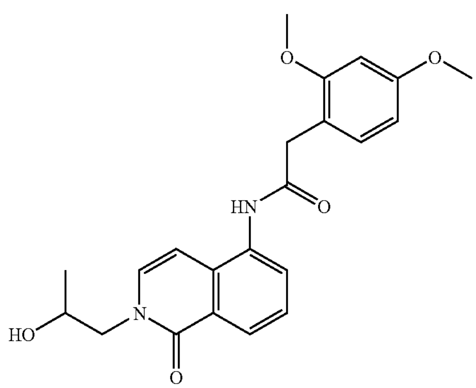 | 396.44 | 397.12 | * |
| 175 | 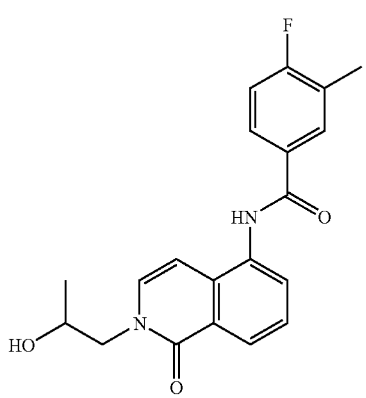 | 354.38 | 355.42 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 176 | 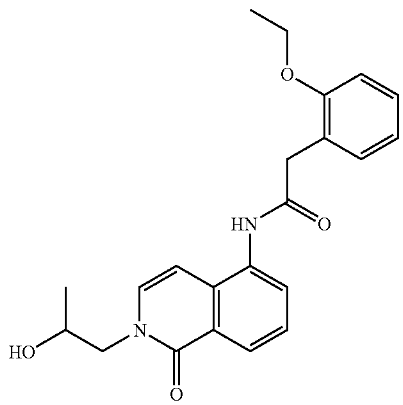 | 380.44 | 381.47 | * |
| 177 | 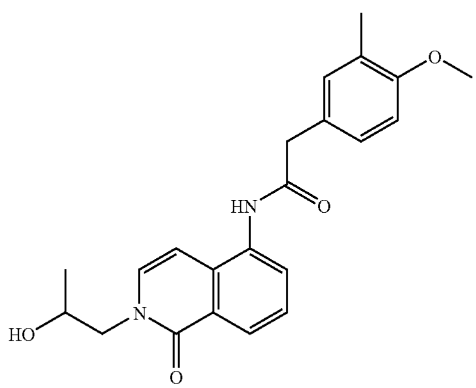 | 380.44 | 381.47 | * |
| 178 | 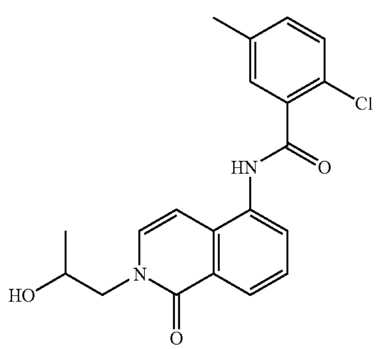 | 370.83 | 371.09 | * |
| 179 | 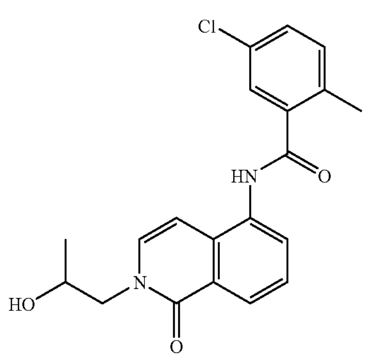 | 370.83 | 371.07 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 180 | 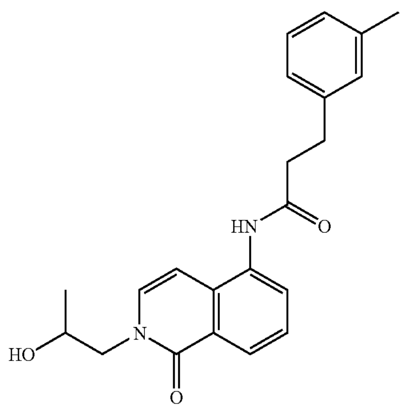 | 364.44 | 365.39 | * |
| 181 | 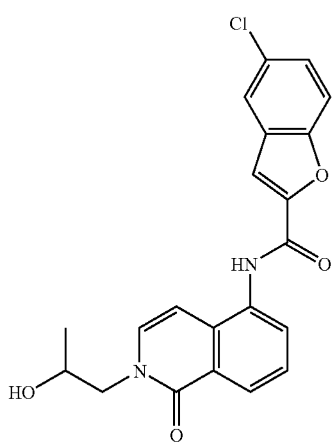 | 396.83 | 397.21 | * |
| 182 | 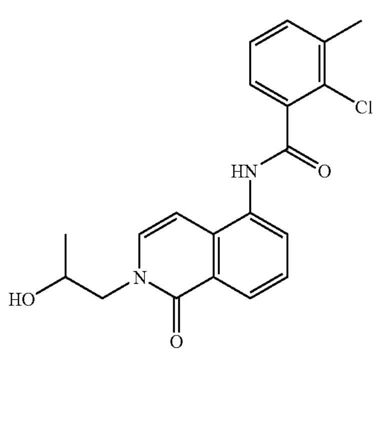 | 370.83 | 371.08 | * |

TABLE 1-continued
| IL-1β % Inhibition of Exemplary Compounds | | | | |
|---|---|---|---|---|
| ID | Structure | MW | MS (Obs) | IL-1β % Inhib. @ 0.3 or 0.1 μM |
| 183 | 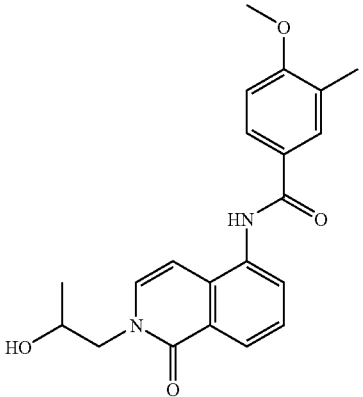 | 366.41 | 367.35 | ** |
| 184 | 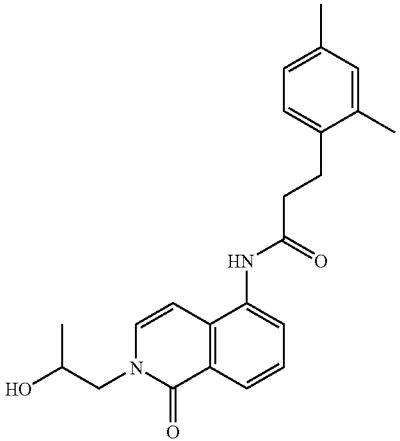 | 378.47 | 379.45 | |
| 185 | 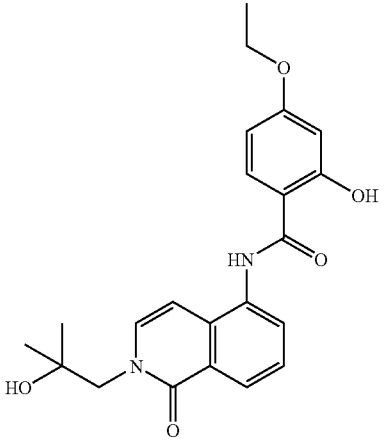 | 396.44 | 397.14 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 186 | 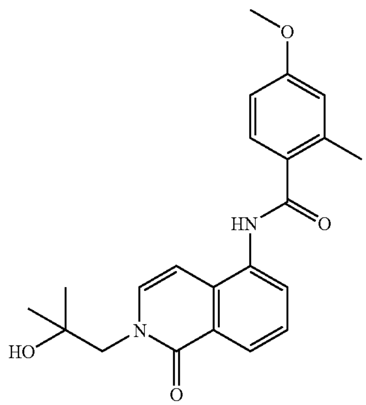 | 380.44 | 381.33 | * |
| 187 | 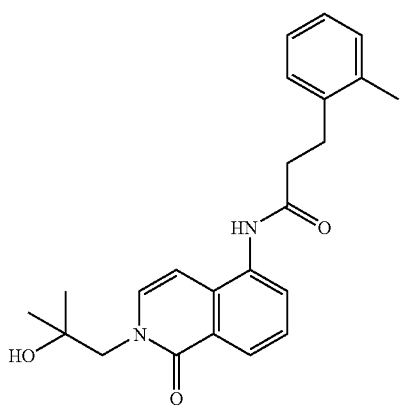 | 378.47 | 379.39 | * |
| 188 | 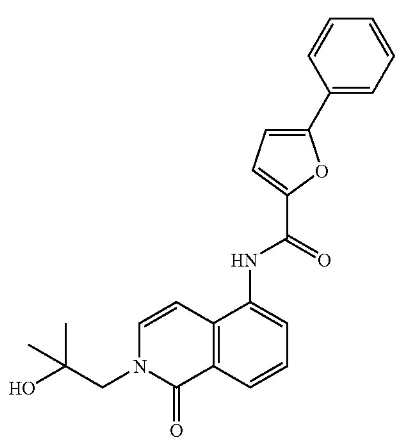 | 402.45 | 403.23 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 189 | 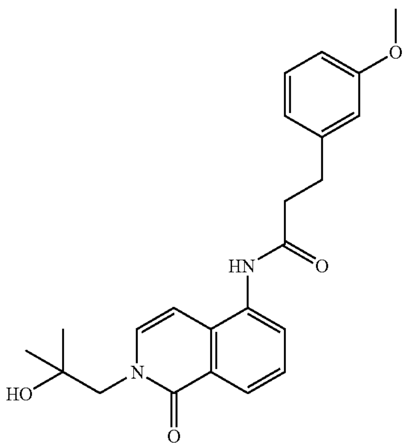 | 394.47 | 395.29 | * |
| 190 | 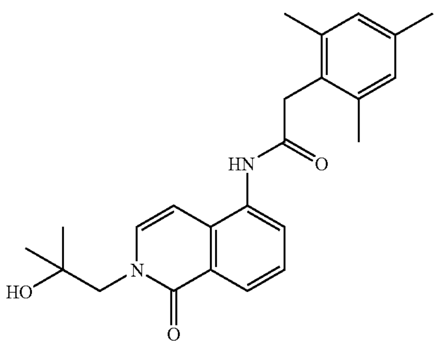 | 392.50 | 393.36 | * |
| 191 | 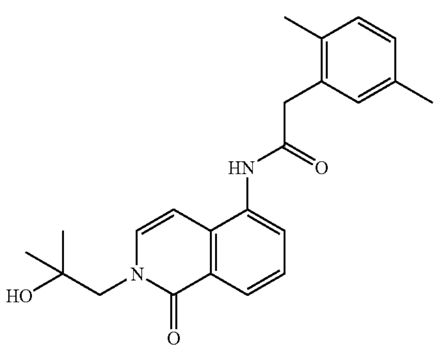 | 378.47 | 379.45 | * |
| 192 | 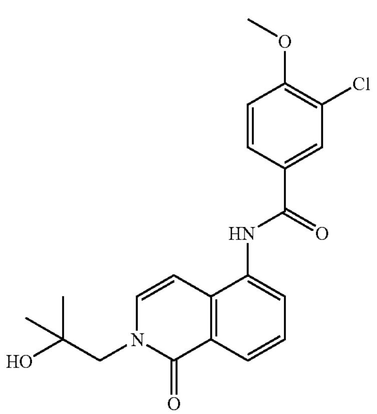 | 400.86 | 401.35 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 193 | 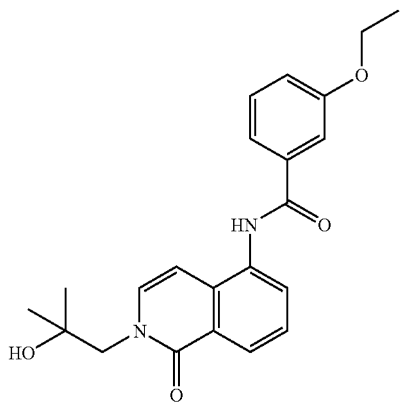 | 380.44 | 381.47 | * |
| 194 | 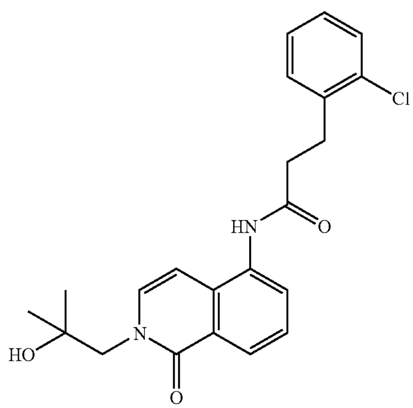 | 398.89 | 399.15 | * |
| 195 | 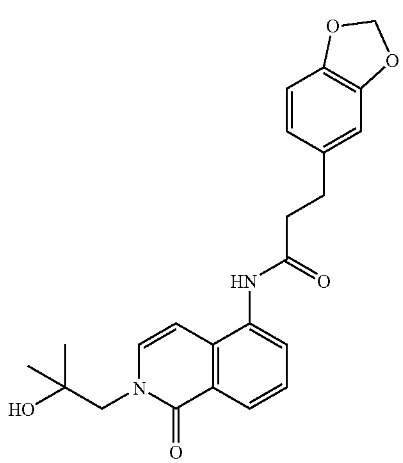 | 408.45 | 409.47 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 196 | 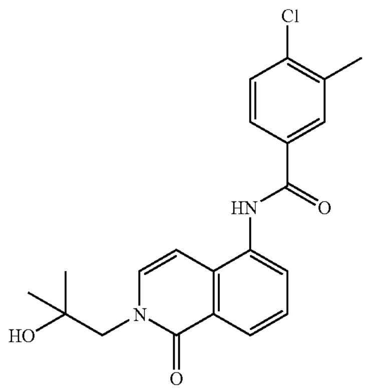 | 384.86 | 385.47 | * |
| 197 | 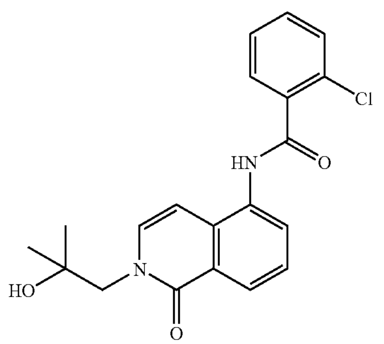 | 370.83 | 371.08 | *** |
| 198 | 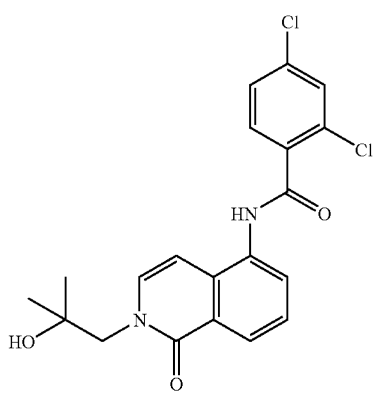 | 405.28 | 405.38 | * |
| 199 | 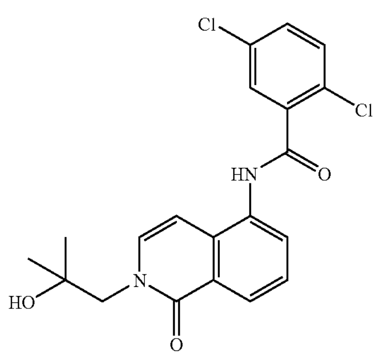 | 405.28 | 405.37 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 200 | 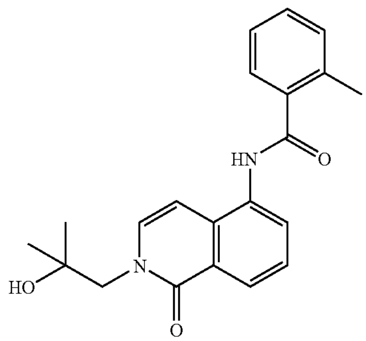 | 350.42 | 351.48 | * |
| 201 | 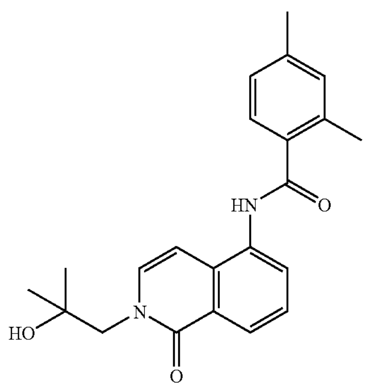 | 364.44 | 365.36 | * |
| 202 | 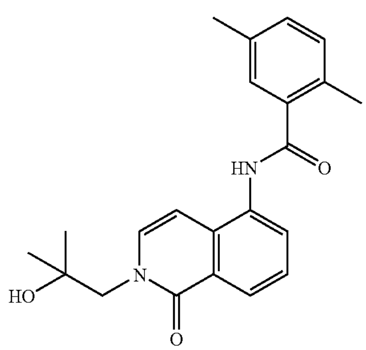 | 364.44 | 365.37 | * |
| 203 | 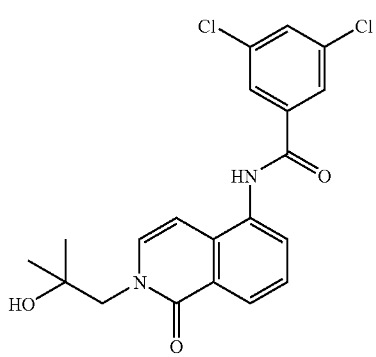 | 405.28 | 405.31 | * |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 204 | 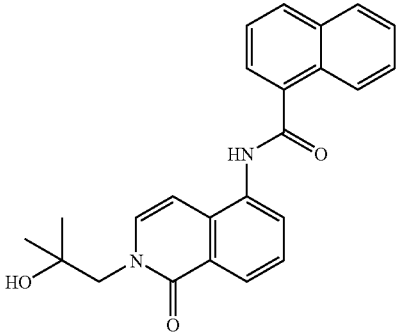 | 386.45 | 387.27 | * |
| 205 | 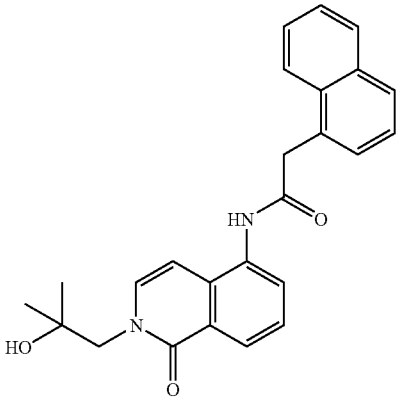 | 400.48 | 401.40 | * |
| 206 | 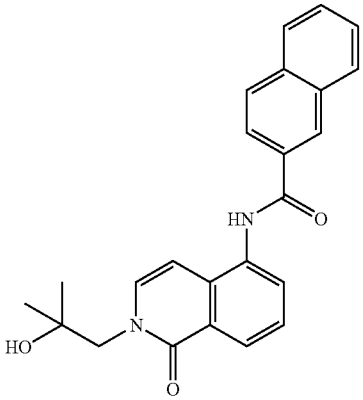 | 386.45 | 387.26 | * |
| 207 | 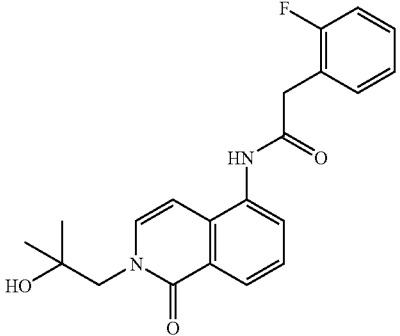 | 368.41 | 369.21 | * |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 208 | 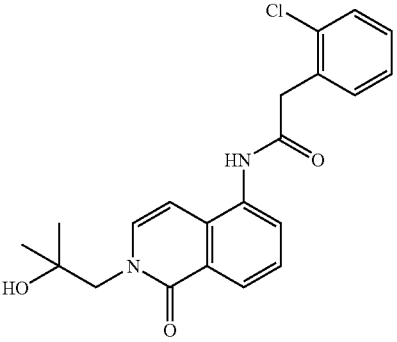 | 384.86 | 385.41 | * |
| 209 | 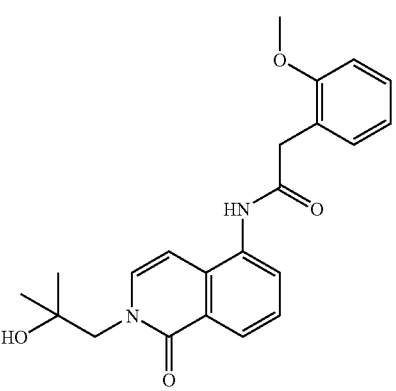 | 380.44 | 381.48 | * |
| 210 | 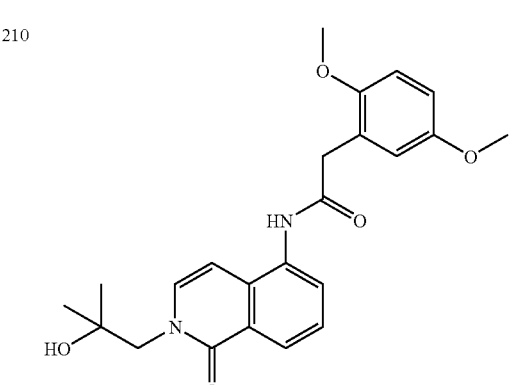 | 410.47 | 411.59 | * |
| 211 | 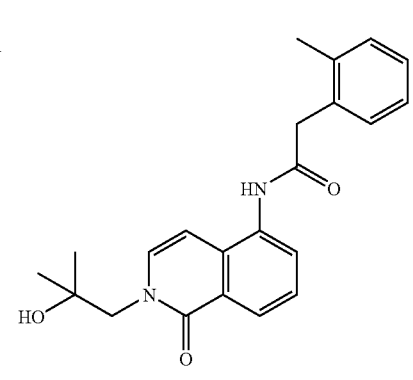 | 364.44 | 365.39 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 212 | 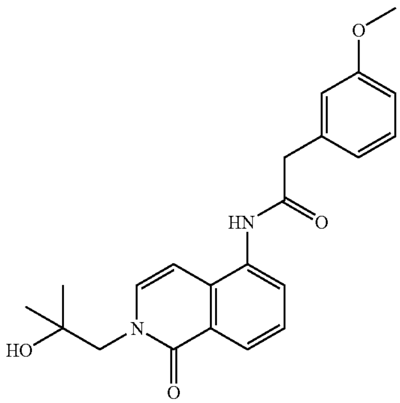 | 380.44 | 381.48 | ** |
| 213 | 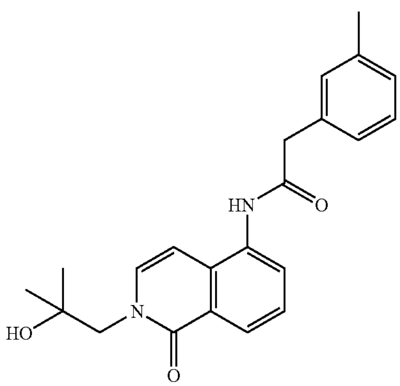 | 364.44 | 365.39 | * |
| 214 | 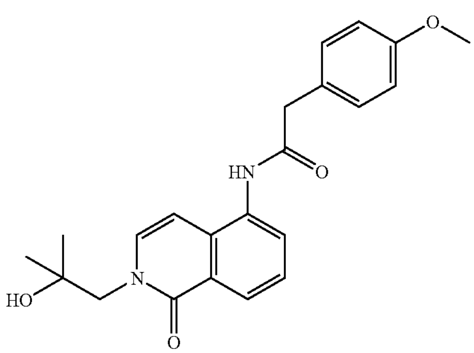 | 380.44 | 381.37 | * |
| 215 | 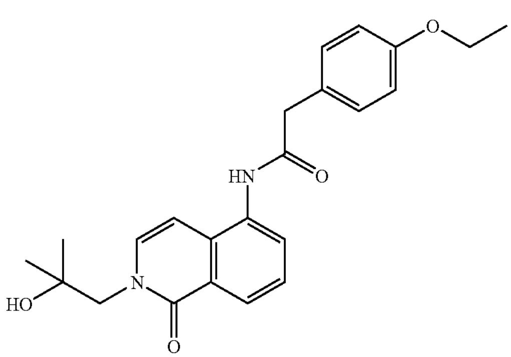 | 394.47 | 395.29 | ** |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 216 | 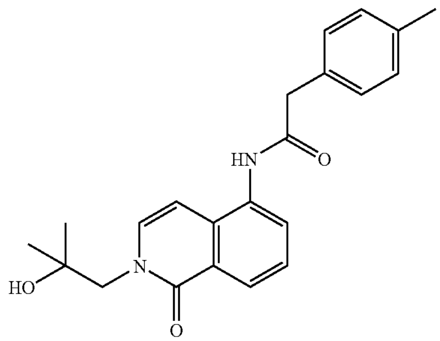 | 364.44 | 365.41 | * |
| 217 | 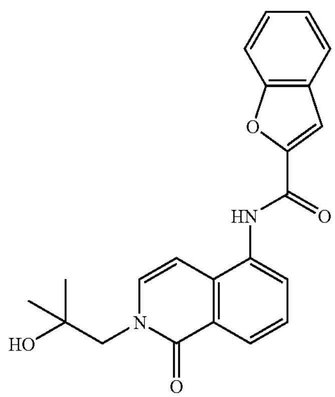 | 376.41 | 377.33 | * |
| 218 | 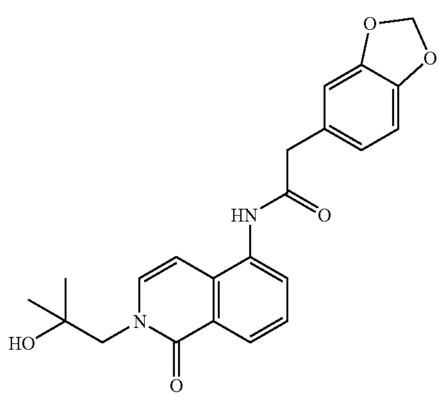 | 394.42 | 395.26 | * |
| 219 | 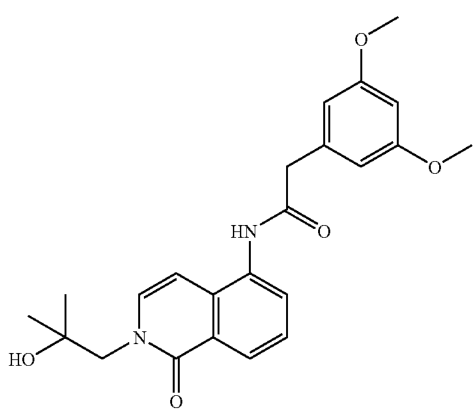 | 410.47 | 411.48 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 220 | 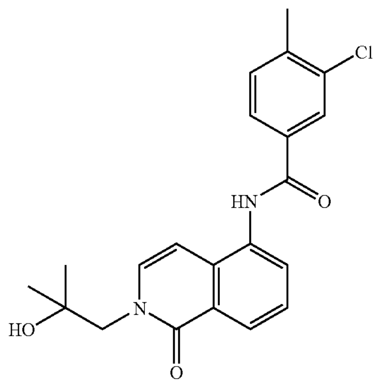 | 384.86 | 385.26 | ** |
| 221 | 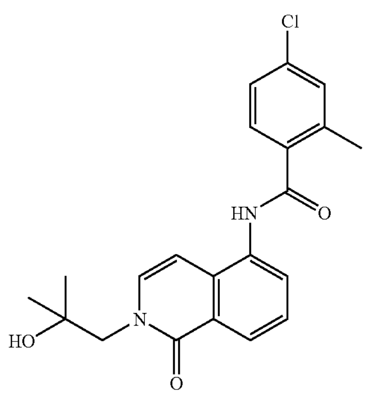 | 384.86 | 385.31 | ** |
| 222 | 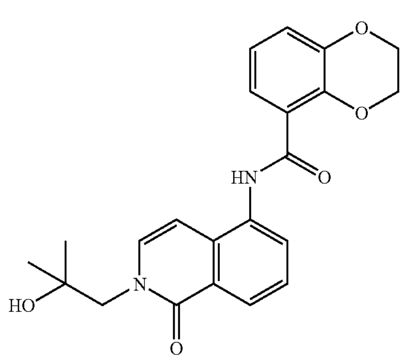 | 394.42 | 395.27 | * |

US 7,816,371 B2
TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 223 | 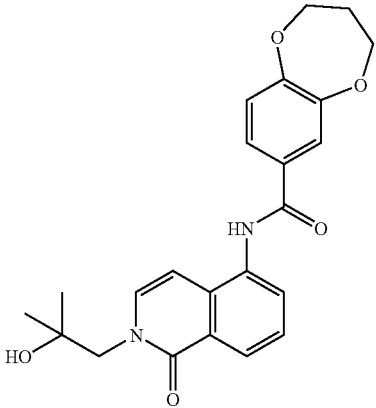 | 408.45 | 409.48 | * |
| 224 | 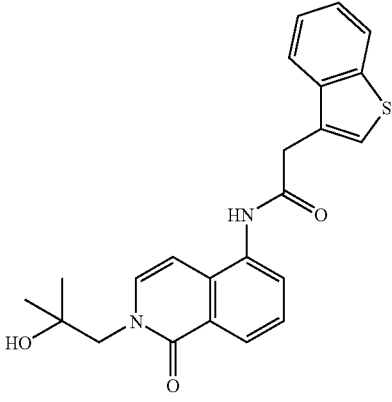 | 406.50 | 407.36 | ** |
| 225 | 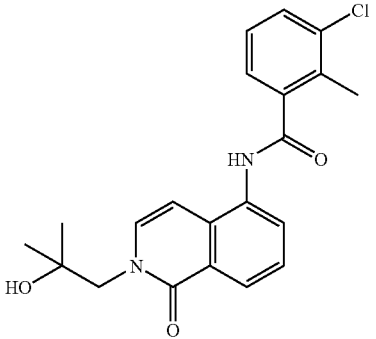 | 384.86 | 385.26 | * |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 226 | 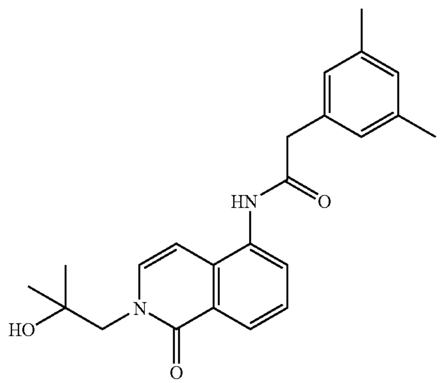 | 378.47 | 379.40 | * |
| 227 | 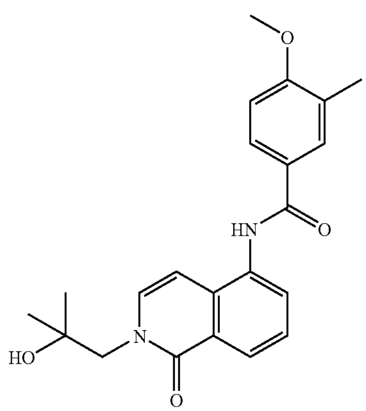 | 380.44 | 381.48 | * |
| 228 | 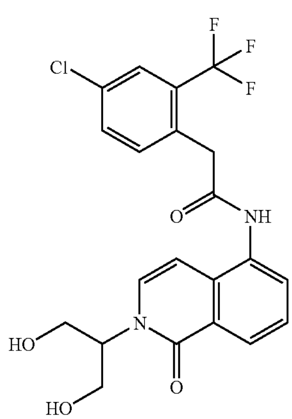 | 454.83 | 455.10 | +++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 229 | 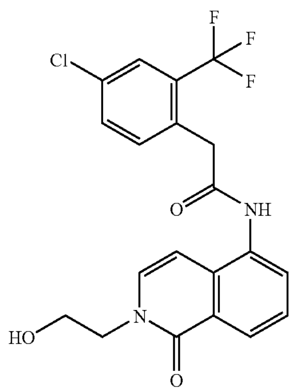 | 424.80 | 425.30 | +++ |
| 230 | 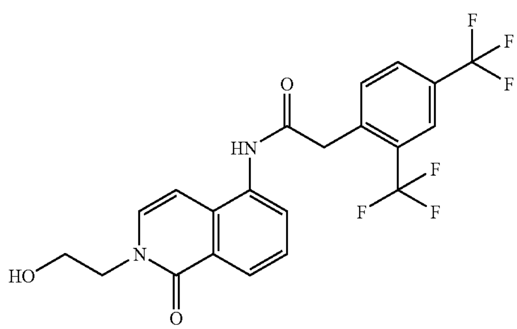 | 458.36 | 459.10 | ++++ |
| 231 | 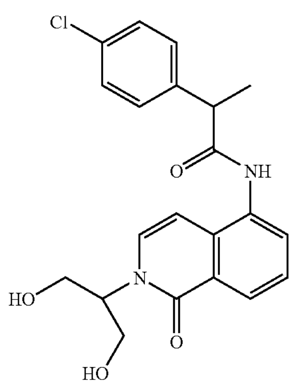 | 400.86 | 401.30 | ++ |
| 232 | 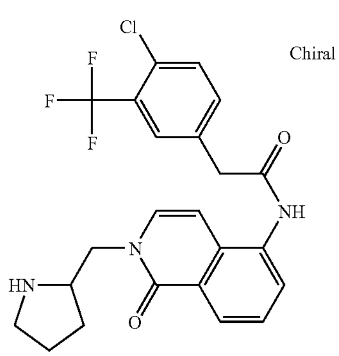 | 463.88 | 464.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 233 | 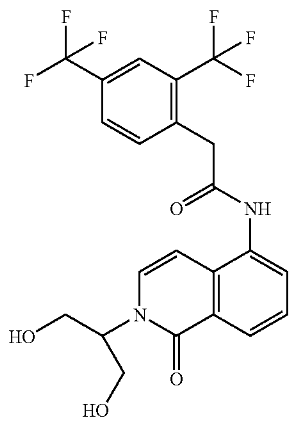 | 488.38 | 489.00 | ++ |
| 234 | 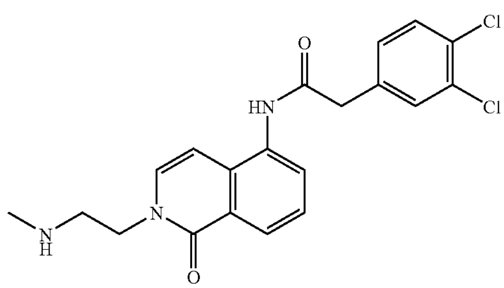 | 404.30 | 403.90 | +++ |
| 235 | 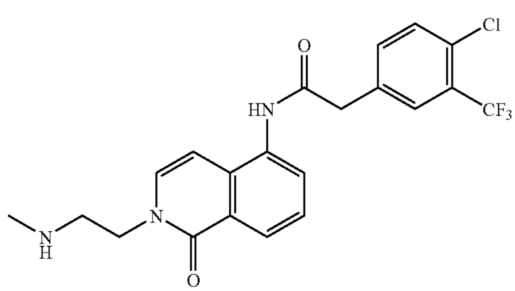 | 437.85 | 437.60 | ++++ |
| 236 | 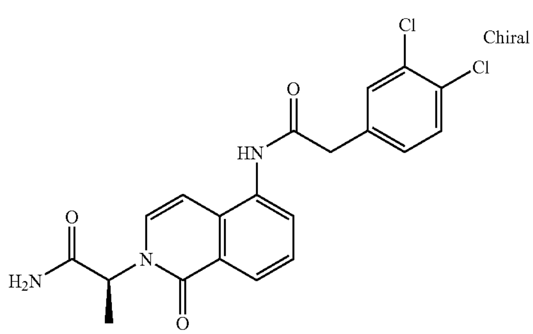 | 418.28 | 418.20 | ++++ |

TABLE 1-continued
IL-1β % Inhibition of Exemplary Compounds
| ID | Structure | MW | MS (Obs) | IL-1β % Inhib. @ 0.3 or 0.1 μM |
|----|-----------|-----|----------|-------------------------------|
| 237 | 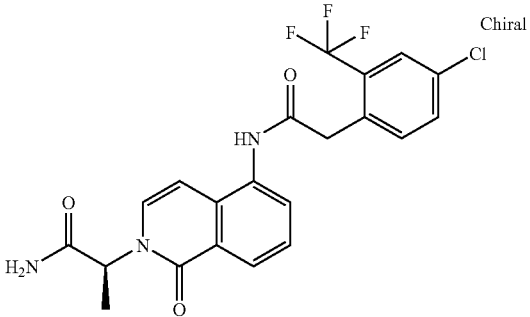 | 451.83 | 452.20 | ++++ |
| 238 | 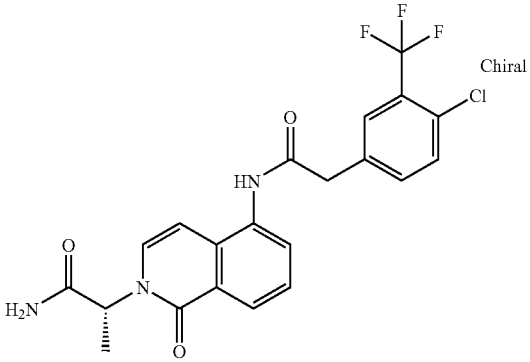 | 451.83 | 452.60 | ++++ |
| 239 | 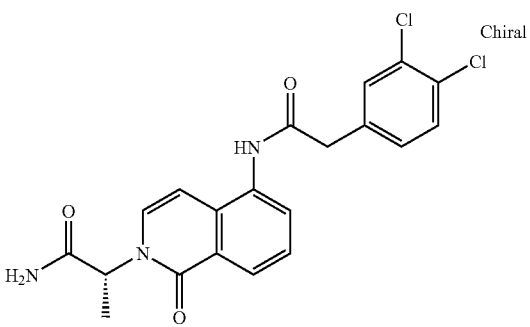 | 418.28 | 418.30 | ++++ |
| 240 | 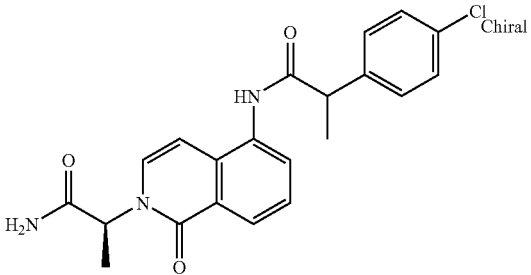 | 397.86 | 398.40 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 241 | 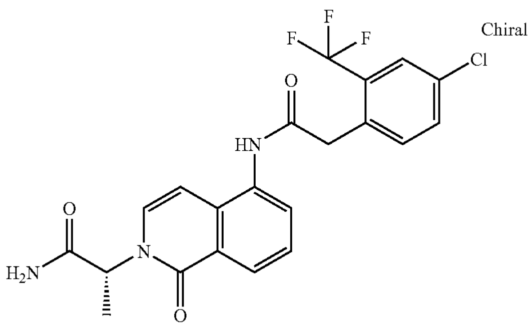 | 451.83 | 452.10 | ++++ |
| 242 | 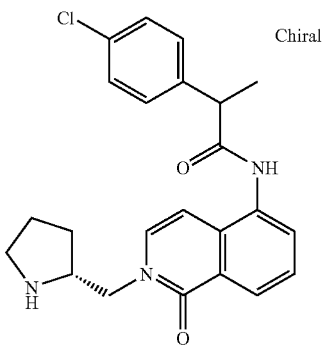 | 409.91 | 409.40 | ++ |
| 243 | 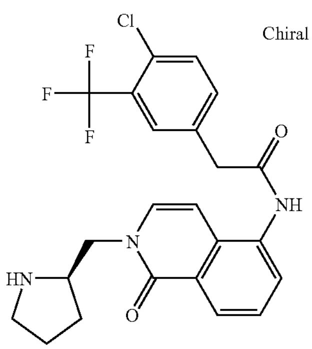 | 463.88 | 464.10 | ++++ |
| 244 | 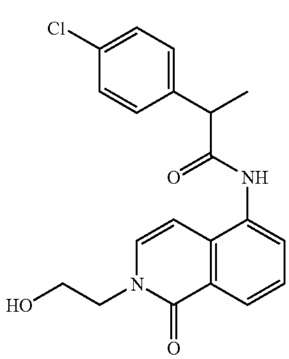 | 370.83 | 371.30 | ++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 245 | 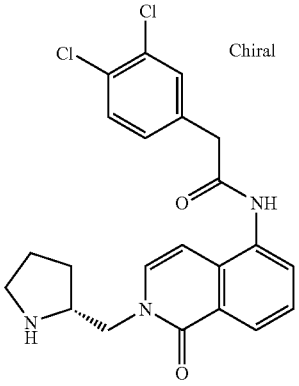 Chiral | 430.33 | 429.70 | ++++ |
| 246 | 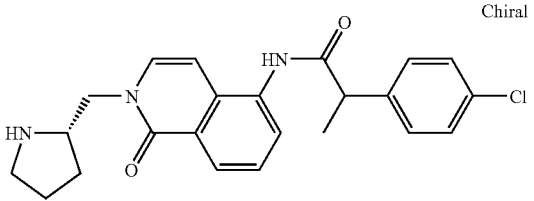 Chiral | 409.91 | 409.60 | +++ |
| 247 | 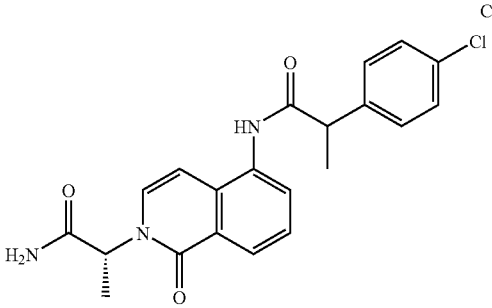 Chiral | 397.86 | 397.50 | ++++ |
| 248 | 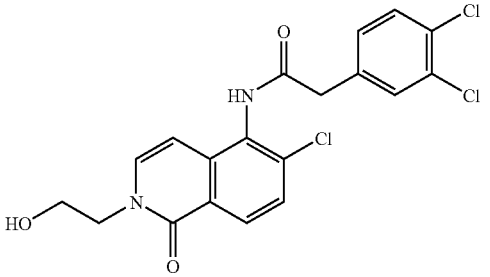 | 425.70 | 426.90 | + |
| 249 | 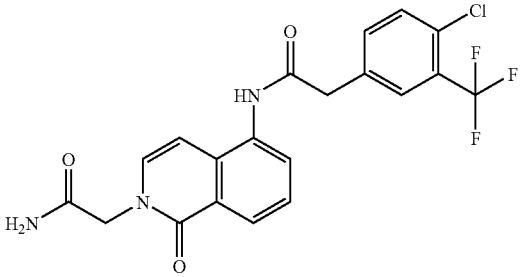 | 437.80 | 437.40 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 250 | 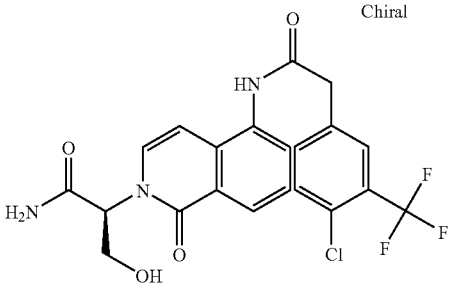 Chiral | 467.83 | 468.30 | ++++ |
| 251 | 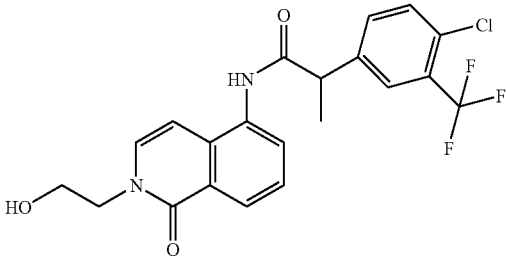 | 438.83 | 438.90 | ++++ |
| 252 | 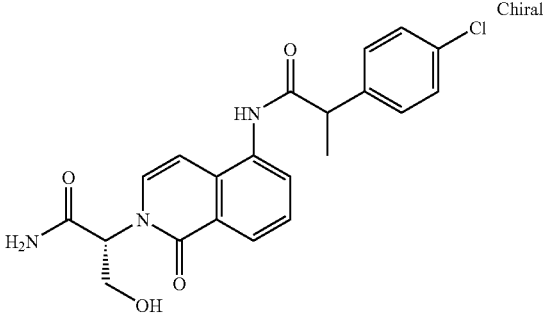 Chiral | 413.86 | 414.30 | +++ |
| 253 | 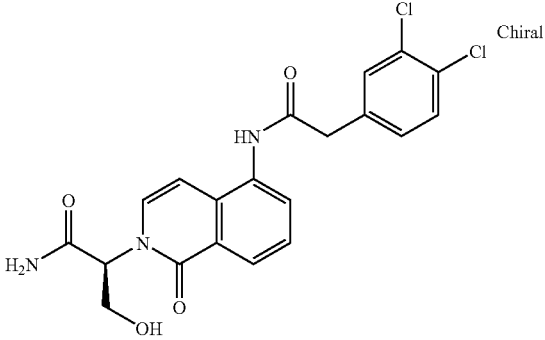 Chiral | 434.28 | 434.10 | ++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 254 | 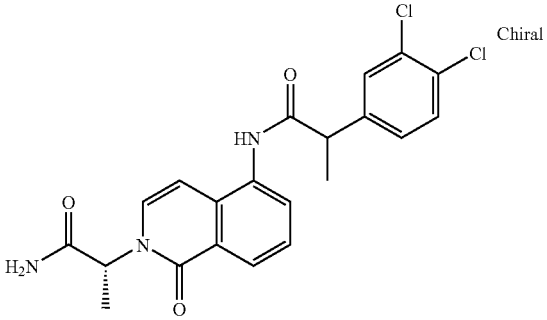 | 432.31 | 433.80 | ++++ |
| 255 | 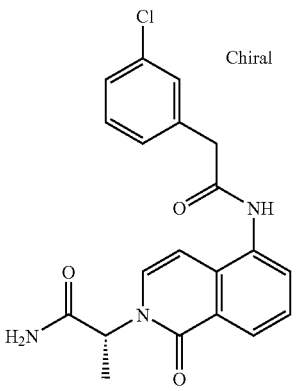 | 383.83 | 385.60 | ++++ |
| 256 | 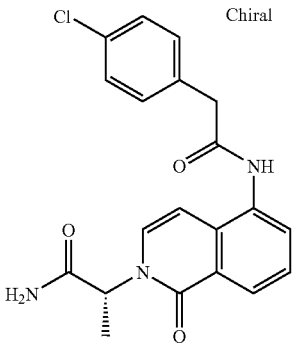 | 383.83 | 383.90 | ++++ |
| 257 | 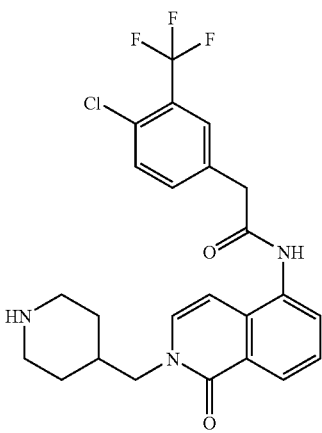 | 477.91 | 478.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 258 | 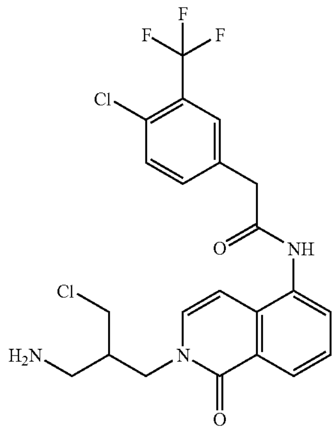 | 486.32 | 486.20 | ++++ |
| 259 | 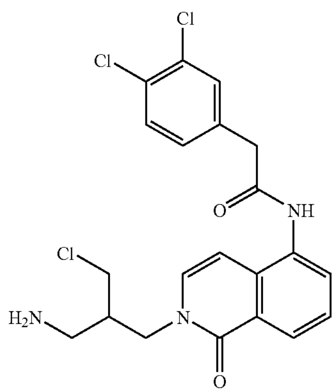 | 452.77 | 453.20 | +++ |
| 260 | 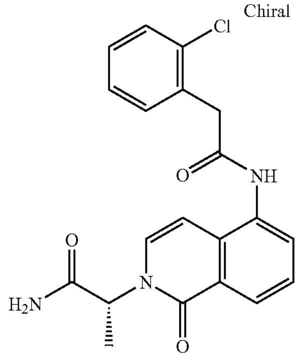 | 383.83 | 384.00 | + |
| 261 | 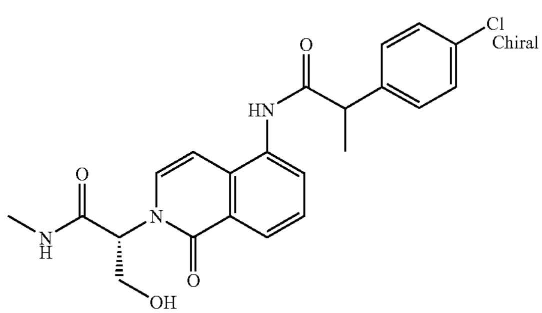 | 427.89 | 427.80 | +++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 262 | 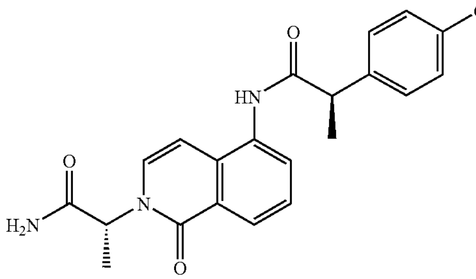 | 397.86 | 400.00 | ++++ |
| 263 | 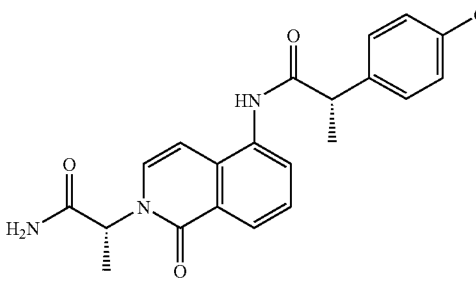 | 397.86 | 398.50 | ++++ |
| 264 | 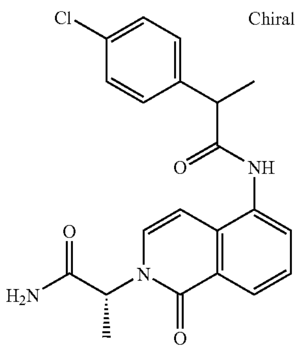 | 411.89 | 412.10 | ++ |
| 265 | 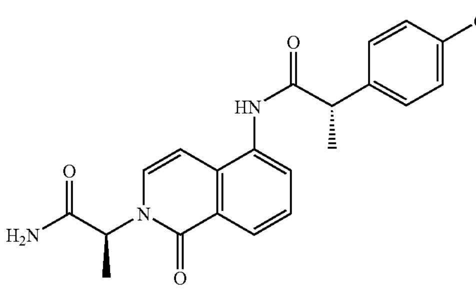 | 397.86 | 398.40 | ++++ |
| 266 | 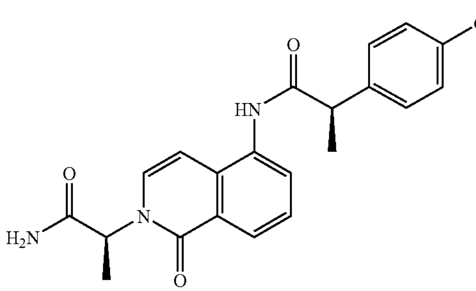 | 397.86 | 397.80 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 267 | 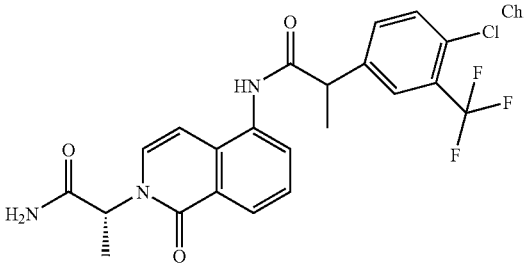 | 465.86 | 466.10 | ++++ |
| 268 | 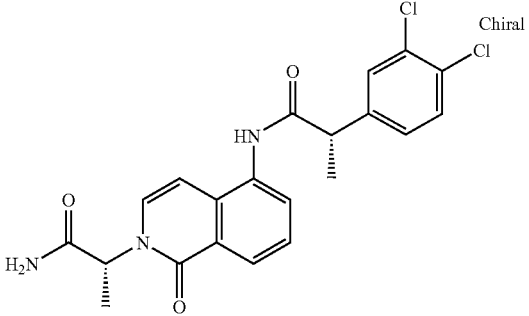 | 432.31 | 432.10 | ++++ |
| 269 | 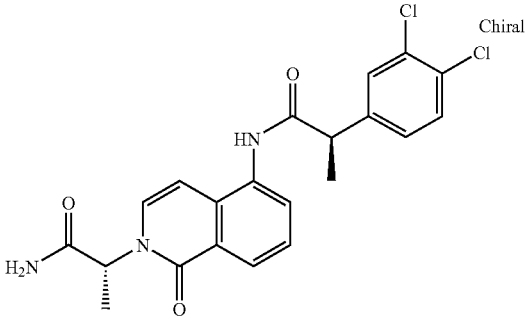 | 432.31 | 433.50 | ++++ |
| 270 | 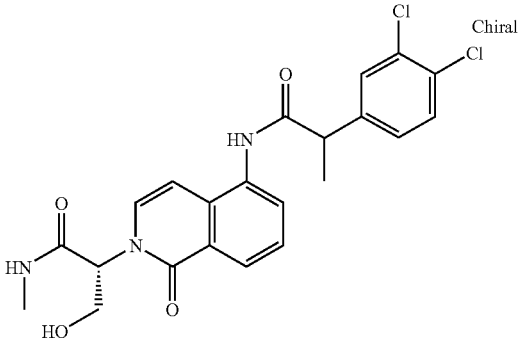 | 462.33 | 462.40 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 271 | 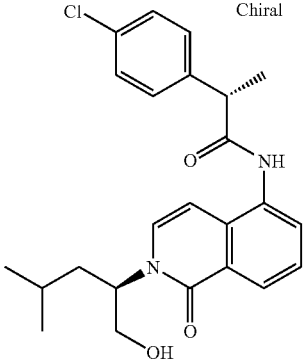 | 426.94 | 427.20 | ++++ |
| 272 | 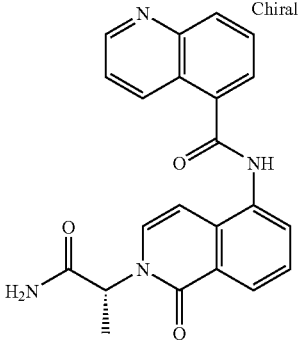 | 386.41 | 386.70 | + |
| 273 | 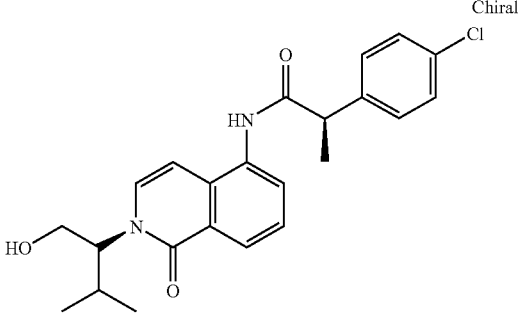 | 412.91 | 413.10 | ++++ |
| 274 | 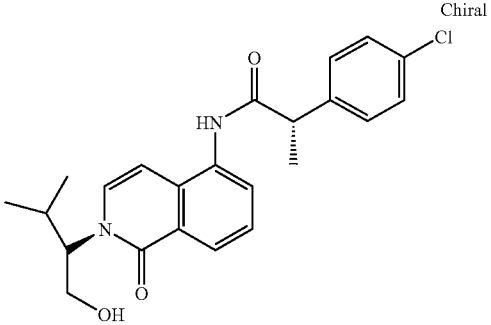 | 412.91 | 413.30 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 275 | 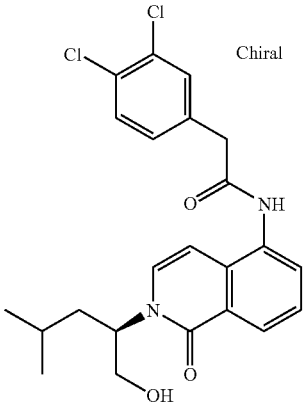 | 447.36 | 447.20 | ++++ |
| 276 | 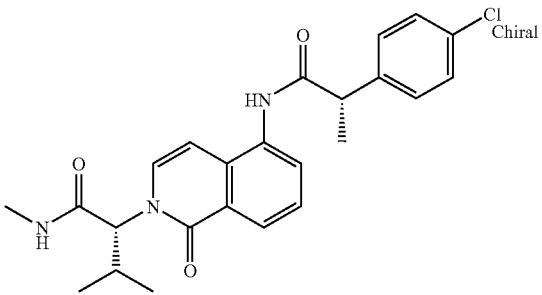 | 439.94 | 440.30 | ++++ |
| 277 | 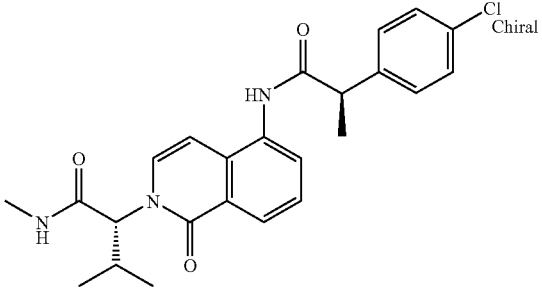 | 439.94 | 440.30 | ++++ |
| 278 | 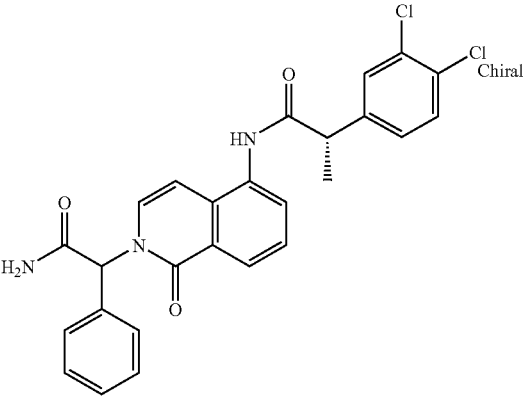 | 494.38 | 494.20 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 279 | 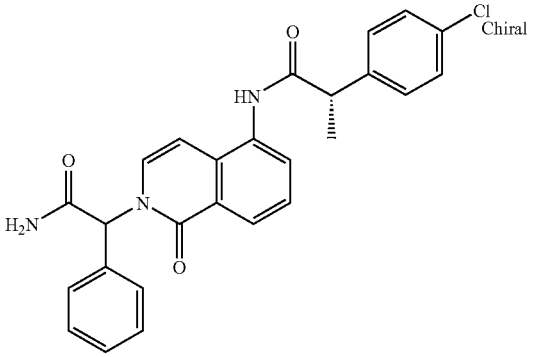 | 459.93 | 460.00 | ++++ |
| 280 | 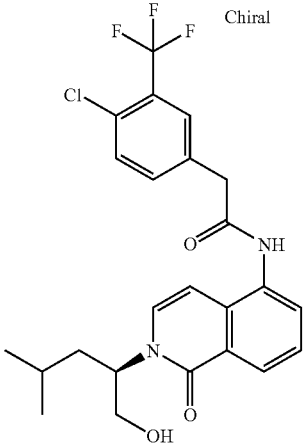 | 480.91 | 481.10 | ++++ |
| 281 | 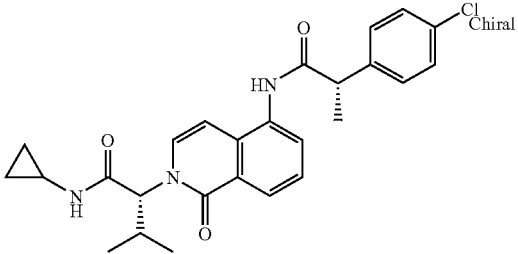 | 465.98 | 465.80 | ++++ |
| 282 | 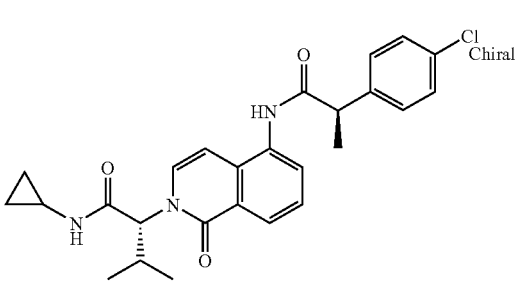 | 465.98 | 466.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 283 | 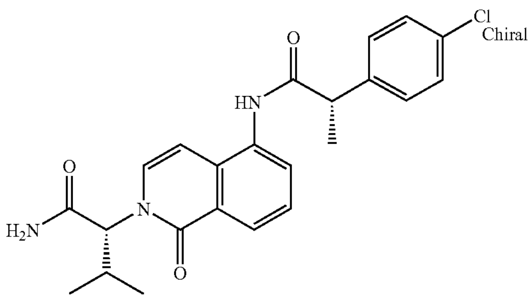 | 425.91 | 426.20 | ++++ |
| 284 | 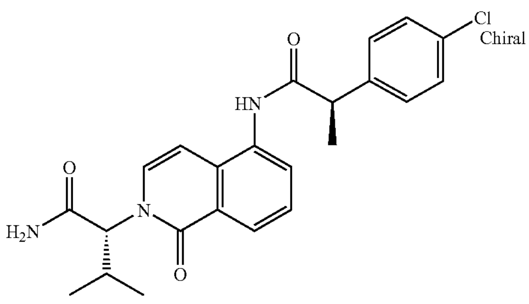 | 425.91 | 426.20 | ++++ |
| 285 | 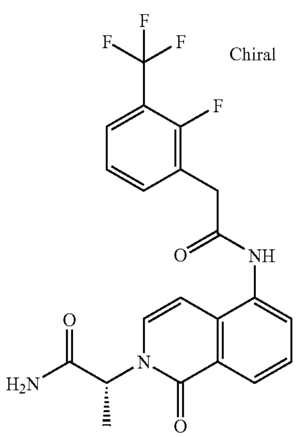 | 435.38 | 436.30 | ++++ |
| 286 | 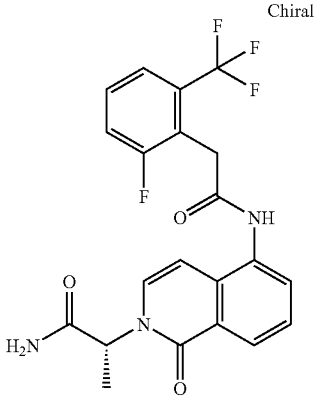 | 435.38 | 436.00 | ++ |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 287 | 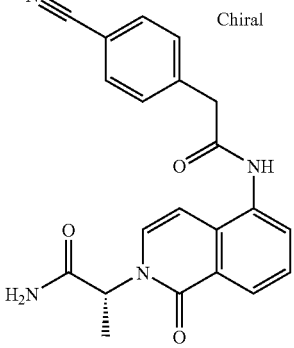 | 374.40 | 374.80 | ++ |
| 288 | 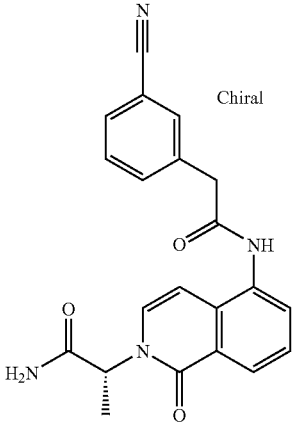 | 374.40 | 374.90 | + |
| 289 | 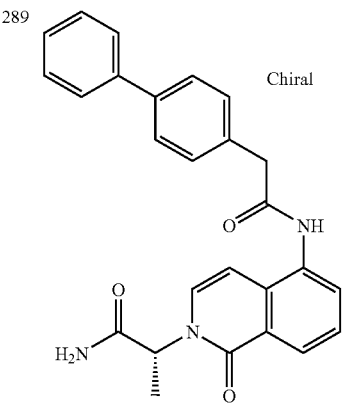 | 425.49 | 426.10 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 290 | 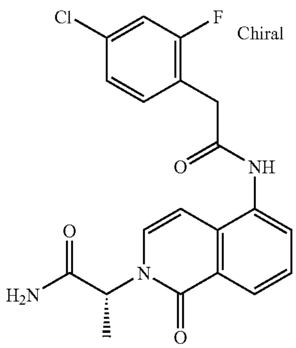 | 401.82 | 402.10 | ++++ |
| 291 | 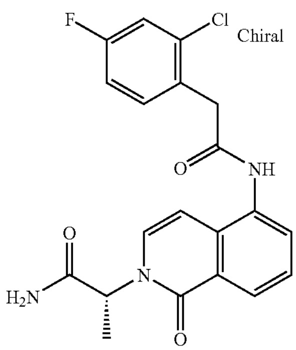 | 401.82 | 402.20 | ++++ |
| 292 | 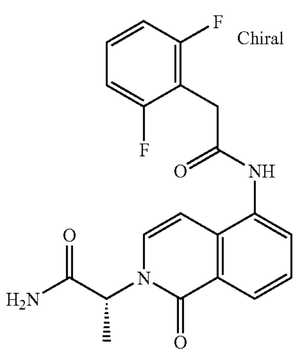 | 385.37 | 386.20 | + |
| 293 | 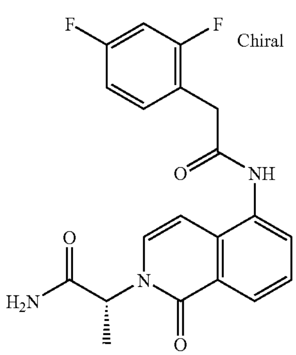 | 85.37 | 386.20 | ++++ |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 294 | 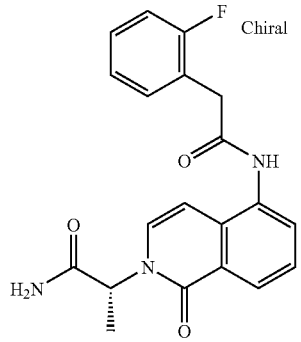 | 367.38 | 367.80 | ++ |
| 295 | 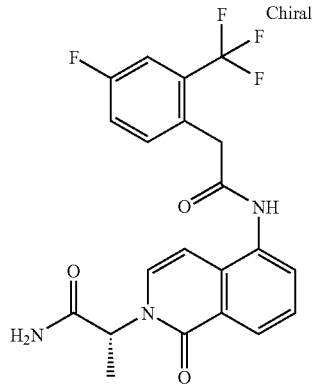 | 435.38 | 436.10 | +++ |
| 296 | 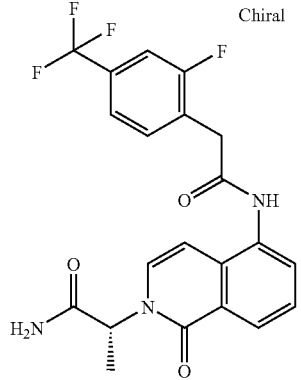 | 435.38 | 436.40 | ++++ |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 297 | | 417.39 | 418.40 | ++++ |
| 298 | | 417.39 | 418.40 | ++++ |
| 299 | | 381.41 | 382.10 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 300 | 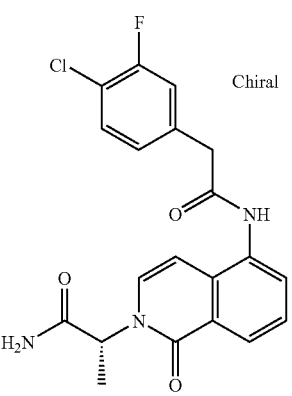 | 401.82 | 402.10 | ++++ |
| 301 | 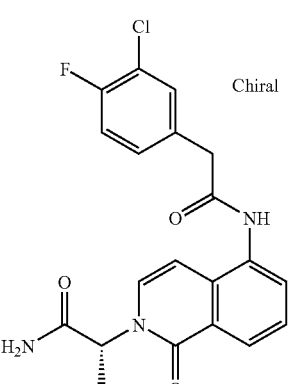 | 401.82 | 402.20 | ++++ |
| 302 | 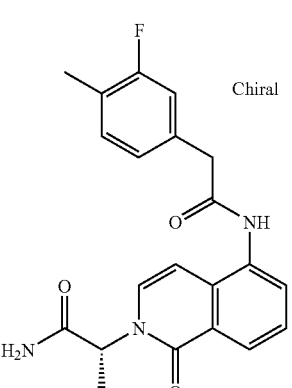 | 381.41 | 382.20 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 303 | 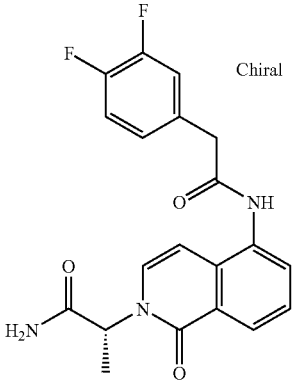 | 385.37 | 386.30 | ++++ |
| 304 | 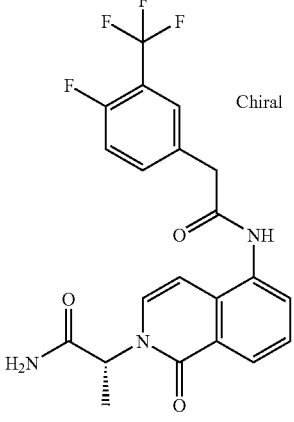 | 435.38 | 436.20 | ++++ |
| 305 | 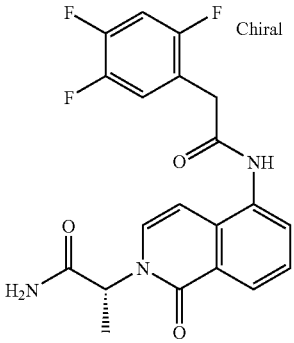 | 403.36 | 404.10 | ++++ |

TABLE 1-continued
IL-1β % Inhibition of Exemplary Compounds
| ID | Structure | MW | MS (Obs) | IL-1β % Inhib. @ 0.3 or 0.1 μM |
|----|-----------|-----|----------|-------------------------------|
| 306 | 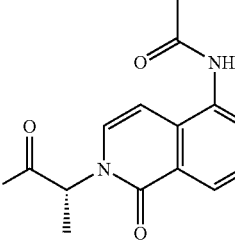 | 435.38 | 436.10 | ++++ |
| 307 | 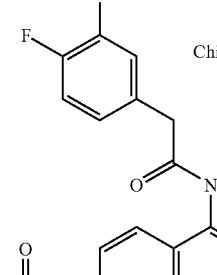 | 446.27 | 448.20 | ++++ |
| 308 | 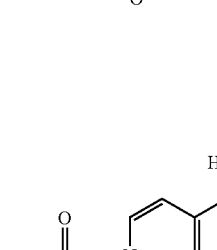 | 437.92 | 438.30 | +++ |
| 309 | 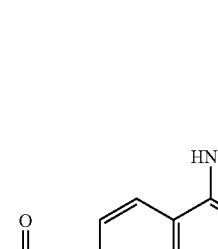 | 350.38 | 351.00 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 310 | 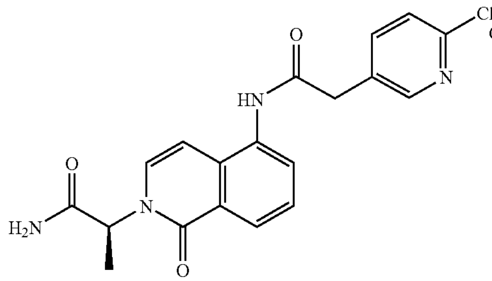 | 384.82 | 385.10 | + |
| 311 | 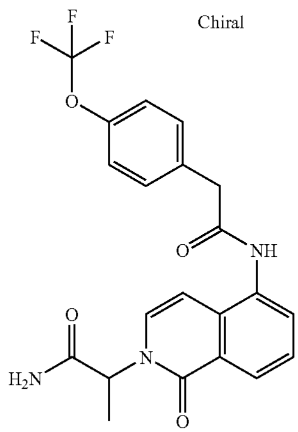 | 433.38 | 434.10 | +++ |
| 312 | 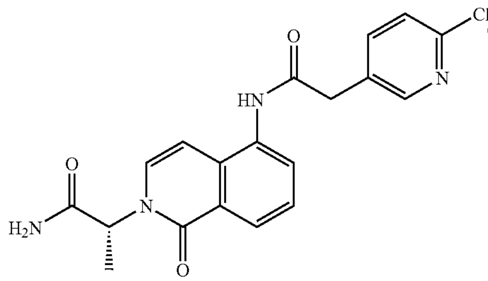 | 384.82 | 385.10 | + |
| 313 | 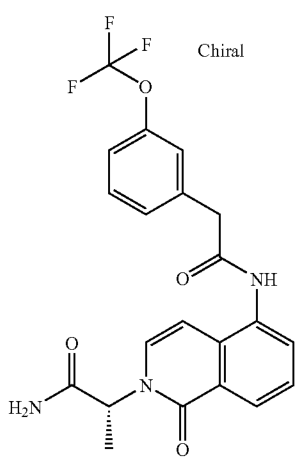 | 433.38 | 434.00 | + |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 314 | 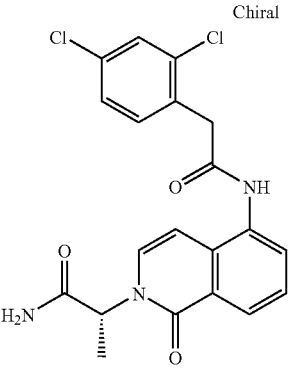 Chiral | 418.28 | 418.10 | ++++ |
| 315 | 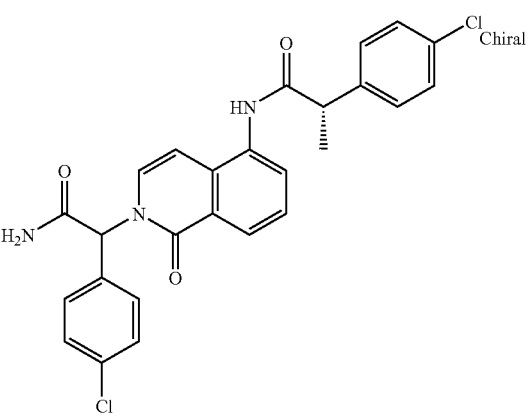 Chiral | 494.38 | 494.20 | +++ |
| 316 | 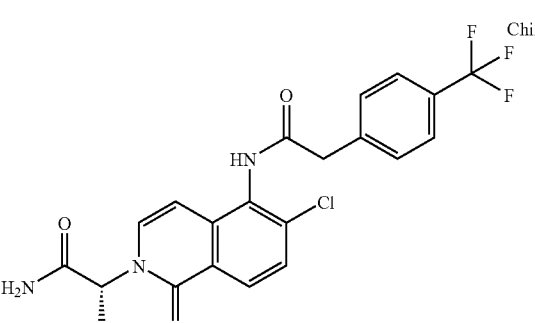 Chiral | 451.83 | 452.20 | +++ |
| 317 | 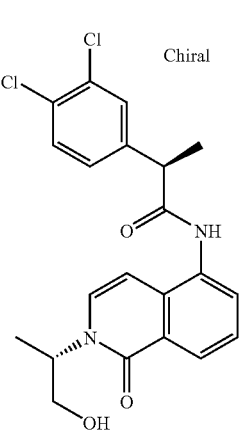 Chiral | 419.31 | 419.30 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 318 | 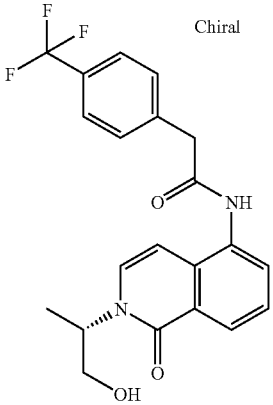 Chiral | 404.39 | 405.00 | ++ |
| 319 | 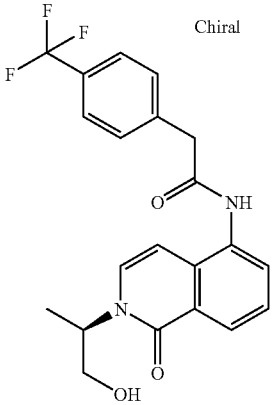 Chiral | 404.39 | 405.10 | ++++ |
| 320 | 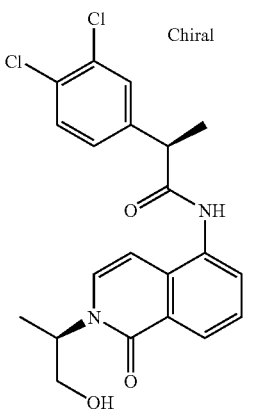 Chiral | 419.31 | 419.30 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 321 | 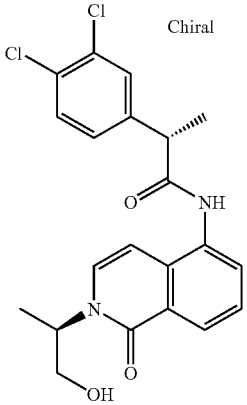 | 419.31 | 419.20 | ++++ |
| 322 | 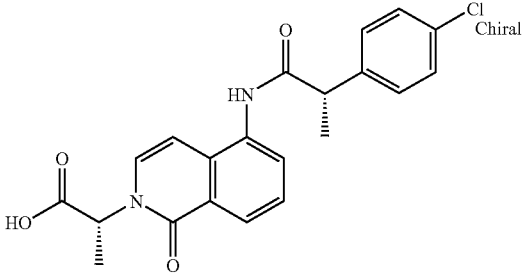 | 398.84 | 399.00 | ++ |
| 323 | 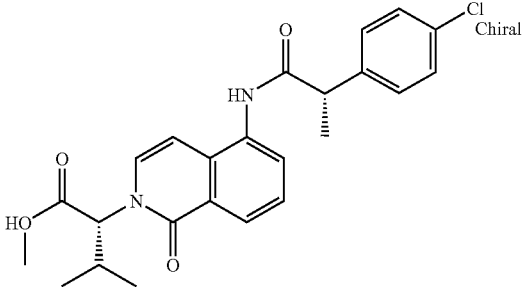 | 426.90 | 427.10 | +++ |
| 324 | 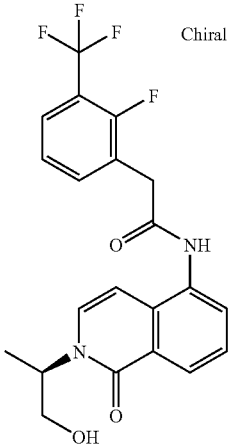 | 422.38 | 423.20 | ++++ |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 325 | 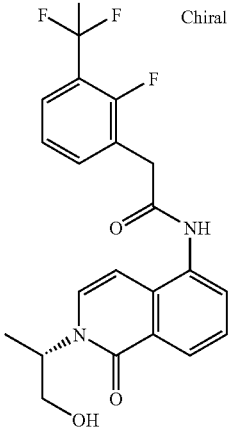 | 422.38 | 422.90 | ++++ |
| 326 | 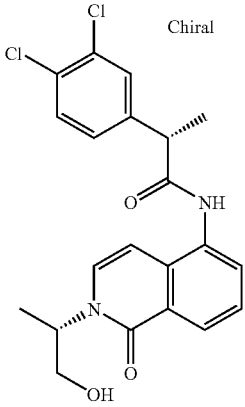 | 419.31 | 419.30 | +++ |
| 327 | 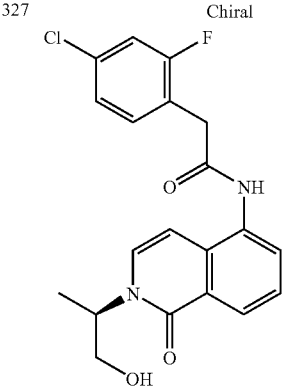 | 388.82 | 389.30 | ++++ |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 328 | 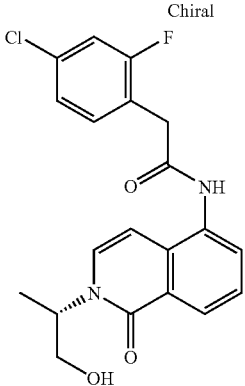 | 388.82 | 389.00 | +++ |
| 329 | 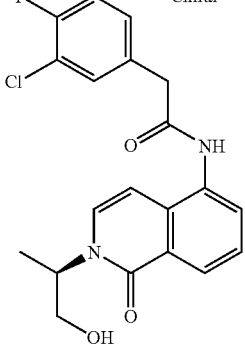 | 388.82 | 389.30 | +++ |
| 330 | 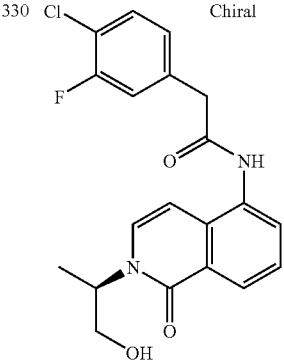 | 388.82 | 389.00 | ++++ |
| 331 | 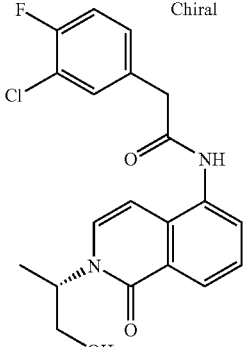 | 388.82 | 389.10 | +++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 332 | 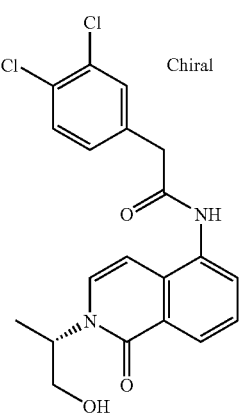 | 405.28 | 405.00 | ++++ |
| 333 | 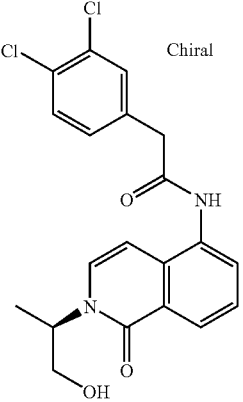 | 405.28 | 405.10 | ++++ |
| 334 | 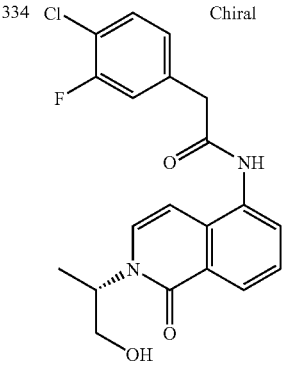 | 388.82 | 389.10 | +++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 335 | 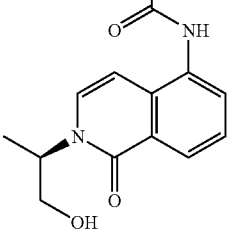 | 422.38 | 423.30 | ++++ |
| 336 | 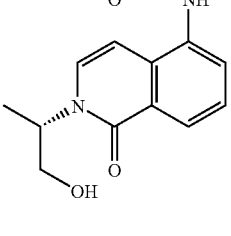 | 422.38 | 423.20 | ++++ |
| 337 | 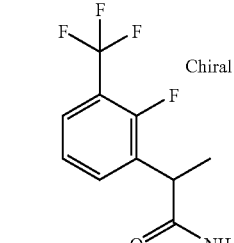 | 449.40<sup>Δ</sup> | 472.40 | ++++ |

TABLE 1-continued
IL-1β % Inhibition of Exemplary Compounds
| ID | Structure | MW | MS (Obs) | IL-1β % Inhib. @ 0.3 or 0.1 μM |
|---|---|---|---|---|
| 338 | 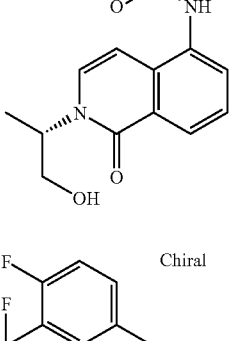 Chiral | 422.38 | 423.30 | ++++ |
| 339 | 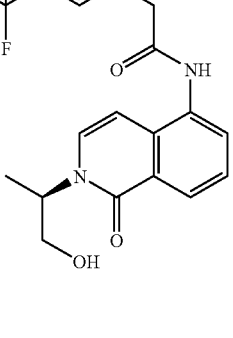 Chiral | 422.38 | 423.20 | ++++ |
| 340 | 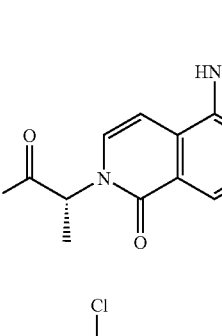 Chiral | 432.21 | 432.10 | ++++ |
| 341 | 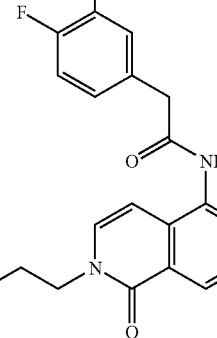 | 374.80 | 374.90 | ++++ |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 342 | | 469.82 | 470.20 | ++++ |
| 343 | | 436.27 | 437.30 | ++ |
| 344 | | 447.41 | 448.30 | ++++ |
| 345 | | 451.83 | 452.10 | ++++ |

TABLE 1-continued

IL-1β % Inhibition of Exemplary Compounds

| ID | Structure | MW | MS (Obs) | IL-1β % Inhib. @ 0.3 or 0.1 μM |
|----|-----------|----|----------|--------------------------------|
| 346 | Chiral | 401.82^Δ | 424.20 | ++++ |
| 347 | Chiral | 435.38^Δ | 458.00 | ++++ |
| 348 | Chiral | 435.38^Δ | 458.00 | ++++ |
| 349 | Chiral | 435.38^Δ | 458.00 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 350 | 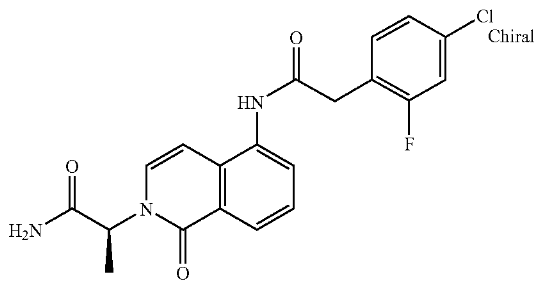 | 401.82<sup>Δ</sup> | 424.00 | ++++ |
| 351 | 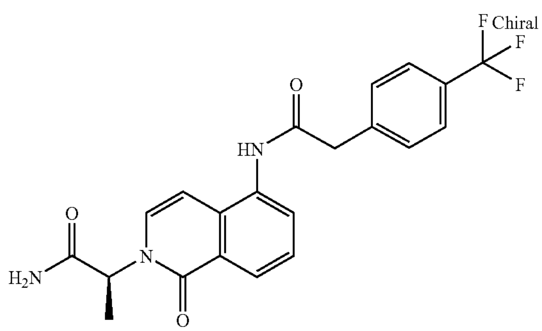 | 417.39<sup>Δ</sup> | 440.30 | ++++ |
| 352 | 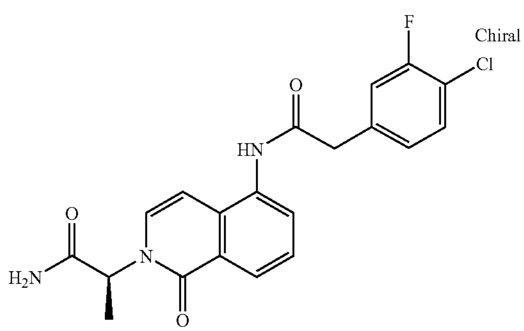 | 401.82<sup>Δ</sup> | 424.10 | ++++ |
| 353 | 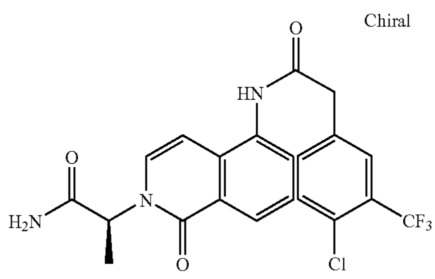 | 451.83<sup>Δ</sup> | 474.10 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 354 | 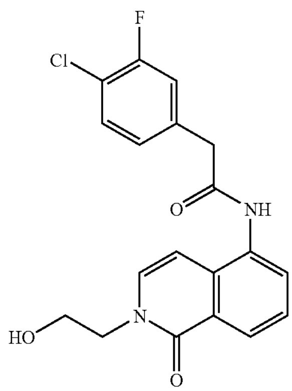 | 374.80 | 375.00 | ++++ |
| 355 | 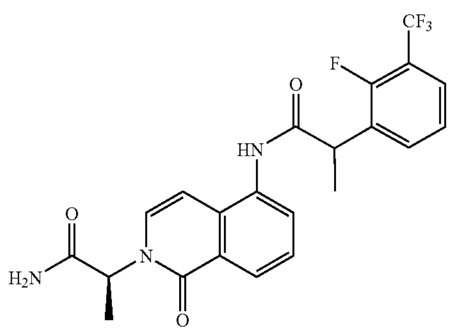 | 449.40^Δ | 472.40 | ++++ |
| 356 | 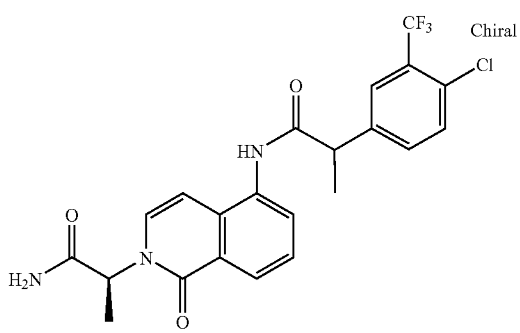 | 465.86^Δ | 488.00 | ++++ |
| 357 | 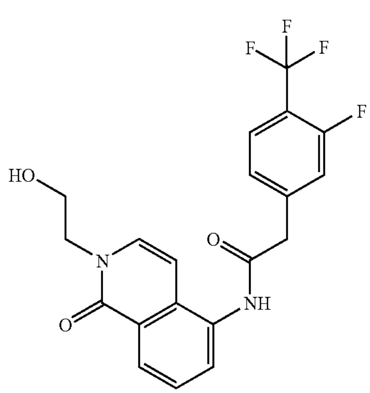 | 408.35 | 409.10 | ++++ |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 358 | | 452.40 | 452.90 | + |
| 359 | | 422.38 | 423.20 | ++++ |
| 361 | | 472.38 | 473.40 | ++++ |

TABLE 1-continued
| | IL-1β % Inhibition of Exemplary Compounds | | | |
|---|---|---|---|---|
| ID | Structure | MW | MS (Obs) | IL-1β % Inhib. @ 0.3 or 0.1 μM |
| 362 | 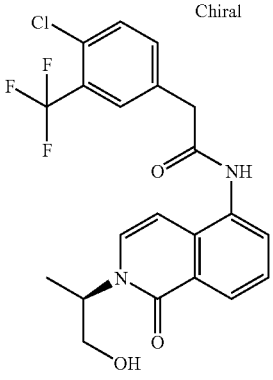 | 438.83 | 439.10 | ++++ |
| 363 | 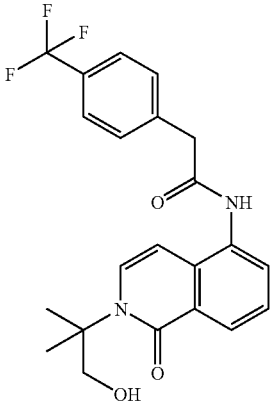 | 418.41 | 419.40 | +++ |
| 364 | 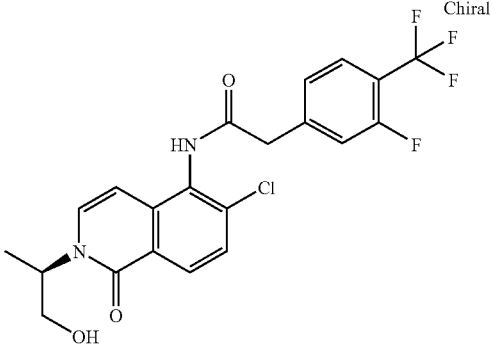 | 438.83 | 439.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 365 | 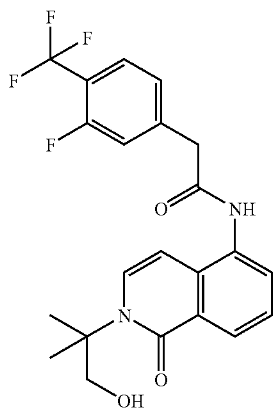 | 436.40 | 437.20 | ++++ |
| 366 | 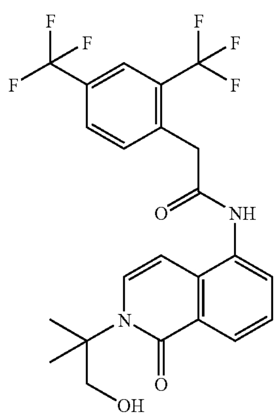 | 486.41 | 487.20 | + |
| 367 | 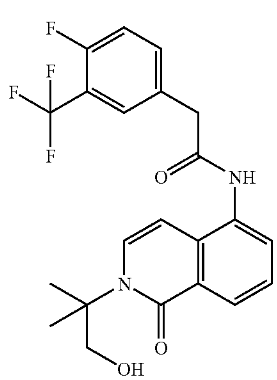 | 436.40 | 437.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|----|-----------|--------|--------|------|
| 368 | 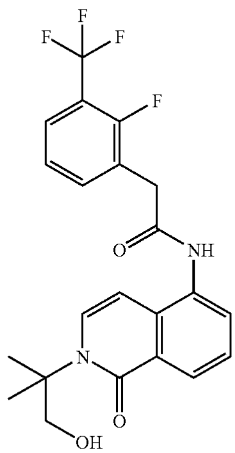 | 436.40 | 437.20 | ++++ |
| 369 | 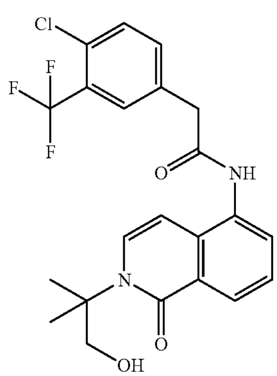 | 452.86 | 453.20 | ++++ |
| 370 | 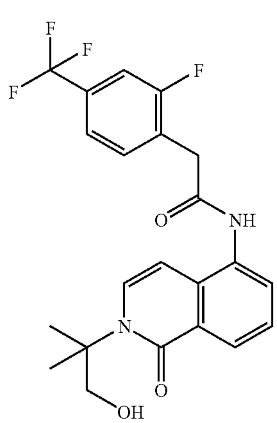 | 436.40 | 437.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 371 | 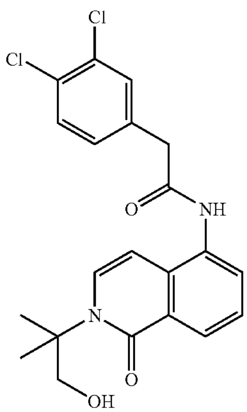 | 419.31 | 419.20 | +++ |
| 372 | 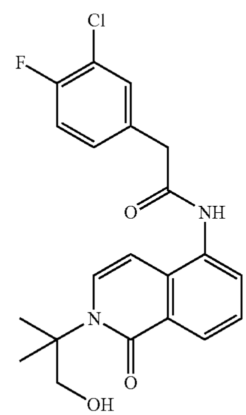 | 402.85 | 403.20 | + |
| 373 | 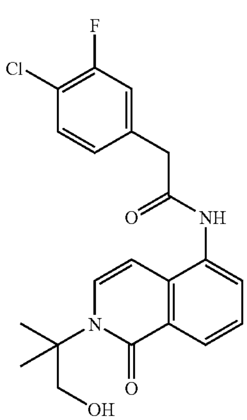 | 402.85 | 403.20 | +++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 374 | 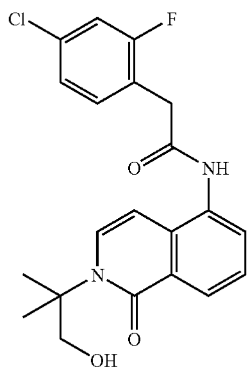 | 402.85 | 403.10 | ++++ |
| 375 | 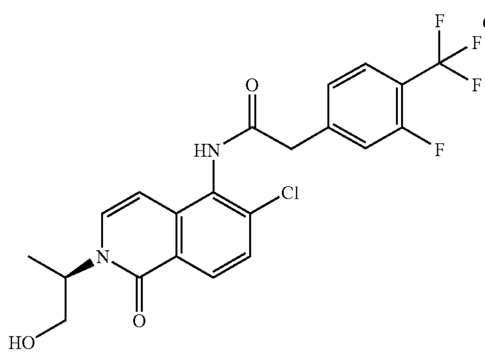 | 456.82 | 457.00 | ++++ |
| 376 | 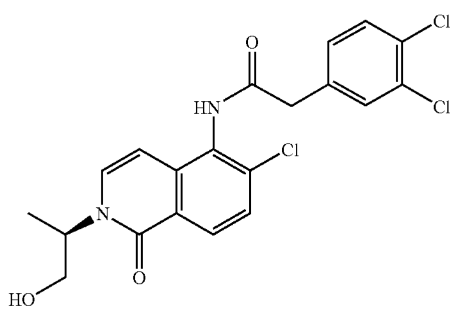 | 439.72 | 440.40 | ++++ |
| 377 | 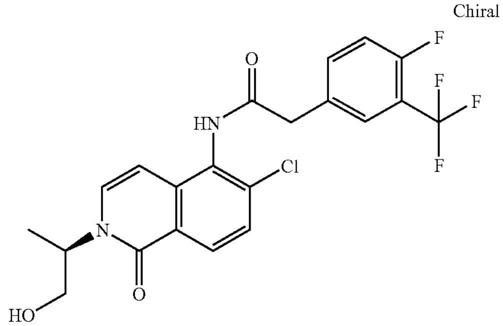 | 456.82 | 457.40 | ++++ |

TABLE 1-continued

| | IL-1β % Inhibition of Exemplary Compounds | | | |
|---|---|---|---|---|
| ID | Structure | MW | MS (Obs) | IL-1β % Inhib. @ 0.3 or 0.1 μM |
| 378 | | 456.82 | 457.40 | ++++ |
| 379 | | 403.36 | 404.10 | ++++ |
| 380 | | 485.38 | 486.30 | ++++ |
| 381 | | 403.36 | 404.20 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 382 | 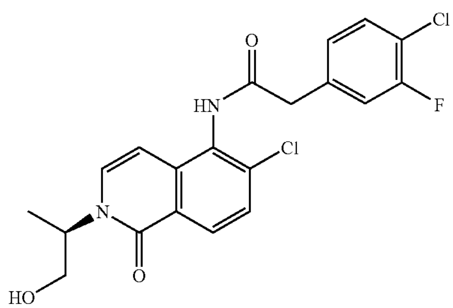 | 423.27 | 423.30 | ++++ |
| 383 | 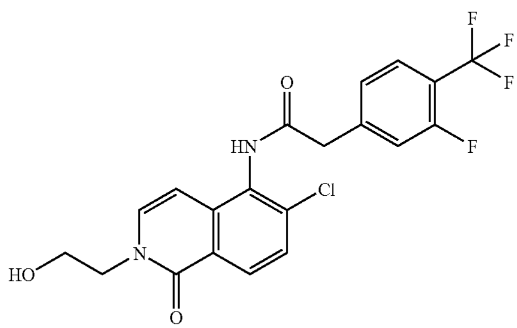 | 442.79 | 443.30 | ++++ |
| 384 | 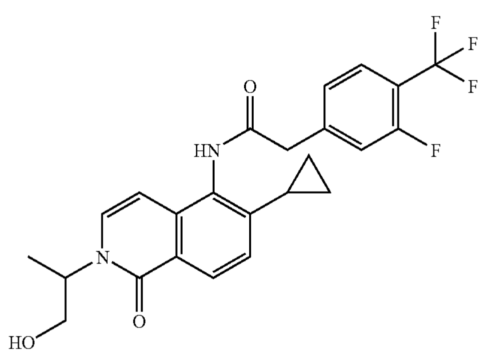 | 462.44 | 463.50 | ++++ |
| 385 | 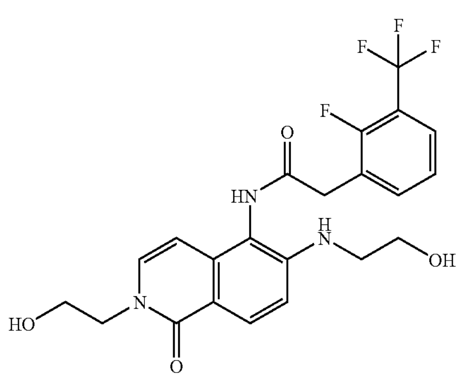 | 467.42 | 468.40 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 386 | 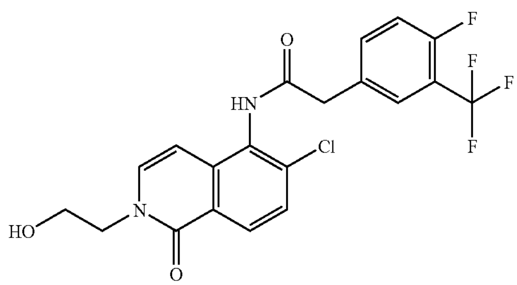 | 442.79 | 443.30 | ++++ |
| 387 | 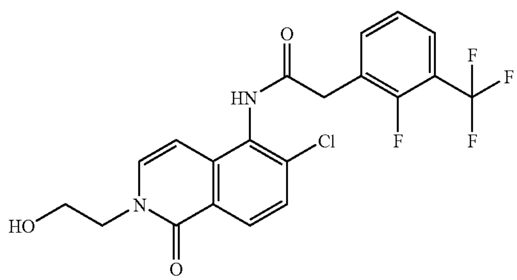 | 442.79 | 443.20 | ++++ |
| 388 | 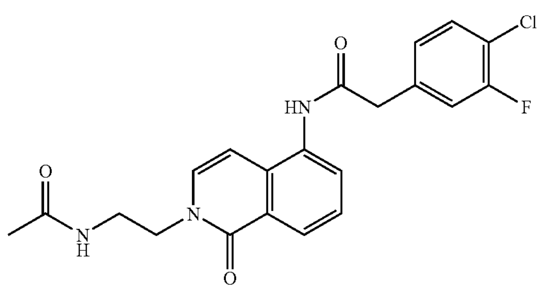 | 415.85 | 416.30 | |
| 389 | 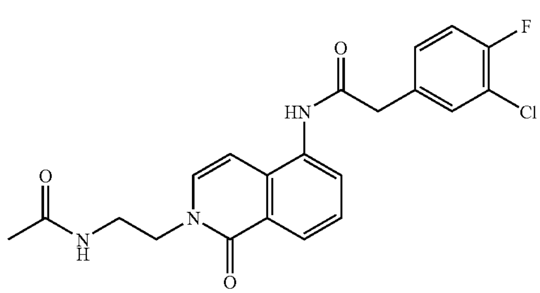 | 415.85 | 416.30 | |
| 390 | 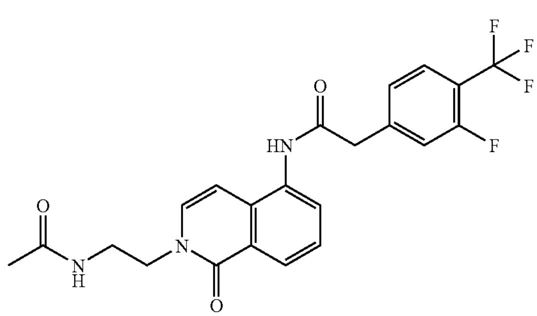 | 449.40 | 449.90 | + |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 391 | 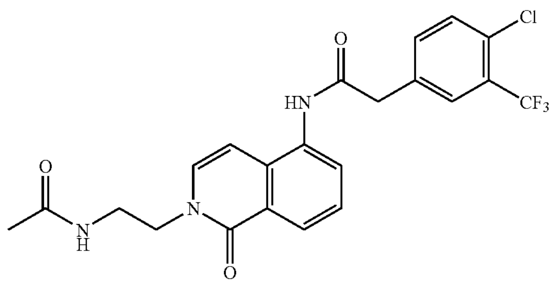 | 465.86 | 466.30 | ++++ |
| 392 | 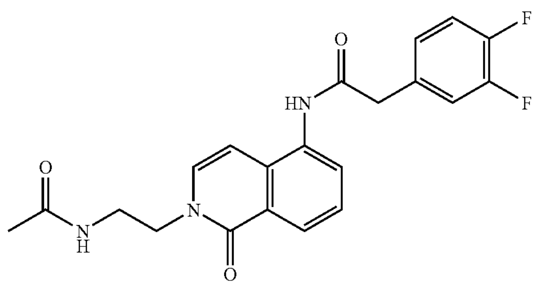 | 399.40 | 400.00 | ++++ |
| 393 | 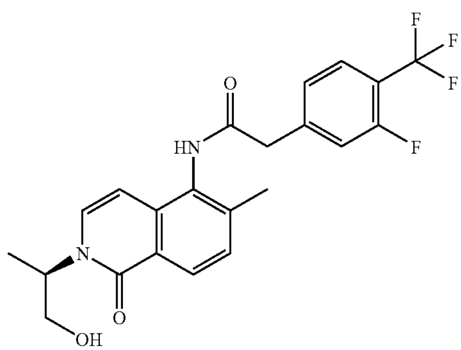 | 436.40 | 437.40 | ++++ |
| 394 | 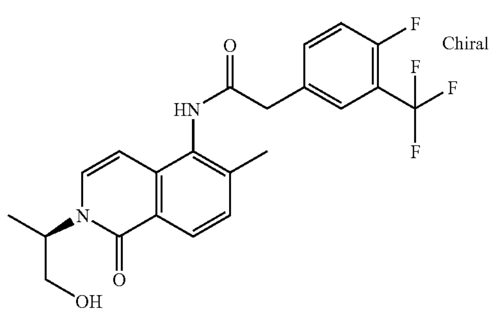 | 436.40 | 437.50 | ++++ |
| 395 | 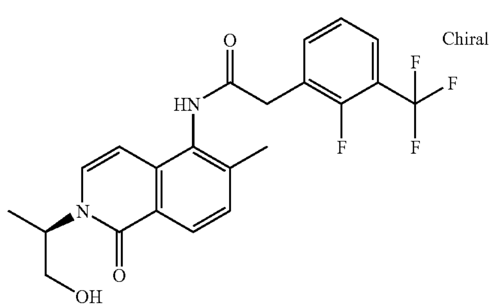 | 436.40 | 437.50 | ++++ |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 396 | 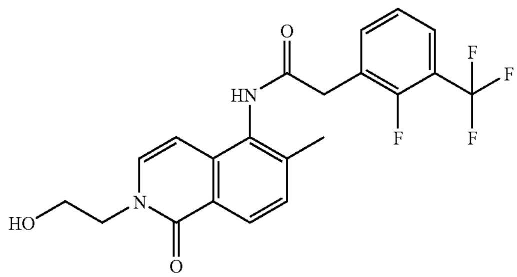 | 422.38 | 423.30 | ++++ |
| 397 | Chiral | 418.41 | 419.40 | ++++ |
| 398 | Chiral | 402.85 | 403.50 | ++++ |
| 399 | 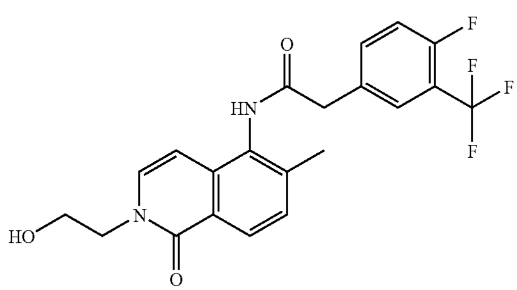 | 422.38 | 423.30 | |

TABLE 1-continued

IL-1β % Inhibition of Exemplary Compounds

| ID | Structure | MW | MS (Obs) | IL-1β % Inhib. @ 0.3 or 0.1 μM |
|---|---|---|---|---|
| 400 | (structure) | 422.38 | 423.20 | ++++ |
| 401 | (structure, Chiral) | 438.42 | 439.5 | ++++ |

IC$_{50}$ Determinations

The compounds set forth in Table 1 were tested for activity in a cellular model as described herein. Specifically, cells were pretreated with differing amounts of the compound under test and released IL-1β determined as in Example 9, above. Measurements were made and IC$_{50}$ values, presented in Table 2, below, were determined by fitting the data to a four parameter logistic equation using GraphPad Prism software (GraphPad Software, Inc.) The equation may be expressed by the following formula:

$$Y = \text{Bottom} + (\text{Top} - \text{Bottom})/(1 + 10\hat{\ }((\text{Log EC50} - X)^* \text{HillSlope}))$$

Where X is the logarithm of concentration, Y is the response and Y starts at Bottom and goes to Top with a sigmoid shape.

TABLE 2

IL-1β IC$_{50}$ for Exemplary Compounds

| ID | IL-1β IC$_{50}$ nM |
|---|---|
| 1 | >1000 |
| 2 | >1000 |
| 3 | 272.40 |
| 4 | 316.90 |
| 5 | >1000 |
| 6 | 311.30 |
| 7 | 288.90 |
| 8 | 30.27 |
| 61 | >1000 |
| 62 | 22.21 |
| 63 | >1000 |
| 64 | 113.00 |

TABLE 2-continued

IL-1β IC$_{50}$ for Exemplary Compounds

| ID | IL-1β IC$_{50}$ nM |
|---|---|
| 65 | 2.21 |
| 66 | 110.10 |
| 67 | >1000 |
| 68 | 720.30 |
| 69 | 10.75 |
| 70 | 405.90 |
| 71 | >1000 |
| 72 | >1000 |
| 73 | 532.00 |
| 74 | >1000 |
| 75 | >1000 |
| 76 | >1000 |
| 77 | >1000 |
| 78 | >1000 |
| 79 | >1000 |
| 80 | 27.52 |
| 81 | 27.75 |
| 82 | 227.70 |
| 228 | 211.90 |
| 229 | 187.10 |
| 230 | 160.50 |
| 231 | 374.10 |
| 232 | 10.67 |
| 233 | 390.70 |
| 234 | 144.50 |
| 235 | 70.57 |
| 236 | 46.59 |
| 237 | 6.27 |
| 238 | 1.26 |
| 239 | 4.05 |
| 240 | 11.77 |

TABLE 2-continued

IL-1β IC$_{50}$ for Exemplary Compounds

| ID | IL-1β IC$_{50}$ nM |
|---|---|
| 241 | 23.61 |
| 242 | 355.80 |
| 243 | 35.79 |
| 245 | 46.45 |
| 246 | 113.30 |
| 247 | 18.78 |
| 248 | >1000 |
| 249 | 4.83 |
| 250 | 15.10 |
| 251 | 57.27 |
| 252 | 160.80 |
| 253 | 762.60 |
| 254 | 25.32 |
| 255 | 21.55 |
| 256 | 34.36 |
| 257 | 38.96 |
| 258 | 9.92 |
| 259 | 208.30 |
| 260 | 694.40 |
| 261 | 188.00 |
| 262 | 73.07 |
| 263 | 13.29 |
| 264 | 442.50 |
| 265 | 15.21 |
| 266 | 38.71 |
| 267 | 3.19 |
| 268 | 3.92 |
| 269 | 8.97 |
| 270 | 37.43 |
| 271 | 60.63 |
| 272 | >1000 |
| 273 | 3.54 |
| 274 | 14.52 |
| 275 | 19.80 |
| 276 | 53.30 |
| 277 | 81.96 |
| 278 | 57.98 |
| 279 | 105.80 |
| 280 | 121.00 |
| 281 | 7.39 |
| 282 | 33.77 |
| 283 | 9.70 |
| 284 | 6.91 |
| 285 | 6.62 |
| 286 | 373.80 |
| 287 | 332.50 |
| 288 | >1000 |
| 289 | 53.04 |
| 290 | 7.63 |
| 291 | 20.60 |
| 292 | >1000 |
| 293 | 44.43 |
| 294 | 663.00 |
| 295 | 184.30 |
| 296 | 17.93 |
| 297 | 16.62 |
| 298 | 7.91 |
| 299 | 24.77 |
| 300 | 5.96 |
| 301 | 3.57 |
| 302 | 32.15 |
| 303 | 15.51 |
| 304 | 5.84 |
| 305 | 36.28 |
| 306 | 5.07 |
| 307 | 18.51 |
| 308 | 302.40 |
| 309 | >1000 |
| 310 | >1000 |
| 311 | 150.40 |
| 312 | >1000 |
| 313 | 713.10 |
| 315 | 220.60 |
| 316 | 2.29 |
| 317 | 93.70 |
| 318 | 132.50 |
| 319 | 25.11 |
| 320 | 9.54 |
| 321 | 13.42 |
| 322 | 571.80 |
| 323 | 320.20 |
| 324 | 22.09 |
| 325 | 84.64 |
| 326 | 122.20 |
| 327 | 39.42 |
| 328 | 202.40 |
| 329 | 205.50 |
| 330 | 13.30 |
| 331 | 163.10 |
| 333 | 1.01 |
| 334 | 202.10 |
| 335 | 9.31 |
| 336 | 49.76 |
| 337 | 9.15 |
| 338 | 48.06 |
| 339 | 10.50 |
| 340 | 18.30 |
| 341 | 52.63 |
| 342 | 7.05 |
| 343 | 395.00 |
| 344 | 48.17 |
| 345 | 112.60 |
| 346 | 66.88 |
| 347 | 31.22 |
| 348 | 20.80 |
| 349 | 48.93 |
| 350 | 13.65 |
| 351 | 35.83 |
| 352 | 32.66 |
| 353 | 29.64 |
| 354 | 84.16 |
| 355 | 36.93 |
| 356 | 15.50 |
| 357 | 14.64 |
| 358 | 438.70 |
| 359 | 43.09 |
| 361 | 14.30 |
| 362 | 1.14 |
| 363 | 167.00 |
| 364 | 10.49 |
| 365 | 41.13 |
| 366 | 788.50 |
| 367 | 106.00 |
| 368 | 60.27 |
| 369 | 14.97 |
| 370 | 134.00 |
| 371 | 156.90 |
| 372 | 420.90 |
| 373 | 258.40 |
| 374 | 175.30 |
| 375 | 4.65 |
| 376 | 13.10 |
| 377 | 0.38 |
| 378 | 31.45 |
| 379 | 30.45 |
| 380 | 64.30 |
| 381 | 32.44 |
| 382 | 6.15 |
| 383 | 6.06 |
| 384 | 8.78 |
| 385 | >1000 |
| 386 | 5.45 |
| 387 | 62.76 |
| 390 | |
| 391 | |
| 392 | |
| 393 | 0.39 |
| 394 | 0.74 |
| 395 | 10.69 |
| 396 | 65.14 |

TABLE 2-continued

IL-1β IC$_{50}$ for Exemplary Compounds

| ID | IL-1β IC$_{50}$ nM |
|---|---|
| 397 | 5.54 |
| 398 | 5.38 |
| 400 | 9.44 |
| 401 | 1.44 |

Half-Life in Human Liver Microsomes (HLM)

Test compounds (1 μM) are incubated with 3.3 mM MgCl$_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH is added into the reaction mixture of P450 group. An aliquot of samples of non-450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/k

The results of the tests and corresponding $T_{1/2}$ values are set forth in Table 3, below.

TABLE 3

T-Half Life In Hours For Exemplary Compounds

| ID | Half Life (hr) |
|---|---|
| 4 | 1.97 |
| 8 | 1.41 |
| 62 | 0.37 |
| 65 | 1.03 |
| 81 | 0.72 |
| 232 | 7.37 |
| 236 | 0.97 |
| 238 | 1.59 |
| 247 | 2.11 |
| 250 | 0.9 |
| 254 | 1.46 |
| 256 | 1.29 |
| 263 | 2.31 |
| 265 | 0.97 |
| 267 | 1.28 |
| 268 | 1.36 |
| 269 | 0.93 |
| 285 | 1.24 |
| 290 | 1.64 |
| 298 | 3.35 |
| 316 | 3.25 |
| 319 | 1.22 |
| 324 | 0.7 |
| 330 | 1.41 |
| 335 | 0.93 |
| 339 | 0.93 |
| 342 | 1.16 |
| 351 | 2.36 |
| 353 | 1.01 |
| 357 | 1.54 |
| 359 | 1.16 |
| 362 | 0.97 |
| 364 | 3.15 |
| 369 | 0.55 |
| 375 | 1.63 |
| 376 | 0.9 |
| 377 | 1.01 |
| 382 | 1.34 |
| 383 | 3.65 |
| 386 | 1.08 |
| 393 | 1.45 |
| 394 | 0.70 |
| 400 | 3.73 |

Pharmacokinetic Evaluation of Compounds Following Intravenous and Oral Administration in Rats.

Male Sprague-Dawley rats are acclimatized for at least 24 hours prior to experiment initiation. During the acclimation period, all animals receive food and water ad libitum. However, food but not water is removed from the animals' cages at least 12 hours before initiation of the experiment. During the first 3 hours of experimentation, the animals receive only water ad libitum. At least three animals each are tested for intravenous and oral dosage. For intravenous formulation, compounds were dissolved (0.25 to 1 mg/mL) in a mixture of 3% dimethyl sulfoxide, 40% PEG 400 and the rest percentage of 40% Captisol in water (w/v). The animals are weighed before dosing. The determined body weight is used to calculate the dose volume for each animal.

Dose volume (mL/kg)=1 mg/kg/formulation concentration (mg/mL)

In instances where the formulation concentrations were less than 0.5 mg/mL, the dosing volume is about 2 mL/kg.

For oral formulation, compounds of this invention are suspended (0.5 to 0.75 mg/mL) in a mixture of 5% of 10% Tween 80 in water (v/v) and 95% of 0.5% methyl cellulose in water (w/v). PO rats are typically dosed through oral gavage following the same dose volume formula as IV to achieve a dose level of 1 to 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite (AUC$_{inf}$). The AUC$_{inf}$ is averaged and the oral bioavailability (% F) for individual animal is calculated as:

AUC$_{inf}$(PO)/AUC$_{inf}$(IV), normalized to their respective dose levels.

The % F is reported as the mean % F of all animals dosed orally with the compound of the invention at the specified level (see Table 4 below).

For the purpose of Table 4, oral bioavailability of each compound is expressed as follows:

| "+" | 0-25% F |
|---|---|
| "++" | 26-50% F |
| "+++" | 51-75% F |
| "++++" | >75% F |

TABLE 4

Oral Bioavailability of Exemplary Compounds

| ID | Oral Bioavailability F (%) |
|---|---|
| 4 | ++++ |
| 8 | + |
| 62 | + |
| 65 | + |
| 81 | + |
| 236 | + |
| 238 | + |
| 247 | ++ |
| 254 | + |
| 256 | + |
| 263 | ++ |
| 265 | ++ |
| 267 | ++ |
| 268 | ++ |
| 269 | ++ |
| 285 | ++ |
| 290 | + |
| 298 | + |
| 316 | ++ |
| 319 | +++ |
| 324 | ++ |
| 330 | ++++ |
| 335 | ++ |
| 339 | +++ |
| 342 | + |
| 351 | + |
| 353 | + |
| 357 | ++++ |
| 359 | ++++ |
| 362 | ++ |
| 364 | ++++ |
| 369 | + |
| 375 | ++++ |
| 376 | ++ |
| 377 | +++ |
| 382 | +++ |
| 383 | ++++ |
| 386 | + |
| 393 | +++ |
| 394 | ++ |
| 395 | ++ |
| 398 | +++ |
| 400 | ++ |

Determination of Aqueous Solubility

The kinetic solubility of a compound can be determined by spiking 10 mM test compound in DMSO solution into 5 to 10 mL buffer at pH 7.4 and pH 2. The mixture was vortexed for 1 hour and equilibrated overnight at room temperature. The mixture was filtered through a saturated filter and the filtrate was analyzed by LC/MS/MS.

The results of the tests and corresponding solubility values are set forth in Table 5, below.

For the purpose of Table 5, solubility of each compound is expressed as follows:

| "+" | 0-25 µM solubility at pH 7.4 |
|---|---|
| "++" | 26-50 µM solubility at pH 7.4 |
| "+++" | 51-75 µM solubility at pH 7.4 |
| "++++" | >75 µM solubility at pH 7.4 |

TABLE 5

Solubility for Exemplary Compounds

| ID | Solubility µM |
|---|---|
| 7 | + |
| 62 | + |
| 69 | + |
| 80 | ++++ |
| 81 | ++++ |
| 237 | ++ |
| 249 | + |
| 250 | ++++ |
| 254 | ++ |
| 256 | + |
| 262 | ++++ |
| 263 | ++++ |
| 265 | ++ |
| 266 | ++++ |
| 267 | +++ |
| 268 | +++ |
| 269 | ++ |
| 283 | ++++ |
| 284 | ++++ |
| 298 | + |
| 300 | + |
| 301 | ++ |
| 304 | + |
| 306 | + |
| 307 | + |
| 316 | + |
| 320 | +++ |
| 324 | ++++ |
| 330 | ++++ |
| 333 | ++++ |
| 335 | ++++ |
| 337 | + |
| 339 | ++++ |
| 351 | + |
| 353 | + |
| 357 | + |
| 359 | + |
| 361 | ++++ |
| 375 | ++++ |
| 376 | ++++ |
| 377 | ++++ |
| 383 | + |
| 386 | + |
| 393 | ++++ |
| 394 | ++++ |
| 395 | ++++ |
| 397 | +++ |
| 398 | ++++ |
| 400 | ++++ |
| 401 | ++++ |

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using Open Eye Software's Lexichem naming tool, Symyx Renaissance Software's Reaction Planner or MDL's ISIS Draw Autonom Software tool and not verified.

What is claimed is:

1. A bicycloheteroaryl compound having a formula:

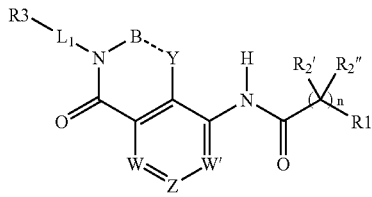

wherein
B and Y are independently selected from $CR^{2a}$ and $CR^{2a}R^{2b}$;
W, W' and Z are independently selected from $CR^4$ and N, provided that all three of W, W' and Z are not N at the same time;
$L^1$ is substituted or unsubstituted $C_1$-$C_5$ alkylene;
n is 0, 1, 2, 3 or 4;
$R^1$ is selected from substituted or unsubstituted 5-13 membered aryl and heteroaryl;
each $R^{2a}$, $R^{2b}$, $R^{2'}$ and $R^{2''}$ is independently selected from hydrogen, halo, substituted or unsubstituted $C_1$-$C_6$ alkyl; or any of $R^{2'}$ and $R^{2''}$ join together to form a cycloalkyl or cycloheteroalkyl ring of 3-7 atoms;
$R^3$ is a hydrogen bond donor group;
each $R^4$ is independently selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;
and the dotted bond is a single or a double bond;
or a pharmaceutically acceptable salt thereof; or a stereoisomer, or an isotopic variant or a tautomer thereof.

2. A compound according to claim 1 wherein each of B and Y is $CH_2$; and the dotted bond is a single bond.

3. A compound according to claim 1 wherein each of B and Y is CH; and the dotted bond is a double bond.

4. A compound according to claim 1 wherein each of $R^{2'}$ and $R^{2''}$ is H.

5. A compound according to claim 1 wherein one of $R^{2'}$ and $R^{2''}$ is independently Me and the other is H.

6. A compound according to claim 1 wherein each of $R^{2'}$ and $R^{2''}$ is Me.

7. A compound according to claim 1 wherein n is 0, 1, or 2.

8. A compound according to claim 1 wherein $R^1$ is selected from a 5-13 membered aryl and heteroaryl, unsubstituted or substituted with one or more substituents independently selected from halo, hydroxyl, amino, cyano, sulfo, sulfanyl, sulfinyl, amido, carboxy, carbalkoxy, alkyl, substituted alkyl, alkenyl, substituted alkenyl, alkynyl, substituted alkynyl, and sulfonamide.

9. A compound according to claim 1 wherein $R^1$ is substituted or unsubstituted aryl.

10. A compound according to claim 1 wherein $R^1$ is substituted or unsubstituted phenyl.

11. A compound according to claim 1 wherein $R^1$ is substituted or unsubstituted pyridyl, substituted or unsubstituted quinoline, substituted or unsubstituted benzodioxole, substituted or unsubstituted benzodioxane, substituted or unsubstituted benzofuran, substituted or unsubstituted benzothiophene, and substituted or unsubstituted benzodioxepine.

12. A compound according to claim 1 wherein the compound is according to formula I, II, III or IV:

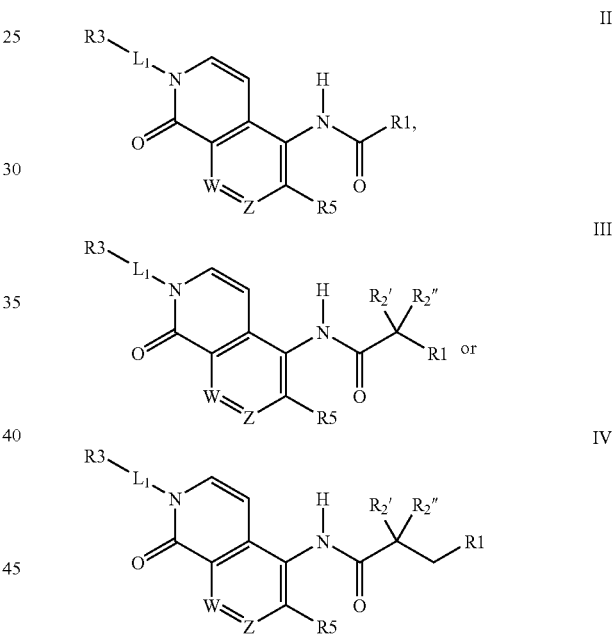

wherein
W is $CR^4$; Z is $CR^4$;
$L^1$, $R^{2'}$, $R^{2''}$, $R^3$ and $R^4$ are as in claim 1;
and $R^5$ is selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt thereof; or a stereoisomer, or an isotopic variant or a tautomer thereof.

13. A compound according to claim 12 wherein each $R^{2'}$ and $R^{2''}$ is H.

14. A compound according to claim 12 wherein $R^{2'}$ is Me; and $R^{2''}$ is H.

15. A compound according to claim 12 wherein $R^1$ is selected from substituted or unsubstituted phenyl.

16. A compound according to claim 1 wherein the compound is according to formula V, VI or VII:

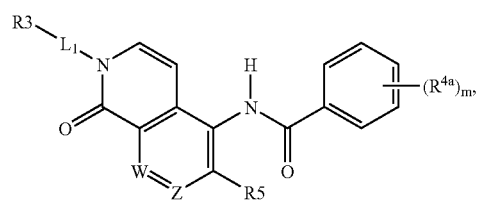

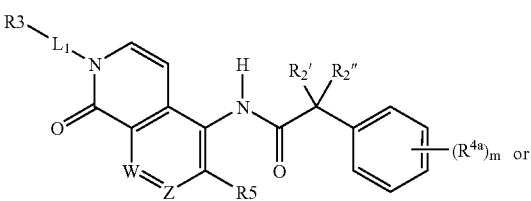

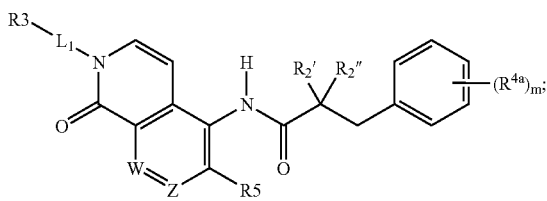

wherein

W is $CR^4$; Z is $CR^4$;

$L^1$, $R^1$ $R^{2'}$, $R^{2''}$, $R^3$ and $R^4$ are as in claim 1;

$R^5$ is selected from H, alkyl, substituted alkyl, acyl, substituted acyl, substituted or unsubstituted acylamino, substituted or unsubstituted alkylamino, substituted or unsubstituted alkylhio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

$R^{4a}$ is selected from hydrogen, alkyl, substituted alkyl, acyl, substituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5;

or a pharmaceutically acceptable salt thereof; or a stereoisomer, or an isotopic variant or a tautomer thereof.

17. A compound according to claim 16 wherein each $R^{2'}$ and $R^{2''}$ is H.

18. A compound according to claim 16 wherein $R^{2'}$ is Me; and $R^{2''}$ is H.

19. A compound according to claim 1 wherein the compound is according to formula VIII, IX or X

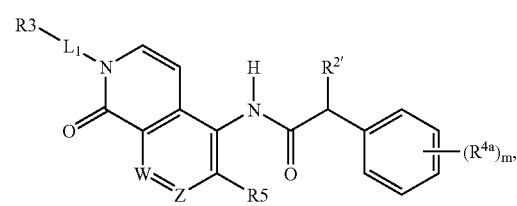

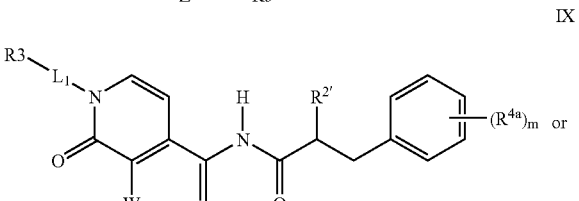

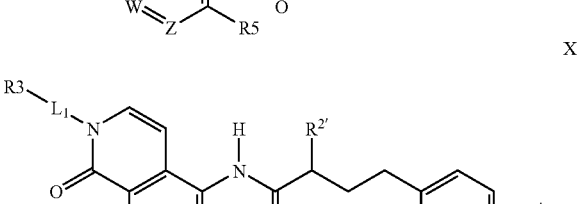

wherein

W is $CR^4$; Z is $CR^4$;

$L^1$, $R^3$ and $R^4$ are as described in claim 1; $R^{2'}$ is H or Me;

$R^5$ is selected from H, alkyl, substituted alkyl, acyl, substituted acyl, substituted or unsubstituted acylamino, substituted or unsubstituted alkylamino, substituted or unsubstituted alkylhio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

$R^{4a}$ is selected from hydrogen, alkyl, substituted alkyl, acyl, substituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5;

or a pharmaceutically acceptable salt thereof; or a stereoisomer, or an isotopic variant or a tautomer thereof.

20. A compound according to either of claim 16 or 19 wherein m is 1, 2 or 3.

21. A compound according to any one of claims 12, 19 and 19, wherein m is 1 or 2 and each $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2H$, SOMe, $SO_2Me$, $SO_3H$, $SO_3Me$, and pyridyl.

22. A compound according to any one of claims 12, 16 and 19, wherein $L^1$ is $C_1$-$C_5$ alkylene unsubstituted or substituted by one or more substituents selected from alkyl, oxo, aryl, hydroxyl, and hydroxyalkyl.

23. A compound according to any one of claims 12, 16 and 19, wherein $L^1$ is a $C_1$-$C_5$ alkylene group substituted with two alkyl groups and wherein any two alkyl groups on the same carbon atom can join together to form a cycloalkyl or cycloheteroalkyl ring of 3-7 atoms.

24. A compound according to any one of claims 12, 16 and 19, wherein $R^3$ is selected from hydroxyl, amino, alkylamino or carbamoyl.

25. A compound according to any one of claims 12, 16 and 19, wherein the group -$L_1$-$R^3$ is selected from

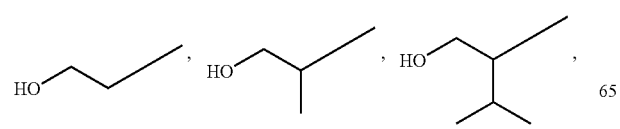

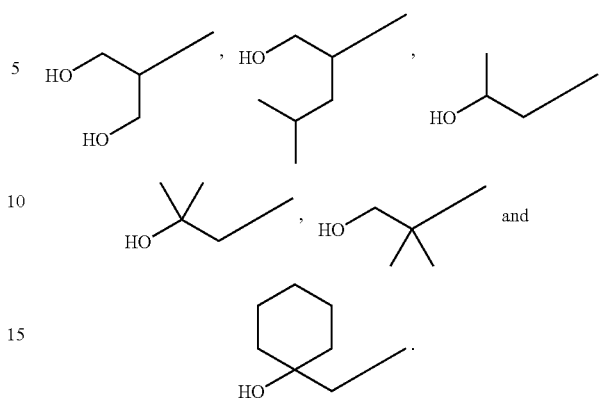

26. A compound according to any one of claims 12, 16 and 19, wherein the group -$L_1$-$R^3$ is selected from

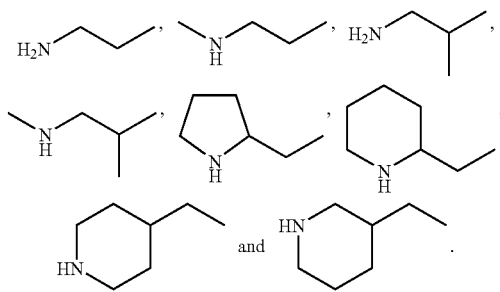

27. A compound according to any one of claims 12, 16 and 19, wherein the group -$L_1$-$R^3$ is selected from

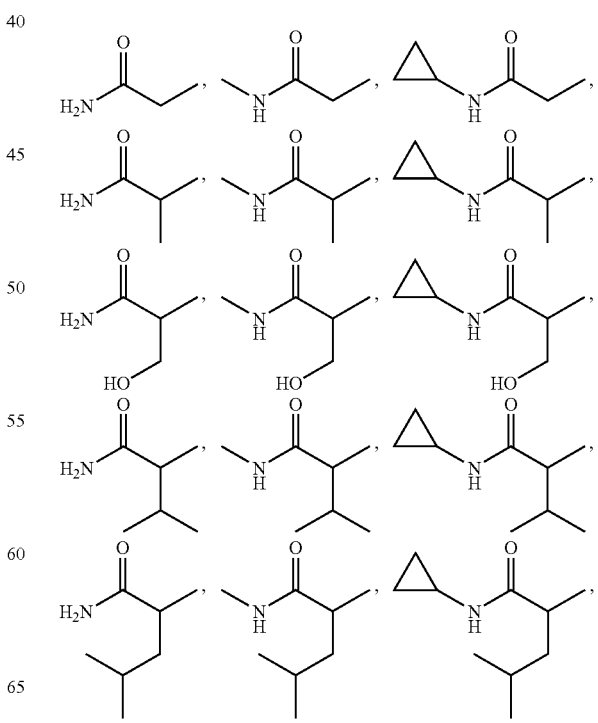

-continued

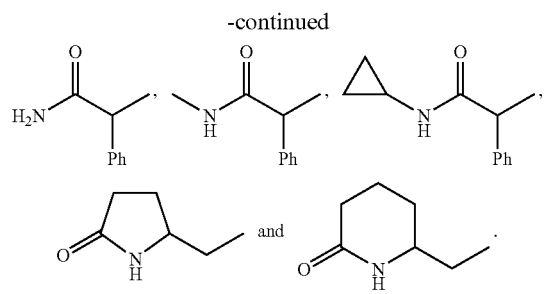

28. A compound according to claim 19 wherein $R^{2'}$ is Me.

29. A compound according to formula XIa, XIb, XIc, XId, XIe, XIf, XIg, XIh, or XIj:

XIa

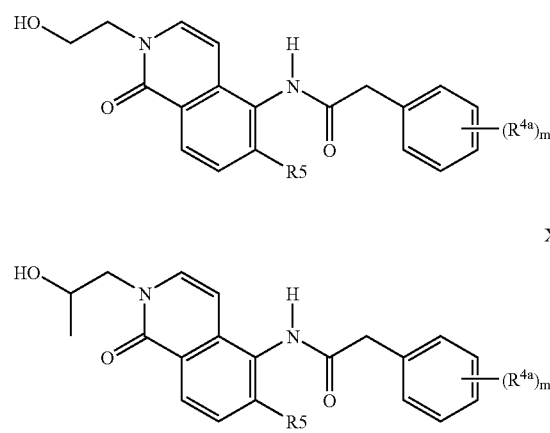

XIb

XIc

XId

XIe

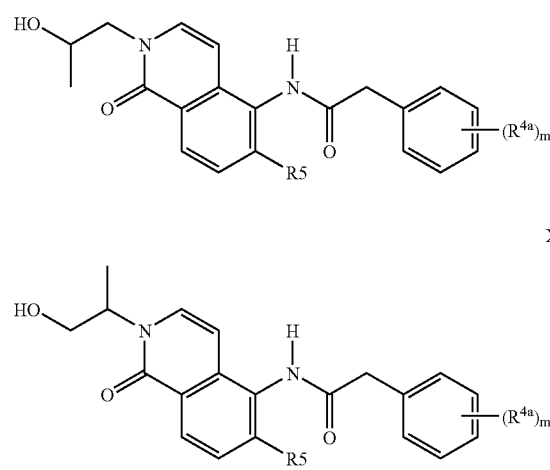

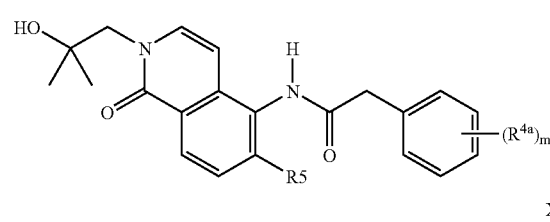

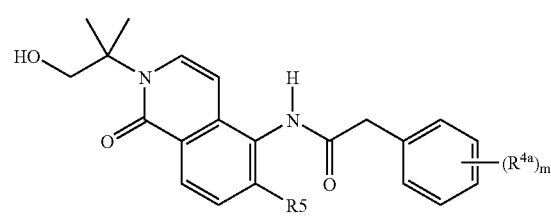

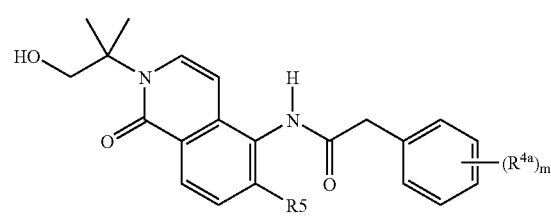

XIf

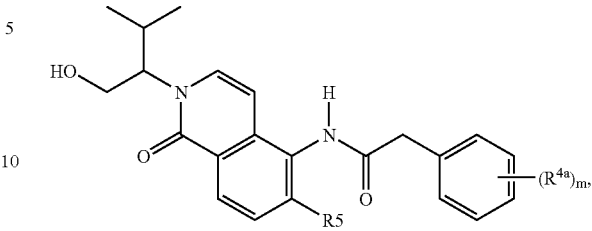

XIg

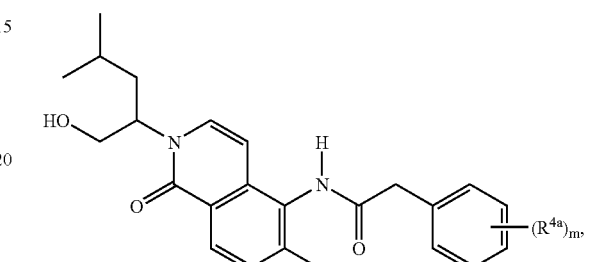

XIh

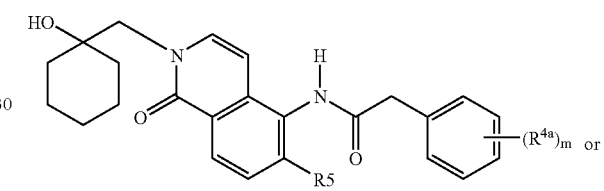 or

XIj

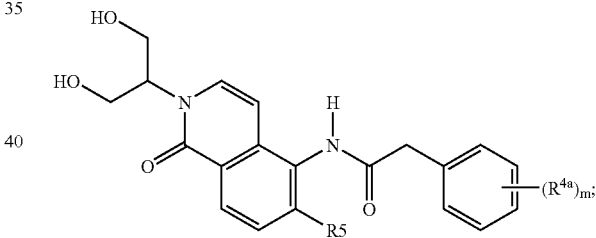

wherein $R^{4a}$ is independently selected from hydrogen, alkyl, substituted alkyl, acyl, substituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5; and $R^5$ is H, alkyl, cylcoalkyl, cycloalkyl, or halo.

30. A compound according to formula XIIa, XIIb or XIIc:

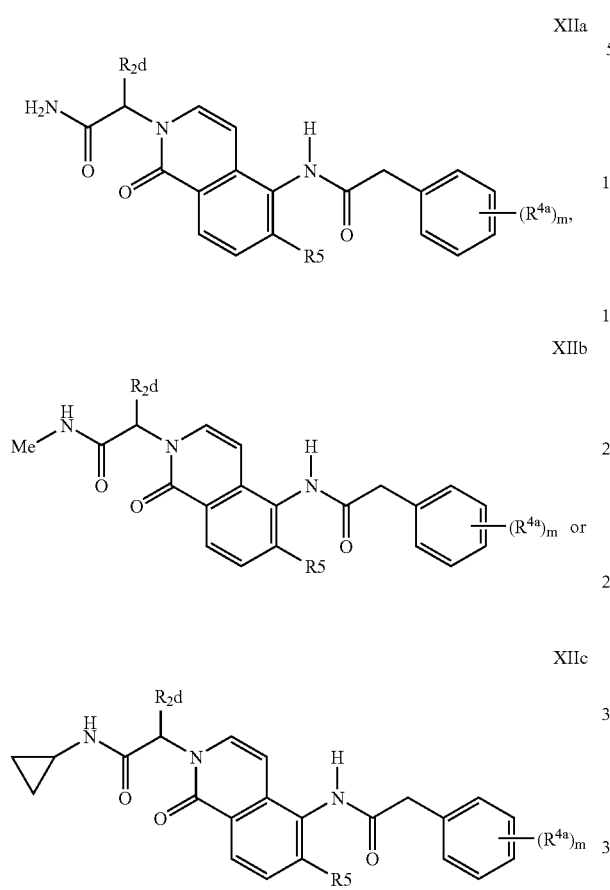

wherein $R^{4a}$ is independently selected from hydrogen alkyl, substituted alkyl, acyl, substituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5; $R^5$ is H, alkyl, cycloalkyl, or halo;

and $R^{2d}$ is selected from hydrogen, alkyl, hydroxyalkyl, and substituted or unsubstituted phenyl.

31. A compound according to claim 30 wherein $R^{2d}$ is methyl, i-Pr or hydroxymethyl.

32. A compound according to formula XIIIa, XIIIb, XIIIc or XIIId:

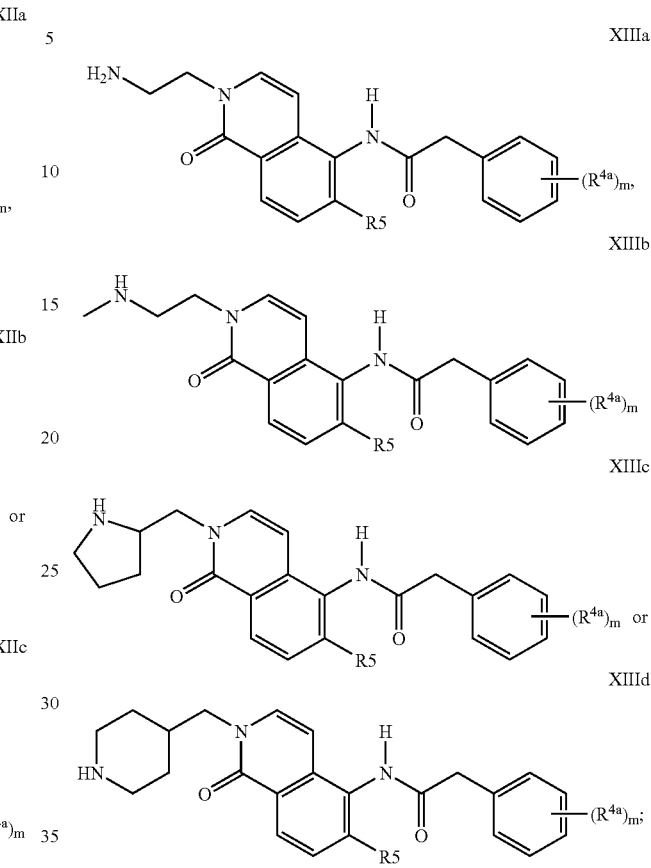

wherein $R^{4a}$ is independently selected from hydrogen, alkyl, substituted alkyl, acyl, substituted acyl, substituted or unsubstituted acylamino, substituted or unsubstituted alkylamino, substituted or unsubstituted alkylhio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-5; and $R^5$ is H, alkyl, cycloalkyl, or halo.

33. A compound according to any one of claims 29, 30, 31, and 32, wherein m is 1, 2 or 3.

34. A compound according to any one of claims 29, 30, and 32, wherein m is 1 or 2 and each $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl.

35. A compound according to any one of claims 16, 19, 29, 30, and 32, wherein m is 1 and $R^{4a}$ is $CF_3$.

36. A compound according to any one of claims 16, 19, 29, 30, and 32, wherein m is 2 and $R^{4a}$ is F and $CF_3$.

37. A compound according to any one of claims 16, 19, 29, 30, and 32, wherein m is 2 and $R^{4a}$ is F and Cl.

38. A compound according to any one of claims 12, 16 and 19, wherein each of W and Z is independently CH.

39. A compound according to any one of claims 12, 16 and 19, wherein W is N.

40. A compound according to any one of claims 12, 16 and 19, wherein W is N and Z is CH.

41. A compound according to any one of claims 12, 16, 19, 29, 30, and 32, wherein $R^5$ is H.

42. A compound according to any one of claims 12, 16, 19, 29, 30, and 32, wherein $R^5$ is Me, cyclopropyl, Cl, F, or $CF_3$.

43. A compound according to claim 1 wherein the compound is selected from

N-[2-(2-Hydroxy-ethyl)-1-oxo-1,2-dihydro-isoquinolin-5-yl]-benzamide;
N-[2-(2-Hydroxy-ethyl)-1-oxo-1,2-dihydro-isoquinolin-5-yl]-2-(4-methoxy-phenyl)-acetamide;
N-[2-(2-Hydroxy-ethyl)-1-oxo-1,2-dihydro-isoquinolin-5-yl]-3-phenyl-propionamide;
2-(4-Chloro-phenyl)-N-[2-(2-hydroxy-ethyl)-1-oxo-1,2-dihydro-isoquinolin-5-yl]-acetamide;
N-[2-(2-Hydroxy-1-hydroxymethyl-ethyl)-1-oxo-1,2-dihydro-isoquinolin-5-yl]-2,4-dimethoxy-benzamide;
N-[2-(2-Hydroxy-ethyl)-1-oxo-1,2-dihydro-isoquinolin-5-yl]-2,4-bis-trifluoromethyl-benzamide;
N-[2-(2-Hydroxy-ethyl)-1-oxo-1,2-dihydro-isoquinolin-5-yl]-2-(4-trifluoromethyl-phenyl)-acetamide;
2-(3,4-Dichloro-phenyl)-N-[2-(2-hydroxy-ethyl)-1-oxo-1,2-dihydro-isoquinolin-5-yl]-acetamide;
5-Phenyl-furan-2-carboxylic acid [2-(1-hydroxy-cyclohexylmethyl)-1-oxo-1,2-dihydro-isoquinolin-5-yl]-amide;
N-[2-(1-Hydroxy-cyclohexylmethyl)-1-oxo-1,2-dihydro-isoquinolin-5-yl]-3-(3-methoxy-phenyl)-propionamide;
N-[2-(1-Hydroxy-cyclohexylmethyl)-1-oxo-1,2-dihydro-isoquinolin-5-yl]-2-(2,4,6-trimethyl-phenyl)-acetamide;
2-(2,5-Dimethyl-phenyl)-N-[2-(1-hydroxy-cyclohexylmethyl)-1-oxo-1,2-dihydro-isoquinolin-5-yl]-acetamide;
3-Chloro-N-[2-(1-hydroxy-cyclohexylmethyl)-1-oxo-1,2-dihydro-isoquinolin-5-yl]-4-methoxy-benzamide;
3-Ethoxy-N-[2-(1-hydroxy-cyclohexylmethyl)-1-oxo-1,2-dihydro-isoquinolin-5-yl]-benzamide;
3-(2-Chloro-phenyl)-N-[2-(1-hydroxy-cyclohexylmethyl)-1-oxo-1,2-dihydro-isoquinolin-5-yl]-propionamide;
3-Benzo[1,3]-dioxol-5-yl-N-[2-(1-hydroxy-cyclohexylmethyl)-1-oxo-1,2-dihydro-isoquinolin-5-yl]-propionamide;
4-Chloro-N-[2-(1-hydroxy-cyclohexylmethyl)-1-oxo-1,2-dihydro-isoquinolin-5-yl]-3-methyl-benzamide;
N-[2-(1-Hydroxy-cyclohexylmethyl)-1-oxo-1,2-dihydro-isoquinolin-5-yl]-2,5-dimethyl-benzamide;
N-[2-(1-Hydroxy-cyclohexylmethyl)-1-oxo-1,2-dihydro-isoquinolin-5-yl]-3,5-dimethoxy-benzamide;
N-[2-(1-Hydroxy-cyclohexylmethyl)-1-oxo-1,2-dihydro-isoquinolin-5-yl]-3-methyl-benzamide;
4-Ethoxy-N-[2-(1-hydroxy-cyclohexylmethyl)-1-oxo-1,2-dihydro-isoquinolin-5-yl]-benzamide;
Biphenyl-4-carboxylic acid [2-(1-hydroxy-cyclohexylmethyl)-1-oxo-1,2-dihydro-isoquinolin-5-yl]-amide;
4-tert-Butyl-N-[2-(1-hydroxy-cyclohexylmethyl)-1-oxo-1,2-dihydro-isoquinolin-5-yl]-benzamide;
N-[2-(1-Hydroxy-cyclohexylmethyl)-1-oxo-1,2-dihydro-isoquinolin-5-yl]-2-phenyl-propionamide;
N-[2-(1-Hydroxy-cyclohexylmethyl)-1-oxo-1,2-dihydro-isoquinolin-5-yl]-3-(4-methoxy-phenyl)-propionamide;
N-[2-(1-Hydroxy-cyclohexylmethyl)-1-oxo-1,2-dihydro-isoquinolin-5-yl]-2-naphthalen-1-yl-acetamide;
Naphthalene-2-carboxylic acid [2-(1-hydroxy-cyclohexylmethyl)-1-oxo-1,2-dihydro-isoquinolin-5-yl]-amide;
2-(2-Fluoro-phenyl)-N-[2-(1-hydroxy-cyclohexylmethyl)-1-oxo-1,2-dihydro-isoquinolin-5-yl]-acetamide;
N-[2-(1-Hydroxy-cyclohexylmethyl)-1-oxo-1,2-dihydro-isoquinolin-5-yl]-2-(2-methoxy-phenyl)-acetamide;
2-(2,5-Dimethoxy-phenyl)-N-[2-(1-hydroxy-cyclohexylmethyl)-1-oxo-1,2-dihydro-isoquinolin-5-yl]-acetamide;
2-(3,4-Dimethoxy-phenyl)-N-[2-(1-hydroxy-cyclohexylmethyl)-1-oxo-1,2-dihydro-isoquinolin-5-yl]-acetamide;
N-[2-(1-Hydroxy-cyclohexylmethyl)-1-oxo-1,2-dihydro-isoquinolin-5-yl]-2-m-tolyl-acetamide;
N-[2-(1-Hydroxy-cyclohexylmethyl)-1-oxo-1,2-dihydro-isoquinolin-5-yl]-2-(4-methoxy-phenyl)-acetamide;
2-(4-Ethoxy-phenyl)-N-[2-(1-hydroxy-cyclohexylmethyl)-1-oxo-1,2-dihydro-isoquinolin-5-yl]-acetamide;
N-[2-(1-Hydroxy-cyclohexylmethyl)-1-oxo-1,2-dihydro-isoquinolin-5-yl]-2-p-tolyl-acetamide;
N-[2-(1-Hydroxy-cyclohexylmethyl)-1-oxo-1,2-dihydro-isoquinolin-5-yl]-4-phenyl-butyramide;
Benzofuran-2-carboxylic acid [2-(1-hydroxy-cyclohexylmethyl)-1-oxo-1,2-dihydro-isoquinolin-5-yl]-amide;
2-Benzol[1,3]-dioxol-5-yl-N-[2-(1-hydroxy-cyclohexylmethyl)-1-oxo-1,2-dihydro-isoquinolin-5-yl]-acetamide;
2-(3,5-Dimethoxy-phenyl)-N-[2-(1-hydroxy-cyclohexylmethyl)-1-oxo-1,2-dihydro-isoquinolin-5-yl]-acetamide;
N-[2-(1-Hydroxy-cyclohexylmethyl)-1-oxo-1,2-dihydro-isoquinolin-5-yl]-4-methoxy-3,5-dimethyl-benzamide;
3-Chloro-N-[2-(1-hydroxy-cyclohexylmethyl)-1-oxo-1,2-dihydro-isoquinolin-5-yl]-4-methyl-benzamide;
4-Chloro-N-[2-(1-hydroxy-cyclohexylmethyl)-1-oxo-1,2-dihydro-isoquinolin-5-yl]-2-methyl-benzamide;
2,3-Dihydro-benzo[1,4]dioxine-5-carboxylic acid [2-(1-hydroxy-cyclohexylmethyl)-1-oxo-1,2-dihydro-isoquinolin-5-yl]-amide;
3,4-Dihydro-2H-benzo[b][1,4]dioxepine-7-carboxylic acid [2-(1-hydroxy-cyclohexylmethyl)-1-oxo-1,2-dihydro-isoquinolin-5-yl]-amide;
2-Benzo[b]thiophen-3-yl-N-[2-(1-hydroxy-cyclohexylmethyl)-1-oxo-1,2-dihydro-isoquinolin-5-yl]-acetamide;
2-(3,5-Dimethyl-phenyl)-N-[2-(1-hydroxy-cyclohexylmethyl)-1-oxo-1,2-dihydro-isoquinolin-5-yl]-acetamide;
2-(2,4-Dimethoxy-phenyl)-N-[2-(1-hydroxy-cyclohexylmethyl)-1-oxo-1,2-dihydro-isoquinolin-5-yl]-acetamide;
4-Fluoro-N-[2-(1-hydroxy-cyclohexylmethyl)-1-oxo-1,2-dihydro-isoquinolin-5-yl]-3-methyl-benzamide;
3-(4-Chloro-phenyl)-N-[2-(1-hydroxy-cyclohexylmethyl)-1-oxo-1,2-dihydro-isoquinolin-5-yl]-propionamide;
2-(2-Ethoxy-phenyl)-N-[2-(1-hydroxy-cyclohexylmethyl)-1-oxo-1,2-dihydro-isoquinolin-5-yl]-acetamide;
2-Chloro-N-[2-(1-hydroxy-cyclohexylmethyl)-1-oxo-1,2-dihydro-isoquinolin-5-yl]-5-methyl-benzamide;
5-Chloro-N-[2-(1-hydroxy-cyclohexylmethyl)-1-oxo-1,2-dihydro-isoquinolin-5-yl]-2-methyl-benzamide;

N-[2-(1-Hydroxy-cyclohexylmethyl)-1-oxo-1,2-dihydro-isoquinolin-5-yl]-3-m-tolyl-propionamide;
5-Chloro-benzofuran-2-carboxylic acid [2-(1-hydroxy-cyclohexylmethyl)-1-oxo-1,2-dihydro-isoquinolin-5-yl]-amide;
2-Chloro-N-[2-(1-hydroxy-cyclohexylmethyl)-1-oxo-1,2-dihydro-isoquinolin-5-yl]-3-methyl-benzamide;
N-[2-(1-Hydroxy-cyclohexylmethyl)-1-oxo-1,2-dihydro-isoquinolin-5-yl]-4-methoxy-3-methyl-benzamide;
3-(2,4-Dimethyl-phenyl)-N-[2-(1-hydroxy-cyclohexylmethyl)-1-oxo-1,2-dihydro-isoquinolin-5-yl]-propionamide;
3-(3-Chloro-phenyl)-N-[2-(1-hydroxy-cyclohexylmethyl)-1-oxo-1,2-dihydro-isoquinolin-5-yl]-propionamide;
N-[2-(1-Hydroxy-cyclohexylmethyl)-1-oxo-1,2-dihydro-isoquinolin-5-yl]-4-isobutyl-benzamide;
N-[2-(2-Hydroxy-ethyl)-1-oxo-1,2,3,4-tetrahydro-isoquinolin-5-yl]-2-(4-trifluoromethyl-phenyl)-acetamide;
3-(3,5-Bis-trifluoromethyl-phenyl)-N-[2-(2-hydroxy-ethyl)-1-oxo-1,2-dihydro-isoquinolin-5-yl]-propionamide;
3-(2,5-Bis-trifluoromethyl-phenyl)-N-[2-(2-hydroxy-ethyl)-1-oxo-1,2-dihydro-isoquinolin-5-yl]-propionamide;
2-(2,3-Dihydro-benzo[1,4]dioxin-6-yl)-N-[2-(2-hydroxy-ethyl)-1-oxo-1,2-dihydro-isoquinolin-5-yl]-acetamide;
2-(3,5-Bis-trifluoromethyl-phenyl)-N-[2-(2-hydroxy-ethyl)-1-oxo-1,2-dihydro-isoquinolin-5-yl]-acetamide;
2-(4-Chloro-3-trifluoromethyl-phenyl)-N-{2-(2-hydroxy-ethyl)-1-oxo-1,2-dihydro-isoquinolin-5-yl}-acetamide;
2-(3-Bromo-4-methoxy-phenyl)-N-[2-(2-hydroxy-ethyl)-1-oxo-1,2-dihydro-isoquinolin-5-yl]-acetamide;
2-(2-Chloro-5-trifluoromethyl-phenyl)-N-[2-(2-hydroxy-ethyl)-1-oxo-1,2-dihydro-isoquinolin-5-yl]-acetamide;
2-(5-Chloro-2-trifluoromethyl-phenyl)-N-{2-(2-hydroxy-ethyl)-1-oxo-1,2-dihydro-isoquinolin-5-yl}-acetamide;
2-(2,4-Dichloro-phenyl)-N-[2-(2-hydroxy-ethyl)-1-oxo-1,2-dihydro-isoquinolin-5-yl]-acetamide;
2-(2,5-Bis-trifluoromethyl-phenyl)-N-[2-(2-hydroxy-ethyl)-1-oxo-1,2-dihydro-isoquinolin-5-yl]-acetamide;
N-[2-(2-Hydroxy-ethyl)-1-oxo-1,2-dihydro-isoquinolin-5-yl]-3-(4-methanesulfonyl-phenyl)-propionamide;
N-[2-(2-Hydroxy-ethyl)-1-oxo-1,2-dihydro-isoquinolin-5-yl]-2-(4-methanesulfonyl-phenyl)-acetamide;
2-(4-Fluoro-phenyl)-N-[2-(2-hydroxy-ethyl)-1-oxo-1,2-dihydro-isoquinolin-5-yl]-acetamide;
N-[2-(2-Hydroxy-ethyl)-1-oxo-1,2-dihydro-isoquinolin-5-yl]-2-phenyl-butyramide;
N-[2-(2-Hydroxy-ethyl)-1-oxo-1,2-dihydro-isoquinolin-5-yl]-2-(3-methoxy-phenyl)-acetamide;
N-[2-(2-Hydroxy-ethyl)-1-oxo-1,2-dihydro-isoquinolin-5-yl]-2-phenyl-acetamide;
2-(2,5-Dimethoxy-phenyl)-N-[2-(2-hydroxy-ethyl)-1-oxo-1,2-dihydro-isoquinolin-5-yl]-acetamide;
2-(4-Chloro-phenyl)-N-[2-(2-hydroxy-ethyl)-1-oxo-1,2-dihydro-isoquinolin-5-yl]-3-methyl-butyramide;
1-(4-Chloro-phenyl)-cyclopentanecarboxylic acid [2-(2-hydroxy-ethyl)-1-oxo-1,2-dihydro-isoquinolin-5-yl]-amide;
2-(3,4-Dichloro-phenyl)-N-[2-(2-hydroxy-1-hydroxymethyl-ethyl)-1-oxo-1,2-dihydro-isoquinolin-5-yl]-acetamide;
2-(4-Chloro-3-trifluoromethyl-phenyl)-N-[2-(2-hydroxy-1-hydroxymethyl--ethyl)-1-oxo-1,2-dihydro-isoquinolin-5-yl]-acetamide;
2-(2,4-Dichloro-phenyl)-N-[2-(2-hydroxy-1-hydroxymethyl-ethyl-ethyl)-1-oxo-1,2-dihydro-isoquinolin-5-yl]-acetamide;
N-{2-(1-Hydroxy-cyclohexylmethyl)-1-oxo-1,2-dihydro-isoquinolin-5-yl}-4-methoxy-2-methyl-benzamide;
N-[2-(1-Hydroxy-cyclohexylmethyl)-1-oxo-1,2-dihydro-isoquinolin-5-yl]-3-o-tolyl-propionamide;
N-{2-(1-Hydroxy-cyclohexylmethyl)-1-oxo-1,2-dihydro-isoquinolin-5-yl}-2,3-dimethyl-benzamide;
N-[2-(1-Hydroxy-cyclohexylmethyl)-1-oxo-1,2-dihydro-isoquinolin-5-yl]-2,4-dimethyl-benzamide;
N-[2-(1-Hydroxy-cyclohexylmethyl)-1-oxo-1,2-dihydro-isoquinolin-5-yl]-3-(2-methoxy-phenyl)-propionamide;
2-(2-Chloro-phenyl)-N-[2-(1-hydroxy-cyclohexylmethyl)-1-oxo-1,2-dihydro-isoquinolin-5-yl]-acetamide;
N-{2-(1-Hydroxy-cyclohexylmethyl)-1-oxo-1,2-dihydro-isoquinolin-5-yl}-2-o-tolyl-acetamide;
N-{2-(2-Hydroxy-1-methyl-ethyl)-1-oxo-1,2-dihydro-isoquinolin-5-yl}-3-o-tolyl-propionamide;
N-[2-(2-Hydroxy-1-methyl-ethyl)-1-oxo-1,2-dihydro-isoquinolin-5-yl]-3-(3-methoxy-phenyl)-propionamide;
3-Chloro-N-{2-(2-hydroxy-1-methyl-ethyl)-1-oxo-1,2-dihydro-isoquinolin-5-yl}-4-methoxy-benzamide;
3-Ethoxy-N-[2-(2-hydroxy-1-methyl-ethyl)-1-oxo-1,2-dihydro-isoquinolin-5-yl]-benzamide;
3-Benzol[1,3]-dioxol-5-yl-N-[2-(2-hydroxy-1-methyl-ethyl)-1-oxo-1,2-dihydro-isoquinolin-5-yl]-propionamide;
2-Chloro-N-[2-(2-hydroxy-1-methyl-ethyl)-1-oxo-1,2-dihydro-isoquinolin-5-yl]-benzamide;
2,4-Dichloro-N-[2-(2-hydroxy-1-methyl-ethyl)-1-oxo-1,2-dihydro-isoquinolin-5-yl]-benzamide;
2,5-Dichloro-N-[2-(2-hydroxy-1-methyl-ethyl)-1-oxo-1,2-dihydro-isoquinolin-5-yl]-benzamide;
N-[2-(2-Hydroxy-1-methyl-ethyl)-1-oxo-1,2-dihydro-isoquinolin-5-yl]-2,3-dimethyl-benzamide;
N-[2-(2-Hydroxy-1-methyl-ethyl)-1-oxo-1,2-dihydro-isoquinolin-5-yl]-2,4-dimethyl-benzamide;
N-[2-(2-Hydroxy-1-methyl-ethyl)-1-oxo-1,2-dihydro-isoquinolin-5-yl]-2,5-dimethyl-benzamide;
4-Ethoxy-N-[2-(2-hydroxy-1-methyl-ethyl)-1-oxo-1,2-dihydro-isoquinolin-5-yl]-benzamide;
Biphenyl-4-carboxylic acid [2-(2-hydroxy-1-methyl-ethyl)-1-oxo-1,2-dihydro-isoquinolin-5-yl]-amide;
N-[2-(2-Hydroxy-1-methyl-ethyl)-1-oxo-1,2-dihydro-isoquinolin-5-yl]-2-phenyl-propionamide;
N-[2-(2-Hydroxy-1-methyl-ethyl)-1-oxo-1,2-dihydro-isoquinolin-5-yl]-3-(2-methoxy-phenyl)-propionamide;
N-[2-(2-Hydroxy-1-methyl-ethyl)-1-oxo-1,2-dihydro-isoquinolin-5-yl]-3-(4-methoxy-phenyl)-propionamide;
Naphthalene-1-carboxylic acid [2-(2-hydroxy-1-methyl-ethyl)-1-oxo-1,2-dihydro-isoquinolin-5-yl]-amide;
N-[2-(2-Hydroxy-1-methyl-ethyl)-1-oxo-1,2-dihydro-isoquinolin-5-yl]-2-(2-methoxy-phenyl)-acetamide;
2-(2,5-Dimethoxy-phenyl)-N-[2-(2-hydroxy-1-methyl-ethyl)-1-oxo-1,2-dihydro-isoquinolin-5-yl]-acetamide;
2-(3,4-Dimethoxy-phenyl)-N-[2-(2-hydroxy-1-methyl-ethyl)-1-oxo-1,2-dihydro-isoquinolin-5-yl]-acetamide;
N-[2-(2-Hydroxy-1-methyl-ethyl)-1-oxo-1,2-dihydro-isoquinolin-5-yl]-2-(4-methoxy-phenyl)-acetamide;
N-[2-(2-Hydroxy-1-methyl-ethyl)-1-oxo-1,2-dihydro-isoquinolin-5-yl]-4-phenyl-butyramide;

Benzofuran-2-carboxylic acid [2-(2-hydroxy-1-methyl-ethyl)-1-oxo-1,2-dihydro-isoquinolin-5-yl]-amide;
2-Benzo[1,3]dioxol-5-yl-N-[2-(2-hydroxy-1-methyl-ethyl)-1-oxo-1,2-dihydro-isoquinolin-5-yl]-acetamide;
2-(3,5-Dimethoxy-phenyl)-N-[2-(2-hydroxy-1-methyl-ethyl)-1-oxo-1,2-dihydro-isoquinolin-5-yl]-acetamide;
3-Chloro-N-[2-(2-hydroxy-1-methyl-ethyl)-1-oxo-1,2-dihydro-isoquinolin-5-yl]-4-methyl-benzamide;
2,3-Dihydro-benzo[1,4]dioxine-5-carboxylic acid [2-(2-hydroxy-1-methyl-ethyl)-1-oxo-1,2-dihydro-isoquinolin-5-yl]-amide;
3,4-Dihydro-2H-benzo[b][1,4]dioxepine-7-carboxylic acid [2-(2-hydroxy-1-methyl-ethyl)-1-oxo-1,2-dihydro-isoquinolin-5-yl]-amide;
3-Chloro-N-[2-(2-hydroxy-1-methyl-ethyl)-1-oxo-1,2-dihydro-isoquinolin-5-yl]-2-methyl-benzamide;
2-(3,5-Dimethyl-phenyl)-N-[2-(2-hydroxy-1-methyl-ethyl)-1-oxo-1,2-dihydro-isoquinolin-5-yl]-acetamide;
2-(2,4-Dimethoxy-phenyl)-N-[2-(2-hydroxy-1-methyl-ethyl)-1-oxo-1,2-dihydro-isoquinolin-5-yl]-acetamide;
2-Chloro-N-[2-(2-hydroxy-1-methyl-ethyl)-1-oxo-1,2-dihydro-isoquinolin-5-yl]-5-methyl-benzamide;
5-Chloro-N-[2-(2-hydroxy-1-methyl-ethyl)-1-oxo-1,2-dihydro-isoquinolin-5-yl]-2-methyl-benzamide;
N-[2-(2-Hydroxy-1-methyl-ethyl)-1-oxo-1,2-dihydro-isoquinolin-5-yl]-4-methoxy-3-methyl-benzamide;
4-Ethoxy-2-hydroxy-N-[2-(2-hydroxy-propyl)-1-oxo-1,2-dihydro-isoquinolin-5-yl]-benzamide;
N-[2-(2-Hydroxy-propyl)-1-oxo-1,2-dihydro-isoquinolin-5-yl]-4-methoxy-2-methyl-benzamide;
N-[2-(2-Hydroxy-propyl)-1-oxo-1,2-dihydro-isoquinolin-5-yl]-3-o-tolyl-propionamide;
5-Phenyl-furan-2-carboxylic acid [2-(2-hydroxy-propyl)-1-oxo-1,2-dihydro-isoquinolin-5-yl]-amide;
N-{2-(2-Hydroxy-propyl)-1-oxo-1,2-dihydro-isoquinolin-5-yl}-3-(3-methoxy-phenyl)-propionamide;
N-[2-(2-Hydroxy-propyl)-1-oxo-1,2-dihydro-isoquinolin-5-yl]-2-(2,4,6-trimethyl-phenyl)-acetamide;
2-(2,5-Dimethyl-phenyl)-N-[2-(2-hydroxy-propyl)-1-oxo-1,2-dihydro-isoquinolin-5-yl]-acetamide;
3-Chloro-N-[2-(2-hydroxy-propyl)-1-oxo-1,2-dihydro-isoquinolin-5-yl]-4-methoxy-benzamide;
3-Ethoxy-N-[2-(2-hydroxy-propyl)-1-oxo-1,2-dihydro-isoquinolin-5-yl]-benzamide;
3-(2-Chloro-phenyl)-N-[2-(2-hydroxy-propyl)-1-oxo-1,2-dihydro-isoquinolin-5-yl]-propionamide;
3-Benzo[1,3]-dioxol-5-yl-N-[2-(2-hydroxy-propyl)-1-oxo-1,2-dihydro-isoquinolin-5-yl]-propionamide;
4-Chloro-N-[2-(2-hydroxy-propyl)-1-oxo-1,2-dihydro-isoquinolin-5-yl]-3-methyl-benzamide;
2-Chloro-N-[2-(2-hydroxy-propyl)-1-oxo-1,2-dihydro-isoquinolin-5-yl]-benzamide;
2,4-Dichloro-N-[2-(2-hydroxy-propyl)-1-oxo-1,2-dihydro-isoquinolin-5-yl]-benzamide;
2,5-Dichloro-N-[2-(2-hydroxy-propyl)-1-oxo-1,2-dihydro-isoquinolin-5-yl]-benzamide;
N-[2-(2-Hydroxy-propyl)-1-oxo-1,2-dihydro-isoquinolin-5-yl]-2-methyl-benzamide;
N-[2-(2-Hydroxy-propyl)-1-oxo-1,2-dihydro-isoquinolin-5-yl]-2,3-dimethyl-benzamide;
N-[2-(2-Hydroxy-propyl)-1-oxo-1,2-dihydro-isoquinolin-5-yl]-2,4-dimethyl-benzamide;
N-[2-(2-Hydroxy-propyl)-1-oxo-1,2-dihydro-isoquinolin-5-yl]-2,5-dimethyl-benzamide;
N-[2-(2-Hydroxy-propyl)-1-oxo-1,2-dihydro-isoquinolin-5-yl]-3,5-dimethoxy-benzamide;
N-[2-(2-Hydroxy-propyl)-1-oxo-1,2-dihydro-isoquinolin-5-yl]-3-methyl-benzamide;
4-Ethoxy-N-[2-(2-hydroxy-propyl)-1-oxo-1,2-dihydro-isoquinolin-5-yl]-benzamide;
Biphenyl-4-carboxylic acid [2-(2-hydroxy-propyl)-1-oxo-1,2-dihydro-isoquinolin-5-yl]-amide;
4-tert-Butyl-N-[2-(2-hydroxy-propyl)-1-oxo-1,2-dihydro-isoquinolin-5-yl]-benzamide;
N-[2-(2-Hydroxy-propyl)-1-oxo-1,2-dihydro-isoquinolin-5-yl]-2-phenyl-propionamide;
N-[2-(2-Hydroxy-propyl)-1-oxo-1,2-dihydro-isoquinolin-5-yl]-3-(2-methoxy-phenyl)-propionamide;
N-[2-(2-Hydroxy-propyl)-1-oxo-1,2-dihydro-isoquinolin-5-yl]-3-(4-methoxy-phenyl)-propionamide;
N-[2-(2-Hydroxy-propyl)-1-oxo-1,2-dihydro-isoquinolin-5-yl]-2-naphthalen-1-yl-acetamide;
Naphthalene-2-carboxylic acid [2-(2-hydroxy-propyl)-1-oxo-1,2-dihydro-isoquinolin-5-yl]-amide;
2-(2-Fluoro-phenyl)-N-[2-(2-hydroxy-propyl)-1-oxo-1,2-dihydro-isoquinolin-5-yl]-acetamide;
2-(2-Chloro-phenyl)-N-[2-(2-hydroxy-propyl)-1-oxo-1,2-dihydro-isoquinolin-5-yl]-acetamide;
N-[2-(2-Hydroxy-propyl)-1-oxo-1,2-dihydro-isoquinolin-5-yl]-2-(2-methoxy-phenyl)-acetamide;
2-(2,5-Dimethoxy-phenyl)-N-[2-(2-hydroxy-propyl)-1-oxo-1,2-dihydro-isoquinolin-5-yl]-acetamide;
N-[2-(2-Hydroxy-propyl)-1-oxo-1,2-dihydro-isoquinolin-5-yl]-2-o-tolyl-acetamide;
N-[2-(2-Hydroxy-propyl)-1-oxo-1,2-dihydro-isoquinolin-5-yl]-2-(3-methoxy-phenyl)-acetamide;
N-[2-(2-Hydroxy-propyl)-1-oxo-1,2-dihydro-isoquinolin-5-yl]-2-m-tolyl-acetamide;
N-[2-(2-Hydroxy-propyl)-1-oxo-1,2-dihydro-isoquinolin-5-yl]-2-(4-methoxy-phenyl)-acetamide;
2-(4-Ethoxy-phenyl)-N-[2-(2-hydroxy-propyl)-1-oxo-1,2-dihydro-isoquinolin-5-yl]-acetamide;
N-[2-(2-Hydroxy-propyl)-1-oxo-1,2-dihydro-isoquinolin-5-yl]-2-p-tolyl-acetamide;
N-[2-(2-Hydroxy-propyl)-1-oxo-1,2-dihydro-isoquinolin-5-yl]-4-phenyl-butyramide;
Benzofuran-2-carboxylic acid [2-(2-hydroxy-propyl)-1-oxo-1,2-dihydro-isoquinolin-5-yl]-amide;
2-Benzo[1,3]-dioxol-5-yl-N-[2-(2-hydroxy-propyl)-1-oxo-1 2-dihydro-isoquinolin-5-yl]-acetamide;
2-(3,5-Dimethoxy-phenyl)-N-[2-(2-hydroxy-propyl)-1-oxo-1,2-dihydro-isoquinolin-5-yl]-acetamide;
N-[2-(2-Hydroxy-propyl)-1-oxo-1,2-dihydro-isoquinolin-5-yl]-4-methoxy-3,5-dimethyl-benzamide;
3-Chloro-N-[2-(2-hydroxy-propyl)-1-oxo-1,2-dihydro-isoquinolin-5-yl]-4-methyl-benzamide;
4-Chloro-N-[2-(2-hydroxy-propyl)-1-oxo-1,2-dihydro-isoquinolin-5-yl]-2-methyl-benzamide;
2,3-Dihydro-benzo[1,4]dioxine-5-carboxylic acid [2-(2-hydroxy-propyl)-1-oxo-1,2-dihydro-isoquinolin-5-yl]-amide;
3,4-Dihydro-2H-benzo[b][1,4]dioxepine-7-carboxylic acid [2-(2-hydroxy-propyl)-1-oxo-1,2-dihydro-isoquinolin-5-yl]-amide;
3-Chloro-N-[2-(2-hydroxy-propyl)-1-oxo-1,2-dihydro-isoquinolin-5-yl]-2-methyl-benzamide;
2-(3,5-Dimethyl-phenyl)-N-[2-(2-hydroxy-propyl)-1-oxo-1,2-dihydro-isoquinolin-5-yl]-acetamide;
2-(2,4-Dimethoxy-phenyl)-N-[2-(2-hydroxy-propyl)-1-oxo-1,2-dihydro-isoquinolin-5-yl]-acetamide;
4-Fluoro-N-[2-(2-hydroxy-propyl)-1-oxo-1,2-dihydro-isoquinolin-5-yl]-3-methyl-benzamide;

2-(2-Ethoxy-phenyl)-N-[2-(2-hydroxy-propyl)-1-oxo-1,2-dihydro-isoquinolin-5-yl]-acetamide;
N-[2-(2-Hydroxy-propyl)-1-oxo-1,2-dihydro-isoquinolin-5-yl]-2-(4-methoxy-3-methyl-phenyl)-acetamide;
2-Chloro-N-[2-(2-hydroxy-propyl)-1-oxo-1,2-dihydro-isoquinolin-5-yl]-5-methyl-benzamide;
5-Chloro-N-[2-(2-hydroxy-propyl)-1-oxo-1,2-dihydro-isoquinolin-5-yl]-2-methyl-benzamide;
N-[2-(2-Hydroxy-propyl)-1-oxo-1,2-dihydro-isoquinolin-5-yl]-3-m-tolyl-propionamide;
5-Chloro-benzofuran-2-carboxylic acid [2-(2-hydroxy-propyl)-1-oxo-1,2-dihydro-isoquinolin-5-yl]-amide;
2-Chloro-N-[2-(2-hydroxy-propyl)-1-oxo-1,2-dihydro-isoquinolin-5-yl]-3-methyl-benzamide;
N-[2-(2-Hydroxy-propyl)-1-oxo-1,2-dihydro-isoquinolin-5-yl]-4-methoxy-3-methyl-benzamide;
3-(2,4-Dimethyl-phenyl)-N-[2-(2-hydroxy-propyl)-1-oxo-1,2-dihydro-isoquinolin-5-yl]-propionamide;
4-Ethoxy-2-hydroxy-N-[2-(2-hydroxy-2-methyl-propyl)-1-oxo-1,2-dihydro-isoquinolin-5-yl]-benzamide;
N-[2-(2-Hydroxy-2-methyl-propyl)-1-oxo-1,2-dihydro-isoquinolin-5-yl]-4-methoxy-2-methyl-benzamide;
N-[2-(2-Hydroxy-2-methyl-propyl)-1-oxo-1,2-dihydro-isoquinolin-5-yl]-3-o-tolyl-propionamide;
5-Phenyl-furan-2-carboxylic acid [2-(2-hydroxy-2-methyl-propyl)-1-oxo-1,2-dihydro-isoquinolin-5-yl]-amide;
N-[2-(2-Hydroxy-2-methyl-propyl)-1-oxo-1,2-dihydro-isoquinolin-5-yl]-3-(3-methoxy-phenyl)-propionamide;
N-[2-(2-Hydroxy-2-methyl-propyl)-1-oxo-1,2-dihydro-isoquinolin-5-yl]-2-(2,4,6-trimethyl-phenyl)-acetamide;
2-(2,5-Dimethyl-phenyl)-N-[2-(2-hydroxy-2-methyl-propyl)-1-oxo-1,2-dihydro-isoquinolin-5-yl]-acetamide;
3-Chloro-N-[2-(2-hydroxy-2-methyl-propyl)-1-oxo-1,2-dihydro-isoquinolin-5-yl]-4-methoxy-benzamide;
3-Ethoxy-N-[2-(2-hydroxy-2-methyl-propyl)-1-oxo-1,2-dihydro-isoquinolin-5-yl]-benzamide;
3-(2-Chloro-phenyl)-N-[2-(2-hydroxy-2-methyl-propyl)-1-oxo-1,2-dihydro-isoquinolin-5-yl]-propionamide;
3-Benzo[1,3]-dioxol-5-yl-N-[2-(2-hydroxy-2-methyl-propyl)-1-oxo-1,2-dihydro-isoquinolin-5-yl]-propionamide;
4-Chloro-N-[2-(2-hydroxy-2-methyl-propyl)-1-oxo-1,2-dihydro-isoquinolin-5-yl]-3-methyl-benzamide;
2-Chloro-N-[2-(2-hydroxy-2-methyl-propyl)-1-oxo-1,2-dihydro-isoquinolin-5-yl]-benzamide;
2,4-Dichloro-N-[2-(2-hydroxy-2-methyl-propyl)-1-oxo-1,2-dihydro-isoquinolin-5-yl]-benzamide;
2,5-Dichloro-N-[2-(2-hydroxy-2-methyl-propyl)-1-oxo-1,2-dihydro-isoquinolin-5-yl]-benzamide;
N-[2-(2-Hydroxy-2-methyl-propyl)-1-oxo-1,2-dihydro-isoquinolin-5-yl]-2-methyl-benzamide;
N-[2-(2-Hydroxy-2-methyl-propyl)-1-oxo-1,2-dihydro-isoquinolin-5-yl]-2,4-dimethyl-benzamide;
N-[2-(2-Hydroxy-2-methyl-propyl)-1-oxo-1,2-dihydro-isoquinolin-5-yl]-2,5-dimethyl-benzamide;
3,5-Dichloro-N-[2-(2-hydroxy-2-methyl-propyl)-1-oxo-1,2-dihydro-isoquinolin-5-yl]-benzamide;
Naphthalene-1-carboxylic acid [2-(2-hydroxy-2-methyl-propyl)-1-oxo-1,2-dihydro-isoquinolin-5-yl]-amide;
N-[2-(2-Hydroxy-2-methyl-propyl)-1-oxo-1,2-dihydro-isoquinolin-5-yl]-2-naphthalen-1-yl-acetamide;
Naphthalene-2-carboxylic acid [2-(2-hydroxy-2-methyl-propyl)-1-oxo-1,2-dihydro-isoquinolin-5-yl]-amide;
2-(2-Fluoro-phenyl)-N-[2-(2-hydroxy-2-methyl-propyl)-1-oxo-1,2-dihydro-isoquinolin-5-yl]-acetamide;
2-(2-Chloro-phenyl)-N-[2-(2-hydroxy-2-methyl-propyl)-1-oxo-1,2-dihydro-isoquinolin-5-yl]-acetamide;
N-[2-(2-Hydroxy-2-methyl-propyl)-1-oxo-1,2-dihydro-isoquinolin-5-yl]-2-(2-methoxy-phenyl)-acetamide;
2-(2,5-Dimethoxy-phenyl)-N-[2-(2-hydroxy-2-methyl-propyl)-1-oxo-1,2-dihydro-isoquinolin-5-yl]-acetamide;
N-[2-(2-Hydroxy-2-methyl-propyl)-1-oxo-1,2-dihydro-isoquinolin-5-yl]-2-o-tolyl-acetamide;
N-[2-(2-Hydroxy-2-methyl-propyl)-1-oxo-1,2-dihydro-isoquinolin-5-yl]-2-(3-methoxy-phenyl)-acetamide;
N-[2-(2-Hydroxy-2-methyl-propyl)-1-oxo-1,2-dihydro-isoquinolin-5-yl]-2-m-tolyl-acetamide;
N-[2-(2-Hydroxy-2-methyl-propyl)-1-oxo-1,2-dihydro-isoquinolin-5-yl]-2-(4-methoxy-phenyl)-acetamide;
2-(4-Ethoxy-phenyl)-N-[2-(2-hydroxy-2-methyl-propyl)-1-oxo-1,2-dihydro-isoquinolin-5-yl]-acetamide;
N-[2-(2-Hydroxy-2-methyl-propyl)-1-oxo-1,2-dihydro-isoquinolin-5-yl]-2-p-tolyl-acetamide;
Benzofuran-2-carboxylic acid [2-(2-hydroxy-2-methyl-propyl)-1-oxo-1,2-dihydro-isoquinolin-5-yl]-amide;
2-Benzo[1,3]-dioxol-5-yl-N-[2-(2-hydroxy-2-methyl-propyl)-1-oxo-1,2-dihydro-isoquinolin-5-yl]-acetamide;
2-(3,5-Dimethoxy-phenyl)-N-[2-(2-hydroxy-2-methyl-propyl)-1-oxo-1,2-dihydro-isoquinolin-5-yl]-acetamide;
3-Chloro-N-[2-(2-hydroxy-2-methyl-propyl)-1-oxo-1,2-dihydro-isoquinolin-5-yl]-4-methyl-benzamide;
4-Chloro-N-[2-(2-hydroxy-2-methyl-propyl)-1-oxo-1,2-dihydro-isoquinolin-5-yl]-2-methyl-benzamide;
2,3-Dihydro-benzo[1,4]dioxine-5-carboxylic acid [2-(2-hydroxy-2-methyl-propyl)-1-oxo-1,2-dihydro-isoquinolin-5-yl]-amide;
3,4-Dihydro-2H-benzo[b][1,4]dioxepine-7-carboxylic acid [2-(2-hydroxy-2-methyl-propyl)-1-oxo-1,2-dihydro-isoquinolin-5-yl]-amide;
2-Benzo[b]thiophen-3-yl-N-[2-(2-hydroxy-2-methyl-propyl)-1-oxo-1,2-dihydro-isoquinolin-5-yl]-acetamide;
3-Chloro-N-[2-(2-hydroxy-2-methyl-propyl)-1-oxo-1,2-dihydro-isoquinolin-5-yl]-2-methyl-benzamide;
2-(3,5-Dimethyl-phenyl)-N-[2-(2-hydroxy-2-methyl-propyl)-1-oxo-1,2-dihydro-isoquinolin-5-yl]-acetamide;
N-[2-(2-Hydroxy-2-methyl-propyl)-1-oxo-1,2-dihydro-isoquinolin-5-yl]-4-methoxy-3-methyl-benzamide;
2-(4-Chloro-2-trifluoromethyl-phenyl)-N-[2-(2-hydroxy-1-hydroxymethyl-ethyl)-1-oxo-1,2-dihydro-isoquinolin-5-yl]-acetamide;
2-(4-Chloro-2-trifluoromethyl-phenyl)-N-[2-(2-hydroxy-ethyl)-1-oxo-1,2-dihydro-isoquinolin-5-yl]-acetamide;
2-(2,4-Bis-trifluoromethyl-phenyl)-N-[2-(2-hydroxy-ethyl)-1-oxo-1,2-dihydro-isoquinolin-5-yl]-acetamide;
2-(4-Chloro-phenyl)-N-[2-(2-hydroxy-1-hydroxymethyl-ethyl)-1-oxo-1,2-dihydro-isoquinolin-5-yl]-propionamide;
2-(4-Chloro-3-trifluoromethyl-phenyl)-N-(1-oxo-2-(S)-1-pyrrolidin-2-ylmethyl-1,2-dihydro-isoquinolin-5-yl)-acetamide;
2-(2,4-Bis-trifluoromethyl-phenyl)-N-[2-(2-hydroxy-1-hydroxymethyl-ethyl)-1-oxo-1,2-dihydro-isoquinolin-5-yl]-acetamide;
2-(3,4-Dichloro-phenyl)-N-[2-(2-methylamino-ethyl)-1-oxo-1,2-dihydro-isoquinolin-5-yl]-acetamide;

2-(4-Chloro-3-trifluoromethyl-phenyl)-N-[2-(2-methylamino-ethyl)-1-oxo-1,2-dihydro-isoquinolin-5-yl]-acetamide;
(S)-2-{5-[2-(3,4-Dichloro-phenyl)-acetylamino]-1-oxo-1H-isoquinolin-2-yl}-propionamide;
(S)-2-{5-[2-(4-Chloro-2-trifluoromethyl-phenyl)-acetylamino]-1-oxo-1H-isoquinolin-2-yl}-propionamide;
(R)-2-{5-[2-(4-Chloro-3-trifluoromethyl-phenyl)-acetylamino]-1-oxo-1H-isoquinolin-2-yl}-propionamide;
(R)-2-{5-[2-(3,4-Dichloro-phenyl)-acetylamino]-1-oxo-1H-isoquinolin-2-yl}-propionamide;
(S)-2-{5-[2-(4-Chloro-phenyl)-propionylamino]-1-oxo-1H-isoquinolin-2-yl}-propionamide;
(R)-2-{5-[2-(4-Chloro-2-trifluoromethyl-phenyl)-acetylamino]-1-oxo-1H-isoquinolin-2-yl}-propionamide;
2-(4-Chloro-phenyl)-N-(1-oxo-2-(R)-1-pyrrolidin-2-ylmethyl-1,2-dihydro-isoquinolin-5-yl)-propionamide;
2-(4-Chloro-3-trifluoromethyl-phenyl)-N-(1-oxo-2-(R)-1-pyrrolidin-2-ylmethyl-1,2-dihydro-isoquinolin-5-yl)-acetamide;
2-(4-Chloro-phenyl)-N-[2-(2-hydroxy-ethyl)-1-oxo-1,2-dihydro-isoquinolin-5-yl]-propionamide;
2-(3,4-Dichloro-phenyl)-N-(1-oxo-2-(R)-1-pyrrolidin-2-ylmethyl-1,2-dihydro-isoquinolin-5-yl)-acetamide;
2-(4-Chloro-phenyl)-N-(1-oxo-2-(S)-1-pyrrolidin-2-ylmethyl-1,2-dihydro-isoquinolin-5-yl)-propionamide;
(R)-2-{5-[2-(4-Chloro-phenyl)-propionylamino]-1-oxo-1H-isoquinolin-2-yl}-propionamide;
N-[6-Chloro-2-(2-hydroxy-ethyl)-1-oxo-1,2-dihydro-isoquinolin-5-yl]-2-(3,4-dichloro-phenyl)-acetamide;
2-{5-[2-(4-Chloro-3-trifluoromethyl-phenyl)-acetylamino]-1-oxo-1H-isoquinolin-2-yl}-acetamide;
(S)-2-{5-[2-(4-Chloro-3-trifluoromethyl-phenyl)-acetylamino]-1-oxo-1H-isoquinolin-2-yl}-3-hydroxy-propionamide;
2-(4-Chloro-3-trifluoromethyl-phenyl)-N-[2-(2-hydroxy-ethyl)-1-oxo-1,2-dihydro-isoquinolin-5-yl]-propionamide;
(R)-2-{5-[2-(4-Chloro-phenyl)-propionylamino]-1-oxo-1H-isoquinolin-2-yl}-3-hydroxy-propionamide;
(S)-2-{5-[2-(3,4-Dichloro-phenyl)-acetylamino]-1-oxo-1H-isoquinolin-2-yl}-3-hydroxy-propionamide;
(R)-2-{5-[2-(3,4-Dichloro-phenyl)-propionylamino]-1-oxo-1H-isoquinolin-2-yl}-propionamide;
(R)-2-{5-[2-(3-Chloro-phenyl)-acetylamino]-1-oxo-1H-isoquinolin-2-yl}-propionamide;
(R)-2-{5-[2-(4-Chloro-phenyl)-acetylamino]-1-oxo-1H-isoquinolin-2-yl}-propionamide;
2-(4-Chloro-3-trifluoromethyl-phenyl)-N-(1-oxo-2-piperidin-4-ylmethyl-1,2-dihydro-isoquinolin-5-yl)-acetamide;
N-[2-(3-Amino-2-chloromethyl-propyl)-1-oxo-1,2-dihydro-isoquinolin-5-yl]-2-(4-chloro-3-trifluoromethyl-phenyl)-acetamide;
N-[2-(3-Amino-2-chloromethyl-propyl)-1-oxo-1,2-dihydro-isoquinolin-5-yl]-2-(3,4-dichloro-phenyl)-acetamide;
(R)-2-{5-[2-(2-Chloro-phenyl)-acetylamino]-1-oxo-1H-isoquinolin-2-yl}-propionamide;
(R)-2-{5-[2-(4-Chloro-phenyl)-propionylamino]-1-oxo-1H-isoquinolin-2-yl}-3-hydroxy-N-methyl-propionamide;
(R)-2-{5-[(R)-2-(4-Chloro-phenyl)-propionylamino]-1-oxo-1H-isoquinolin-2-yl}-propionamide;
(R)-2-{5-[(S)-2-(4-Chloro-phenyl)-propionylamino]-1-oxo-1H-isoquinolin-2-yl}-propionamide;
N-[2-((R)-1-Carbamoyl-ethyl)-1-oxo-1,2-dihydro-isoquinolin-5-yl]-2-(4-chloro-phenyl)-isobutyramide;
(S)-2-{5-[(S)-2-(4-Chloro-phenyl)-propionylamino]-1-oxo-1H-isoquinolin-2-yl}-propionamide;
(S)-2-{5-[(R)-2-(4-Chloro-phenyl)-propionylamino]-1-oxo-1H-isoquinolin-2-yl}-propionamide;
(R)-2-{5-[2-(4-Chloro-3-trifluoromethyl-phenyl)-propionylamino]-1-oxo-1H-isoquinolin-2-yl}-propionamide;
(R)-2-{5-[(S)-2-(3,4-Dichloro-phenyl)-propionylamino]-1-oxo-1H-isoquinolin-2-yl}-propionamide;
(R)-2-{5-[(R)-2-(3,4-Dichloro-phenyl)-propionylamino]-1-oxo-1H-isoquinolin-2-yl}-propionamide;
(R)-2-{5-[2-(3,4-Dichloro-phenyl)-propionylamino]-1-oxo-1H-isoquinolin-2-yl}-3-hydroxy-N-methyl-propionamide;
(S)-2-(4-Chloro-phenyl)-N-[2-((R)-1-hydroxymethyl-3-methyl-butyl)-1-oxo-1,2-dihydro-isoquinolin-5-yl]-propionamide;
Quinoline-5-carboxylic acid [2-((R)-1-carbamoyl-ethyl)-1-oxo-1,2-dihydro-isoquinolin-5-yl]-amide;
(R)-2-(4-Chloro-phenyl)-N-[(R)-2-(1-hydroxymethyl-2-methyl-propyl)-1-oxo-1,2-dihydro-isoquinolin-5-yl]-propionamide;
(S)-2-(4-Chloro-phenyl)-N-[2-((R)-1-hydroxymethyl-2-methyl-propyl)-1-oxo-1,2-dihydro-isoquinolin-5-yl]-propionamide;
2-(3,4-Dichloro-phenyl)-N-[2-((R)-1-hydroxymethyl-3-methyl-butyl)-1-oxo-1,2-dihydro-isoquinolin-5-yl]-acetamide;
(R)-2-{5-[(S)-2-(4-Chloro-phenyl)-propionylamino]-1-oxo-1H-isoquinolin-2-yl}-3,N-dimethyl-butyramide;
(R)-2-{5-[(R)-2-(4-Chloro-phenyl)-propionylamino]-1-oxo-1H-isoquinolin-2-yl}-3,N-dimethyl-butyramide;
(S)—N-[2-((R)-Carbamoyl-phenyl-methyl)-1-oxo-1,2-dihydro-isoquinolin-5-yl]-2-(3,4-dichloro-phenyl)-propionamide;
(S)—N-[2-((R)-Carbamoyl-phenyl-methyl)-1-oxo-1,2-dihydro-isoquinolin-5-yl]-2-(4-chloro-phenyl)-propionamide;
2-(4-Chloro-3-trifluoromethyl-phenyl)-N-{2-((R)-1-hydroxymethyl-3-methyl-butyl)-1-oxo-1,2-dihydro-isoquinolin-5-yl}-acetamide;
(R)-2-{5-[(S)-2-(4-Chloro-phenyl)-propionylamino]-1-oxo-1H-isoquinolin-2-yl}-N-cyclopropyl-3-methyl-butyramide;
(R)-2-{5-((R)-2-(4-Chloro-phenyl)-propionylamino-1-1-oxo-1H-isoquinolin-2-yl}-N-cyclopropyl-3-methyl-butyramide;
(R)-2-{5-[(S)-2-(4-Chloro-phenyl)-propionylamino]-1-oxo-1H-isoquinolin-2-yl]-3-methyl-butyramide;
(R)-2-{5-[(R)-2-(4-Chloro-phenyl)-propionylamino]-1-oxo-1H-isoquinolin-2-yl}-3-methyl-butyramide;
(R)-2-{5-[2-(2-Fluoro-3-trifluoromethyl-phenyl)-acetylamino]-1-oxo-1H-isoquinolin-2-yl}-propionamide;
(R)-2-{5-[2-(2-Fluoro-6-trifluoromethyl-phenyl)-acetylamino]-1-oxo-1H-isoquinolin-2-yl}-propionamide;
(R)-2-{5-[2-(4-Cyano-phenyl)-acetylamino]-1-oxo-1H-isoquinolin-2-yl}-propionamide;
(R)-2-{5-[2-(3-Cyano-phenyl)-acetylamino]-1-oxo-1H-isoquinolin-2-yl}-propionamide;
(R)-2-{5-(2-Biphenyl-4-yl-acetylamino)-1-oxo-1H-isoquinolin-2-yl}-propionamide;
(R)-2-{5-[2-(4-Chloro-2-fluoro-phenyl)-acetylamino]-1-oxo-1H-isoquinolin-2-yl}-propionamide;
(R)-2-{5-[2-(2-Chloro-4-fluoro-phenyl)-acetylamino]-1-oxo-1H-isoquinolin-2-yl}-propionamide;

(R)-2-{5-[2-(2,6-Difluoro-phenyl)-acetylamino]-1-oxo-1H-isoquinolin-2-yl}-propionamide;
(R)-2-{5-[2-(2,4-Difluoro-phenyl)-acetylamino]-1-oxo-1H-isoquinolin-2-yl}-propionamide;
(R)-2-{5-[2-(2-Fluoro-phenyl)-acetylamino]-1-oxo-1H-isoquinolin-2-yl}-propionamide;
(R)-2-{5-[2-(4-Fluoro-2-trifluoromethyl-phenyl)-acetylamino]-1-oxo-1H-isoquinolin-2-yl}-propionamide;
(R)-2-{5-[2-(2-Fluoro-4-trifluoromethyl-phenyl)-acetylamino]-1-oxo-1H-isoquinolin-2-yl}-propionamide;
(R)-2-{1-Oxo-5-[2-(3-trifluoromethyl-phenyl)-acetylamino]-1H-isoquinolin-2-yl}-propionamide;
(R)-2-{1-Oxo-5-[2-(4-trifluoromethyl-phenyl)-acetylamino]-1H-isoquinolin-2-yl}-propionamide;
(R)-2-{5-[2-(4-Fluoro-phenyl)-propionylamino]-1-oxo-1H-isoquinolin-2-yl}-propionamide;
(R)-2-{5-[2-(4-Chloro-3-fluoro-phenyl)-acetylamino]-1-oxo-1H-isoquinolin-2-yl}-propionamide;
(R)-2-{5-[2-(3-Chloro-4-fluoro-phenyl)-acetylamino]-1-oxo-1H-isoquinolin-2-yl}-propionamide;
(R)-2-{5-[2-(3-Fluoro-4-methyl-phenyl)-acetylamino]-1-oxo-1H-isoquinolin-2-yl}-propionamide;
(R)-2-{5-[2-(3,4-Difluoro-phenyl)-acetylamino]-1-oxo-1H-isoquinolin-2-yl}-propionamide;
(R)-2-{5-[2-(4-Fluoro-3-trifluoromethyl-phenyl)-acetylamino]-1-oxo-1H-isoquinolin-2-yl}-propionamide;
(R)-2-{1-Oxo-5-[2-(2,4,5-trifluoro-phenyl)-acetylamino]-1H-isoquinolin-2-yl}-propionamide;
(R)-2-{5-[2-(3-Fluoro-4-trifluoromethyl-phenyl)-acetylamino]-1-oxo-1H-isoquinolin-2-yl}-propionamide;
(R)-2-{5-[2-(3-Bromo-4-fluoro-phenyl)-acetylamino]-1-oxo-1H-isoquinolin-2-yl}-propionamide;
(R)-2-{5-[(S)-2-(4-Chloro-phenyl)-propionylamino]-1-oxo-1H-isoquinolin-2-yl}N-cyclopropyl-propionamide;
(R)-2-{1-Oxo-5-(2-pyridin-2-yl-acetylamino)-1H-isoquinolin-2-yl}-propionamide;
(S)-2-{5-[2-(6-Chloro-pyridin-3-yl)-acetylamino]-1-oxo-1H-isoquinolin-2-yl}-propionamide;
(R)-2-{1-oxo-5-[2-(4-trifluoromethoxy-phenyl)-acetylamino]-1H-isoquinolin-2-yl}-propionamide;
(R)-2-{5-[2-(6-Chloro-pyridin-3-yl)-acetylamino]-1-oxo-1H-isoquinolin-2-yl}-propionamide;
(R)-2-{1-oxo-5-[2-(3-trifluoromethoxy-phenyl)-acetylamino]-1H-isoquinolin-2-yl}-propionamide;
(R)-2-{5-[2-(2,4-Dichloro-phenyl)-acetylamino]-1-oxo-1H-isoquinolin-2-yl}-propionamide;
(S)—N-{2-[Carbamoyl-(4-chloro-phenyl)-methyl]-1-oxo-1,2-dihydro-isoquinolin-5-yl}-2-(4-chloro-phenyl)-propionamide;
(R)-2-{6-Chloro-1-oxo-5-[2-(4-trifluoromethyl-phenyl)-acetylamino]-1H-isoquinolin-2-yl}-propionamide;
(R)-2-(3,4-Dichloro-phenyl)-N-[2-((S)-2-hydroxy-1-methyl-ethyl)-1-oxo-1,2-dihydro-isoquinolin-5-yl]-propionamide;
N-[2-((S)-2-Hydroxy-1-methyl-ethyl)-1-oxo-1,2-dihydro-isoquinolin-5-yl]-2-(4-trifluoromethyl-phenyl)-acetamide;
N-[2-((R)-2-Hydroxy-1-methyl-ethyl)-1-oxo-1,2-dihydro-isoquinolin-5-yl]-2-(4-trifluoromethyl-phenyl)-acetamide;
(R)-2-(3,4-Dichloro-phenyl)-N-[2-((R)-2-hydroxy-1-methyl-ethyl)-1-oxo-1,2-dihydro-isoquinolin-5-yl]-propionamide;
(S)-2-(3,4-Dichloro-phenyl)-N-[2-((R)-2-hydroxy-1-methyl-ethyl)-1-oxo-1,2-dihydro-isoquinolin-5-yl]-propionamide;
(R)-2-{5-[(S)-2-(4-Chloro-phenyl)-propionylamino]-1-oxo-1H-isoquinolin-2-yl}-propionic acid;
(R)-2-{5-[(S)-2-(4-Chloro-phenyl)-propionylamino]-1-oxo-1H-isoquinolin-2-yl}-3-methyl-butyric acid;
2-(2-Fluoro-3-trifluoromethyl-phenyl)-N-[2-((R)-2-hydroxy-1-methyl-ethyl)-1-oxo-1,2-dihydro-isoquinolin-5-yl]-acetamide;
2-(2-Fluoro-3-trifluoromethyl-phenyl)-N-[2-((S)-2-hydroxy-1-methyl-ethyl)-1-oxo-1,2-dihydro-isoquinolin-5-yl]-acetamide;
(S)-2-(3,4-Dichloro-phenyl)-N-[2-((S)-2-hydroxy-1-methyl-ethyl)-1-oxo-1,2-dihydro-isoquinolin-5-yl]-propionamide;
2-(4-Chloro-2-fluoro-phenyl)-N-[2-((R)-2-hydroxy-1-methyl-ethyl)-1-oxo-1,2-dihydro-isoquinolin-5-yl]-acetamide;
2-(4-Chloro-2-fluoro-phenyl)-N-[2-((S)-2-hydroxy-1-methyl-ethyl)-1-oxo-1,2-dihydro-isoquinolin-5-yl]-acetamide;
2-(3-Chloro-4-fluoro-phenyl)-N-[2-((R)-2-hydroxy-1-methyl-ethyl)-1-oxo-1,2-dihydro-isoquinolin-5-yl]-acetamide;
2-(4-Chloro-3-fluoro-phenyl)-N-[2-((R)-2-hydroxy-1-methyl-ethyl)-1-oxo-1,2-dihydro-isoquinolin-5-yl]-acetamide;
2-(3-Chloro-4-fluoro-phenyl)-N-[2-((S)-2-hydroxy-1-methyl-ethyl)-1-oxo-1,2-dihydro-isoquinolin-5-yl]-acetamide;
2-(3,4-Dichloro-phenyl)-N-[2-((S)-2-hydroxy-1-methyl-ethyl)-1-oxo-1,2-dihydro-isoquinolin-5-yl]-acetamide;
2-(3,4-Dichloro-phenyl)-N-{2-((R)-2-hydroxy-1-methyl-ethyl)-1-oxo-1,2-dihydro-isoquinolin-5-yl}-acetamide;
2-(4-Chloro-3-fluoro-phenyl)-N-[2-((S)-2-hydroxy-1-methyl-ethyl)-1-oxo-1,2-dihydro-isoquinolin-5-yl]-acetamide;
2-(3-Fluoro-4-trifluoromethyl-phenyl)-N-[2-((R)-2-hydroxy-1-methyl-ethyl)-1-oxo-1,2-dihydro-isoquinolin-5-yl]-acetamide;
2-(3-Fluoro-4-trifluoromethyl-phenyl)-N-[2-((S)-2-hydroxy-1-methyl-ethyl)-1-oxo-1,2-dihydro-isoquinolin-5-yl]-acetamide;
(R)-2-{5-[2-(2-Fluoro-3-trifluoromethyl-phenyl)-propionylamino]-1-oxo-1H-isoquinolin-2-yl}-propionamide;
2-(4-Fluoro-3-trifluoromethyl-phenyl)-N-[2-((S)-2-hydroxy-1-methyl-ethyl)-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-1-oxo-1,2-dihydro-isoquinolin-5-yl]-acetamide;
(R)-2-{6-Chloro-5-[(S)-2-(4-chloro-phenyl)-propionylamino]-1-oxo-1H-isoquinolin-2-yl}-propionamide;
2-(3-Chloro-4-fluoro-phenyl)-N-[2-(2-hydroxy-ethyl)-1-oxo-1,2-dihydro-isoquinolin-5-yl]-acetamide;
(R)-2-{6-Chloro-5-[2-(2-fluoro-3-trifluoromethyl-phenyl)-acetylamino]-1-oxo-1H-isoquinolin-2-yl}-propionamide;
(R)-2-{6-Chloro-5-[2-(4-chloro-2-fluoro-phenyl)-acetylamino]-1-oxo-1H-isoquinolin-2-yl}-propionamide;
(R)-2-{6-Methoxy-1-oxo-5-[2-(4-trifluoromethyl-phenyl)-acetylamino]-1H-isoquinolin-2-yl}-propionamide;
(S)-2-{6-Chloro-1-oxo-5-[2-(4-trifluoromethyl-phenyl)-acetylamino]-1-1H-isoquinolin-2-yl}-propionamide;
(S)-2-{5-[2-(3-Chloro-4-fluoro-phenyl)-acetylamino]-1-oxo-1H-isoquinolin-2-yl}-propionamide;
(S)-2-{5-[2-(3-Fluoro-4-trifluoromethyl-phenyl)-acetylamino]-1-oxo-1H-isoquinolin-2-yl}-propionamide;

(S)-2-{5-[2-(4-Fluoro-3-trifluoromethyl-phenyl)-acetylamino]-1-oxo-1H-isoquinolin-2-yl}-propionamide;
(S)-2-{5-[2-(2-Fluoro-3-trifluoromethyl-phenyl)-acetylamino]-1-oxo-1H-isoquinolin-2-yl}-propionamide;
(S)-2-{5-[2-(4-Chloro-2-fluoro-phenyl)-acetylamino]-1-oxo-1H-isoquinolin-2-yl}-propionamide;
(S)-2-{1-Oxo-5-[2-(4-trifluoromethyl-phenyl)-acetylamino]-1H-isoquinolin-2-yl}-propionamide;
(S)-2-{5-[2-(4-Chloro-3-fluoro-phenyl)-acetylamino]-1-oxo-1H-isoquinolin-2-yl}-propionamide;
(S)-2-{5-[2-(4-Chloro-3-trifluoromethyl-phenyl)-acetylamino]-1-oxo-1H-isoquinolin-2-yl}-propionamide;
2-(4-Chloro-3-fluoro-phenyl)-N-[2-(2-hydroxy-ethyl)-1-oxo-1,2-dihydro-isoquinolin-5-yl]-acetamide;
(S)-2-{5-[2-(2-Fluoro-3-trifluoromethyl-phenyl)-propionylamino]-1-oxo-1H-isoquinolin-2-yl}-propionamide;
(S)-2-{5-[2-(4-Chloro-3-trifluoromethyl-phenyl)-propionylamino]-1-oxo-1H-isoquinolin-2-yl}-propionamide;
2-(3-Fluoro-4-trifluoromethyl-phenyl)-N-[2-(2-hydroxy-ethyl)-1-oxo-1,2-dihydro-isoquinolin-5-yl]-acetamide;
2-(3-Fluoro-4-trifluoromethyl-phenyl)-N-[2-((R)-2-hydroxy-1-methyl-ethyl)-6-methoxy-1-oxo-1,2-dihydro-isoquinolin-5-yl]-acetamide;
2-(2-Fluoro-4-trifluoromethyl-phenyl)-N-[2-((R)-2-hydroxy-1-methyl-ethyl)-1-oxo-1,2-dihydro-isoquinolin-5-yl]-acetamide;
2-(2,4-Bis-trifluoromethyl-phenyl)-N-[2-((R)-2-hydroxy-1-methyl-ethyl)-1-oxo-1,2-dihydro-isoquinolin-5-yl]-acetamide;
2-(4-Chloro-3-trifluoromethyl-phenyl)-N-[2-((R)-2-hydroxy-1-methyl-ethyl)-1-oxo-1,2-dihydro-isoquinolin-5-yl]-acetamide;
N-[2-(2-Hydroxy-1,1-dimethyl-ethyl)-1-oxo-1,2-dihydro-isoquinolin-5-yl]-2-(4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(4-trifluoromethyl-phenyl)-acetamide;
2-(3-Fluoro-4-trifluoromethyl-phenyl)-N-[2-(2-hydroxy-1,1-dimethyl-ethyl)-1-oxo-1,2-dihydro-isoquinolin-5-yl]-acetamide;
2-(2,4-Bis-trifluoromethyl-phenyl)-N-[2-(2-hydroxy-1,1-dimethyl-ethyl)-1-oxo-1,2-dihydro-isoquinolin-5-yl]-acetamide;
2-(4-Fluoro-3-trifluoromethyl-phenyl)-N-[2-(2-hydroxy-1,1-dimethyl-ethyl)-1-oxo-1,2-dihydro-isoquinolin-5-yl]-acetamide;
2-(2-Fluoro-3-trifluoromethyl-phenyl)-N-[2-(2-hydroxy-1,1-dimethyl-ethyl)-1-oxo-1,2-dihydro-isoquinolin-5-yl]-acetamide;
2-(4-Chloro-3-trifluoromethyl-phenyl)-N-[2-(2-hydroxy-1,1-dimethyl-ethyl)-1-oxo-1,2-dihydro-isoquinolin-5-yl]-acetamide;
2-(2-Fluoro-4-trifluoromethyl-phenyl)-N-[2-(2-hydroxy-1,1-dimethyl-ethyl)-1-oxo-1,2-dihydro-isoquinolin-5-yl]-acetamide;
2-(3,4-Dichloro-phenyl)-N-[2-(2-hydroxy-1,1-dimethyl-ethyl)-1-oxo-1,2-dihydro-isoquinolin-5-yl]-acetamide;
2-(3-Chloro-4-fluoro-phenyl)-N-[2-(2-hydroxy-1,1-dimethyl-ethyl)-1-oxo-1,2-dihydro-isoquinolin-5-yl]-acetamide;
2-(4-Chloro-3-fluoro-phenyl)-N-[2-(2-hydroxy-1,1-dimethyl-ethyl)-1-oxo-1,2-dihydro-isoquinolin-5-yl]-acetamide;
2-(4-Chloro-2-fluoro-phenyl)-N-[2-(2-hydroxy-1,1-dimethyl-ethyl)-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3,4-dichloro-phenyl)-acetamide;
N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;
N-[6-Chloro-2-((R)-2-hydroxy-1-methyl-ethyl)-1-oxo-1,2-dihydro-isoquinolin-5-yl]-2-(2-fluoro-4-trifluoromethyl-phenyl)-acetamide;
(R)-2-{1-Oxo-5-[2-(2,3,4-trifluoro-phenyl)-acetylamino]-1H-isoquinolin-2-yl}-propionamide;
(R)-2-{5-[2-(2,4-Bis-trifluoromethyl-phenyl)-acetylamino]-1-oxo-1H-isoquinolin-2-yl}-propionamide;
(R)-2-{1-Oxo-5-[2-(3,4,5-trifluoro-phenyl)-acetylamino]-1H-isoquinolin-2-yl}-propionamide;
2-(4-Chloro-3-fluoro-phenyl)-N-[6-chloro-2-((R)-2-hydroxy-1-methyl-ethyl)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(3-fluoro-4-trifluoromethyl-phenyl)-acetamide;
N-[6-Cyclopropyl-2-((R)-2-hydroxy-1-methyl-ethyl)-1-oxo-1,2-dihydro-isoquinolin-5-yl]-2-(3-fluoro-4-trifluoromethyl-phenyl)-acetamide;
2-(2-Fluoro-3-trifluoromethyl-phenyl)-N-[2-(2-hydroxy-ethyl)-6-(2-hydroxy-ethylamino)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(4-fluoro-3-trifluoromethyl-phenyl)-acetamide;
N-[6-Chloro-2-(2-hydroxy-ethyl)-1-oxo-1,2-dihydro-isoquinolin-5-yl]-2-(2-fluoro-3-trifluoromethyl-phenyl)-acetamide;
N-[2-(2-Acetylamino-ethyl)-1-oxo-1,2-dihydro-isoquinolin-5-yl]-2-(4-chloro-3-fluoro-phenyl)-acetamide;
N-[2-(2-Acetylamino-ethyl)-1-oxo-1,2-dihydro-isoquinolin-5-yl]-2-(3-chloro-4-fluoro-phenyl)-acetamide;
N-[2-(2-Acetylamino-ethyl)-1-oxo-1,2-dihydro-isoquinolin-5-yl]-2-(3-fluoro-4-trifluoromethyl-phenyl)-acetamide;
N-[2-(2-Acetylamino-ethyl)-1-oxo-1,2-dihydro-isoquinolin-5-yl]-2-(4-chloro-3-trifluoromethyl-phenyl)-acetamide;
N-[2-(2-Acetylamino-ethyl)-1-oxo-1,2-dihydro-isoquinolin-5-yl]-2-(3,4-difluoro-phenyl)-acetamide;
2-(3-Fluoro-4-trifluoromethyl-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-(2-hydroxy-ethyl)-6-methyl-1-oxo-1,2-dihydro-isoquinolin-5-yl]-acetamide;
N-[2-((R)-2-Hydroxy-1-methyl-ethyl)-6-methyl-1-oxo-1,2-dihydro-isoquinolin-5-yl]-2-(4-trifluoromethyl-phenyl)-acetamide;

2-(4-Chloro-3-fluoro-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-[2-(2-hydroxy-ethyl)-6-methyl-1-oxo-1,2-dihydro-isoquinolin-5-yl]-acetamide; and
2-(3-Fluoro-4-trifluoromethyl-phenyl)-N-[2-((R)-2-hydroxy-1-methyl-ethyl)-6-methyl-1-oxo-1,2,3,4-tetrahydro-isoquinolin-5-yl]-acetamide.

44. A compound according to claim 1 wherein the compound is selected from 2-(4-Chloro-phenyl)-N-[2-(2-hydroxy-ethyl)-1-oxo-1,2-dihydro-isoquinolin-5-yl]-acetamide;
2-(3,4-Dichloro-phenyl)-N-[2-(2-hydroxy-ethyl)-1-oxo-1,2-dihydro-isoquinolin-5-yl]-acetamide;
3-(2,5-Bis-trifluoromethyl-phenyl)-N-[2-(2-hydroxy-ethyl)-1-oxo-1,2-dihydro-isoquinolin-5-yl]-propionamide;
2-(4-Chloro-3-trifluoromethyl-phenyl)-N-[2-(2-hydroxy-ethyl)-1-oxo-1,2-dihydro-isoquinolin-5-yl]-acetamide;
2-(4-Chloro-3-trifluoromethyl-phenyl)-N-[2-(2-hydroxy-1-hydroxymethyl-ethyl)-1-oxo-1,2-dihydro-isoquinolin-5-yl]-acetamide;
2-(4-Chloro-3-trifluoromethyl-phenyl)-N-(1-oxo-2-(S)-1-pyrrolidin-2-ylmethyl-1,2-dihydro-isoquinolin-5-yl)-acetamide;
(S)-2-{5-[2-(3,4-Dichloro-phenyl)-acetylamino]-1-oxo-1H-isoquinolin-2-yl}-propionamide;
(R)-2-{5-[2-(4-Chloro-3-trifluoromethyl-phenyl)-acetylamino]-1-oxo-1H-isoquinolin-2-yl}-propionamide;
(R)-2-{5-[2-(4-Chloro-phenyl)-propionylamino]-1-oxo-1H-isoquinolin-2-yl}-propionamide;
(S)-2-{5-[2-(4-Chloro-3-trifluoromethyl-phenyl)-acetylamino]-1-oxo-1H-isoquinolin-2-yl}-3-hydroxy-propionamide;
(R)-2-{5-[2-(3,4-Dichloro-phenyl)-propionylamino]-1-oxo-1H-isoquinolin-2-yl}-propionamide;
(R)-2-{5-[2-(4-Chloro-phenyl)-acetylamino]-1-oxo-1H-isoquinolin-2-yl}-propionamide;
(R)-2-{5-[(S)-2-(4-Chloro-phenyl)-propionylamino]-1-oxo-1H-isoquinolin-2-yl}-propionamide;
(S)-2-{5-[(S)-2-(4-Chloro-phenyl)-propionylamino]-1-oxo-1H-isoquinolin-2-yl}-propionamide;
(R)-2-{5-[2-(4-Chloro-3-trifluoromethyl-phenyl)-propionylamino]-1-oxo-1H-isoquinolin-2-yl}-propionamide;
(R)-2-{5-[(S)-2-(3,4-Dichloro-phenyl)-propionylamino]-1-oxo-1H-isoquinolin-2-yl}-propionamide;
(R)-2-{5-[(R)-2-(3,4-Dichloro-phenyl)-propionylamino]-1-oxo-1H-isoquinolin-2-yl}-propionamide;
(R)-2-{5-[2-(2-Fluoro-3-trifluoromethyl-phenyl)-acetylamino]-1-oxo-1H-isoquinolin-2-yl}-propionamide;
(R)-2-{5-[2-(4-Chloro-2-fluoro-phenyl)-acetylamino]-1-oxo-1H-isoquinolin-2-yl}-propionamide;
(R)-2-{1-Oxo-5-[2-(4-trifluoromethyl-phenyl)-acetylamino]-1H-isoquinolin-2-yl}-propionamide;
(R)-2-{6-Chloro-1-oxo-542-(4-trifluoromethyl-phenyl)-acetylamino]-1H-isoquinolin-2-yl}-propionamide;
N-[2-((R)-2-Hydroxy-1-methyl-ethyl)-1-oxo-1,2-dihydro-isoquinolin-5-yl]-2-(4-trifluoromethyl-phenyl)-acetamide;
2-(2-Fluoro-3-trifluoromethyl-phenyl)-N-[2-((R)-2-hydroxy-1-methyl-ethyl)-1-oxo-1,2-dihydro-isoquinolin-5-yl]-acetamide;
2-(4-Chloro-3-fluoro-phenyl)-N-[2-((R)-2-hydroxy-1-methyl-ethyl)-1-oxo-1,2-dihydro-isoquinolin-5-yl]-acetamide;
2-(3-Fluoro-4-trifluoromethyl-phenyl)-N-[2-((R)-2-hydroxy-1-methyl-ethyl)-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-1-oxo-1,2-dihydro-isoquinolin-5-yl]-acetamide;
(R)-2-{6-Chloro-5-[2-(2-fluoro-3-trifluoromethyl-phenyl)-acetylamino]-1-oxo-1H-isoquinolin-2-yl}-propionamide;
(S)-2-{1-Oxo-5-[2-(4-trifluoromethyl-phenyl)-acetylamino]-1H-isoquinolin-2-yl}-propionamide;
(S)-2-{5-[2-(4-Chloro-3-trifluoromethyl-phenyl)-acetylamino]-1-oxo-1H-isoquinolin-2-yl}-propionamide;
2-(3-Fluoro-4-trifluoromethyl-phenyl)-N-[2-(2-hydroxy-ethyl)-1-oxo-1,2-dihydro-isoquinolin-5-yl]-acetamide;
2-(2-Fluoro-4-trifluoromethyl-phenyl)-N-[2-((R)-2-hydroxy-1-methyl-ethyl)-1-oxo-1,2-dihydro-isoquinolin-5-yl]-acetamide;
2-(4-Chloro-3-trifluoromethyl-phenyl)-N-[2-((R)-2-hydroxy-1-methyl-ethyl)-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(4-trifluoromethyl-phenyl)-acetamide;
2-(4-Chloro-3-trifluoromethyl-phenyl)-N-[2-(2-hydroxy-1,1-dimethyl-ethyl)-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3,4-dichloro-phenyl)-acetamide;
N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;
2-(4-Chloro-3-fluoro-phenyl)-N-[6-chloro-2-((R)-2-hydroxy-1-methyl-ethyl)-1-oxo-1,2-dihydro-isoquinolin-5-yl]acetamide;
N-[6-Chloro-2-(2-hydroxy-ethyl)-1-oxo-1,2-dihydro-isoquinolin-5-yl]-2-(3-fluoro-4-trifluoromethyl-phenyl)-acetamide;
N-[6-Chloro-2-(2-hydroxy-ethyl)-1-oxo-1,2-dihydro-isoquinolin-5-yl]-2-(4-fluoro-3-trifluoromethyl-phenyl)-acetamide;
2-(3-Fluoro-4-trifluoromethyl-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide; and
2-(3-Fluoro-4-trifluoromethyl-phenyl)-N-[2-(2-hydroxy-ethyl)-6-methyl-1-oxo-1,2-dihydro-isoquinolin-5-yl]-acetamide.

45. A compound according to claim 1 wherein the compound is selected from 2-(2-Fluoro-3-trifluoromethyl-phenyl)-N-[2-((R)-2-hydroxy-1-methyl-ethyl)-1-oxo-1,2-dihydro-isoquinolin-5-yl]-acetamide;
2-(4-Chloro-3-fluoro-phenyl)-N-[2-((R)-2-hydroxy-1-methyl-ethyl)-1-oxo-1,2-dihydro-isoquinolin-5-yl]-acetamide;
2-(3,4-Dichloro-phenyl)-N-[2-((R)-2-hydroxy-1-methyl-ethyl)-1-oxo-1,2-dihydro-isoquinolin-5-yl]-acetamide;

2-(3-Fluoro-4-trifluoromethyl-phenyl)-N-{2-((R)-2-hydroxy-1-methyl-ethyl)-1-oxo-1,2-dihydro-isoquinolin-5-yl}-acetamide;

N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;

N-[6-Chloro-2-((R)-2-hydroxy-1-methyl-ethyl)-1-oxo-1,2-dihydro-isoquinolin-5-yl]-2-(3,4-dichloro-phenyl)-acetamide;

N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;

2-(3-Fluoro-4-trifluoromethyl-phenyl)-N-[2-((R)-2-hydroxy-1-methyl-ethyl)-6-methyl-1-oxo-1,2-dihydro-isoquinolin-5-yl]-acetamide;

2-(4-Fluoro-3-trifluoromethyl-phenyl)-N-{2-((R)-2-hydroxy-1-methyl-ethyl)-6-methyl-1-oxo-1,2-dihydro-isoquinolin-5-yl}-acetamide;

2-(2-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;

N-[2-((R)-2-Hydroxy-1-methyl-ethyl)-6-methyl-1-oxo-1,2-dihydro-isoquinolin-5-yl]-2-(4-trifluoromethyl-phenyl)-acetamide;

2-(4-Chloro-3-fluoro-phenyl)-N-[2-((R)-2-hydroxy-1-methyl-ethyl)-6-methyl-1-oxo-1,2-dihydro-isoquinolin-5-yl]-acetamide;

2-(3-Fluoro-4-trifluoromethyl-phenyl)-N-[2-(2-hydroxy-ethyl)-6-methyl-1-oxo-1,2-dihydro-isoquinolin-5-yl]-acetamide;

2-(3-Fluoro-4-trifluoromethyl-phenyl)-N-[2-((R)-2-hydroxy-1-methyl-ethyl)-6-methyl-1-oxo-1,2,3,4-tetrahydro-isoquinolin-5-yl]-acetamide;

(R)-2-{5-[(S)-2-(4-Chloro-phenyl)-propionylamino]-1-oxo-1H-isoquinolin-2-yl}-3-methyl-butyramide; and (R)-2-{5-[(R)-2-(4-Chloro-phenyl)-propionylamino]-1-oxo-1H-isoquinolin-2-yl}-3-methyl-butyramide.

46. A pharmaceutical composition comprising a pharmaceutically acceptable carrier and a pharmaceutically effective amount of a compound of claim 1.

47. The pharmaceutical composition of claim 46, wherein the carrier is a parenteral carrier.

48. The pharmaceutical composition of claim 46, wherein the carrier is an oral carrier.

49. The pharmaceutical composition of claim 46, wherein the carrier is a topical carrier.

50. A method for treating in a mammal a disease or condition that is causally related to the aberrant activity of the P2X$_7$ receptor in vivo, which comprises administering to the mammal an effective disease-treating or condition-treating amount of a compound according to claim 1, or a pharmaceutical composition according to claim 46, wherein the disease or condition is selected from a pain condition, and an inflammatory disease or condition.

51. A method for treating in a mammal a disease or condition selected from: pain including acute, inflammatory and neuropathic pain, chronic pain, dental pain and headache including migraine, cluster headache and tension headache; and diseases and disorders which are mediated by or result in inflammation, arthritis, rheumatoid arthritis and osteoarthritis, diseases and disorders which are mediated by or result in neuroinflammation, and inflammatory bowel disease, which comprises administering to the mammal an effective disease-treating or condition-treating amount of a compound according to claim 1, or a pharmaceutical composition of claim 46.

52. The method of claim 51, wherein the disease or condition is rheumatoid arthritis.

53. The method of claim 51, wherein the disease or condition is osteoarthritis.

54. The method of claim 51, wherein the disease or condition is pain.

55. The method of claim 51, wherein the disease or condition is neuropathic pain.

56. The method of claim 55, wherein the pain is associated with a condition selected from the group consisting of post-mastectomy pain syndrome, stump pain, phantom limb pain, oral neuropathic pain, Charcot's pain, toothache, venomous snake bite, spider bite, insect sting, postherpetic neuralgia, diabetic neuropathy, reflex sympathetic dystrophy, trigeminal neuralgia, osteoarthritis, rheumatoid arthritis, fibromyalgis, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia splenopalatine neuralgia, supraorbital neuralgia, vidian neuralgia, sinus headache, tension headache, labor, childbirth, intestinal gas, menstruation, cancer, and trauma.

* * * * *